US012466835B1

(12) United States Patent
Bakale et al.

(10) Patent No.: US 12,466,835 B1
(45) Date of Patent: Nov. 11, 2025

(54) SOLID FORMS OF MACROCYCLIC COMPOUNDS, SALTS AND FORMULATIONS THEREOF, AND METHODS OF PREPARING AND USING THE SAME

(71) Applicant: Kura Oncology, Inc., San Diego, CA (US)

(72) Inventors: Roger Paul Bakale, Cardiff, CA (US); Kenneth K. Liu, Fremont, CA (US); Yun Shan, San Diego, CA (US); Xiufeng Sun, Oceanside, CA (US); Patricia Andres, Bend, OR (US); Song Chen, Beijing (CN); Yue Lu, Ningbo (CN); Licheng Song, Beijing (CN); Catalina Ferrer, Groningen (NL); Ana Rita Neves, Frankfurt am Main (DE)

(73) Assignee: Kura Oncology, Inc., San Diego, CA (US)

( * ) Notice: Subject to any disclaimer, the term of this patent is extended or adjusted under 35 U.S.C. 154(b) by 0 days.

(21) Appl. No.: 18/935,332

(22) Filed: Nov. 1, 2024

Related U.S. Application Data

(63) Continuation of application No. PCT/CN2024/096480, filed on May 30, 2024.

(30) Foreign Application Priority Data

May 31, 2023 (WO) ................ PCT/CN2023/097389

(51) Int. Cl.

| | |
|---|---|
| ***C07D 491/08*** | (2006.01) |
| ***A61K 9/20*** | (2006.01) |
| ***A61K 9/28*** | (2006.01) |
| ***A61K 31/4748*** | (2006.01) |

(52) U.S. Cl.

CPC .......... *C07D 491/08* (2013.01); *A61K 9/2009* (2013.01); *A61K 9/2013* (2013.01); *A61K 9/2027* (2013.01); *A61K 9/2054* (2013.01); *A61K 9/2095* (2013.01); *A61K 9/282* (2013.01); *A61K 9/2853* (2013.01); *A61K 31/4748* (2013.01)

(58) Field of Classification Search

CPC .................................................... C07D 491/08

See application file for complete search history.

(56) References Cited

U.S. PATENT DOCUMENTS 12,018,011 B2 * 6/2024 Zhu ...................... C07D 401/10

FOREIGN PATENT DOCUMENTS

| | | |
|---|---|---|
| WO | WO 1997021701 A1 | 6/1997 |
| WO | WO 2023102378 A1 | 6/2023 |

OTHER PUBLICATIONS

Chemical Abstract Service, STN Database, Registry No. 1639044-71-5 [online][Entered STN: Dec. 18, 2014] (Year: 2014).

Chemical Abstract Service, STN Database, Registry No. 190441-46-4 [online][Entered STN: Dec. 18, 2014] (Year: 1997).

Dinsmore et al., "Conformational Restriction of Flexible Ligands Guided by the Transferred NOE Experiment: Potent Macrocyclic Inhibitors of Farnesyltransferase," Journal of the American Chemical Society 123(9):2107-2108 (2001).

Driggers et al., "The exploration of macrocycles for drug discovery—an underexploited structural class," Nature Reviews Drug Discovery 7(7):608-624 (2008).

International Search Report and Written Opinion for International Patent Application No. PCT/CN2024/096480 mailed Aug. 28, 2024 (12 pages).

Kraus et al., "Second Generation Analogues of the Cancer Drug Clinical Candidate Tipifarnib for Anti-Chagas Disease Drug Discovery," Journal of Medicinal Chemistry 53(10):3887-3898 (2010).

Yu et al., "Discovery of novel inhibitors for human farnesyltransferase (hFTase) via structure-based virtual screenings," Med Chem Comm 4(6):962-971 (2013).

* cited by examiner

*Primary Examiner* — Kevin E Weddington

(74) *Attorney, Agent, or Firm* — Jones Day

(57) ABSTRACT

The present disclosure relates to solid forms of Compound 1, or a pharmaceutically acceptable form thereof, a pharmaceutically acceptable salt of Compound 1, or pharmaceutically acceptable solvate thereof, pharmaceutical compositions comprising the same, methods of preparing the same, and methods of treating cancer dependent on a farnesylated protein, using the same.

28 Claims, 51 Drawing Sheets

4/51

Figure 1:
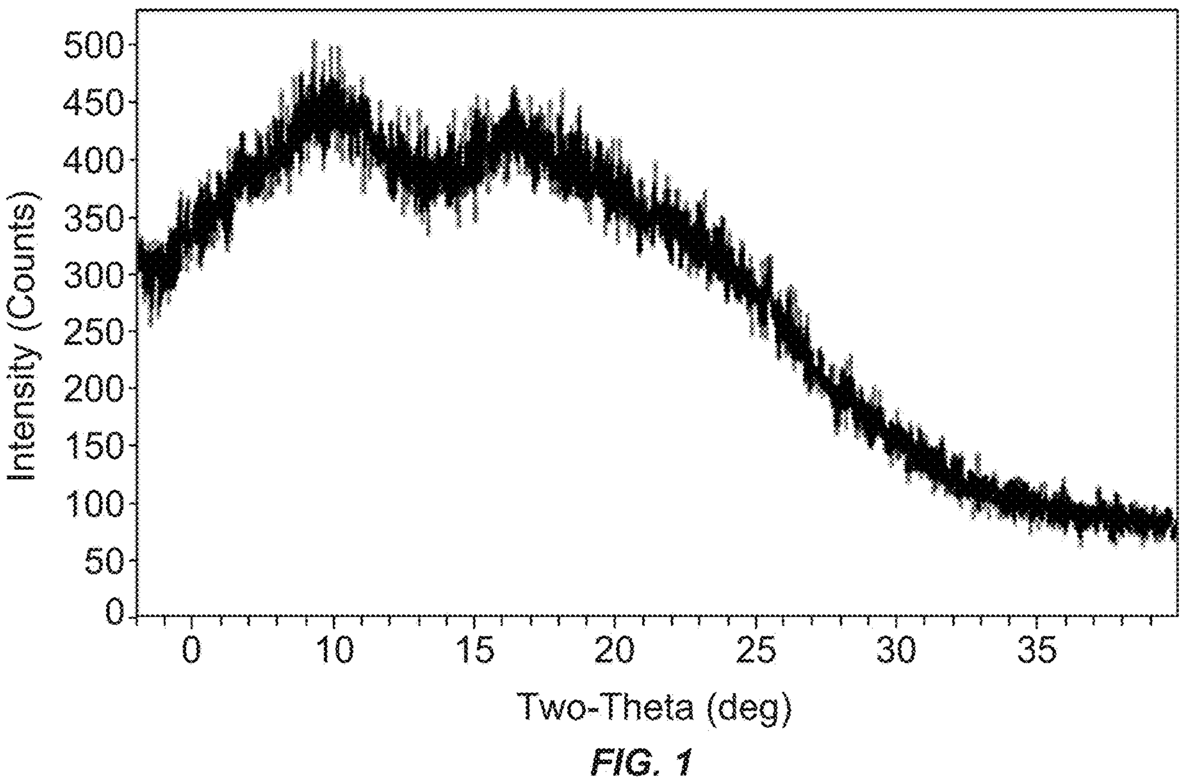

SOLID FORMS OF MACROCYCLIC COMPOUNDS, SALTS AND FORMULATIONS THEREOF, AND METHODS OF PREPARING AND USING THE SAME

1. CROSS-REFERENCE

This application is a continuation of International Application No. PCT/CN2024/096480, filed May 30, 2024, which claims priority pursuant to 35 U.S.C. § 365(b) to International Patent Application No. PCT/CN2023/097389, filed May 31, 2023. Each of the foregoing related applications is herein incorporated by reference in its entirety.

2. FIELD

Provided herein are solid forms of Compound 1, or a pharmaceutically acceptable form thereof, a pharmaceutically acceptable salt of Compound 1, or pharmaceutically acceptable solvate thereof, pharmaceutical compositions comprising the same, methods of preparing the same, and methods of treating cancer dependent on a farnesylated protein, using the same.

3. SUMMARY

In one aspect is solid form comprising Compound 1, or a pharmaceutically acceptable salt and/or solvate thereof:

Compound 1

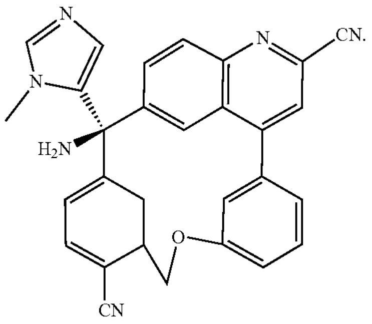

In another aspect is a pharmaceutically acceptable salt of Compound 1, or an isotopologue thereof, or a pharmaceutically acceptable solvate of the pharmaceutically acceptable salt.

In another aspect is a pharmaceutical composition comprising: i) a solid form comprising Compound 1, or a pharmaceutically acceptable salt and/or solvate thereof, in an amount from about 0.1 mg to about 200 mg, and ii) one or more pharmaceutically acceptable excipients.

In another aspect is a method of preparing a pharmaceutical composition, as provided herein, comprising: i) optionally, de-lumping the solid form of the Compound 1, or pharmaceutically acceptable salt and/or solvate thereof; ii) mixing the solid form of the Compound 1, or pharmaceutically acceptable salt and/or solvate thereof, with a disintegrant, a glidant, and a first portion of a filler to form a first blend; iii) de-lumping the first blend to form a de-lumped first blend; iv) de-lumping a second portion of the filler; v) blending the de-lumped first blend and the de-lumped second portion of the filler to form a second blend; vi) blending the second blend with a lubricant to form a lubricated blend; and vii) compressing the lubricated blend, optionally with a rotary press, into a tablet.

In another aspect is a method of preparing a pharmaceutical composition, as provided herein, comprising: i) optionally, de-lumping the solid form of the Compound 1, or pharmaceutically acceptable salt and/or solvate thereof; ii) mixing the solid form of the Compound 1, or pharmaceutically acceptable salt and/or solvate thereof, with a filler, a glidant, and a first portion of a disintegrant to form a first blend; iii) de-lumping and then blending the first blend to form a second blend; iv) blending the second blend with a first portion of a lubricant to form a lubricated intragranular blend; v) forming granules from the intragranular blend, for example, with a roller compactor and screen; vi) blending the granules with a second portion of the disintegrant and a second portion of the lubricant to form a lubricated final blend; and vii) compressing the lubricated final blend, optionally with a rotary press, into a tablet.

In another aspect is a method of preparing the pharmaceutical composition, as provided herein, comprising: i) optionally, de-lumping the solid form of the Compound 1, or pharmaceutically acceptable salt and/or solvate thereof; ii) granulating the solid form of the Compound 1, or pharmaceutically acceptable salt and/or solvate thereof, a filler, a glidant, and a disintegrant with a binder and water to form wet granules; iii) drying the wet granules to form dry granules; iv) blending the granules with a lubricant to form a lubricated final blend; and v) compressing the lubricated final blend, optionally with a rotary press, into a tablet.

In another aspect is a process for preparing Compound 1:

Compound 1

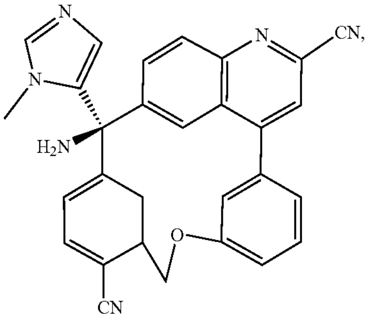

or a pharmaceutically acceptable form thereof, comprising:

(a) reacting racemic Compound 19:

Compound 19

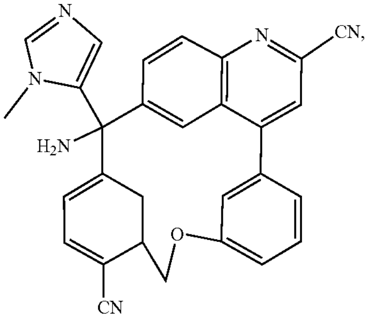

with a chiral acid in a solvent to form a diastereomeric salt of Compound 1 and a diastereomeric salt of Compound 2:

Compound 2

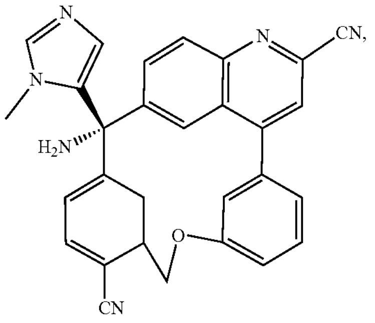

wherein one of the two diastereomeric salts precipitates selectively from the solvent and the other of the two diastereomeric salts is selectively soluble in the solvent;

(b) separating the precipitate from the solvent;

(c) reacting the diastereomeric salt of Compound 1 with a base to provide Compound 1, and (d) optionally, recrystallizing Compound 1, optionally from ACN/water in a ratio of about 2:1 to about 1:5, optionally about 1:1 to about 1:3.

In another aspect is a process for preparing Compound 1:

Compound 1

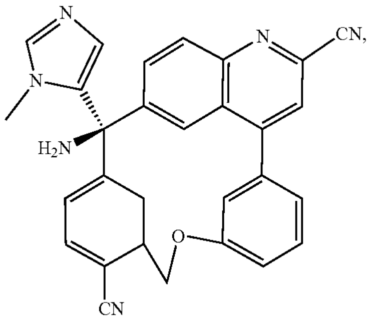

or a pharmaceutically acceptable form thereof, comprising reacting Compound 18A:

Compound 19

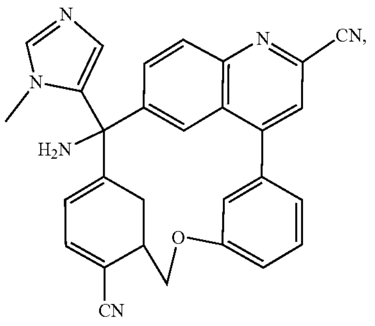

with a cyanide equivalent and a palladium catalyst, optionally in the presence of zinc source and/or a phosphine ligand, to provide Compound 19:

Compound 19

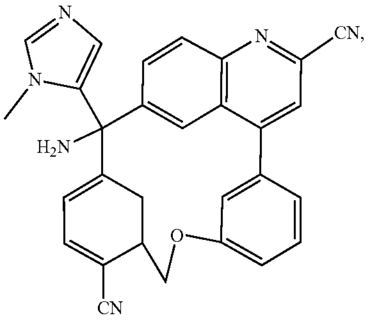

and purifying racemic Compound 19 by chiral separation to provide Compound 1.

In another aspect is a process for preparing Compound 9 comprising reacting Compound 7:

Compound 7

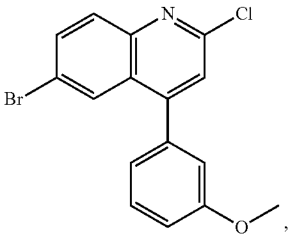

with a demethylating agent to form Compound 8:

Compound 8

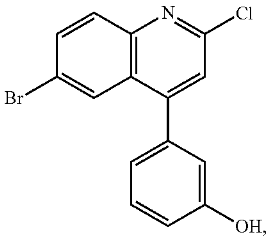

and reacting Compound & with TBSCl and a base to form Compound 9.

In another aspect is a process for preparing Compound 11:

Compound 11

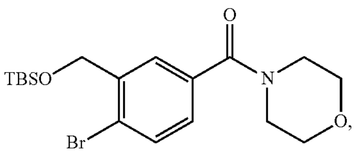

comprising reacting Compound 23:

Compound 23

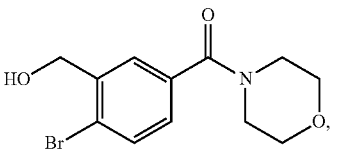

with TBSCl in the presence of a base to form Compound 11.

In another aspect is a process for preparing Compound 19:

Compound 19

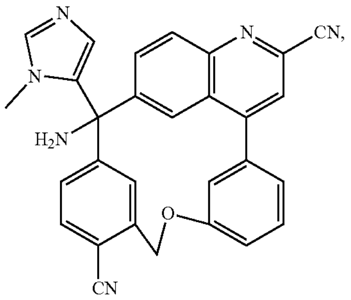

comprising chlorinating Compound 17:

Compound 17

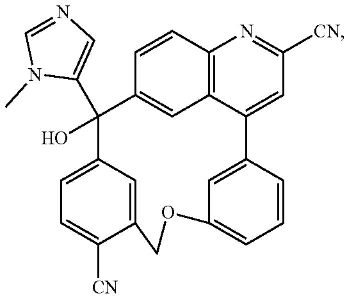

with a chlorinating agent to form Compound 18:

Compound 18

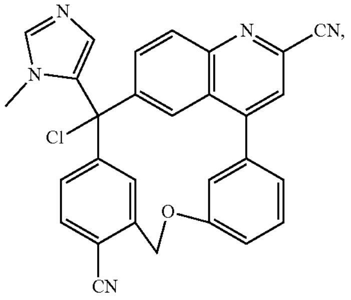

and reacting Compound 18 with an ammonia equivalent to form Compound 19.

In another aspect is a process for preparing Compound 14:

Compound 14

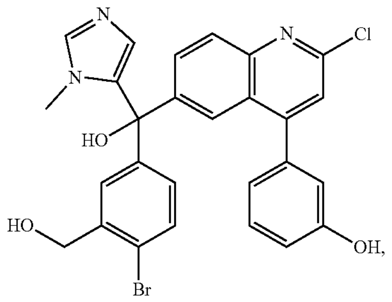

comprising deprotecting Compound 13:

Compound 13

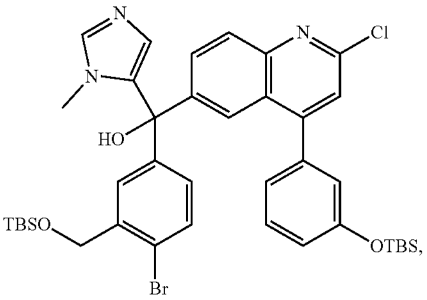

under deprotecting conditions to form Compound 14.

In another aspect is a process for preparing Compound 12:

Compound 12

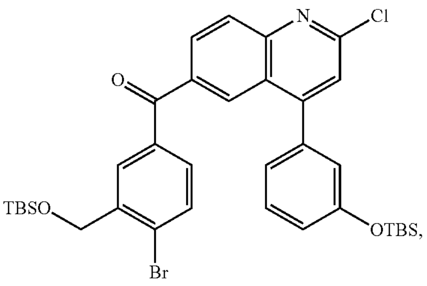

comprising condensing Compound 11:

Compound 11

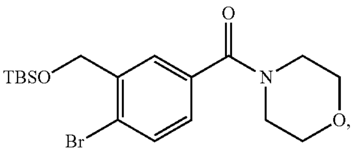

with Compound 9;

Compound 9

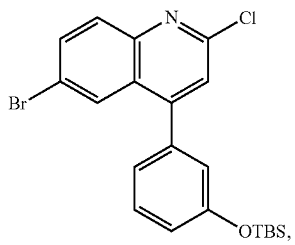

to form Compound 12.

In another aspect is a process for preparing Compound 13, comprising coupling Compound 12 with 1-methylimidazole to form Compound 13.

In another aspect is a compound selected from:

(12)

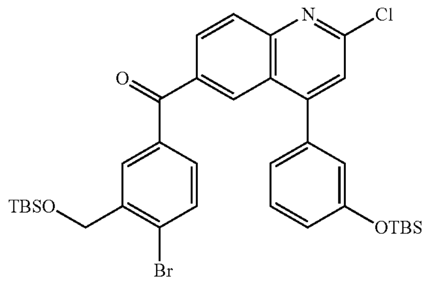

(13)

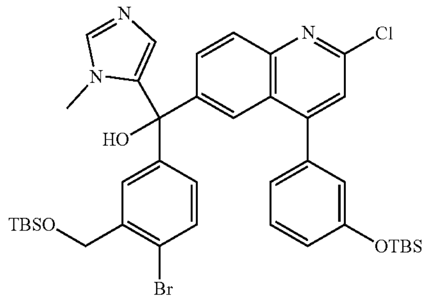

(7)

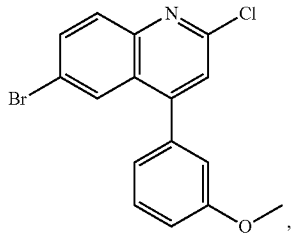

(11)

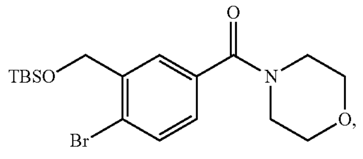

and

-continued (23)

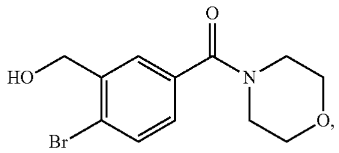

and salts thereof.

In another aspect is a (R)-chlocyphos, (S)-chlocyphos, (+)-tartaric acid, (−)-tartaric acid, (+)-camphorsulfonic acid, (−)-camphorsulfonic acid, L-(−)-di-p-anisoyltartaric acid, D-(+)-di-p-anisoyltartaric acid, L-(−)-di-toluoyltartaric acid, D-(+)-di-toluoyltartaric acid, (R)-BINAP phosphate, (S)-BINAP phosphate, di-benzoyl-1-tartaric acid, or di-benzoyl-D-tartaric acid salt of Compound 1 or Compound 2.

In another aspect is a method of inhibiting a farnesyltransferase, comprising contacting the farnesyltransferase with an effective amount of a solid form of Compound 1, as provided herein, a pharmaceutically acceptable salt of Compound 1, or an isotopologue thereof, or a pharmaceutically acceptable solvate of the pharmaceutically acceptable salt, as provided herein, or with a pharmaceutical composition comprising the same, as provided herein, optionally wherein the farnesyltransferase is present in a cell, optionally wherein the contacting of the farnesyltransferase takes place in a cell, optionally wherein the cell is in a subject, optionally wherein the cell is a mammalian cell, optionally wherein the cell is a human cell, and optionally wherein the subject suffers from a cancer dependent on a farnesylated protein.

In another aspect is a method of treating cancer dependent on a farnesylated protein in a subject, comprising administering a therapeutically effective amount of a solid form of Compound 1, as provided herein, a pharmaceutically acceptable salt of Compound 1, or a isotopologue thereof, or a pharmaceutically acceptable solvate of the pharmaceutically acceptable salt, as provided herein, or with a pharmaceutical composition comprising the same, as provided herein, to the subject having cancer dependent on a farnesylated protein, optionally wherein the subject is human.

4. BRIEF DESCRIPTION OF THE FIGURES

FIG. 1: provides a representative X-ray powder diffraction (XRPD) pattern of amorphous form of a free base of Compound 1.

Figure 2:
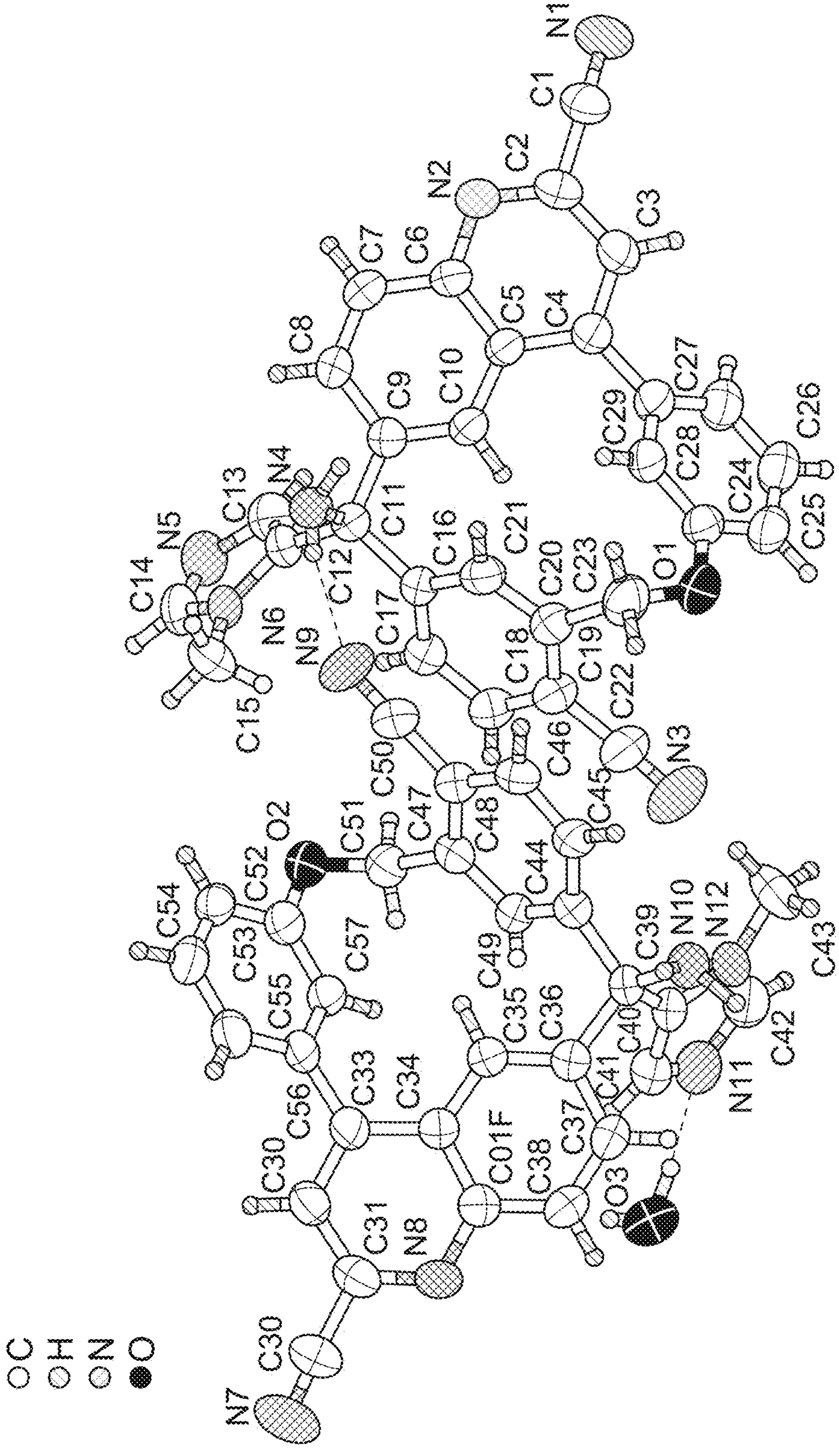

FIG. 2: provides a representative Oak Ridge Thermal Ellipsoid Plot (ORTEP) illustration of a single crystal analysis of Form 1 of a free base, hemi-hydrate of Compound 1.

Figure 3:
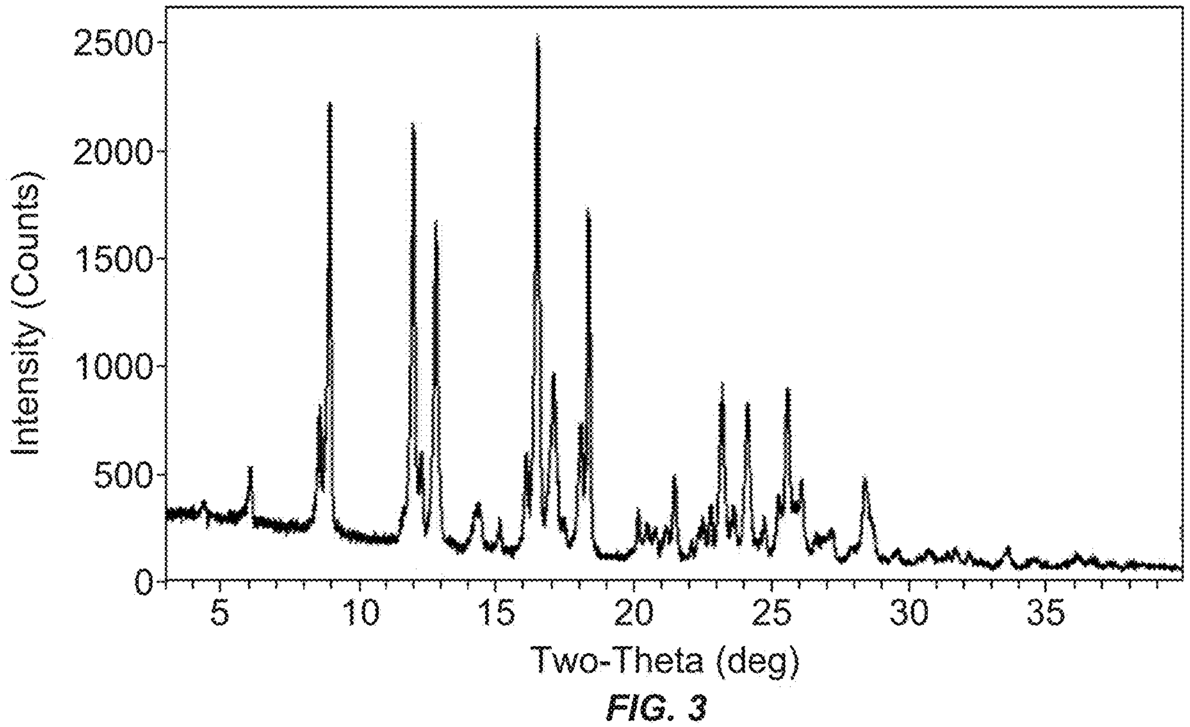

FIG. 3 provides a representative XRPD pattern of Form 1 of a free base, hemi-hydrate of Compound 1.

Figure 4:
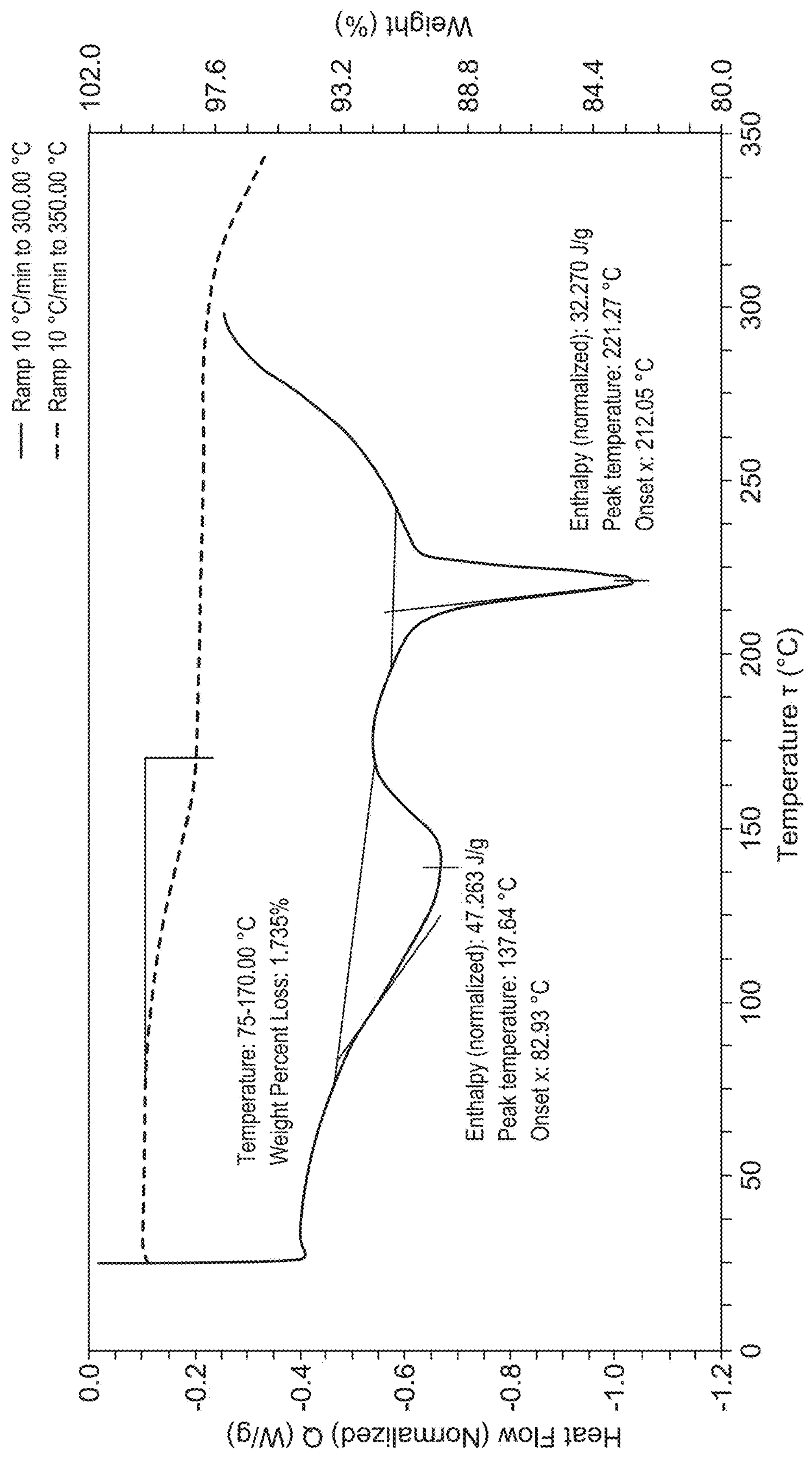

FIG. 4 provides representative DSC and TGA thermograms of Form 1 of a free base, hemi-hydrate of Compound 1.

Figure 5:
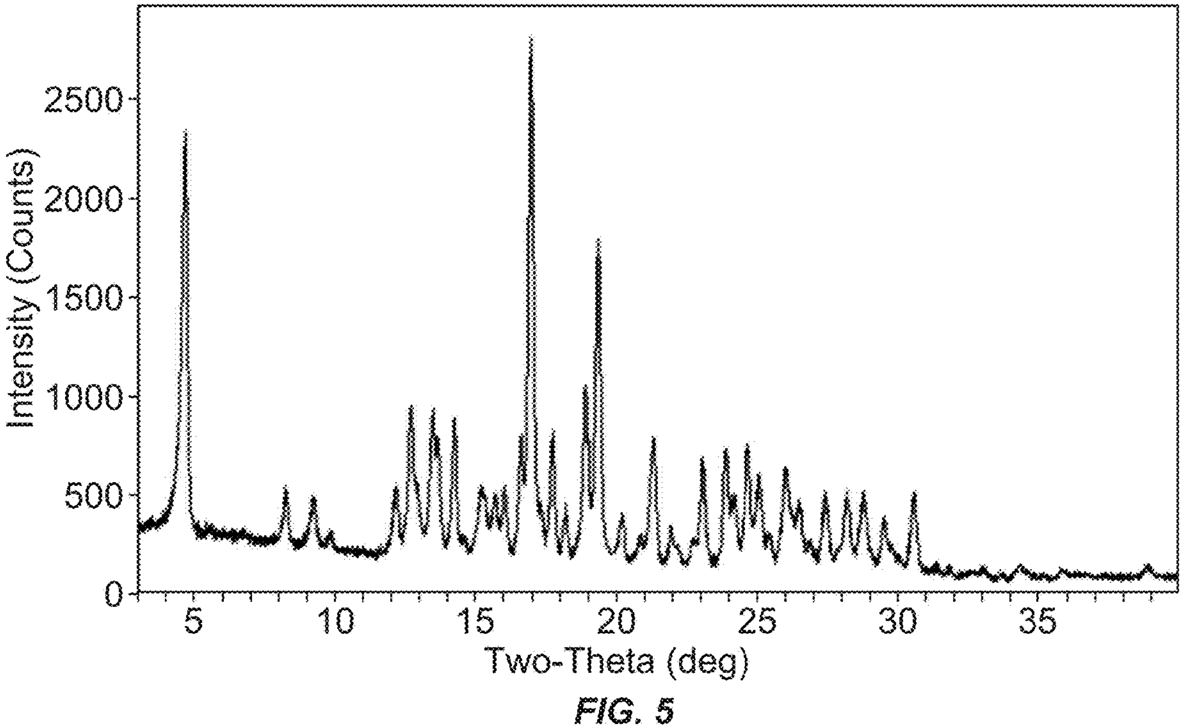

FIG. 5 provides a representative XRPD pattern of Form 2 of a benzoate salt of Compound 1.

Figure 6:
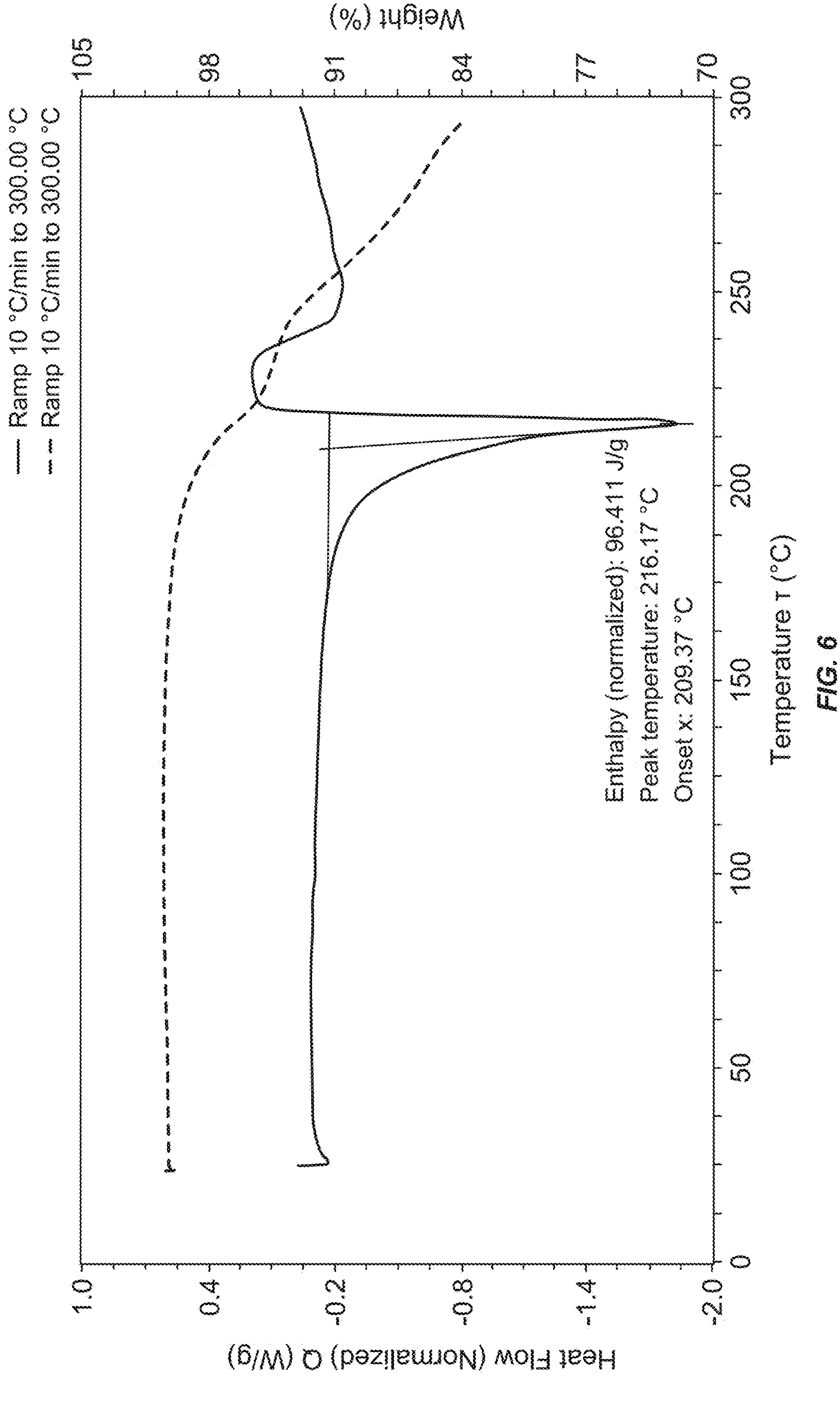

FIG. 6 provides representative DSC and TGA thermograms of Form 2 of a benzoate salt of Compound 1.

Figure 7:
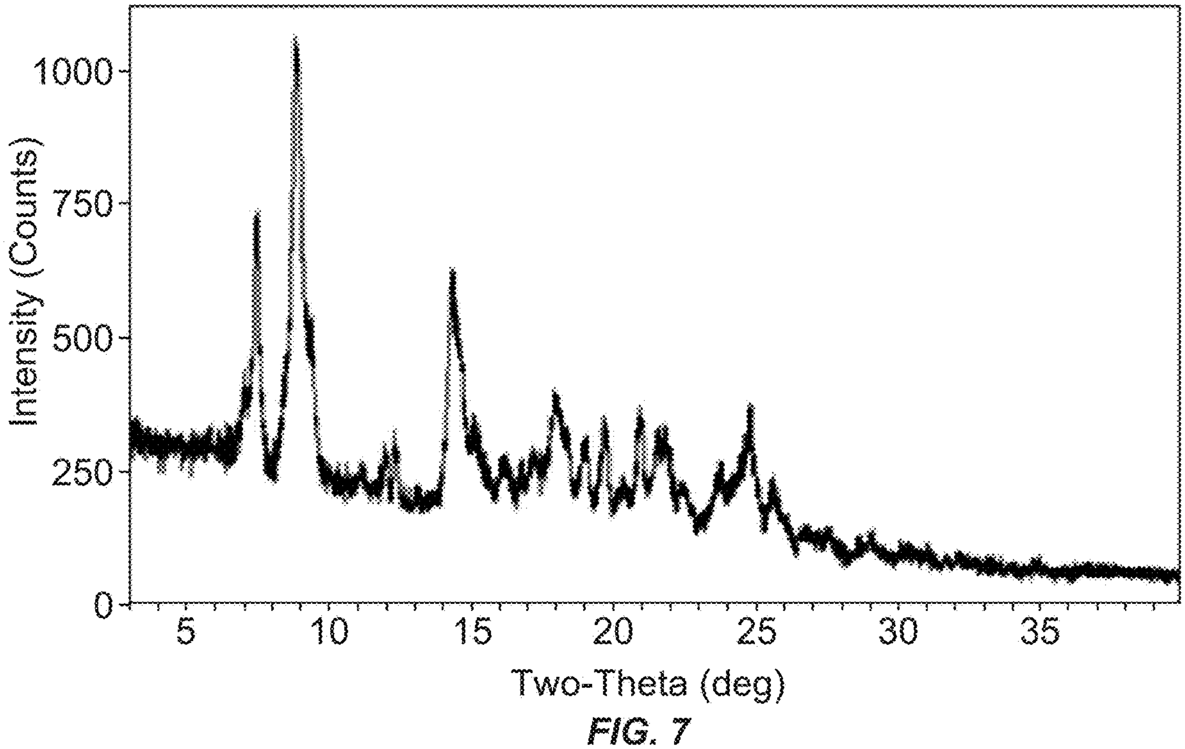

FIG. 7 provides a representative XRPD pattern of Form 3 of a besylate (benzenesulfonic acid) salt of Compound 1.

Figure 8:
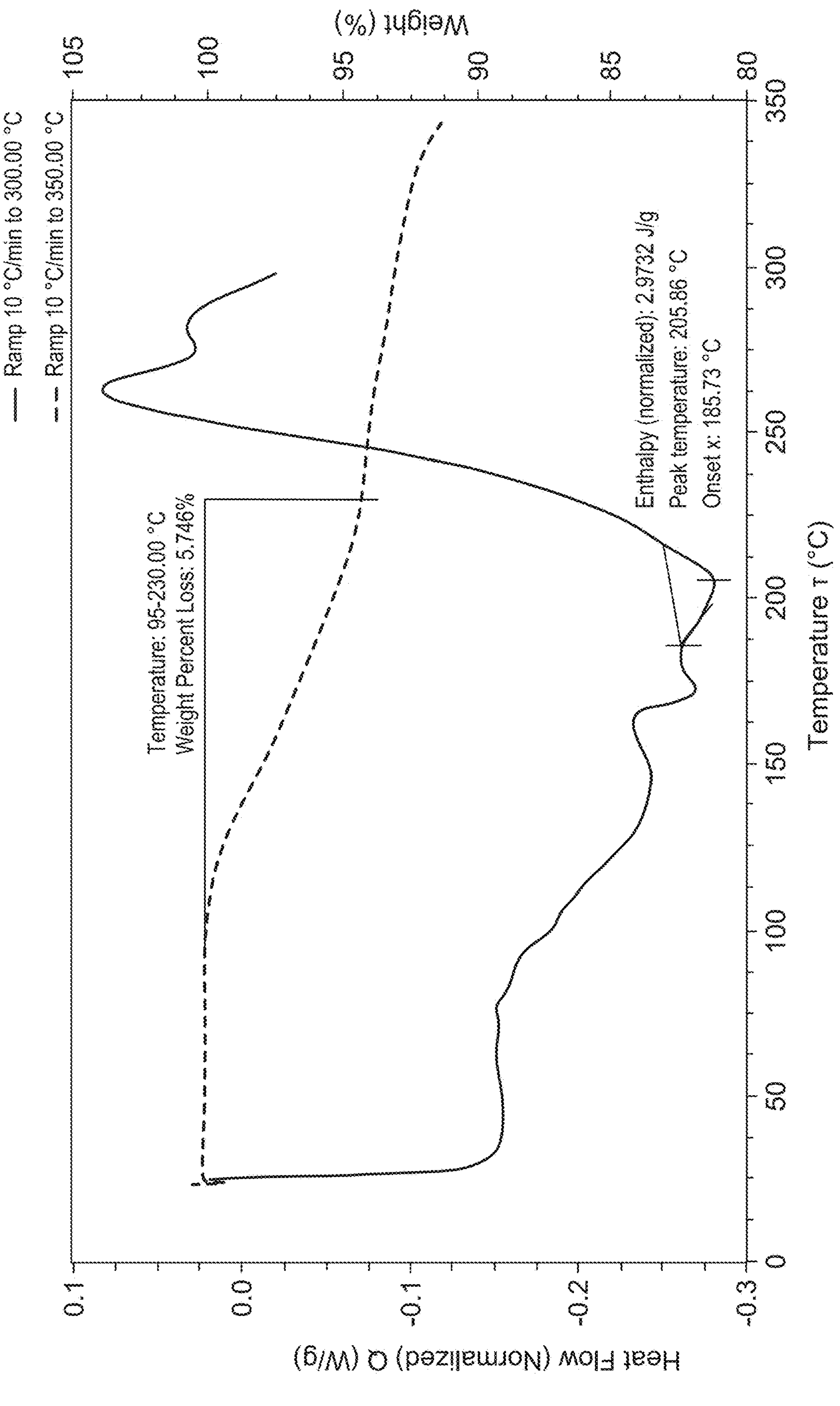

FIG. 8 provides representative DSC and TGA thermograms of Form 3 of a besylate (benzenesulfonic acid) salt of Compound 1.

Figure 9:
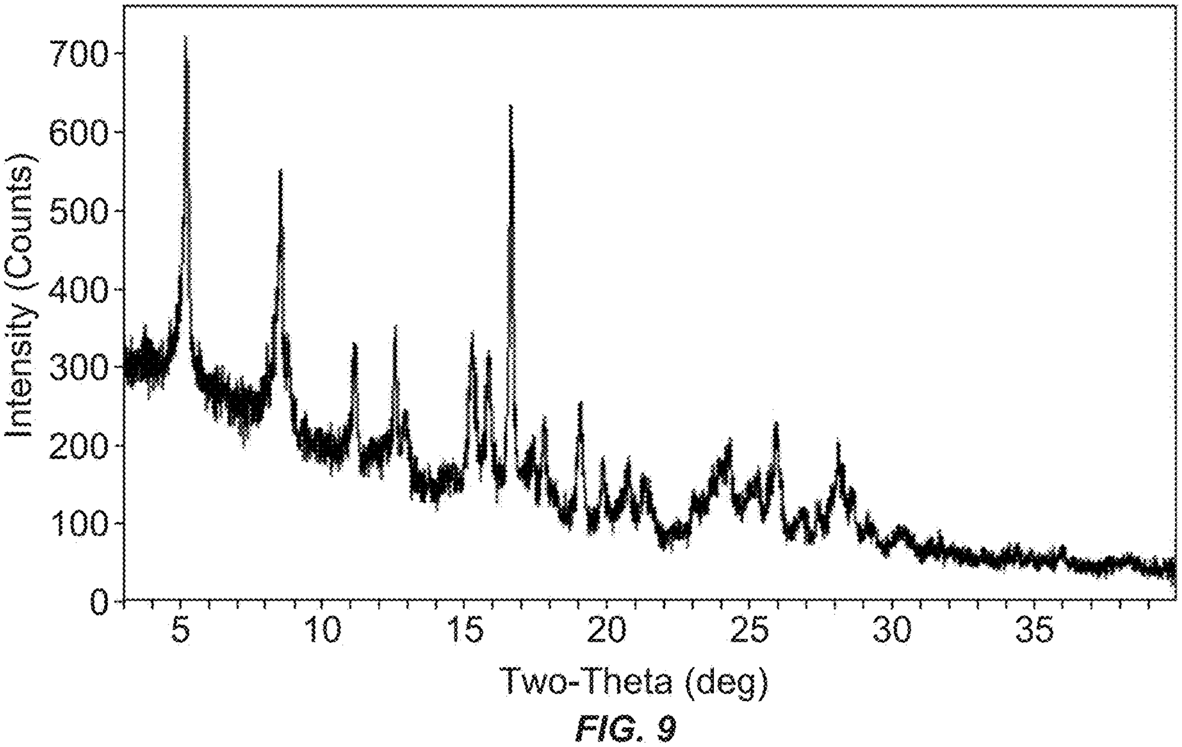

FIG. 9 provides a representative XRPD pattern of Form 4 of a chloride salt of Compound 1.

Figure 10:
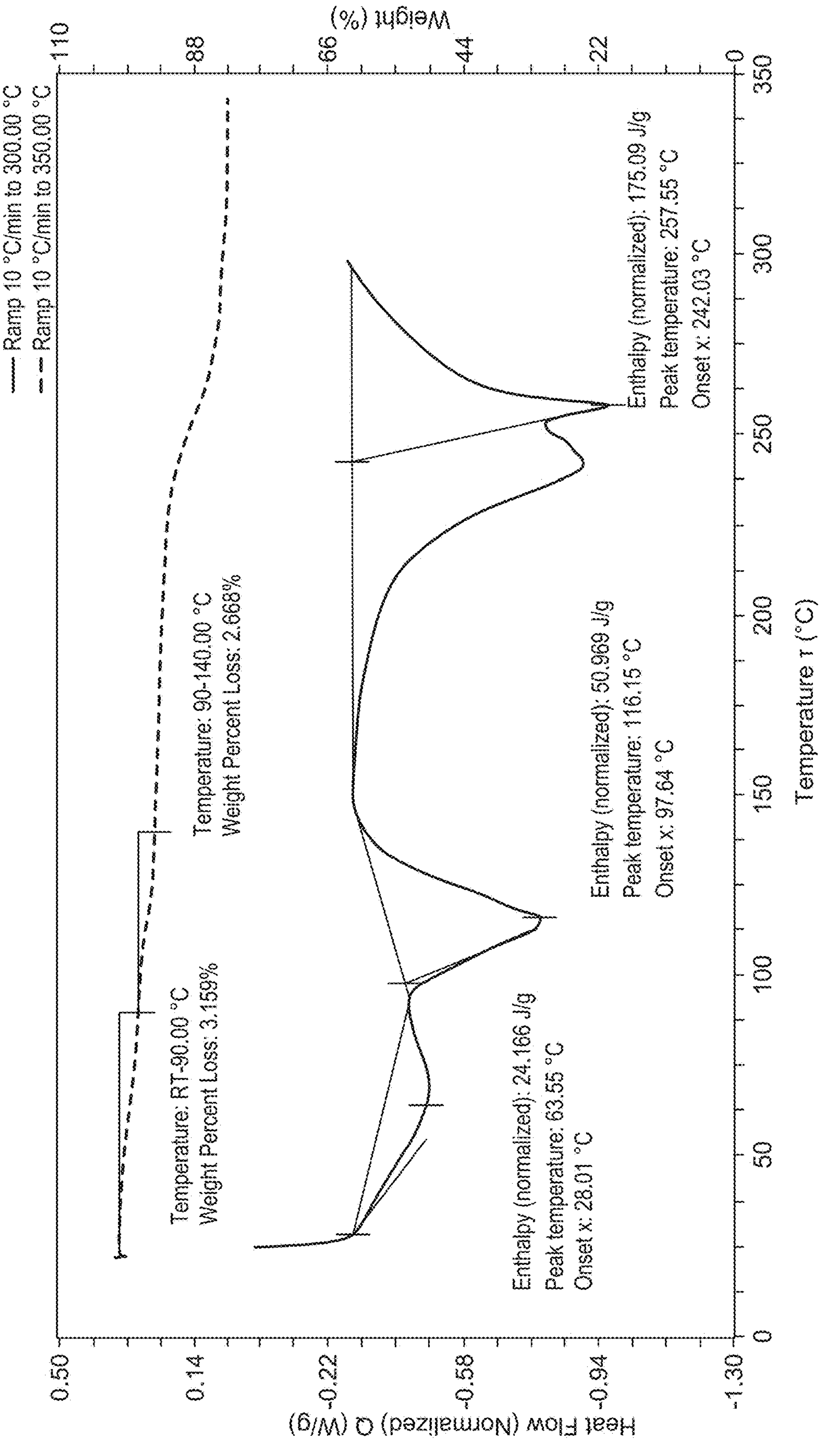

FIG. 10 provides representative DSC and TGA thermograms of Form 4 of a chloride salt of Compound 1.

Figure 11:
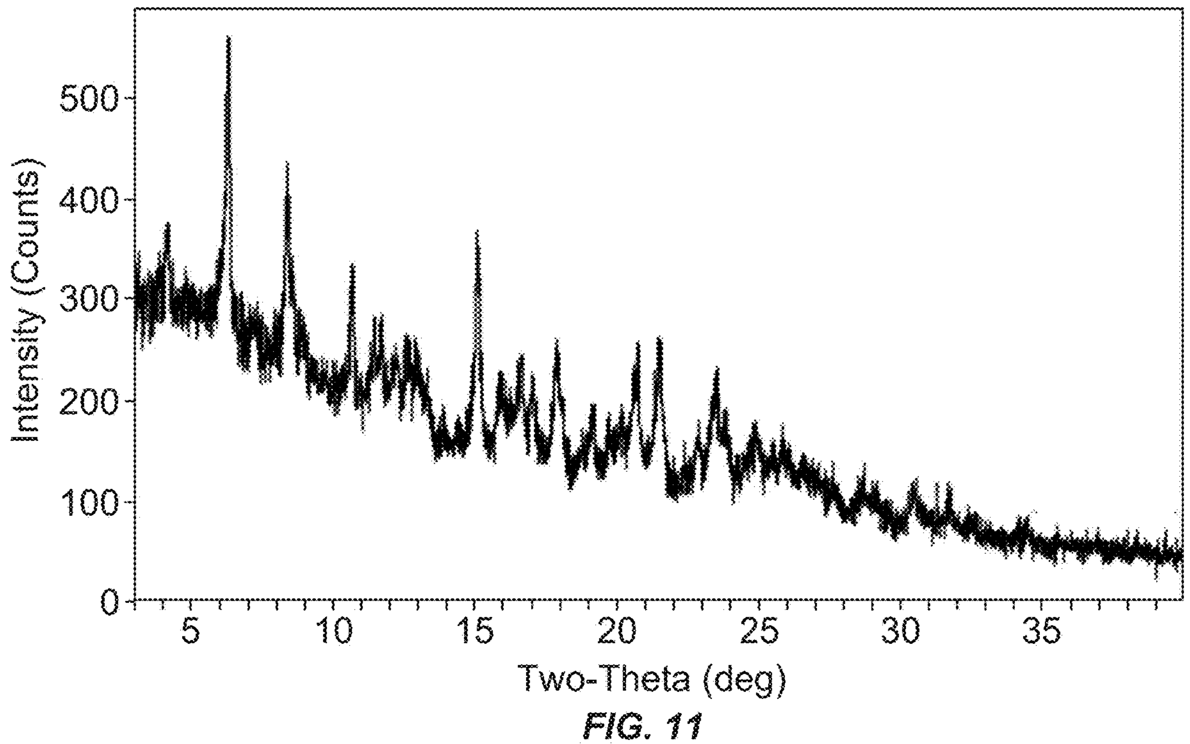

FIG. 11 provides a representative XRPD pattern of Form 5 of a chloride salt of Compound 1.

Figure 12:
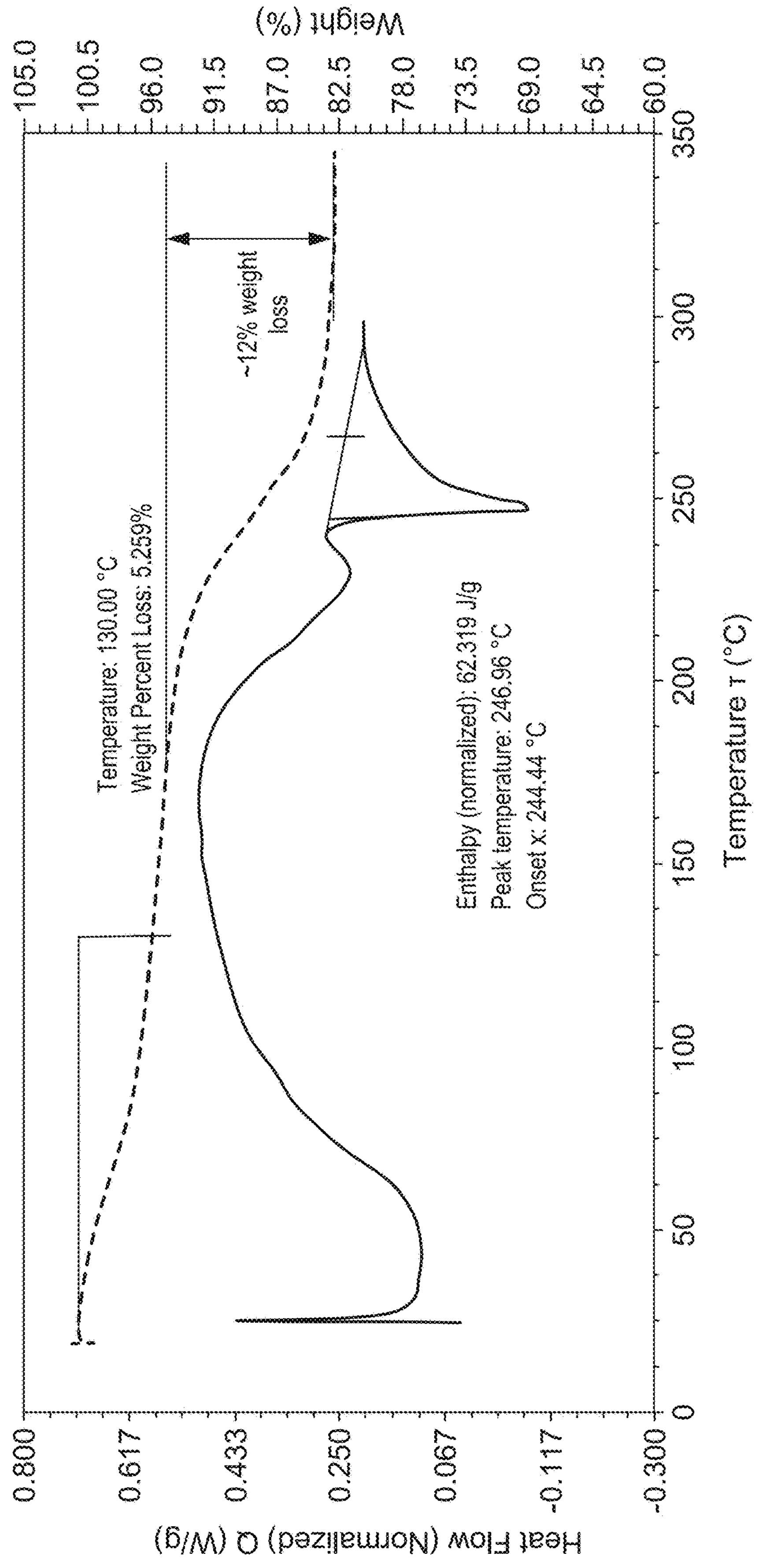

FIG. 12 provides representative DSC and TGA thermograms of Form 5 of a chloride salt of Compound 1.

Figure 13:
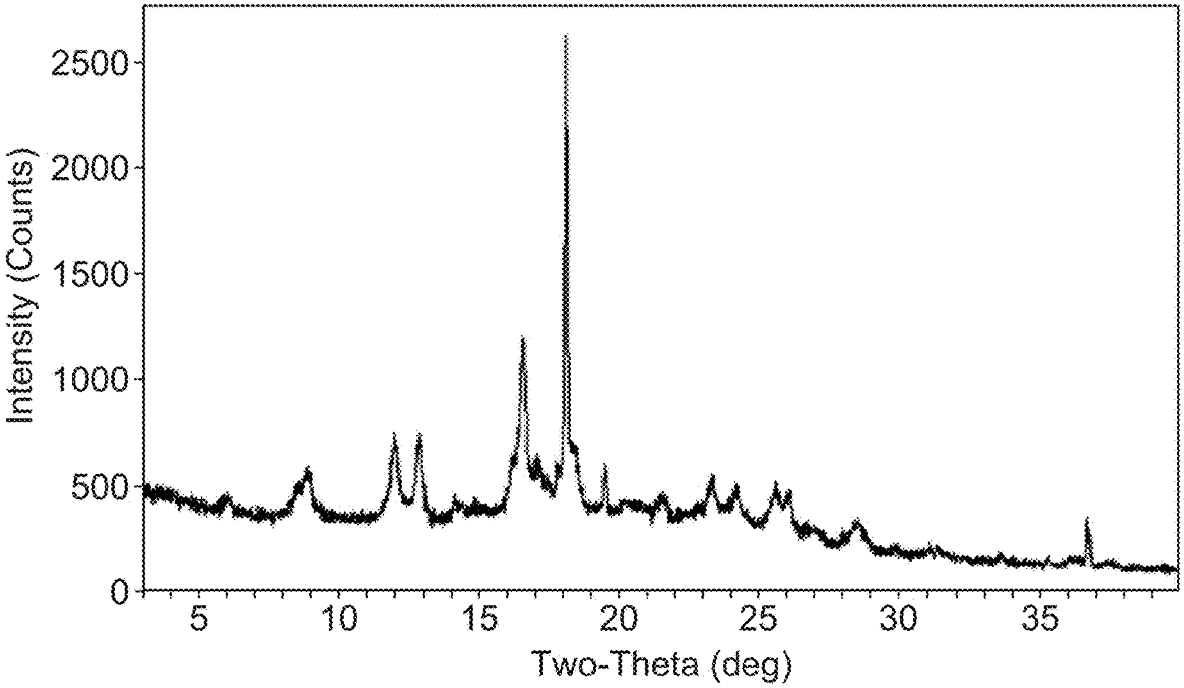

FIG. 13 provides a representative XRPD pattern of Form 6 of a citrate salt of Compound 1.

Figure 14:
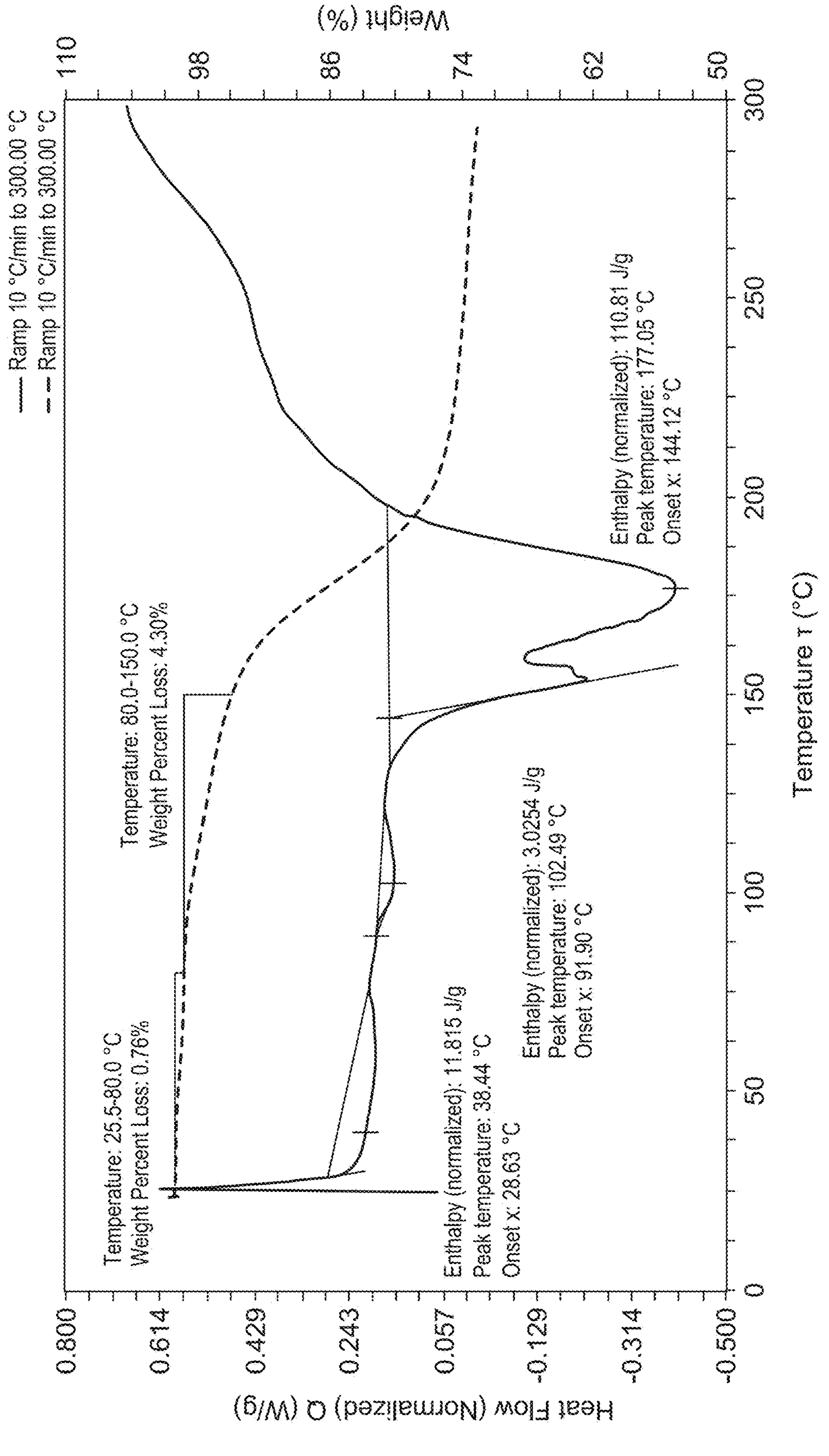

FIG. 14 provides representative DSC and TGA thermograms of Form 6 of a citrate salt of Compound 1.

Figure 15:
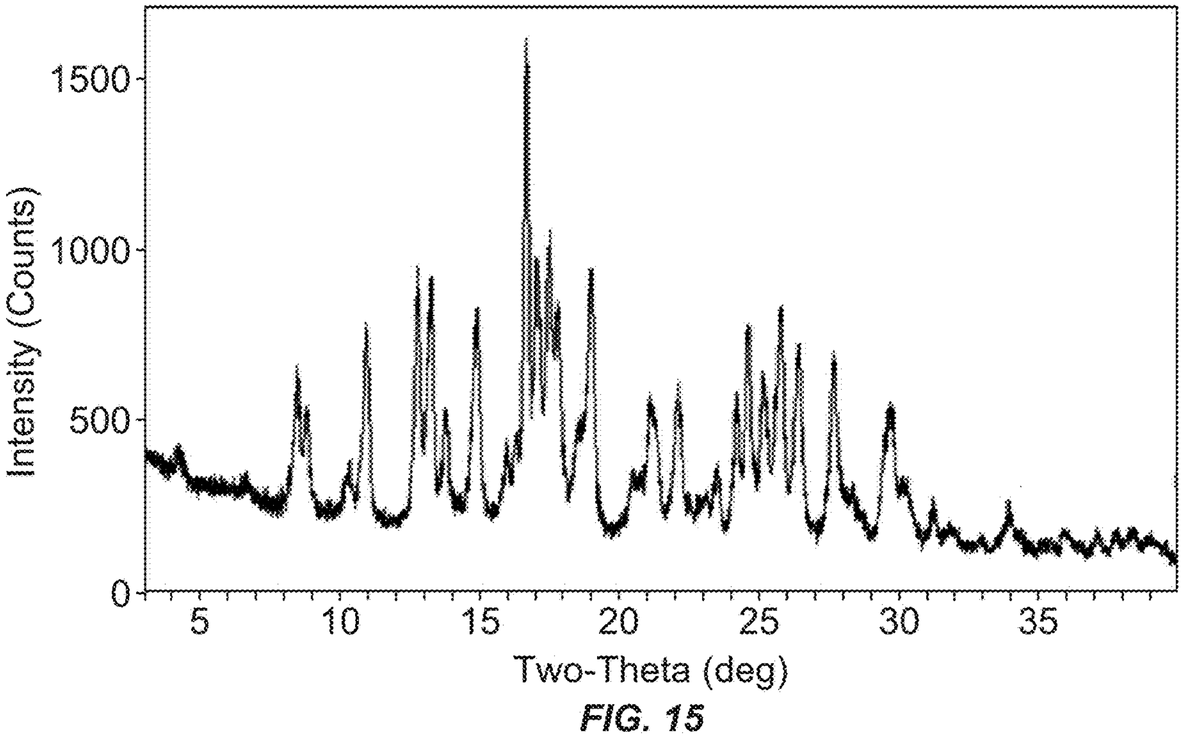

FIG. 15 provides a representative XRPD pattern of Form 7 of a citrate salt of Compound 1.

Figure 16:
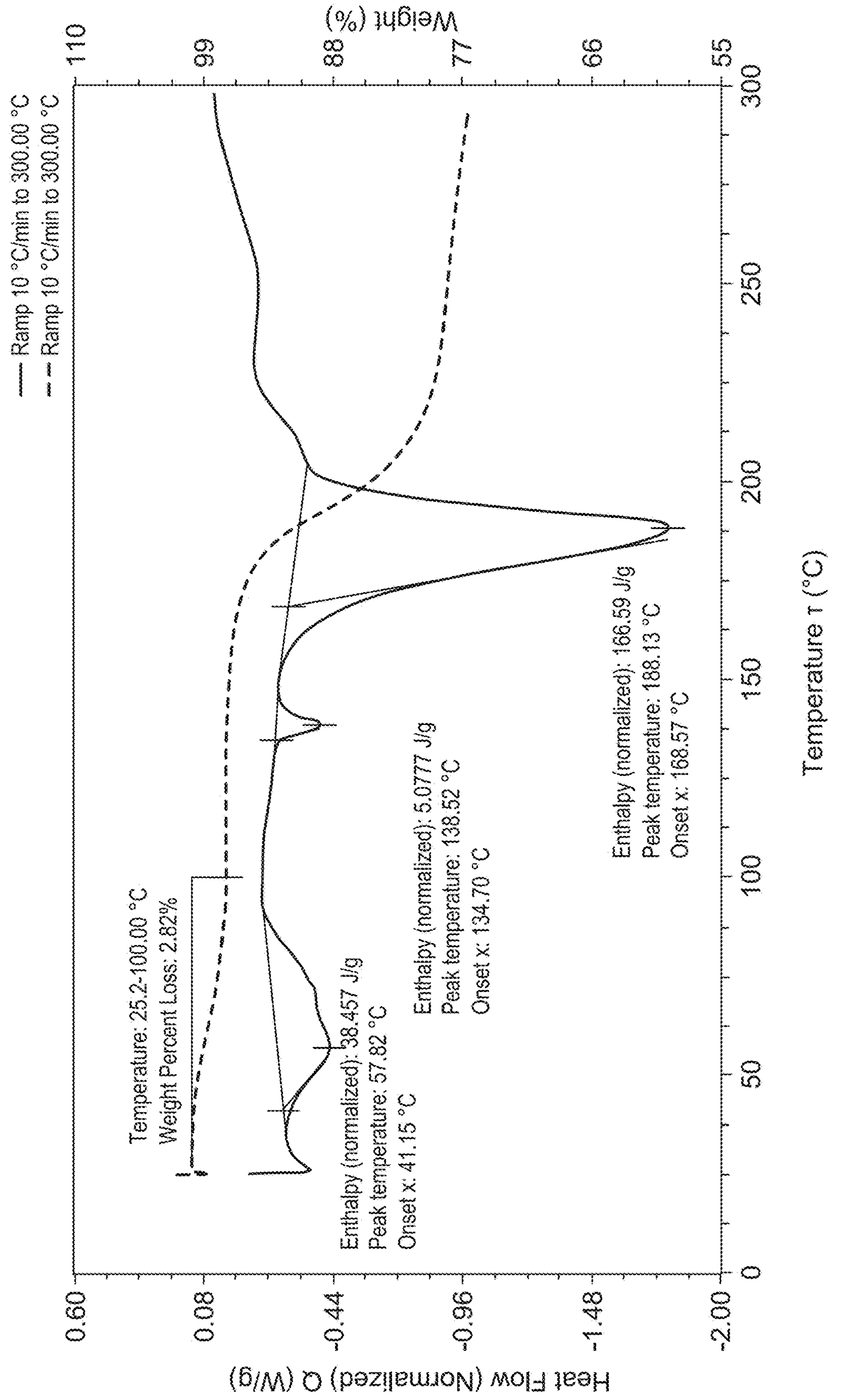

FIG. 16 provides representative DSC and TGA thermograms of Form 7 of a citrate salt of Compound 1.

Figure 17:
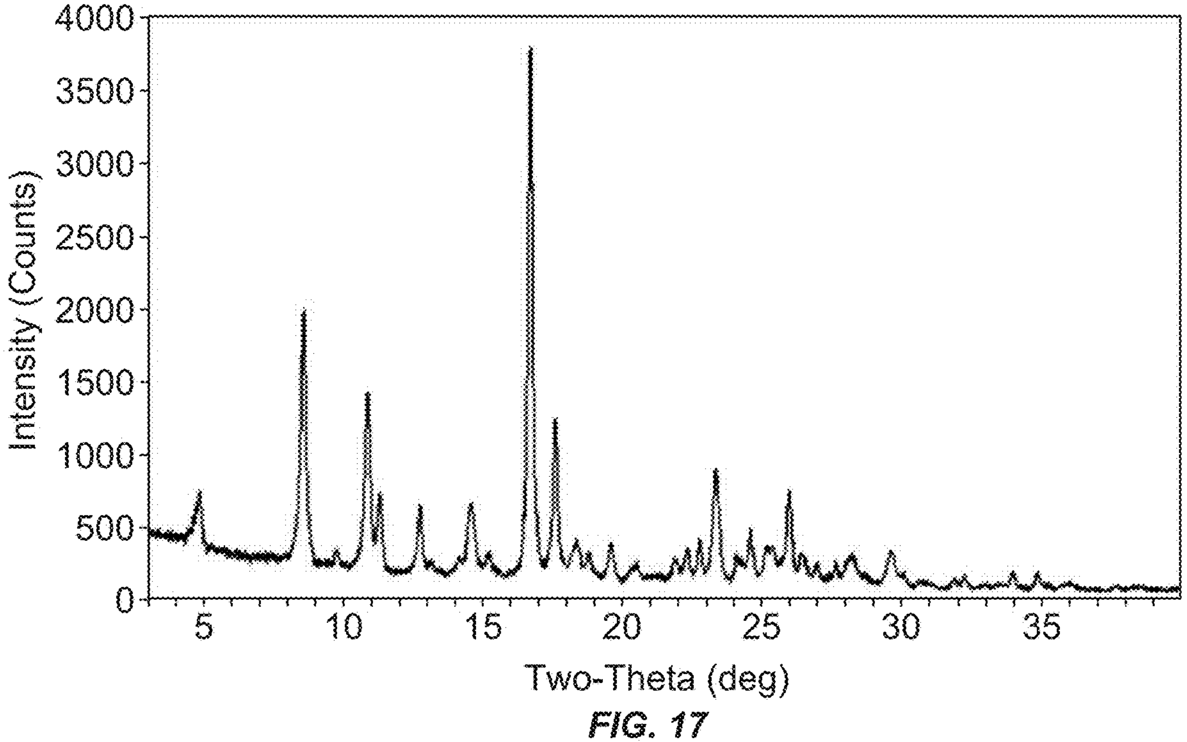

FIG. 17 provides a representative XRPD pattern of Form 8 of a fumarate salt of Compound 1.

Figure 18:
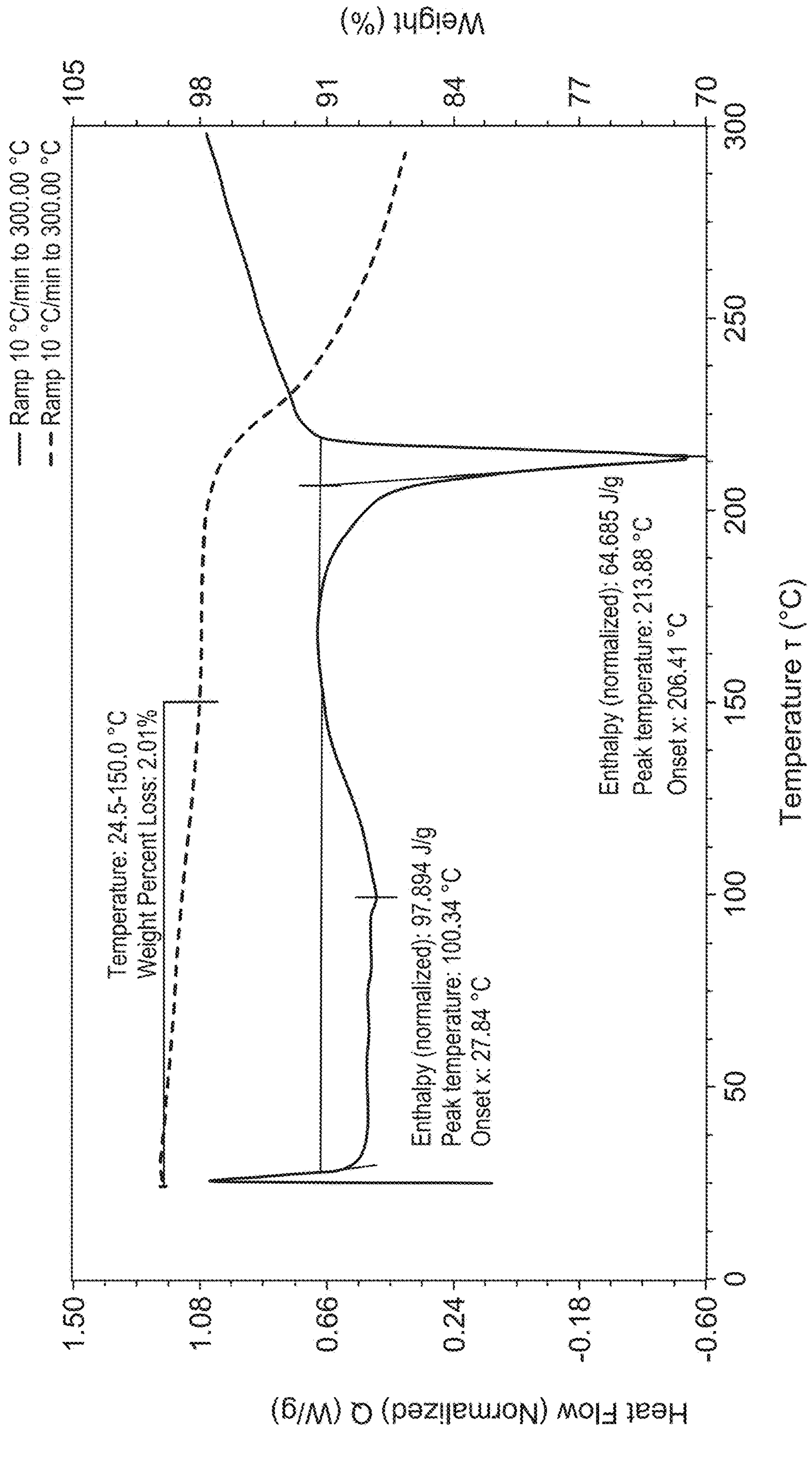

FIG. 18 provides representative DSC and TGA thermograms of Form 8 of a fumarate salt of Compound 1.

Figure 19:
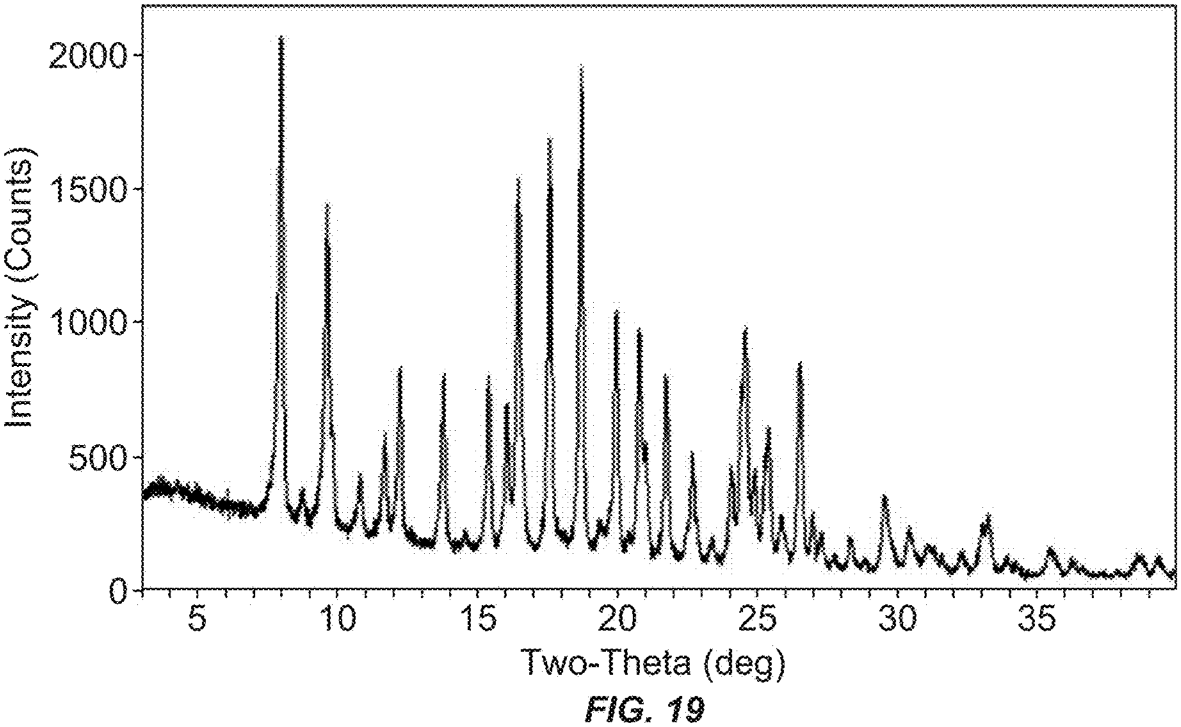

FIG. 19 provides a representative XRPD pattern of Form 9 of a gentisate salt of Compound 1.

Figure 20:
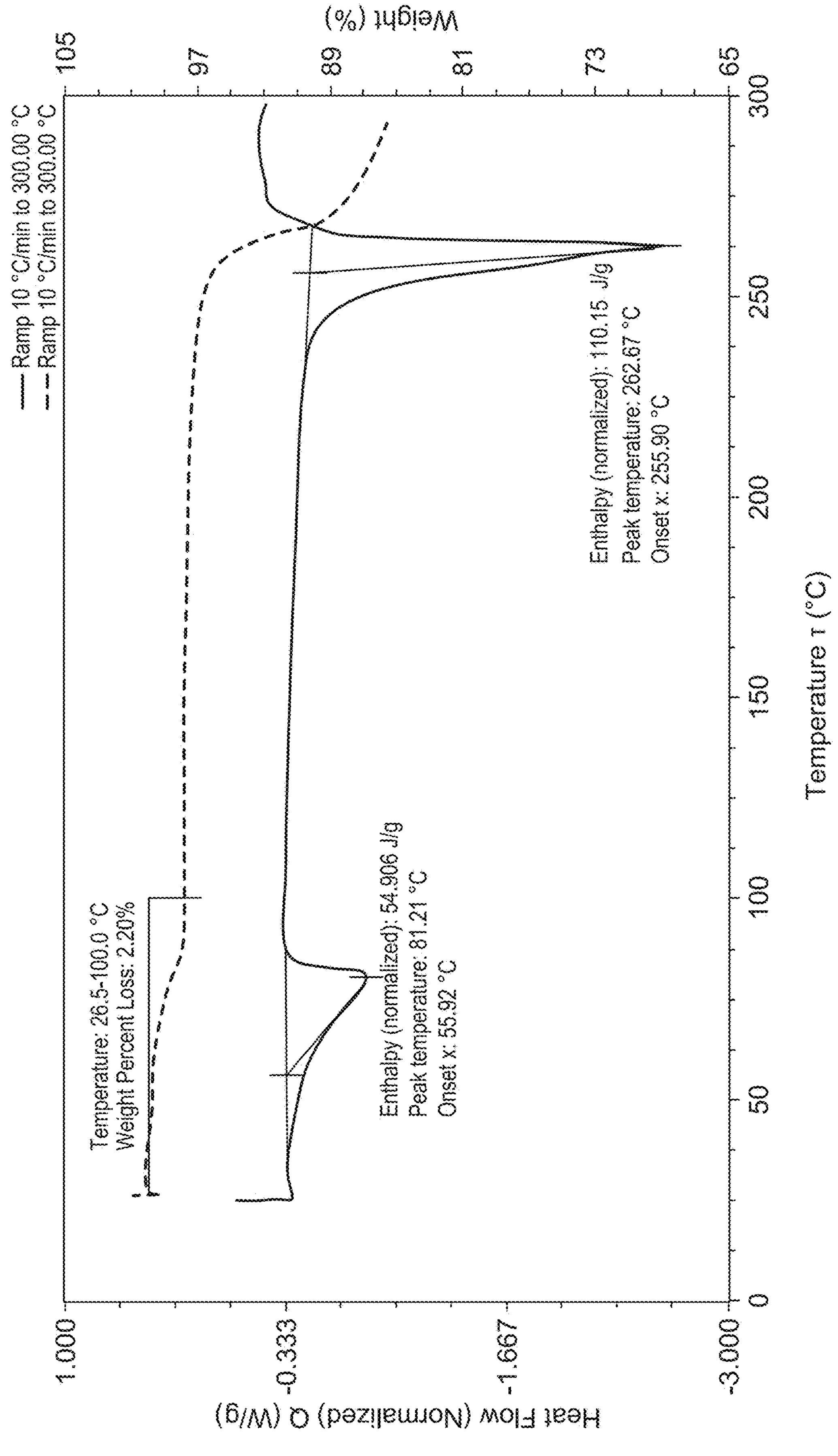

FIG. 20 provides representative DSC and TGA thermograms of Form 9 of a gentisate salt of Compound 1.

Figure 21:
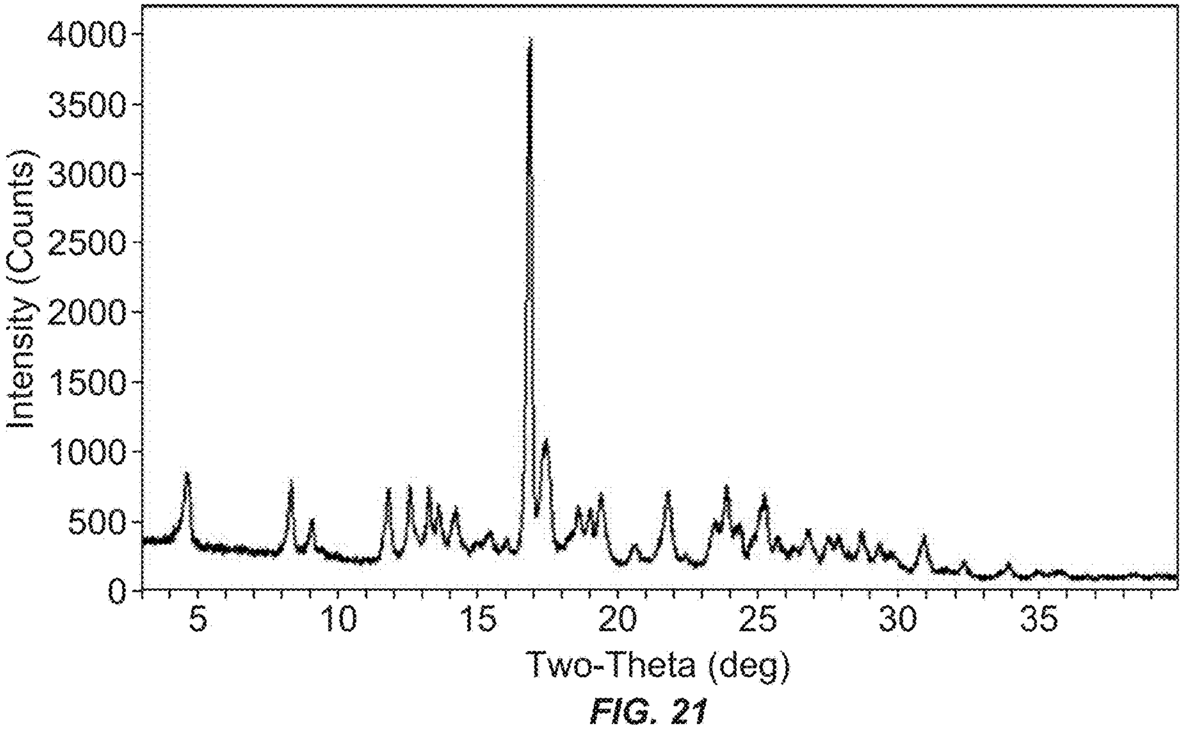

FIG. 21 provides a representative XRPD pattern of Form 10 of a gentisate salt of Compound 1.

Figure 22:
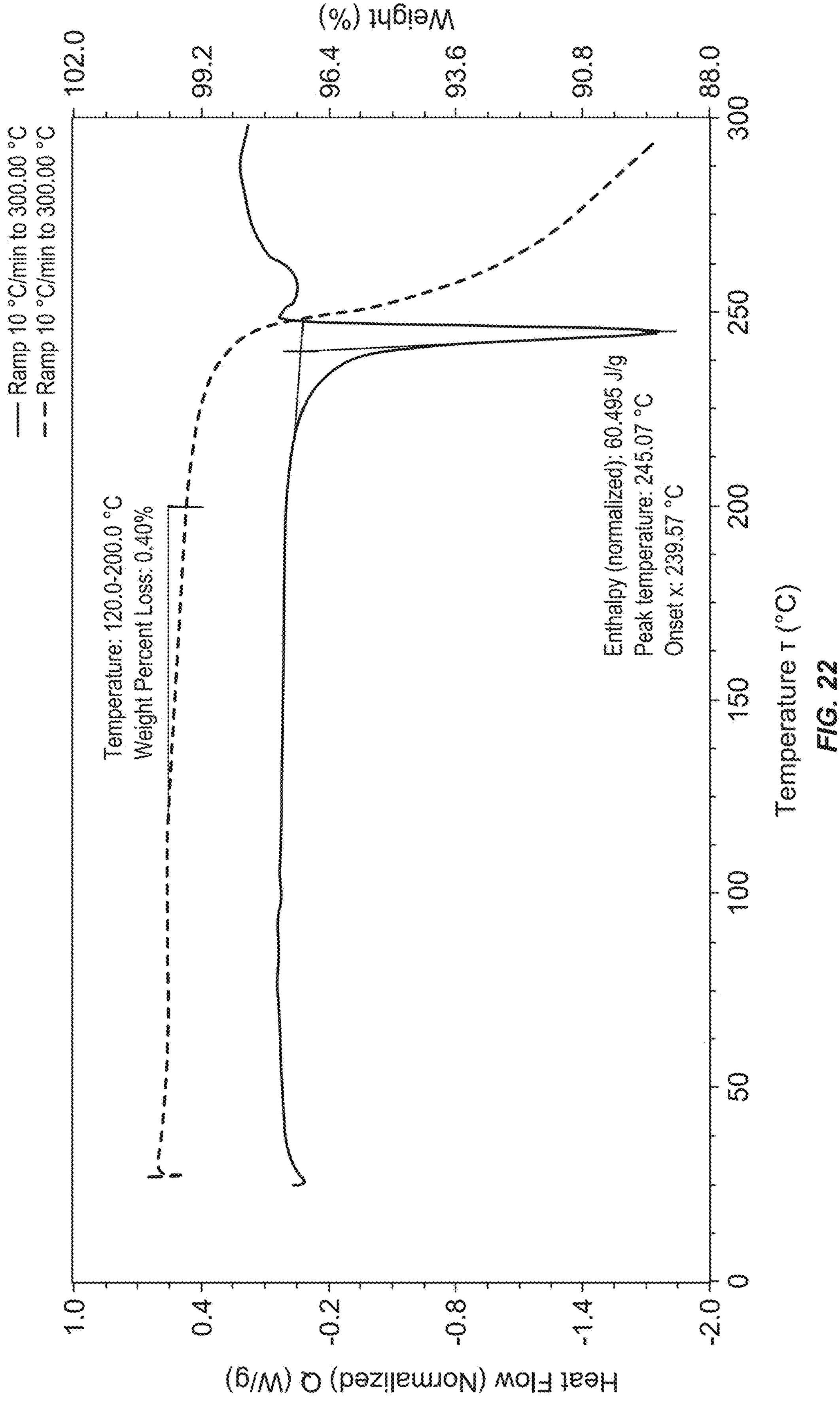

FIG. 22 provides representative DSC and TGA thermograms of Form 10 of a gentisate salt of Compound 1.

Figure 23:
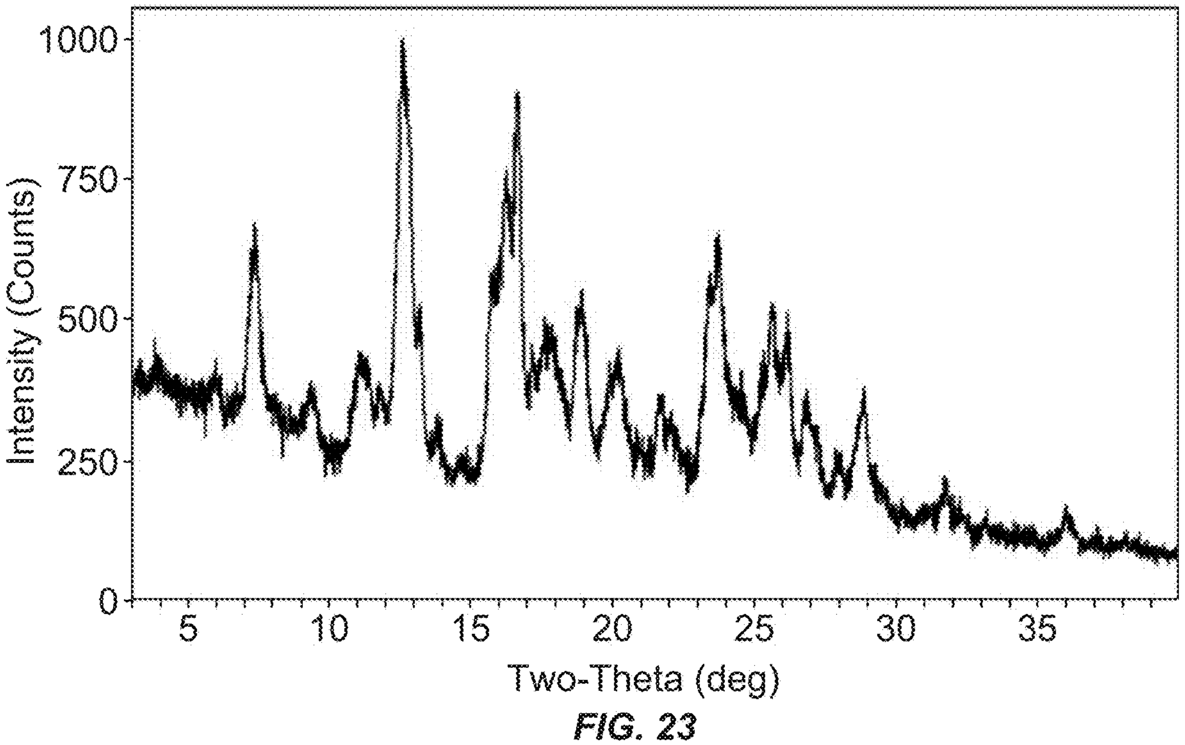

FIG. 23 provides a representative XRPD pattern of Form 11 of a glycolate salt of Compound 1.

Figure 24:
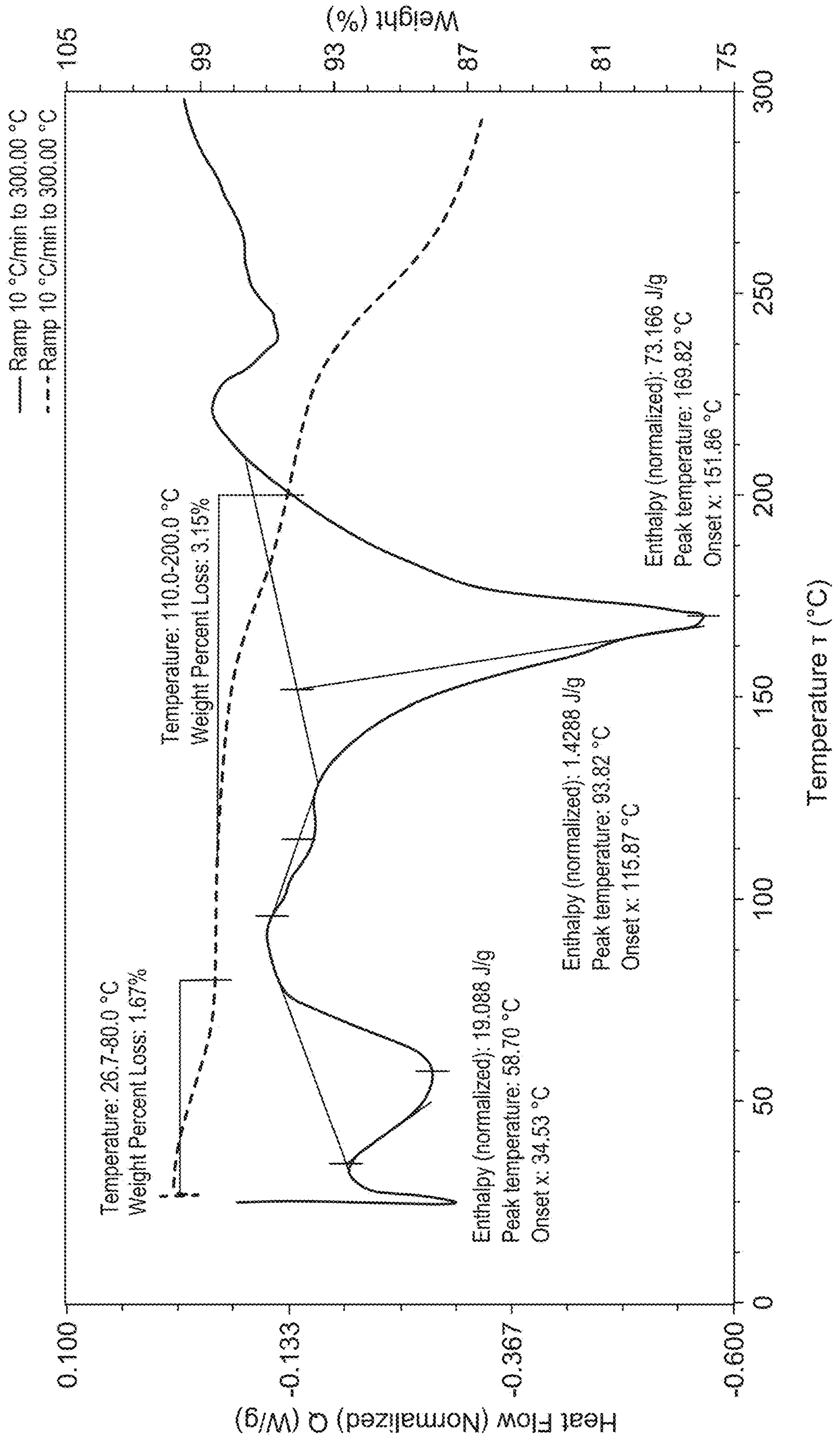

FIG. 24 provides representative DSC and TGA thermograms of Form 11 of a glycolate salt of Compound 1.

Figure 25:
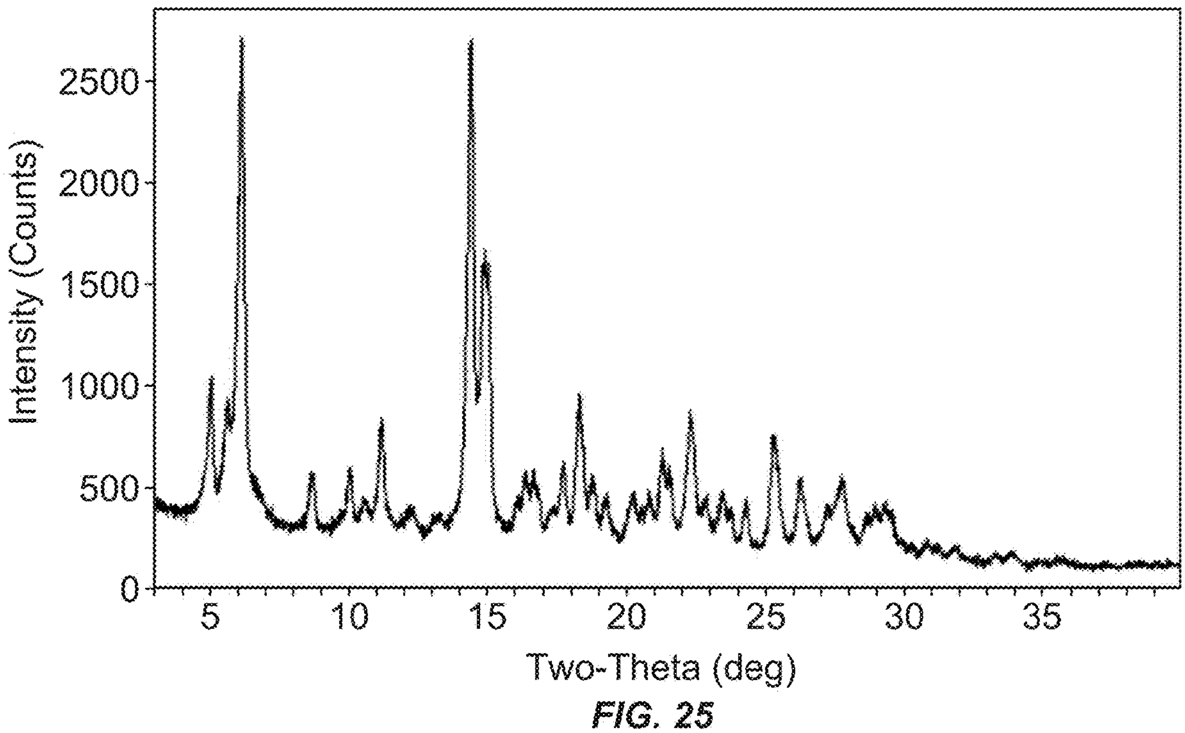

FIG. 25 provides a representative XRPD pattern of Form 12 of a 1-hydroxy-2-naphthoate salt of Compound 1.

Figure 26:
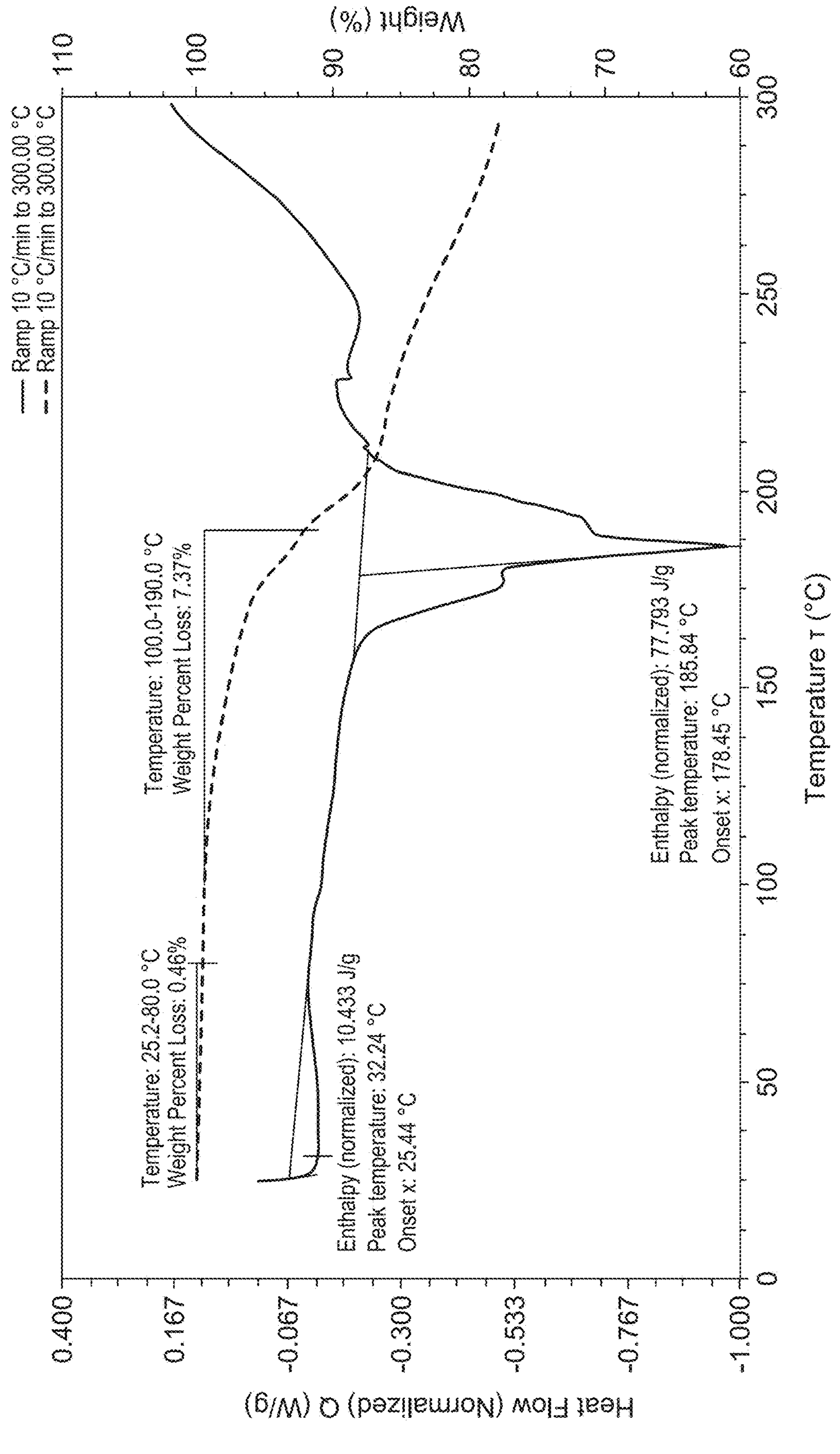

FIG. 26 provides representative DSC and TGA thermograms of Form 12 of a 1-hydroxy-2-naphthoate salt of Compound 1.

Figure 27:
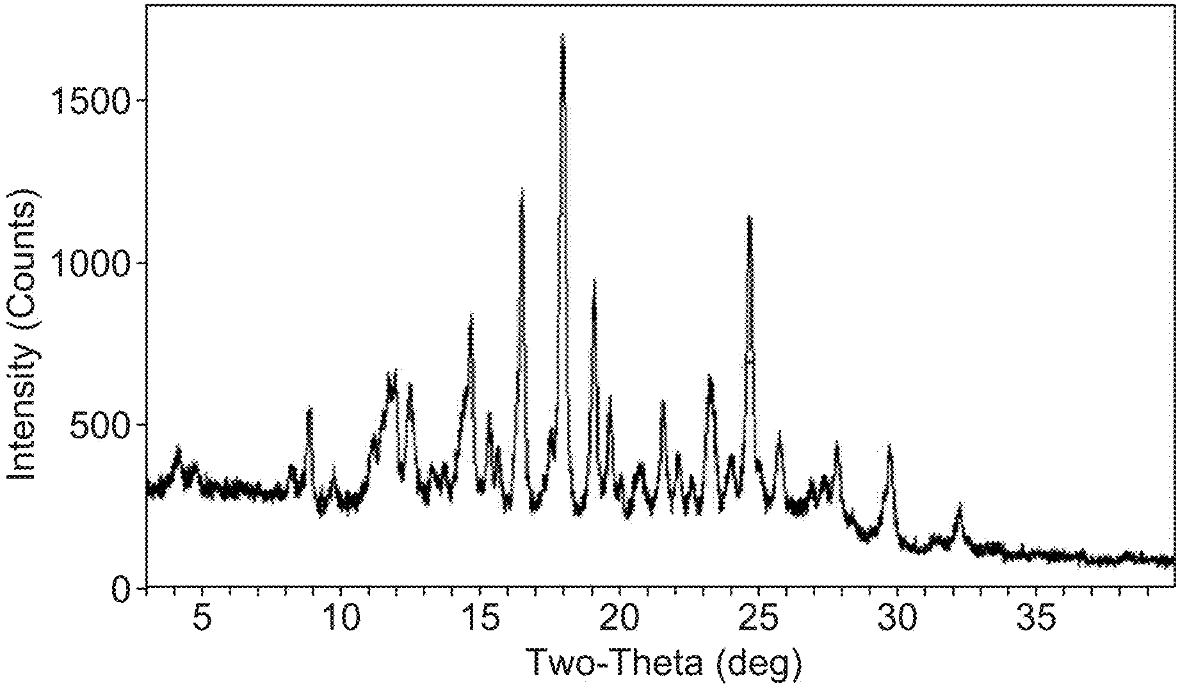

FIG. 27 provides a representative XRPD pattern of Form 13 of a 1-hydroxy-2-naphthoate salt of Compound 1.

Figure 28:
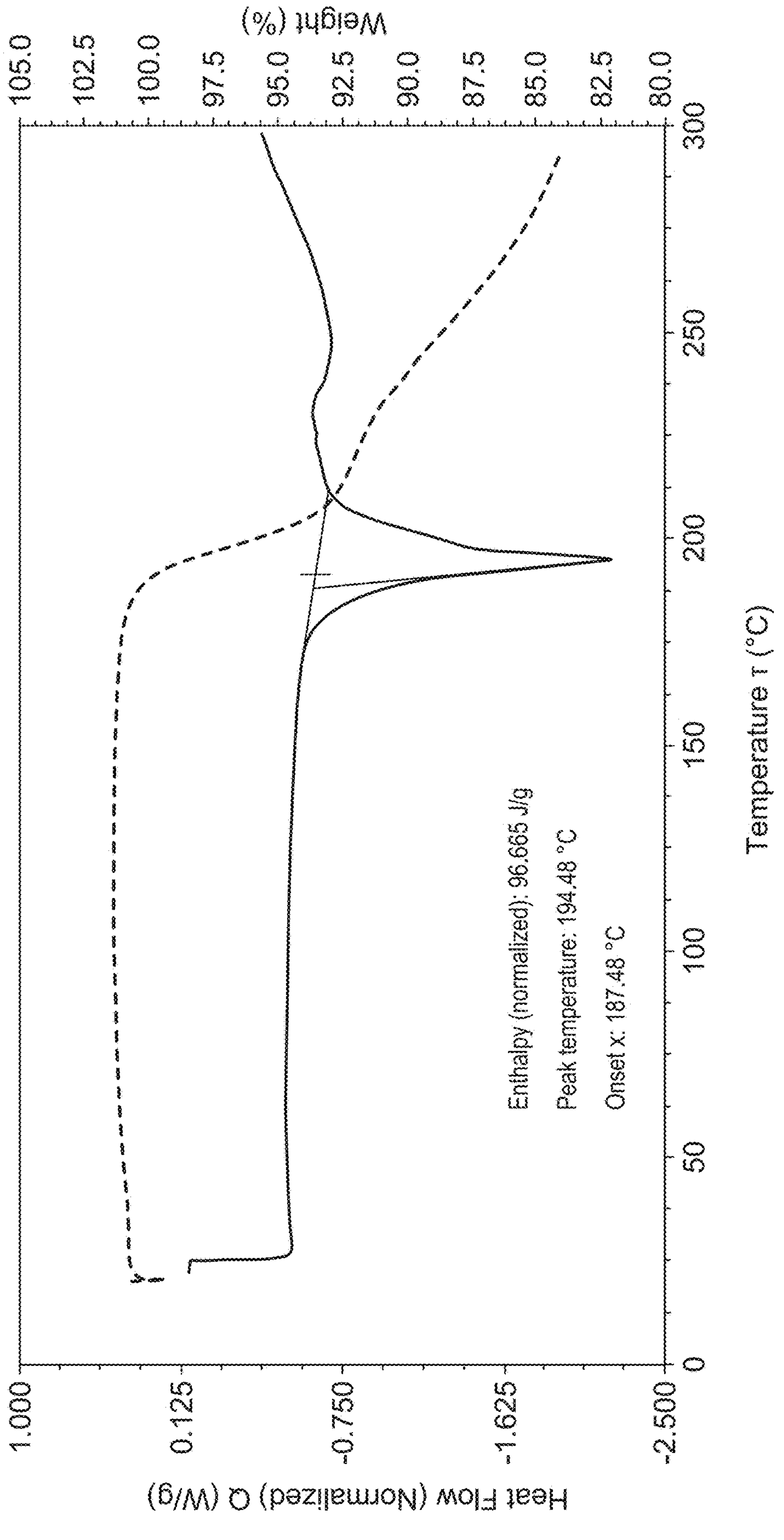

FIG. 28 provides representative DSC and TGA thermograms of Form 13 of a 1-hydroxy-2-naphthoate salt of Compound 1.

Figure 29:
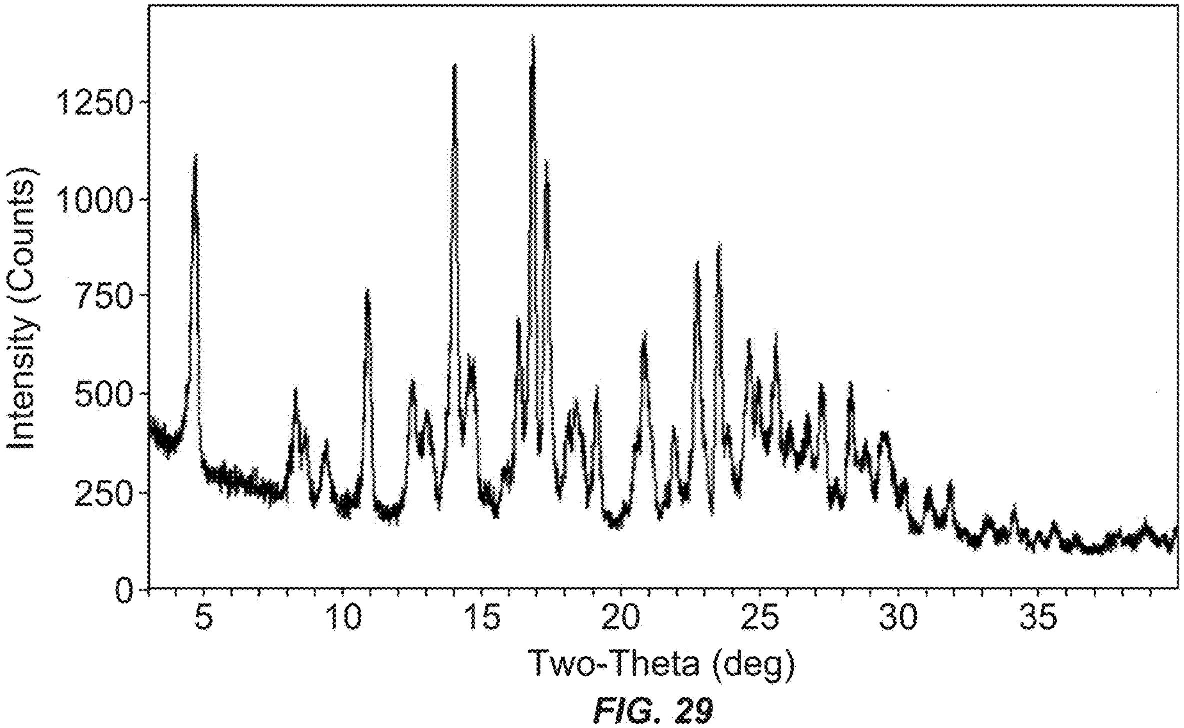

FIG. 29 provides a representative XRPD pattern of Form 14 of a malate salt of Compound 1.

Figure 30:
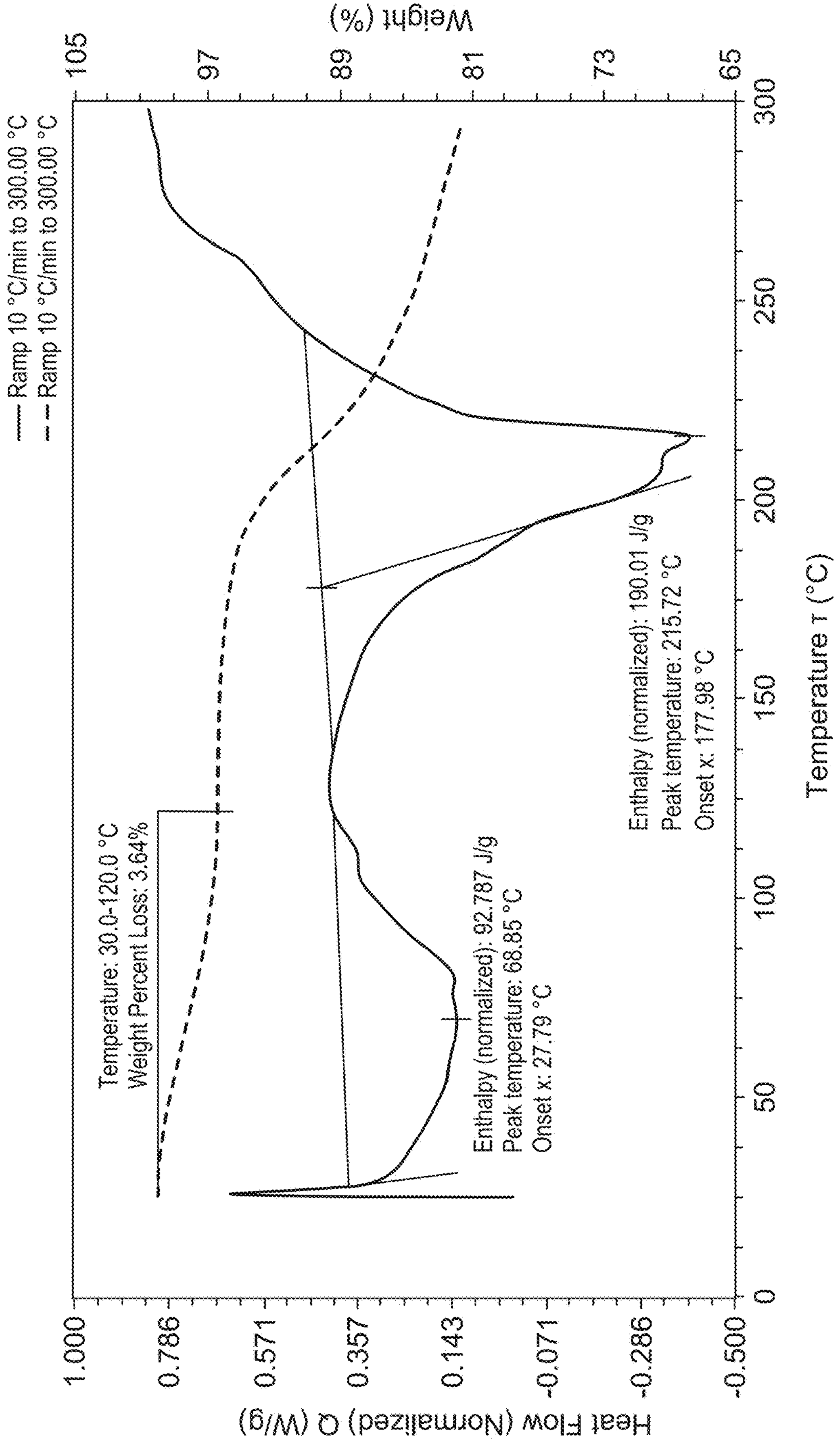

FIG. 30 provides representative DSC and TGA thermograms of Form 14 of a malate salt of Compound 1.

Figure 31:
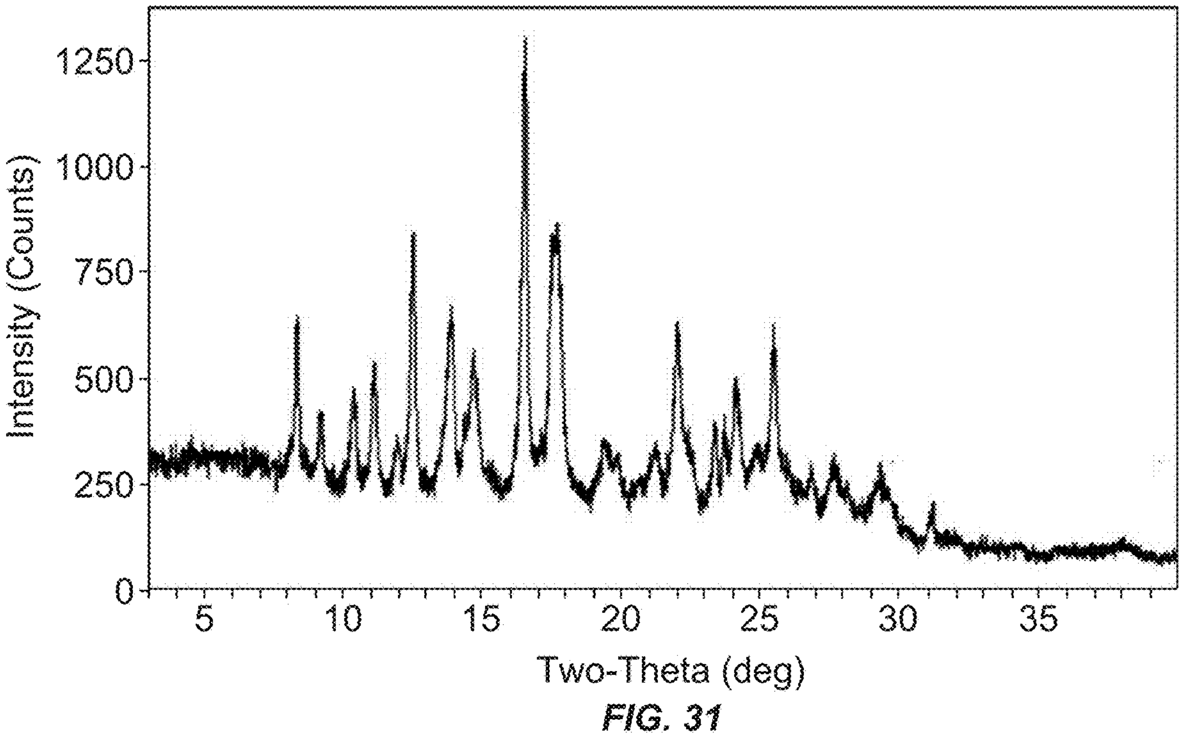

FIG. 31 provides a representative XRPD pattern of Form 15 of a malate salt of Compound 1.

Figure 32:
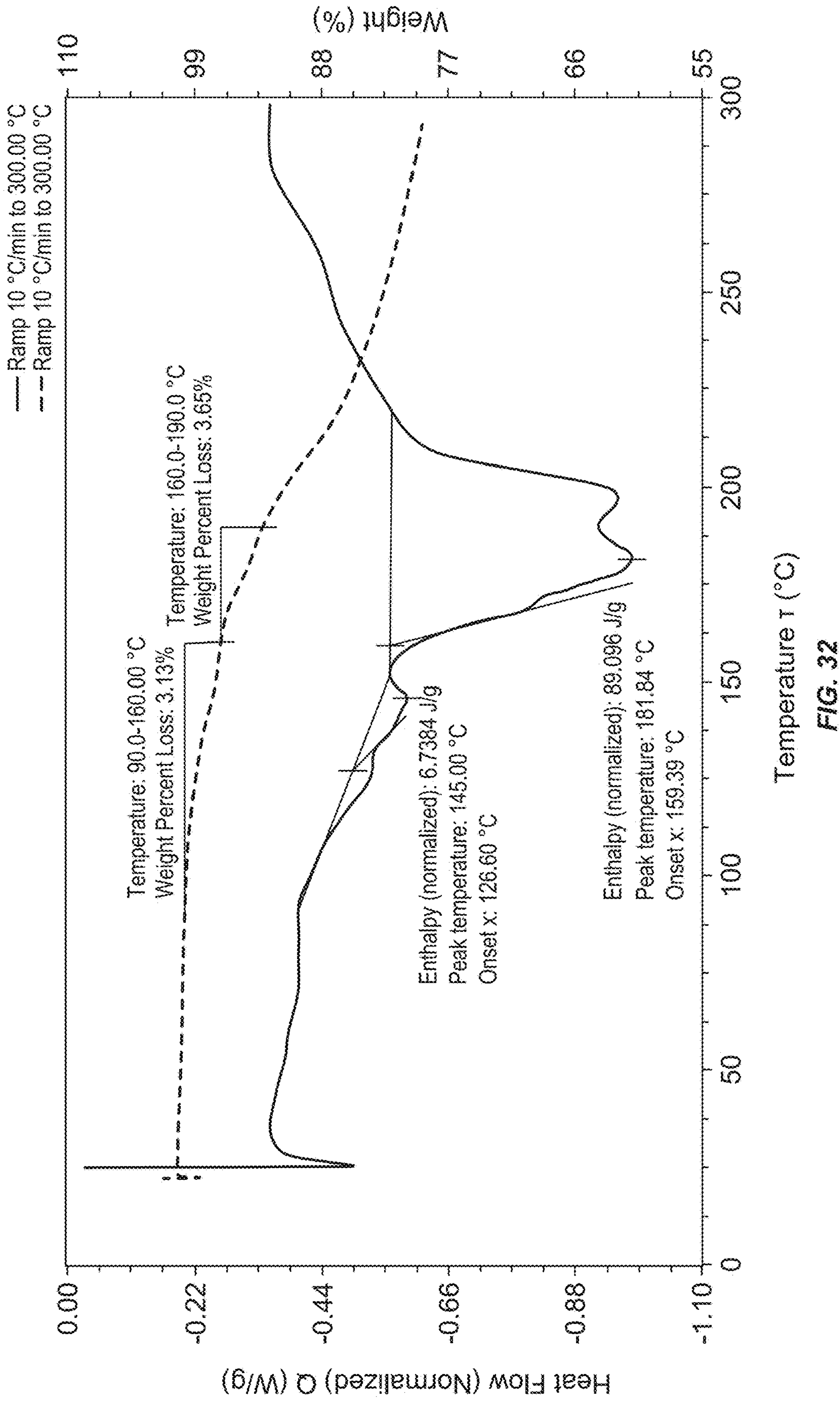

FIG. 32 provides representative DSC and TGA thermograms of Form 15 of a malate salt of Compound 1.

Figure 33:
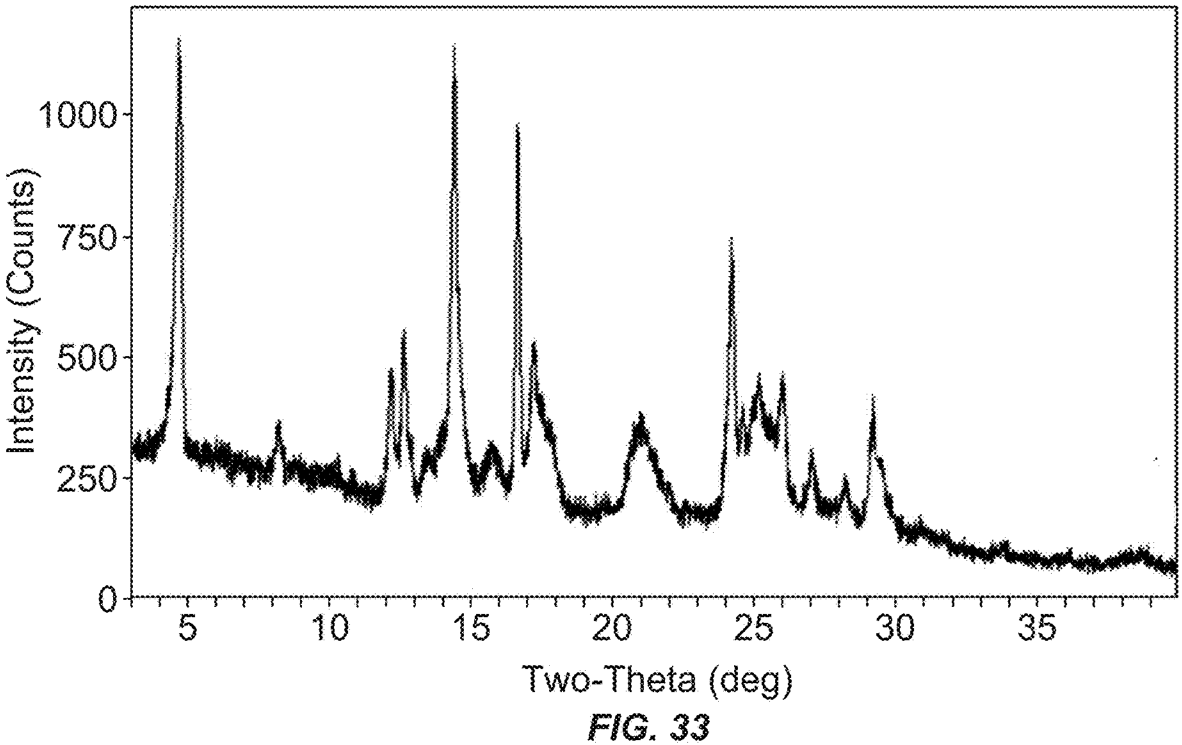

FIG. 33 provides a representative XRPD pattern of Form 16 of a maleate salt of Compound 1.

Figure 34:
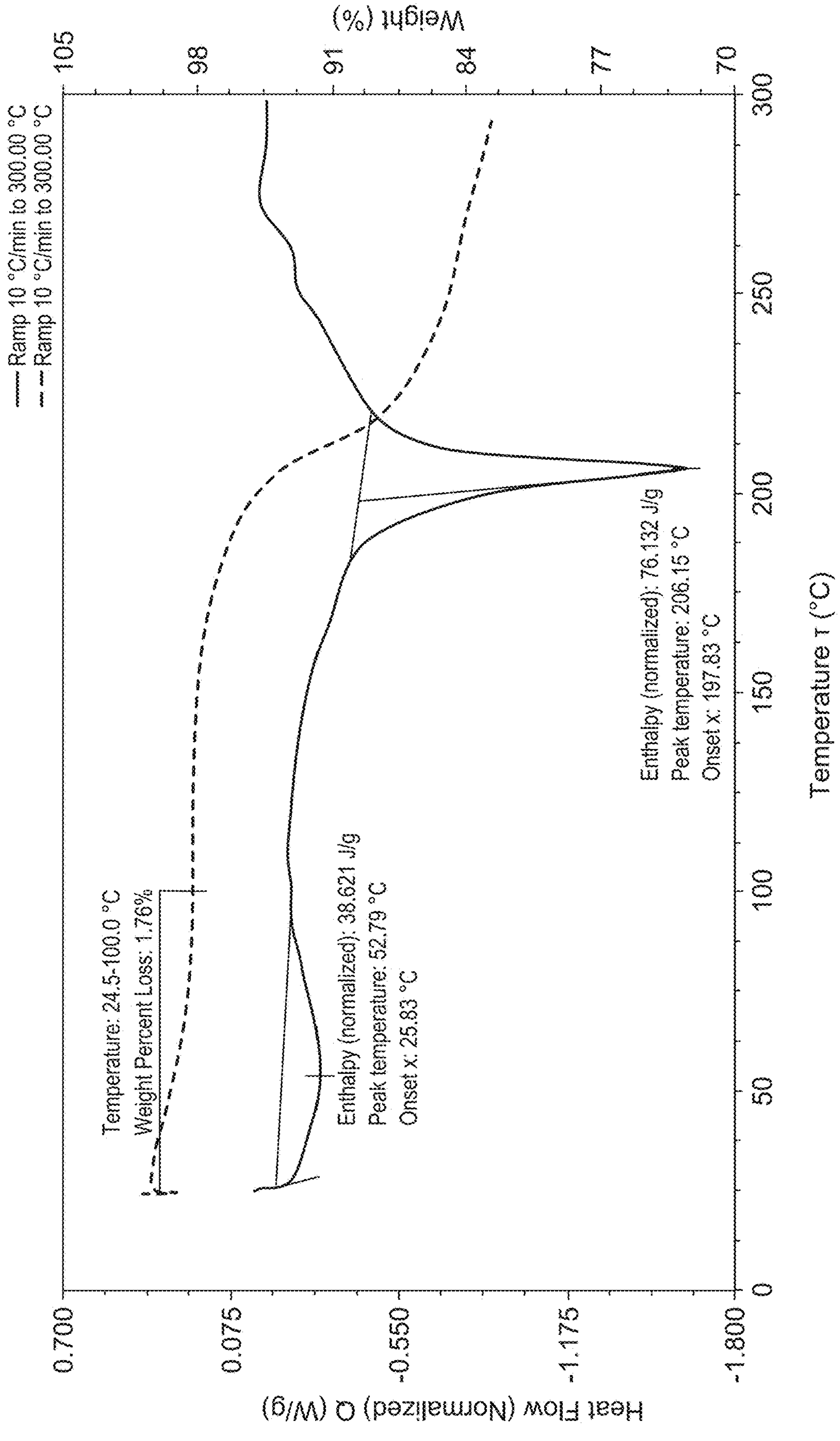

FIG. 34 provides representative DSC and TGA thermograms of Form 16 of a maleate salt of Compound 1.

Figure 35:
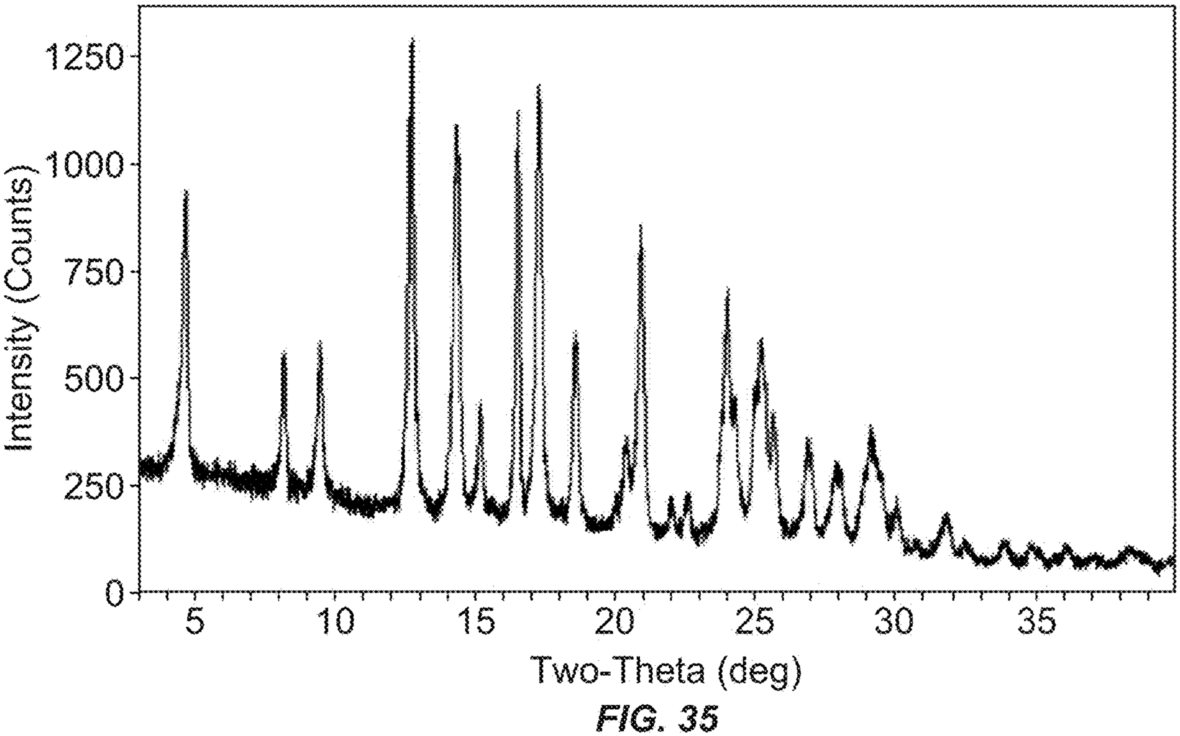

FIG. 35 provides a representative XRPD pattern of Form 17 of a maleate salt of Compound 1.

Figure 36:
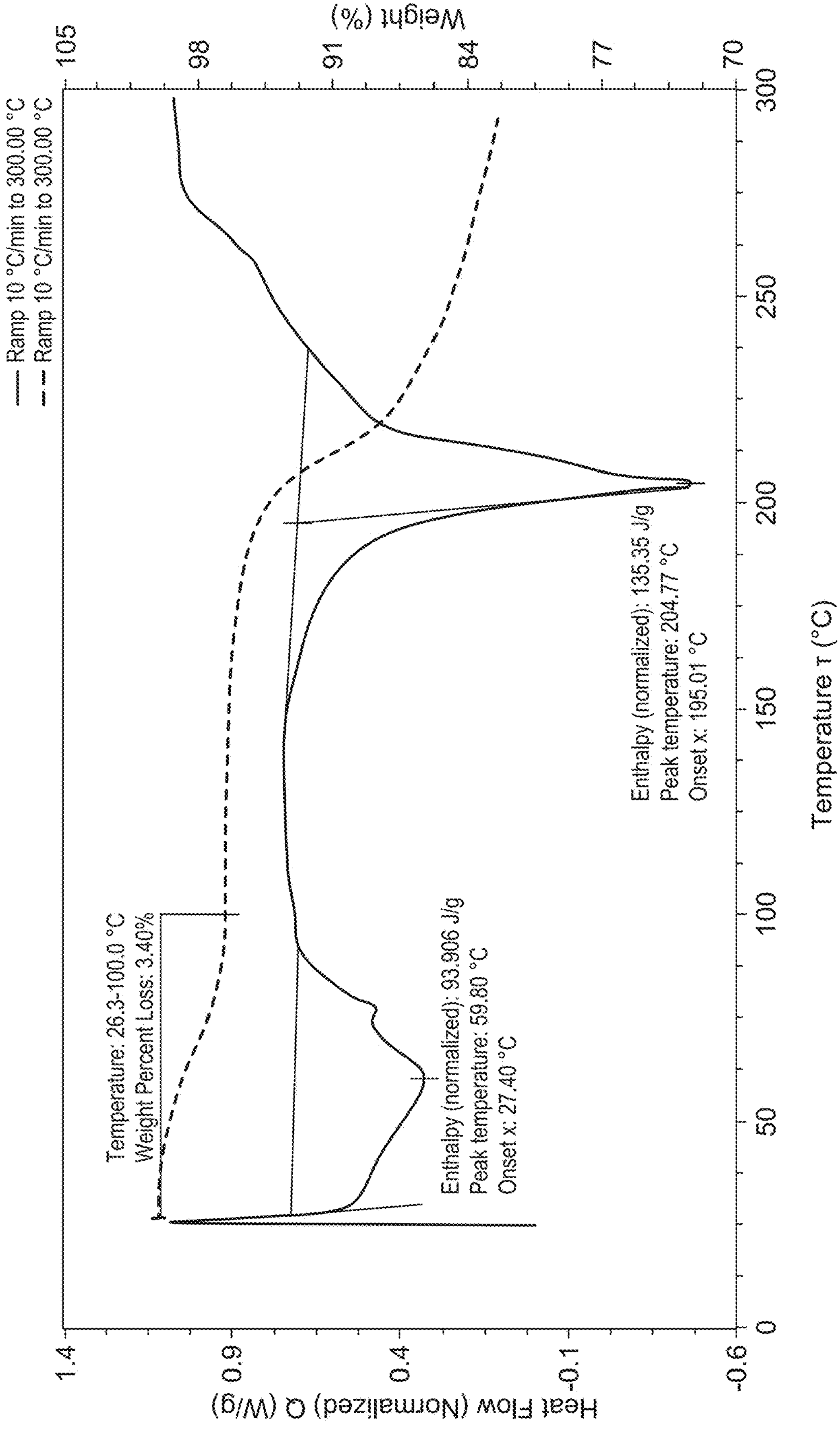

FIG. 36 provides representative DSC and TGA thermograms of Form 17 of a maleate salt of Compound 1.

Figure 37:
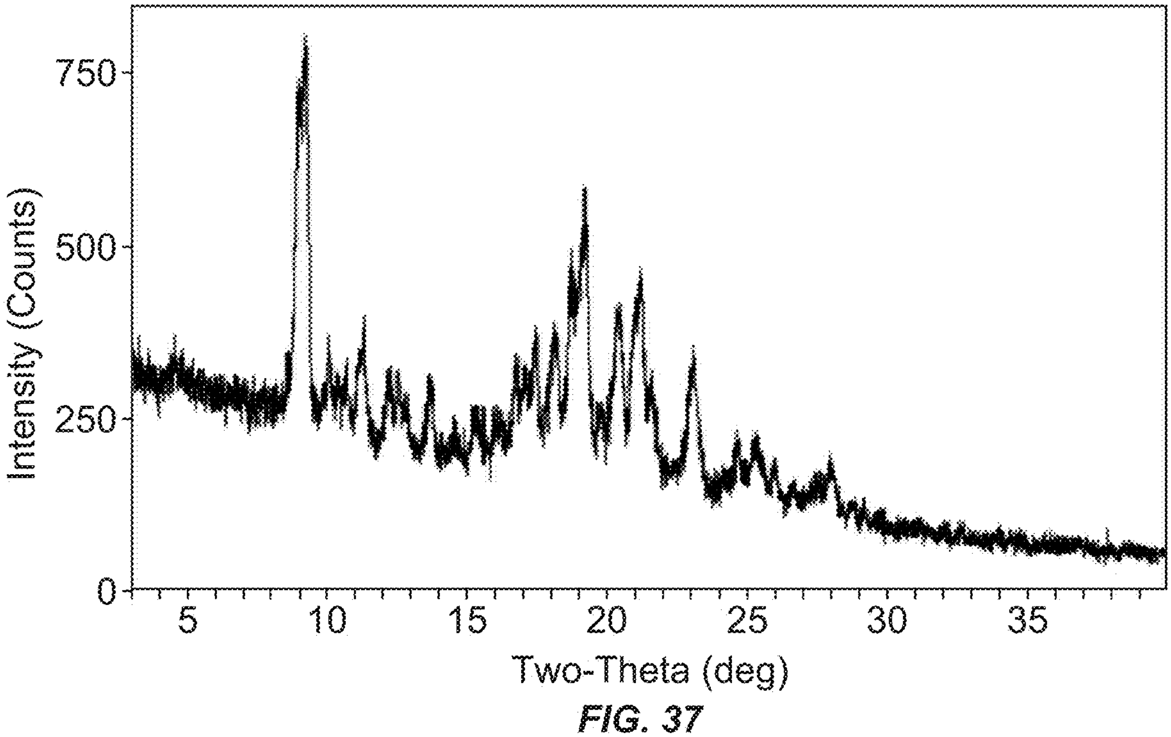

FIG. 37 provides a representative XRPD pattern of Form 18 of a mesylate salt of Compound 1.

Figure 38:
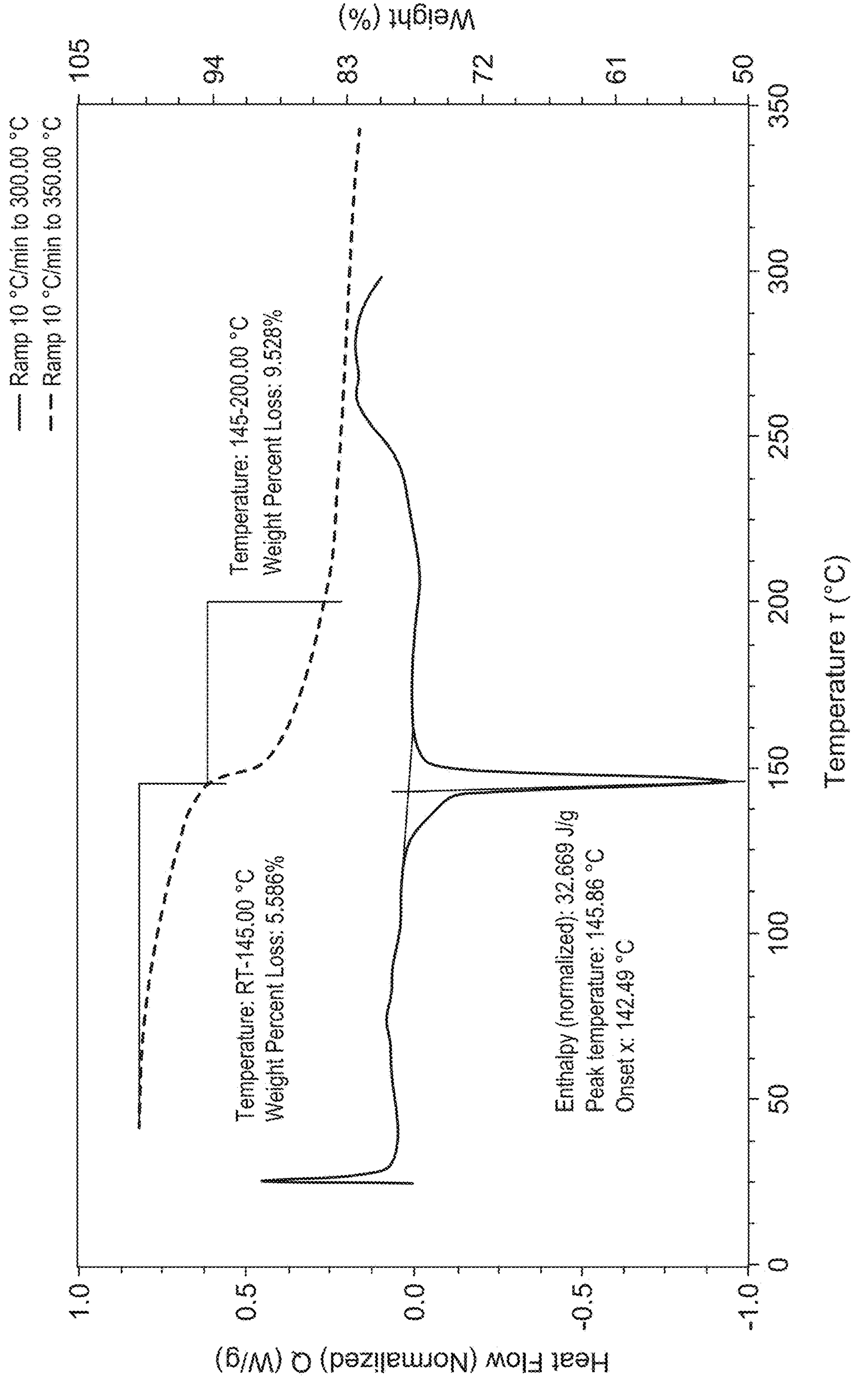

FIG. 38 provides representative DSC and TGA thermograms of Form 18 of a mesylate salt of Compound 1.

Figure 39:
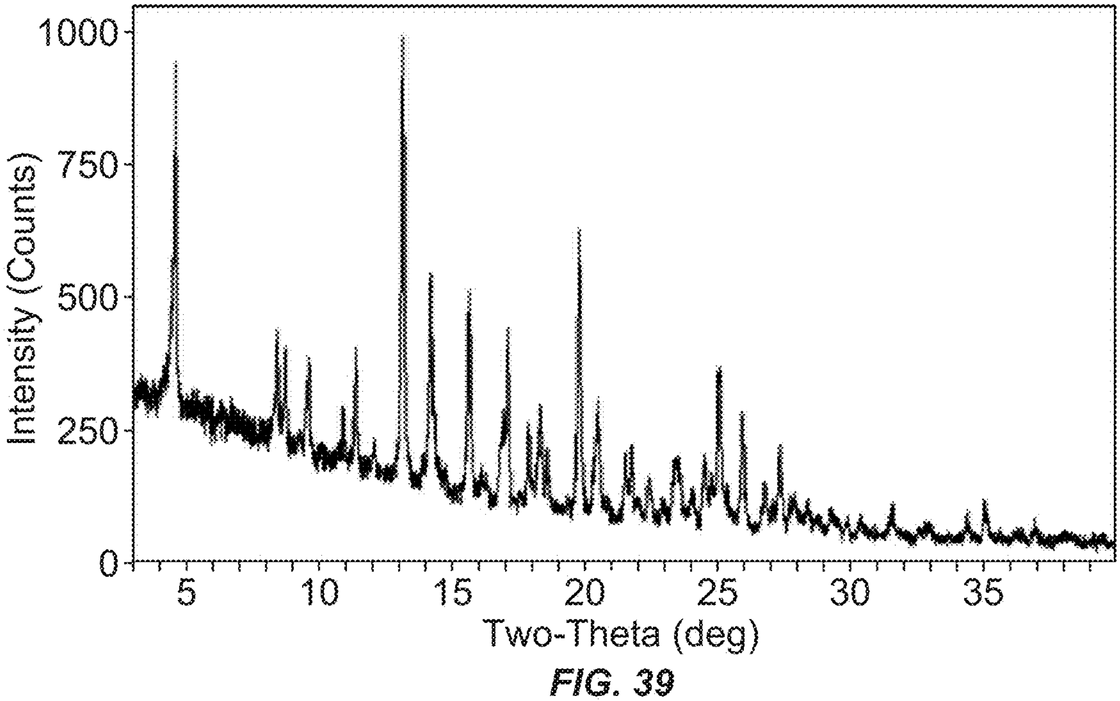

FIG. 39 provides a representative XRPD pattern of Form 19 of a oxalate salt of Compound 1.

Figure 40:
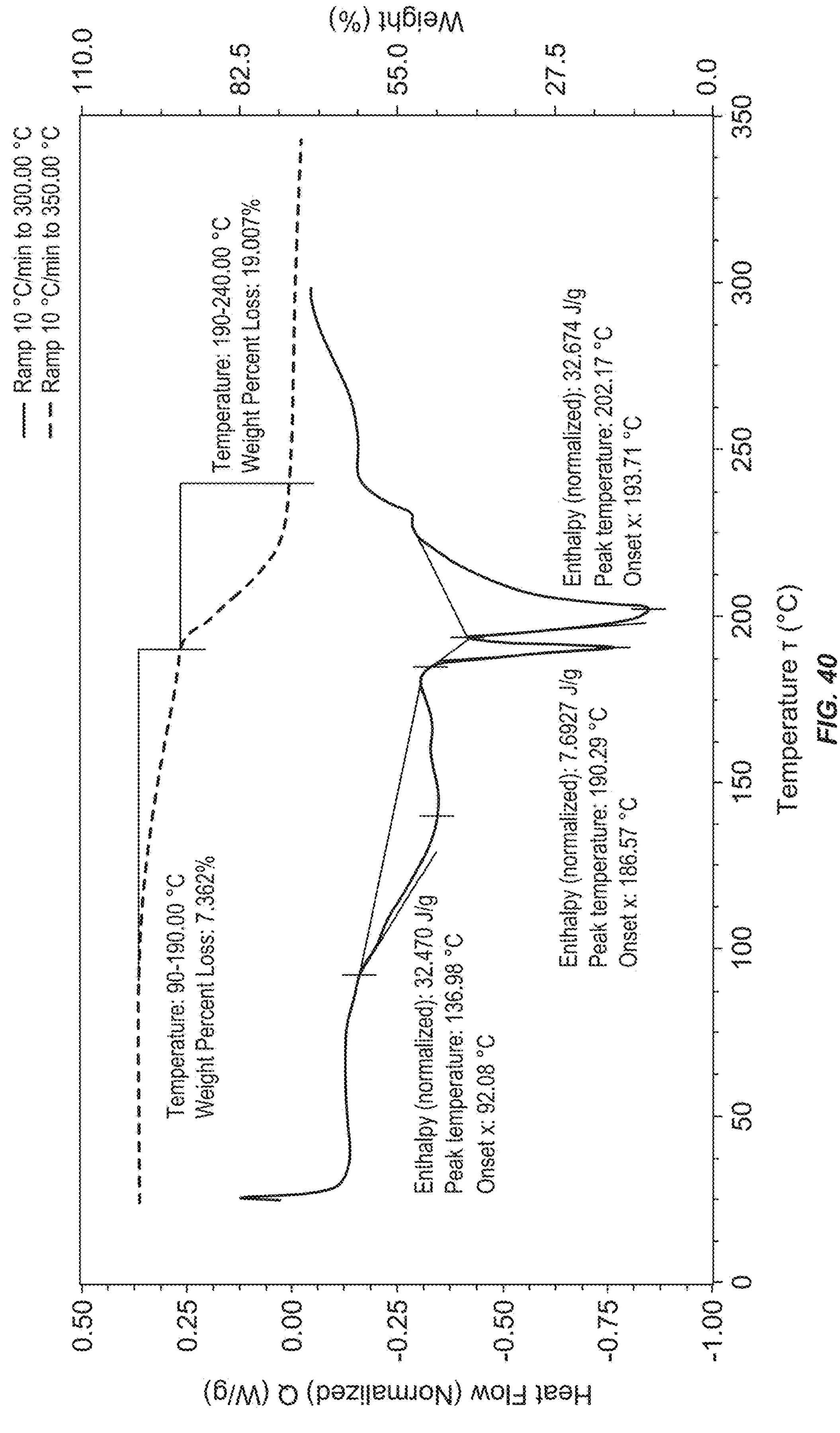

FIG. 40 provides representative DSC and TGA thermograms of Form 19 of a oxalate salt of Compound 1.

Figure 41:
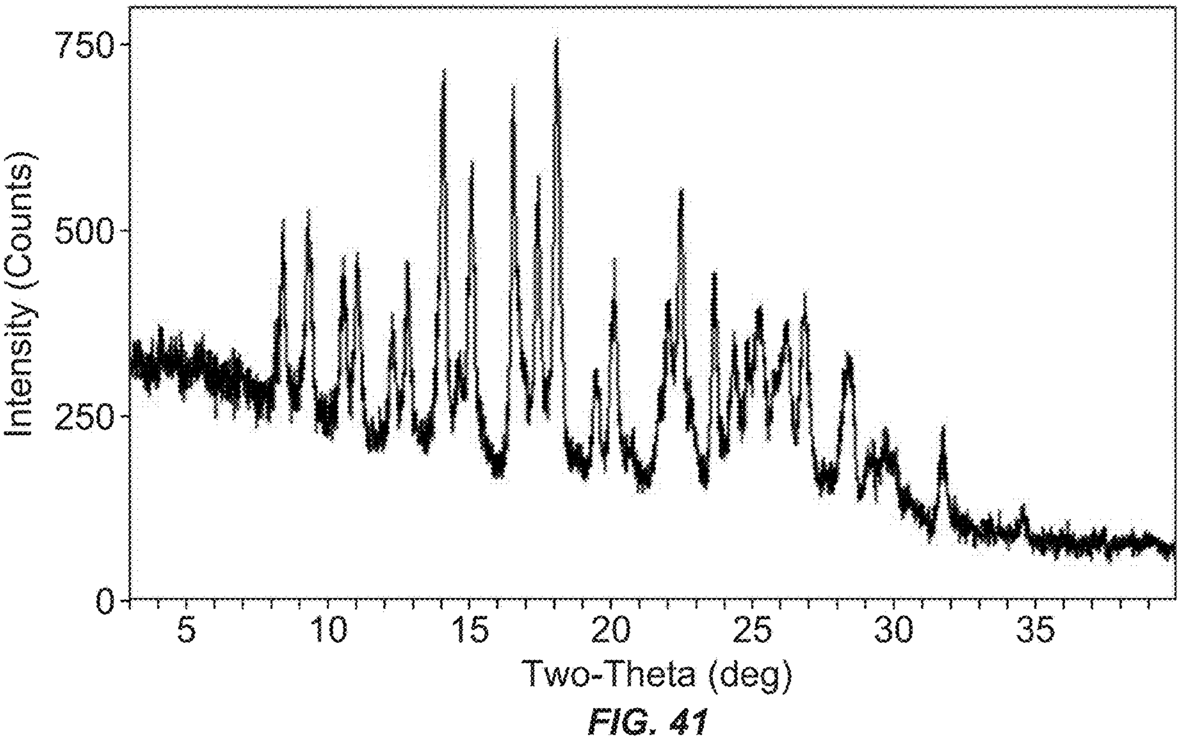

FIG. 41 provides a representative XRPD pattern of Form 20 of a phosphate salt of Compound 1.

Figure 42:
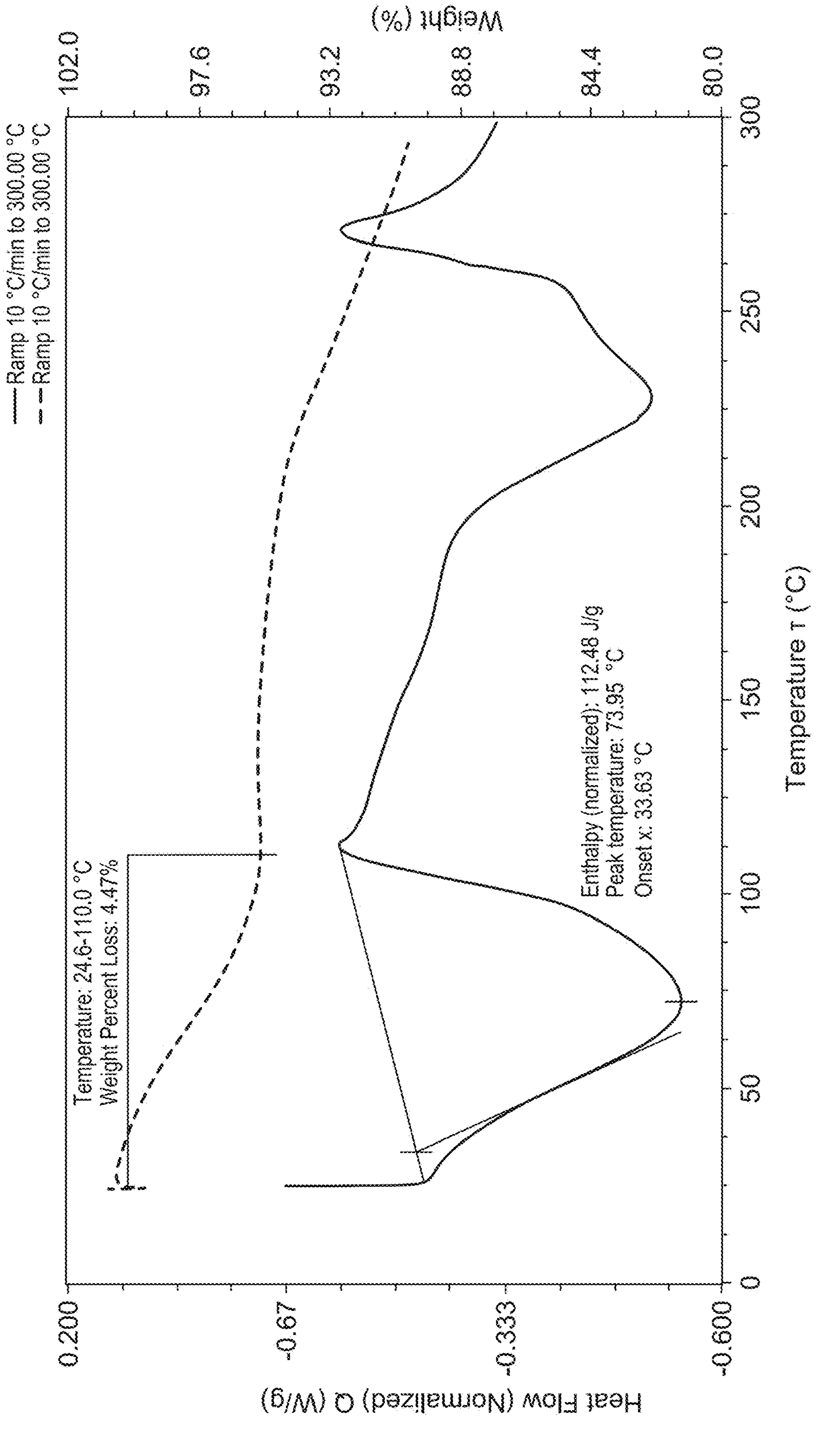

FIG. 42 provides representative DSC and TGA thermograms of Form 20 of a phosphate salt of Compound 1.

Figure 43:
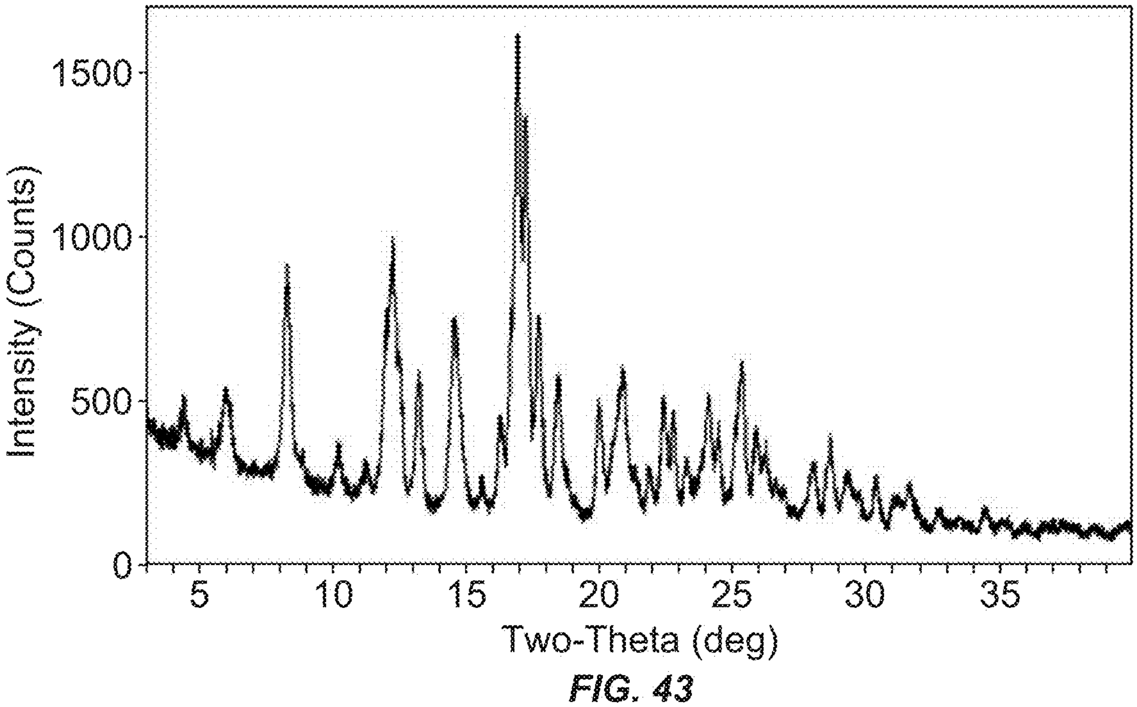

FIG. 43 provides a representative XRPD pattern of Form 21 of a tartrate salt of Compound 1.

Figure 44:
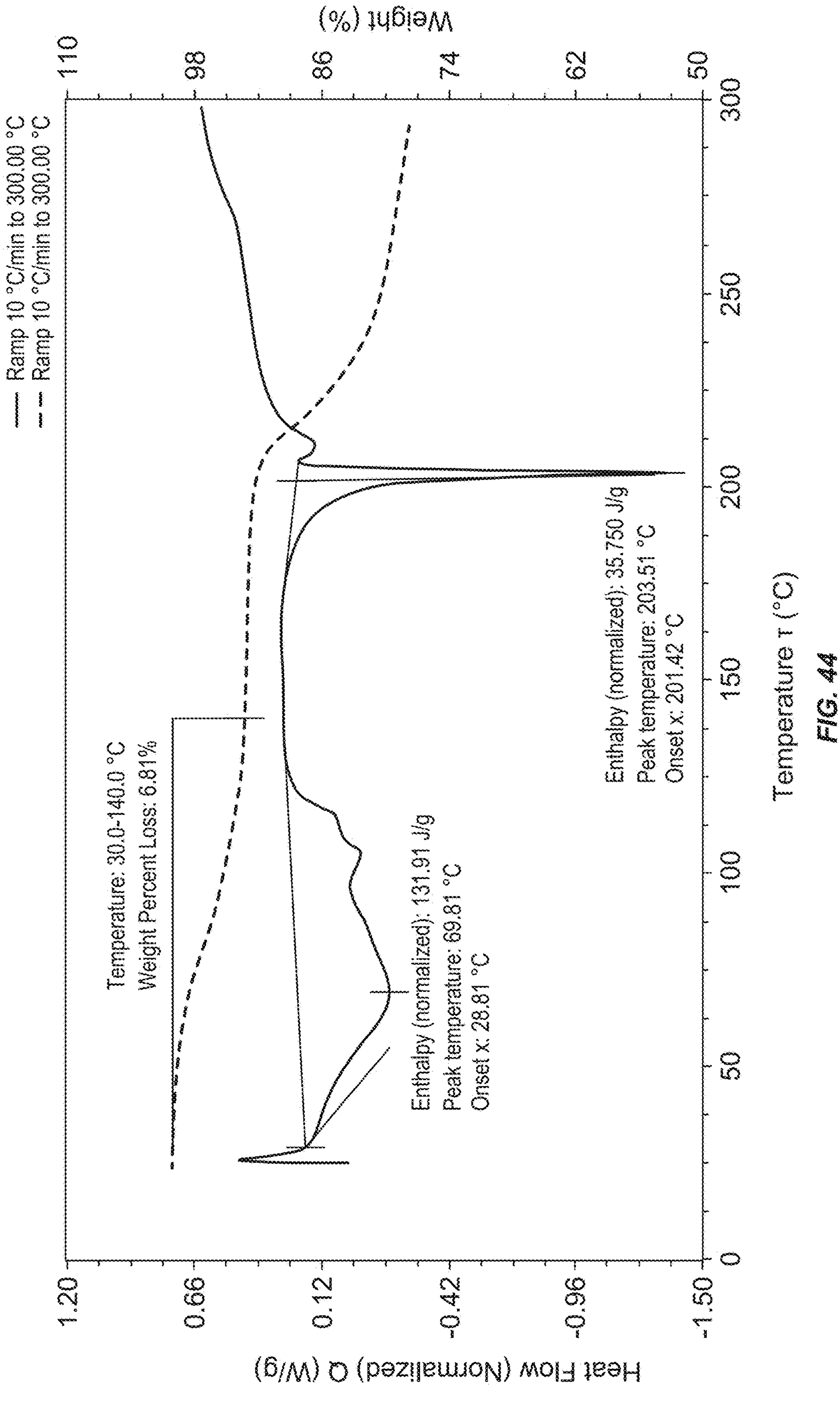

FIG. 44 provides representative DSC and TGA thermograms of Form 21 of a tartrate salt of Compound 1.

Figure 45:
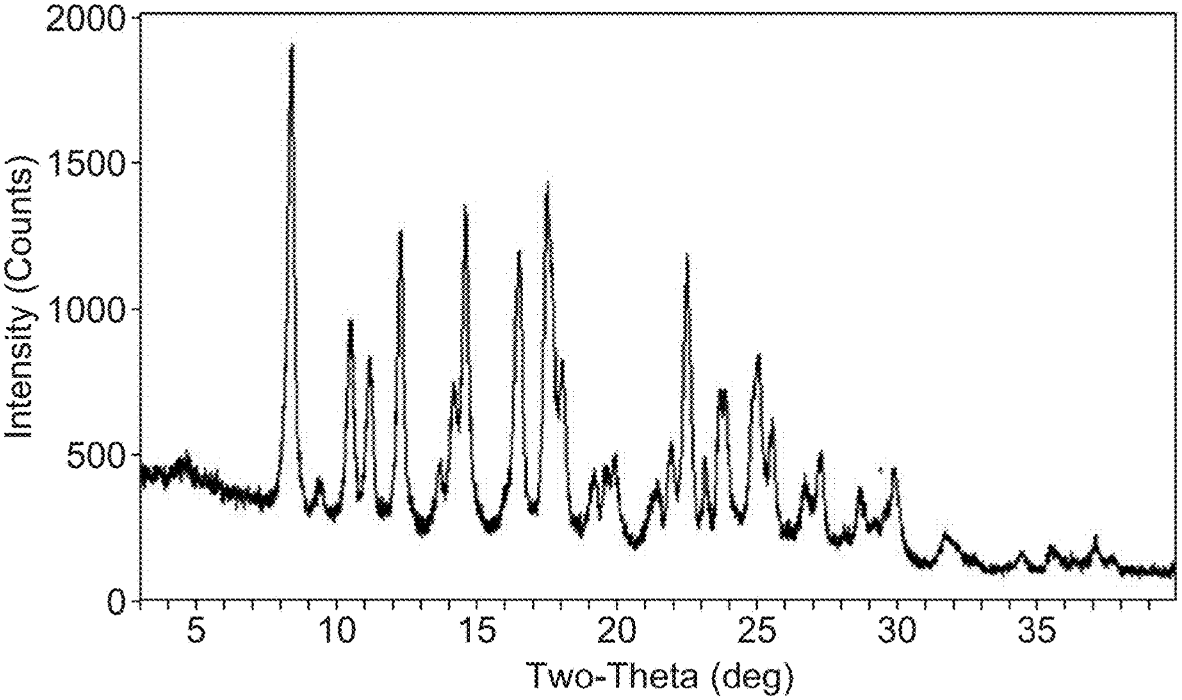

FIG. 45 provides a representative XRPD pattern of Form 22 of a tartrate salt of Compound 1.

Figure 46:
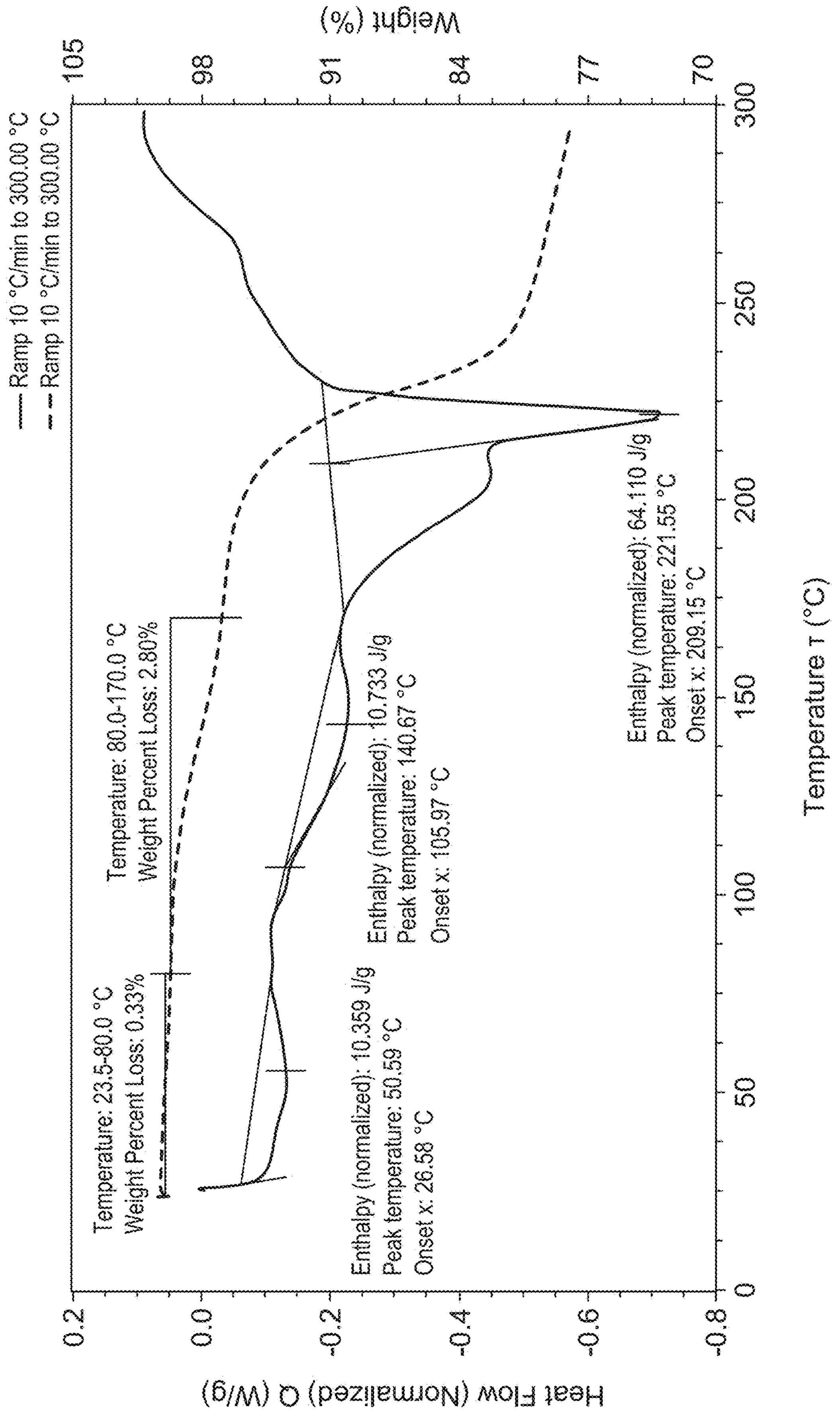

FIG. 46 provides representative DSC and TGA thermograms of Form 22 of a tartrate salt of Compound 1.

Figure 47:
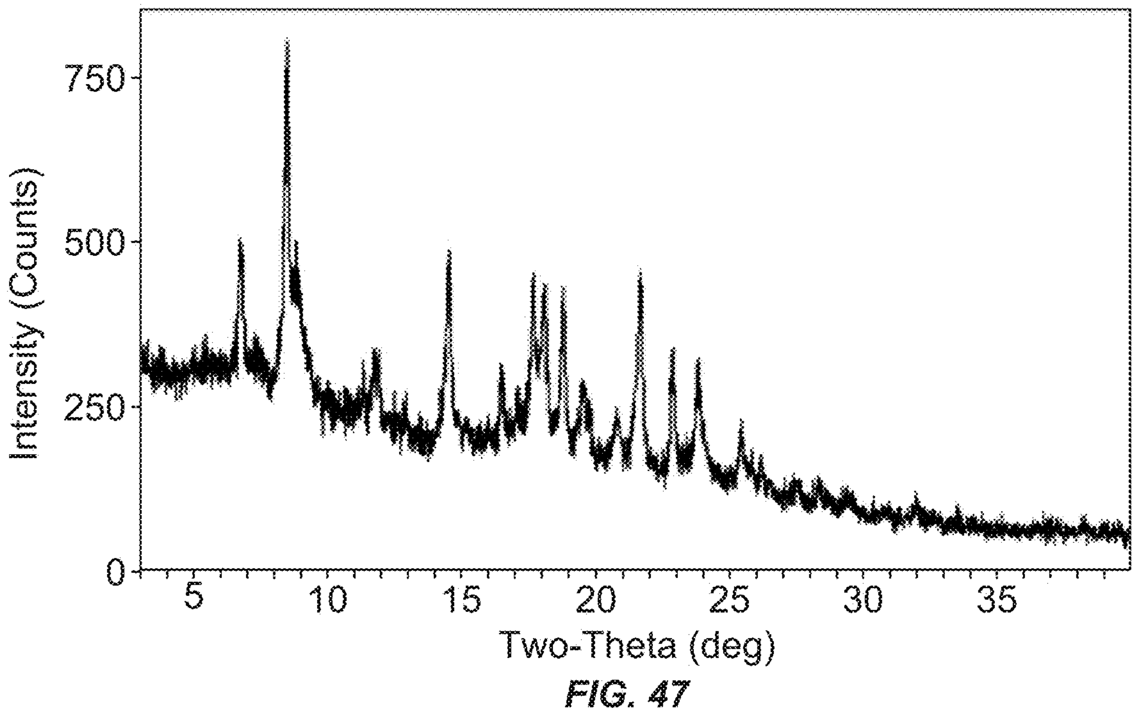

FIG. 47 provides a representative XRPD pattern of Form 23 of a tosylate salt of Compound 1.

Figure 48:
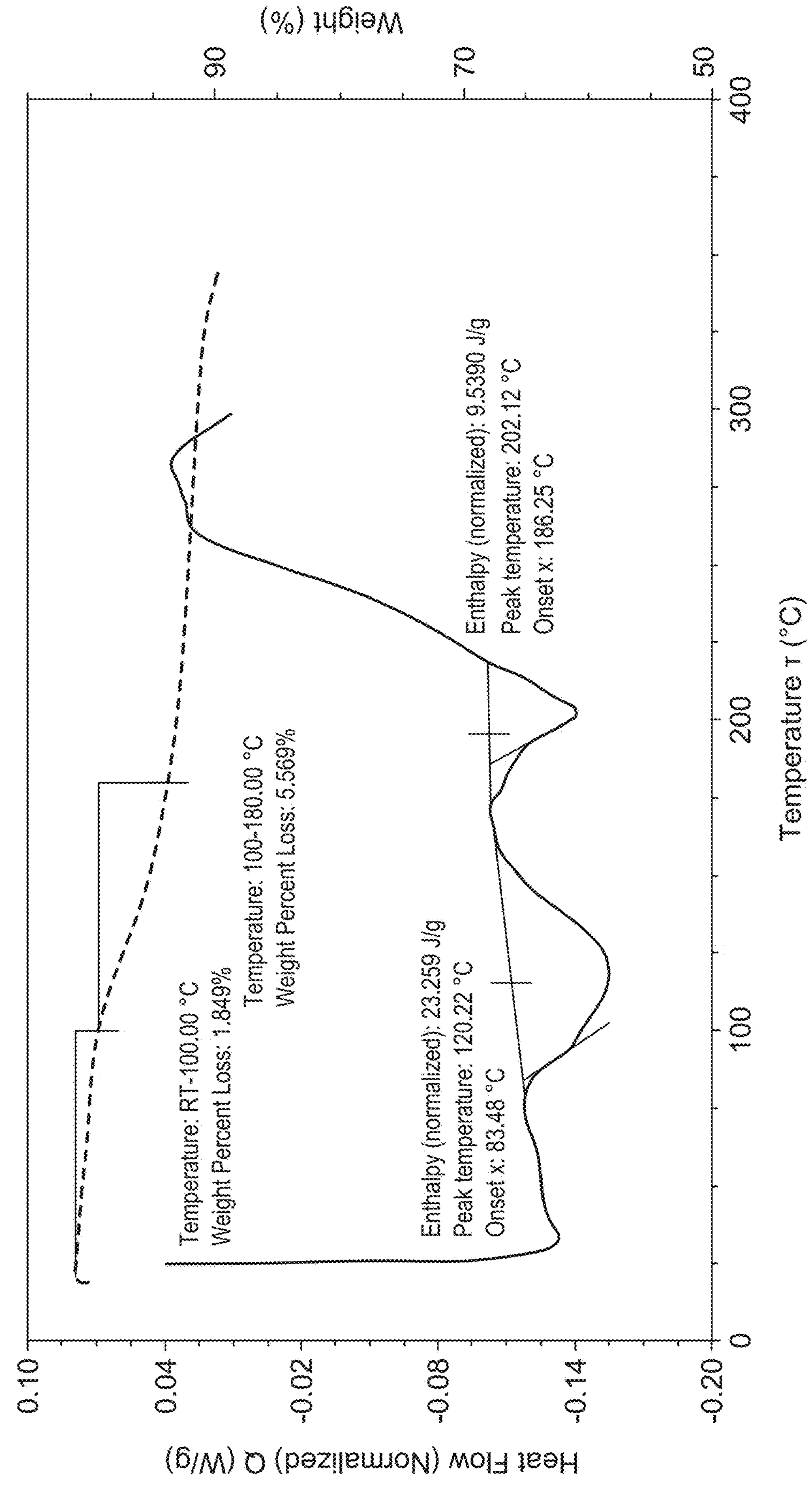

FIG. 48 provides representative DSC and TGA thermograms of Form 23 of a tosylate salt of Compound 1.

Figure 49:
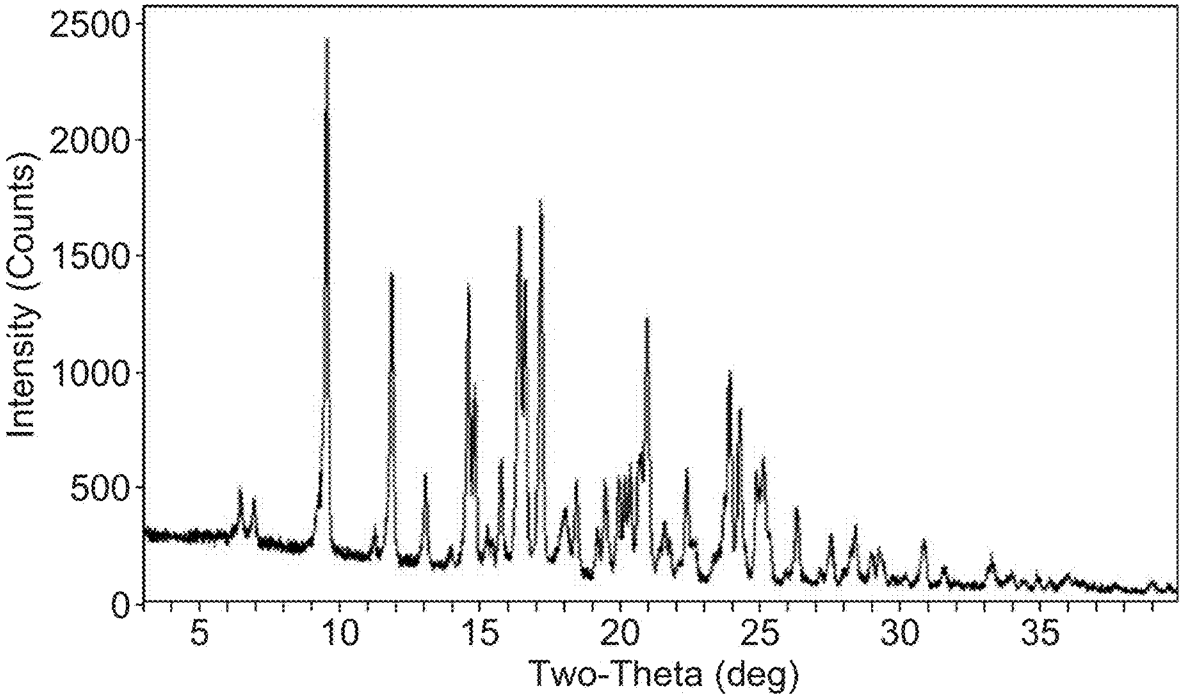

FIG. 49 provides a representative XRPD pattern of Form 24 of a free base, anhydrate of Compound 1.

Figure 50:
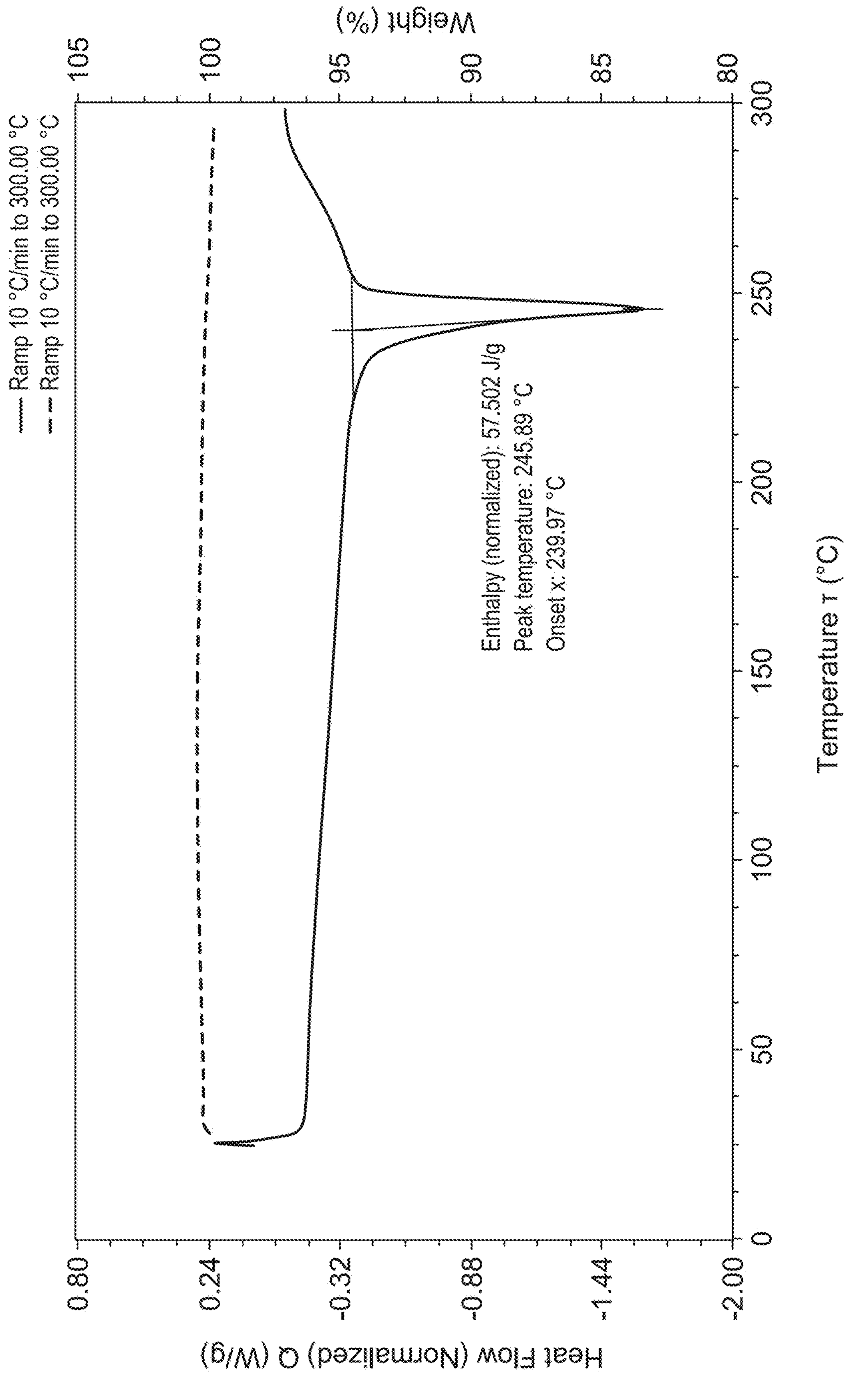

FIG. 50 provides representative DSC and TGA thermograms of Form 24 of a free base, anhydrate of Compound 1.

Figure 51:
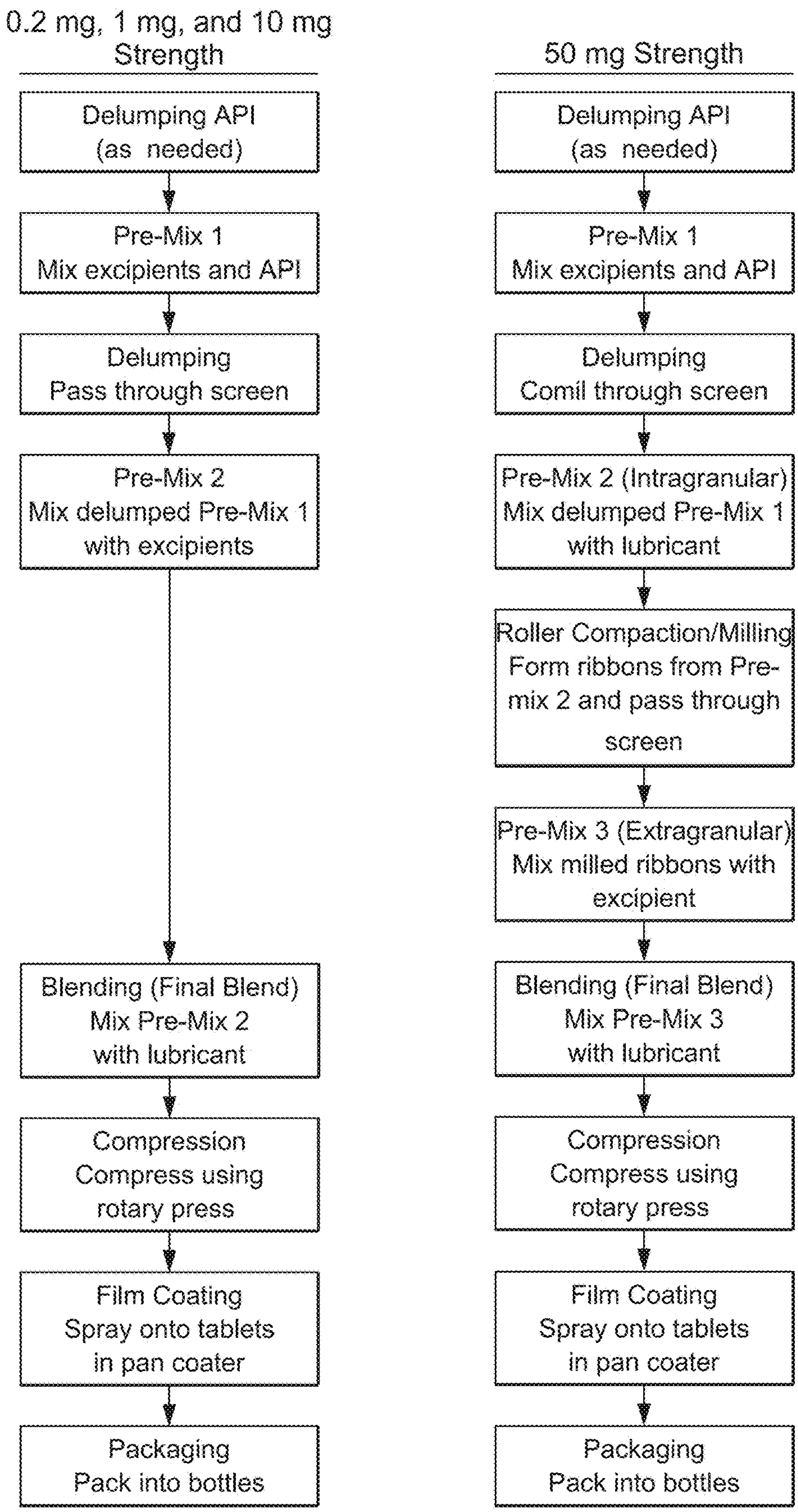

FIG. 51 illustrates exemplary processes for preparing tablets having strengths of 0.2 mg, 1 mg, 10 mg, and 50 mg of Compound 1, or a pharmaceutically acceptable salt and/or solvate thereof (free base equivalent amount).

5. DETAILED DESCRIPTION

Unless defined otherwise, all technical and scientific terms used herein have the same meaning as is commonly understood by one of ordinary skill in the art. In the event that there are a plurality of definitions for a term herein, those in this section prevail unless stated otherwise.

As used herein, and in the specification and the accompanying claims, the indefinite articles "a" and "an" and the definite article "the" include plural as well as single referents unless the context clearly indicates otherwise.

When ranges are used herein for physical properties, such as molecular weight, or chemical properties, such as chemical formulae, all combinations and subcombinations of ranges, including the endpoint numbers on both limits of the range, and specific embodiments therein are intended to be included. As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. For example, in some embodiments, the value of XRPD peak position may vary by up to ±0.2 degrees 2θ while still describing the particular XRPD peak. For example, in some embodiments, the value of a DSC thermal event having an onset temperature or a DSC peak temperature (each expressed in degrees Celsius (° C.)) may vary by up to ±2° C. while still describing the particular temperature. As used herein, a tilde (i.e., "~") preceding a numerical value or range of values indicates "about" or "approximately."

The term "between" includes the endpoint numbers on both limits of the range. For example, the range described by "between 3 and 5" is inclusive of the numbers "3" and "5".

As used herein, the term "API correction factor" is understood to refer to a correction factor calculation that is used to characterize a particular lot of an active pharmaceutical ingredient (API), which is determined based on the purity of API, the amount of any water and any residual solvent content present, and residue on ignition (ROI): API correction factor=(purity of API)*(1−water content−residual solvent−ROI). Purity of API is determined using methods known in the art, for example, HPLC and/or $^1$H NMR. Water content is determined using methods known in the art, for example, Karl Fischer analysis. ROI is determined using methods known in the art, for example, ignition of a sample and heating the residue at elevated temperature, such as about 450 to about 600° C., and weighing the remaining material. The API correction factor used therein is at least about 0.95, or at least about 0.96, or at least about 0.97, or at least about 0.98, or at least about 0.99. In some aspects, the API correction factor is at least 0.97, or is from about 0.97 to about 0.98.

As used herein, the term "administer," "administering," or "administration" refers to the act of delivering, or causing to be delivered, a compound or a pharmaceutical composition to the body of a subject by a method described herein or otherwise known in the art. Administering a compound or a pharmaceutical composition includes prescribing a compound or a pharmaceutical composition to be delivered into the body of a patient. Exemplary forms of administration include oral dosage forms, such as tablets, capsules, syrups, suspensions; injectable dosage forms, such as intravenous (IV), intramuscular (IM), or intraperitoneal (IP); transdermal dosage forms, including creams, jellies, powders, or patches; buccal dosage forms; inhalation powders, sprays, suspensions, and rectal suppositories. In some embodiments, the form of administration is an oral dosage form, such as a tablet.

As used herein, a "pharmaceutically acceptable form" of compounds disclosed herein includes, but is not limited to, a pharmaceutically acceptable salt, solvate, isomer, and isotopologue (i.e., isotopically labeled derivative), of compounds disclosed herein, which includes combinations thereof (e.g., a solvate of a pharmaceutically acceptable salt, or an isomer and/or isotopologue of a compound or of a solvate, salt, or solvate of salt of such compound). In some embodiments, a "pharmaceutically acceptable form" includes, but is not limited to, a pharmaceutically acceptable salt, solvate, isomer (e.g., tautomer or stereoisomer), and isotopologue (i.e., isotopically labeled derivative) of Compound 1 as disclosed herein, and combinations thereof.

In some embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describe pharmaceutically acceptable salts in detail (see *J. Pharm. Sci.* (1977) 66:1-19). Pharmaceutically acceptable salts of the compounds provided herein include those derived from suitable pharmaceutically acceptable inorganic and organic acids and bases, such as suitable inorganic and organic addition acids and bases. For example, the pharmaceutically acceptable salt of the compounds provided herein is derived from suitable a pharmaceutically acceptable inorganic or organic acid, such as suitable inorganic or organic addition acid, which is sometimes referred to as the conjugate acid. In some embodiments, the pharmaceutically acceptable salt includes, but is not limited to, a benzoate salt, a besylate salt, a chloride salt, a citrate salt, a fumarate salt, a gentisate salt, a glutarate salt, a glycolate salt, a hippurate salt, a 1-hydroxy-2-naphthoate salt, a malate salt, a maleate salt, a mesylate salt, an oxalate salt, a phosphate salt, a sulfate salt, a tartrate salt, or a tosylate salt. In some embodiments, a pharmaceutically acceptable salt of Compound 1, or a pharmaceutically acceptable solvate and/or isotopologue form thereof, is or comprises Compound 1, or pharmaceutically acceptable solvate and/or isotopologue form thereof, and a conjugate acid (a pharmaceutically acceptable salt) in a molar ratio in the range of about 2:1 to about 1:2. In some embodiments, a solid form comprises a pharmaceutically acceptable salt of Compound 1, or a pharmaceutically acceptable solvate and/or isotopologue form thereof, and a conjugate acid (a pharmaceutically acceptable salt) in a molar ratio in the range of about 2:1 to about 1:2. In some embodiments, the molar ratio of the Compound 1 or pharmaceutically acceptable solvate thereof to the conjugate acid ranges from about 2:1 to about 0.1:1. In some embodiments, the molar ratio of the Compound 1 or pharmaceutically acceptable solvate thereof to the conjugate acid ranges from about 2:1 to about 1:1. In some embodiments, the molar ratio of the Compound 1 or pharmaceutically acceptable solvate thereof to the conjugate acid ranges from about 0.1:1 to about 1:2. In some embodiments, the molar ratio of the Compound 1 or pharmaceutically acceptable solvate thereof to the conjugate acid ranges from about 1:1 to about 1:2. In some embodiments, the molar ratio of the Compound 1 or pharmaceutically acceptable solvate and/or isotopologue form thereof, and the conjugate acid (the pharmaceutically acceptable salt) is about 2:1, about 1.9:1, about 1.8:1, about 1.7:1, about 1.6:1, about 1.5:1, about 1.4:1, about 1.3:1, about 1.2:1, about 1.1:1, about 1:1, about 0.9:1, about 0.8:1, about 0.7:1, about 0.6:1, about 0.5:1, about 1:0.5, about 1:0.6, about 1:0.7, about 1:0.8, about 1:0.9, about 1:1.1, about 1:1.2, about 1:1.3, about 1:1.4, about 1:1.5, about 1:1.6, about 1:1.7, about 1:1.8, about 1:1.9, or about 1:2, such as about 2:1, about 1:1, or about 1:2. In some embodiments, the molar ratio of the Compound 1 or pharmaceutically acceptable solvate thereof to the conjugate acid is about 1:2. In some embodiments, the molar ratio of the Compound 1 or pharmaceutically acceptable solvate thereof to the conjugate acid is about 1:1. In some embodiments, the molar ratio of the Compound 1 or pharmaceutically acceptable solvate thereof to the conjugate acid is about 2:1.

In some embodiments, the pharmaceutically acceptable form of a compound disclosed herein is exclusive of a salt form (i.e., is not a salt), sometimes referred to as a free form or free base form, of a compound disclosed herein. In some embodiments, a free base form of a compound disclosed herein is a pharmaceutically acceptable solvate and/or isotopologue form of said compound. In some embodiments, a free base form of a compound disclosed herein is a pharmaceutically acceptable solvate form of said compound.

In some embodiments, the pharmaceutically acceptable form is a solvate (e.g., a hydrate). As used herein, the terms "solvate," "pharmaceutically acceptable solvate," or "pharmaceutically acceptable solvent," refer to a compound that further includes a stoichiometric or non-stoichiometric amount of solvent bound by non-covalent intermolecular forces. In some embodiments, the solvate is a crystalline form of a molecule, atom, and/or ions that further comprises molecules of a solvent or solvents incorporated into the crystalline lattice structure. The solvent molecules in the solvate may be present in a regular arrangement and/or a non-ordered arrangement. In some embodiments, the solvate may comprise either a stoichiometric or nonstoichiometric amount of the solvent molecules. For example, a solvate with a nonstoichiometric amount of solvent molecules may result from partial loss of solvent from the solvate. Solvates may occur as dimers or oligomers comprising more than one molecule or Compound ABC within the crystalline lattice structure. The solvate can be of a disclosed compound or a pharmaceutically acceptable salt thereof. Where the solvent is water, the solvate is a "hydrate." In some embodiments, the solvate is a hydrate. Pharmaceutically acceptable solvates and hydrates are complexes that, for example, can include 0.1, 0.25, 0.50, 0.75, or 1 solvent or water molecules, or can include 1 to about 100, or 1 to about 10, or one to about 2, about 3 or about 4, solvent or water molecules. In some embodiments, a pharmaceutically acceptable solvate of Compound 1, or a pharmaceutically acceptable salt and/or isotopologue form thereof, is or comprises Compound 1, or pharmaceutically acceptable salt and/or isotopologue form thereof, and a pharmaceutically acceptable solvent in a molar ratio in the range of about 2:1 to about 1:2. In some embodiments, the molar ratio of Compound 1 to the solvent ranges from about 2:1 to about 0.1:1. In some embodiments, the molar ratio of Compound 1 to the solvent ranges from about 2:1 to about 1:1. In some embodiments, the molar ratio of Compound 1 to the solvent ranges from about 0.1:1 to about 1:2. In some embodiments, the molar ratio of Compound 1 to the solvent ranges from about 1:1 to about 1:2. In some embodiments, the molar ratio of the Compound 1 to the solvent is about 2:1, about 1.9:1, about 1.8:1, about 1.7:1, about 1.6:1, about 1.5:1, about 1.4:1, about 1.3:1, about 1.2:1, about 1.1:1, about 1:1, about 0.9:1, about 0.8:1, about 0.7:1, about 0.6:1, about 0.5:1, about 1:0.5, about 1:0.6, about 1:0.7, about 1:0.8, about 1:0.9, about 1:1.1, about 1:1.2, about 1:1.3, about 1:1.4, about 1:1.5, about 1:1.6, about 1:1.7, about 1:1.8, about 1:1.9, or about 1:2, such as about 2:1, about 1:1, or about 1:2. In some embodiments, the molar ratio of the Compound 1 to the solvent is about 1:2 (i.e., bis-solvate). In some embodiments, the molar ratio of the Compound 1 to the solvent is about 1:1 (i.e., mono-solvate). In some embodiments, the molar ratio of the Compound 1 to the solvent is about 2:1 (i.e., hemi-solvate). In some embodiments, the pharmaceutically acceptable solvent (solvate) is or may comprise a hydrate, a hemi-hydrate, an iso-butyl acetate solvate, an iso-propyl acetate solvate, a tetrahydrofuran solvate, an acetone solvate, an acetonitrile solvate, or combinations thereof. For example, in some embodiments, the pharmaceutically acceptable solvate is water, and the molar ratio of the Compound 1 to the solvent is about 1:2 (also referred to as a hemi-hydrate). In some embodiments, the pharmaceutically acceptable solvate of Compound 1, or a pharmaceutically acceptable salt and/or isotopologue form thereof, is a solid form of the Compound 1.

In some embodiments, the term a "pharmaceutically acceptable salt or solvate" of compounds disclosed herein includes, but is not limited to, a pharmaceutically acceptable salt and/or solvate, of compounds disclosed herein, which includes combinations thereof (e.g., a solvate of a pharmaceutically acceptable salt), and further includes isotopologues thereof (i.e., isotopically labeled derivative) of the compound or of the solvate, salt, or solvate of salt of such compound.

In some embodiments, the pharmaceutically acceptable form of a compound disclosed herein is exclusive of a solvate form, sometimes referred to as a non-solvate, of a compound disclosed herein. For example, the pharmaceutically acceptable form of a compound disclosed herein may be exclusive of water, sometimes referred to as an anhydrate, of a compound disclosed herein. In some embodiments, a non-solvate form of a compound disclosed herein is a pharmaceutically acceptable salt and/or isotopologue form of said compound. In some embodiments, a non-solvate form of a compound disclosed herein is a pharmaceutically acceptable salt form of said compound. Unless otherwise specified, it is understood that a non-solvate form of a compound has a residual amount of solvate at about 5% or less, about 4% or less, about 3% or less, about 2% or less, about 1% or less, about 0.5% or less, or about 0.25% or less. For example, an anhydrate form of a compound has a residual amount of water at about 5% or less, about 4% or less, about 3% or less, about 2% or less, about 1% or less, about 0.5% or less, or about 0.25% or less.

In some embodiments, the pharmaceutically acceptable form is an isomer. "Isomers" are different compounds that have the same molecular formula. In some embodiments, the isomer may be a stereoisomer. In some embodiments, the isomer may be a tautomer. In some embodiments, the isomer may be a geometric isomer. "Stereoisomers" are isomers that differ only in the way the atoms are arranged in space. Stereoisomers include, for example, enantiomers, diastereomers, and atopisomers. Atropisomers are stereoisomers that arise because of hindered rotation about a single bond, where energy differences due to steric strain or other factors create a barrier to rotation sufficient to allow for identification and potentially isolation of individual conformers. As used herein, the term "isomer" includes any and all geometric isomers and stereoisomers. For example, "isomers" include geometric double bond cis- and trans-isomers, also termed E- and Z-isomers; atropisomers; R- and S-enantiomers; diastereomers, (d)-isomers and (l)-isomers, racemic mixtures thereof; and other mixtures thereof, as falling within the scope of this disclosure.

It is further understood that reference to a compound as disclosed herein having one or more stereocenters without designating the specific chirality (e.g., R- or S-enantiomer) will be understood to refer to the compound as racemic mixture (or a mixture of diastereomers), while inclusion of R- or S-designations will be understood to refer to an enantiomer (or a diastereomer) form of the compound, such as an enantiomerically (or diastereomerically) enriched form of the compound, or an enantiomeric excess of the specified enantiomer form of the compound, in accordance with discussion above regarding enantiomeric enriched and enantiomeric excess. Notation of a compound with an R- or S-designation is understood to include an enantiomerically enriched or an enantiomeric excess of the specified enantiomer of the compound, and not limited to only 100% of the single specified enantiomer of the compound.

It should be noted that if there is a discrepancy between a depicted structure and a name for that structure, the depicted structure is to be accorded more weight.

"Enantiomers" are a pair of stereoisomers that are non-superimposable mirror images of each other. A mixture of a pair of enantiomers in any proportion can be known as a "racemic" mixture. The term "(±)" or "(rac)" is used to designate a racemic mixture where appropriate. "Diastereoisomers" are stereoisomers that have at least two asymmetric atoms, but which are not mirror-images of each other. The absolute stereochemistry can be specified according to the Cahn-Ingold-Prelog R—S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures.

Stereoisomers, such as optically active (+) and (−), or optically active (R)- and(S)-isomers, can be asymmetrically synthesized or prepared, for example, using chiral synthons or chiral reagents, or resolved using techniques, such as chromatography on a chiral stationary phase. For example, the stereoisomers can be isolated from mixtures by methods known to those skilled in the art, including chiral high pressure liquid chromatography (HPLC) and the formation and crystallization of chiral salts; or preferred isomers can be prepared by asymmetric syntheses. See, e.g., Jacques, J., et al., (Wiley-Interscience, New York, 1981); Wilen, S. H., et al., *Tetrahedron* 33:2725(1977); Eliel, E. L., *Stereochemistry of Carbon Compounds* (McGraw-Hill, NY, 1962); Wilen, S. H., *Tables of Resolving Agents and Optical Resolutions* p. 268 (E. L. Eliel, Ed., Univ. of Notre Dame Press, Notre Dame, IN, 1972); Todd, M., *Separation Of Enantiomers: Synthetic Methods* (Wiley-VCH Verlag gmbH & Co. KGaA, Weinheim, Germany, 2014); Toda, F., *Enantiomer Separation: Fundamentals and Practical Methods* (Springer Science & Business Media, 2007); Subramanian, G. *Chiral Separation Techniques: A Practical Approach* (John Wiley & Sons, 2008); Ahuja, S., *Chiral Separation Methods for Pharmaceutical and Biotechnological Products* (John Wiley & Sons, 2011).

It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its(S) form.

In some embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a double bond, or a triple bond to a single bond, or vice versa). "Tautomerization" includes prototropic or proton-shift tautomerization, which is considered a subset of acid base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. The concentrations of the isomeric forms will depend on the environment the compound is found in and may be different depending upon, for example, whether the compound is a solid or is in an organic or aqueous solution. Exemplary tautomerizations include, but are not limited to, keto-enol; amide-imide; lactam-lactim; enamine-imine; and enamine-(a different) enamine tautomerizations. For example, in aqueous solution, pyrazoles may exhibit the following isomeric forms, which are referred to as tautomers of each other:

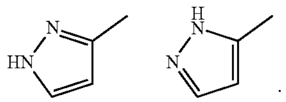

As readily understood by one skilled in the art, a wide variety of functional groups and other structures may exhibit tautomerism and all tautomers of a compound are within the scope of the compound as provided herein.

In some embodiments, the pharmaceutically acceptable form is an isotopologue. As used herein, the term "isotopologue" refers to isotopically-enriched compounds which are identical to those recited herein, but for the fact that one or more atoms are replaced by an atom having an atomic mass or mass number different from the atomic mass or mass number usually found in nature. Unless otherwise stated, structures depicted herein are also meant to include compounds which differ only in the presence of one or more isotopically enriched atoms. Examples of isotopes that can be incorporated into compounds described herein include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{32}P$, $^{33}P$, $^{33}S$, $^{34}S$, $^{35}S$, $^{36}S$, $^{18}F$, $^{35}Cl$, $^{36}Cl$, and $^{37}Cl$, respectively, each of which is also within the scope of this description. For example, compounds having the present structures except for the replacement or enrichment of a hydrogen by deuterium or tritium at one or more atoms in the molecule, are within the scope of this disclosure. In some embodiments, provided herein are isotopically labeled compounds having one or more hydrogen atoms replaced by or enriched by deuterium. In some embodiments, provided herein are isotopically labeled compounds having one or more hydrogen atoms replaced by or enriched by tritium. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. Isotopically-enriched compounds, such as Compound 1, or a pharmaceutically acceptable form thereof, including a solid form of Compound 1, or a pharmaceutically acceptable form thereof, can generally be prepared using procedures known to persons of ordinary skill in the art by substituting an appropriate isotopically-enriched reagent for a non-isotopically-enriched reagent. Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In some embodiments, provided herein are isotopically labeled compounds having one or more hydrogen atoms replaced by or enriched by deuterium. In some embodiments, provided herein are isotopically labeled compounds having 1-3 hydrogen atoms replaced by or enriched by deuterium. In some embodiments, provided herein are isotopically labeled compounds having one or more hydrogen atoms replaced by or enriched by tritium. In some embodiments, provided herein are isotopically labeled compounds having one or more carbon atoms replaced or enriched by $^{13}C$. In some embodiments, provided herein are isotopically labeled compounds having one or more carbon atoms replaced or enriched by $^{14}C$.

When the compounds are enriched with deuterium, the deuterium-to-hydrogen ratio on the deuterated atoms of the molecule substantially exceeds the naturally occurring deuterium-to-hydrogen ratio.

As used herein and unless otherwise specified, the terms "solid form" and related terms refer to a physical form which is not predominantly in a liquid or a gaseous state. As used herein, the terms "solid form" and "solid forms" encompass semi-solids. Solid forms may be crystalline, amorphous, partially crystalline, partially amorphous, or mixtures of forms.

The solid forms provided herein may have varying degrees of crystallinity or lattice order. The solid forms provided herein are not limited by any particular degree of crystallinity or lattice order, and may be 0-100% crystalline. Methods of determining the degree of crystallinity are known to those of ordinary skill in the, such as those described in Suryanarayanan, R., *X-Ray Power Diffractometry*, Physical Characterization of Pharmaceutical Salts, H. G. Brittain, Editor, Mercel Dekkter, Murray Hill, N.J., 1995, pp. 187-199, which is incorporated herein by reference in its entirety. In some embodiments, the solid forms provided herein are about 0, 5, 10, 15, 20, 25, 30, 35, 40, 45, 50, 55, 60, 65, 70, 75, 80, 85, 90, 95 or 100% crystalline, such as about 90%, about 95%, about 96%, about 97%, about 98%, about 98.5%, about 99%, or about 99.5%, crystalline, or greater.

As used herein and unless otherwise specified, the term "crystalline" and related terms used herein, when used to describe a substance, component, product, or form, mean that the substance, component, product, or form is substantially crystalline, for example, as determined by X-ray diffraction. See, e.g., *Remington: The Science and Practice of Pharmacy,* 21$^{st}$ edition, Lippincott, Williams and Wilkins, Baltimore, MD (2005); *The United States Pharmacopeia,* 23$^{rd}$ edition, 1843-1844(1995).

As used herein and unless otherwise specified, the term "crystal form," "crystal forms," and related terms herein refer to solid forms that are crystalline. Crystal forms include single-component crystal forms and multiple-component crystal forms, and include, but are not limited to, polymorphs, solvates, hydrates, and other molecular complexes, as well as salts, solvates of salts, hydrates of salts, co-crystals of salts, other molecular complexes of salts, and polymorphs thereof. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous form(s) and/or other crystal form(s) on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

A "single-component" solid form comprising a compound consists essentially of the compound. A "multiple-component" solid form comprising a compound comprises a significant quantity of one or more additional species, such as ions and/or molecules, within the solid form. For example, in certain embodiments, a crystalline multiple-component solid form comprising a compound further comprises one or more species non-covalently bonded at regular positions in the crystal lattice. For another example, in certain embodiments, an amorphous multiple-component solid form comprising a compound further comprises one or more polymer (s), and the compound is dispersed in a solid matrix that comprises the polymer(s).

Crystal forms of a substance may be obtained by a number of methods. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, and solvent-drop grinding.

Unless otherwise specified, the terms "polymorph." "polymorphic form," "polymorphs," "polymorphic forms," and related terms herein refer to two or more crystal forms that consist essentially of the same molecule, molecules or ions. Like different crystal forms, different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing (for example, one polymorph might be more likely to form solvates or might be difficult to filter and wash free of impurities, and particle shape and size distribution might be different between polymorphs).

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure. In certain embodiments, an amorphous form of a substance may comprise additional components or ingredients (for example, an additive, a polymer, or an excipient that may serve to further stabilize the amorphous form). In certain embodiments, amorphous form may be a solid solution.

Amorphous forms of a substance can be obtained by a number of methods. Such methods include, but are not limited to, heating, melt cooling, rapid melt cooling, solvent evaporation, rapid solvent evaporation, desolvation, sublimation, grinding, ball-milling, cryo-grinding, spray drying, and freeze drying.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder. In some embodiments, an XRPD pattern is obtained using Cu Kα radiation. In some embodiments, the peaks listed for an XRPD pattern have a relative intensity of greater than about 5%, greater than about 10%, greater than about 15%, or greater than about 20%. In some embodiments, the ramp rate (heating rate) for a DSC is about 10° C. per minute. In some embodiments, slow heating rate such as 0.5-2.0° C. per minute can be used for more accurate DSC testing. The sample pans used in a DSC testing include, e.g., aluminum, platinum, and stainless steel pans. The pans can have different configurations, e.g., open, pinhole, or hermetically-sealed pans. In some embodiments, the ramp rate for a TGA is about 10° C. per minute.

Unless otherwise specified, the terms "X-ray powder diffraction", "powder X-ray diffraction", "PXRD", and "XRPD" are used interchangeably in this application.

Solid forms may exhibit distinct physical characterization data that are unique to a particular solid form, such as the crystal forms provided herein. These characterization data may be obtained by various techniques known to those skilled in the art, including for example X-ray powder diffraction, differential scanning calorimetry, thermal gravimetric analysis, and nuclear magnetic resonance spectroscopy. The data provided by these techniques may be used to identify a particular solid form. One skilled in the art can determine whether a solid form is one of the forms provided herein by performing one of these characterization techniques and determining whether the resulting data "matches" or "substantially matches" the reference data provided herein, which is identified as being characteristic of a particular solid form. Characterization data that "matches" or "substantially matches" those of a reference solid form is understood by those skilled in the art to correspond to the same solid form as the reference solid form. In analyzing whether data "match" or "substantially match," a person of ordinary skill in the art understands that particular characterization data points may vary to a reasonable extent while still describing a given solid form, due to, for example, experimental error and routine sample-to-sample analysis variation. For example, an XRPD pattern, DSC thermogram or TGA thermal curve that "matches" or "substantially matches" with one or more figures herein showing an XRPD pattern or DSC thermogram or TGA thermal curve, respectively, is one that would be considered by one skilled in the art to represent the same single crystalline form of the compound as the sample of the compound that provided the pattern or thermogram or thermal curve of one or more figures provided herein. Thus, an XRPD pattern or DSC thermogram or TGA thermal curve that matches or is substantially in accordance may be identical to that of one of the figures or, more likely, may be somewhat different from one or more of the figures. For example, an XRPD pattern that is somewhat different from one or more of the figures may not necessarily show each of the lines of the diffraction pattern presented herein and/or may show a slight change in appearance or intensity of the lines or a shift in the position of the lines. These differences typically result from differences in the conditions involved in obtaining the data or differences in the purity of the sample used to obtain the data. A person skilled in the art is capable of determining if a sample of a crystalline compound is of the same form as or a different form from a form disclosed herein by comparison of the XRPD pattern or DSC thermogram or TGA thermal curve of the sample and the corresponding XRPD pattern or DSC thermogram or TGA thermal curve disclosed herein.

"Substantially pure," when used without further qualification, means the compound has a purity greater than about 90 weight percent, for example, greater than about 90, 91, 92, 93, 94, 95, 96, 97, 98, or 99 weight percent, and also including a purity equal to about 100 weight percent, based on the weight of the compound. The remaining material may comprise other form(s) of the compound and/or reaction impurities and/or processing impurities arising from its preparation. If the compound is "substantially pure" with respect to the presence of the other remaining materials, it can be referred to as "substantially physically pure". When qualified, "substantially pure" means that the indicated compound contains less than about 10%, less than about 5%, less than about 4%, less than about 3%, less than about 2%, less than about 1%, less than about 0.5%, or less than about 0.1% by weight of the indicated impurity. In some embodiments, the solid forms, e.g., crystal or amorphous forms, provided herein are substantially pure, i.e., substantially free of other solid forms and/or of other chemical compounds, containing less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds. For example, in some embodiments, the solid form of Compound 1 is substantially pure (e.g., having the purity of at least about 90 wt. %, at least about 95 wt. %, at least about 96 wt. %, at least about 97 wt. %, at least about 98 wt. %, or at least about 99 wt. %). Purity can be assessed using techniques known in the art, for example, using an HPLC assay.

"Substantially pure" can also be qualified. If the compound is "substantially pure" with respect to the presence of chemical impurities (e.g., reaction impurities and/or processing impurities arising from its preparation), it can be referred to as "substantially chemically pure." If the compound is "substantially pure" with respect to the presence of another stereoisomer, such as the other enantiomer, it can be referred to as "substantially stereoisomerically pure," such as "substantially enantiomerically pure," respectively. As used herein and unless otherwise indicated, the term stereoisomerically pure means one stereoisomer of a compound that is substantially free of other stereoisomers of that compound.

As used herein, and unless otherwise indicated, a chemical compound, solid form, or composition that is "substantially free" of another chemical compound, solid form, or composition means that the compound, solid form, or composition contains, in certain embodiments, less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

As used herein, and unless otherwise specified, a solid form that is "substantially physically pure" is substantially free from other solid forms. In certain embodiments, a crystal form that is substantially physically pure contains less than about 50%, 45%, 40%, 35%, 30%, 25%, 20%, 15%, 10% 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

As used herein, and unless otherwise specified, a solid form that is "substantially chemically pure" is substantially free from other chemical compounds (i.e., chemical impurities). In certain embodiments, a solid form that is substantially chemically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

For instance, an enantiomer can, in some embodiments, be provided substantially free of the corresponding enantiomer, and can also be referred to as "optically enriched," "enantiomerically enriched," "enantiomerically pure" and "non-racemic," as used interchangeably herein, in which the amount of one enantiomer is greater than the amount of that one enantiomer in a control mixture of the racemic composition (e.g., greater than 1:1 by weight). A typical enantiomerically pure compound comprises greater than about 80% by weight of one enantiomer of the compound and less than about 20% by weight of other enantiomer of the compound, greater than about 90% by weight of one enantiomer of the compound and less than about 10% by weight of the other enantiomer of the compound, greater than about 95% by weight of one enantiomer of the compound and less than about 5% by weight of the other enantiomer of the compound, or greater than about 97% by weight of one enantiomer of the compound and less than about 3% by weight of the other enantiomer of the compound.

For example, an enantiomerically enriched preparation of the S enantiomer, means a preparation of the compound having greater than about 50% by weight of the S enantiomer relative to the total weight of the preparation (e.g., total weight of S and R isomers), such as greater than about 60% by weight, greater than about 70% by weight, or greater than about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have greater than about 85% by weight of one enantiomer relative to the total weight of the preparation, such as greater than about 90%, greater than about 95%, greater than about 96%, greater than about 97%, greater than about 98%, greater than about 98.5%, greater than about 99%, greater than about 99.5% by weight. In some embodiments, the solid form of Compound 1 (i.e., (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile) is enantiomerically pure (i.e., substantially free of Compound 2 (i.e., (R)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile). In some embodiments, the solid form of Compound 1 is substantially enantiomerically pure with the other enantiomer (e.g., Compound 2, the R enantiomer) present less than about 10%, less than about 5%, less than about 4%, less than about 3%, less than about 2%, less than about 1%, less than about 0.5%, or less than about 0.1% by weight. In some embodiments, the solid form of Compound 1 is substantially enantiomerically pure (e.g., having the enantiomeric purity of at least about 98.0 wt. %, at least about 98.5 wt. %, at least about 99.0 wt. %, at least about 99.5 wt. %, or at least about 99.9 wt. %).

The use of stereoisomerically pure forms of such compounds, as well as the use of mixtures of those forms, are encompassed by the embodiments provided herein. For example, mixtures comprising equal or unequal amounts of the enantiomers of a particular compound may be used in methods and compositions provided herein.

The "enantiomeric excess" or "% enantiomeric excess" of composition, for example a composition comprising a mixture of enantiomers of a compound, can be calculated using the equation shown below. In the example shown below, a mixture containing 90% of one enantiomer, e.g., an S enantiomer, and 10% of the other enantiomer, e.g., an R enantiomer, is said to have an enantiomeric excess of 80%.

$$ee = (99 - 10)/100 = 80\%.$$

For example, in some embodiments, a compound described herein is a mixture of enantiomers of the compound (racemic) and contains an enantiomeric excess of greater than about 5%, about 10%, about 20%, about 30%, about 40%, about 50%, about 60%, about 70%, about 80%, about 90%, about 95%, about 96%, about 97%, about 98%, about 98.5%, about 99%, or about 99.5%, of one enantiomer relative to the other enantiomer, such as an excess of the S enantiomer relative to the R enantiomer. For example, a compound provided herein may have greater than about 95% ee, such as about 96% ee, about 97% ee, about 98% ee, about 98.5% ee, about 99% ee, or about 99.5% ee of a single enantiomer. In some embodiments, the mixture of enantiomers of the compound (racemic) has an enantiomeric excess of about 55% to about 99.5%, about 60% to about 99.5%, about 65% to about 99.5%, about 70% to about 99.5%, about 75% to about 99.5%, about 80% to about 99.5%, about 85% to about 99.5%, about 90% to about 99.5%, about 95% to about 99.5%, about 96% to about 99.5%, about 97% to about 99.5%, about 98% to about 99.5%, or about 99% to about 99.5%, or more than about 99.5%, of one enantiomer relative to the other enantiomer, such as an enantiomeric excess of the S enantiomer relative to the R enantiomer.

As used herein, the term "pharmaceutically acceptable excipient" is understood to mean a carrier, excipient, or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which a therapeutic agent is administered. Such pharmaceutical carriers can be sterile liquids, such as water and oils, including those of petroleum, animal, vegetable, or synthetic origin, such as peanut oil, soybean oil, mineral oil, sesame oil, and the like. Water is a specific carrier for intravenously administered pharmaceutical compositions. Saline solutions and aqueous dextrose and glycerol solutions can also be employed as liquid carriers, particularly for injectable solutions. For example, the term pharmaceutically acceptable carrier, excipient or diluent includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions. Typical compositions and dosage forms comprise one or more excipients. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. Examples of excipients that can be used in oral dosage forms provided herein include, but are not limited to, fillers, glidants, disintegrants, lubricants, or binders, or combinations thereof.

Definitions of specific functional groups and chemical terms are described in more detail below. The chemical elements are identified in accordance with the Periodic Table of the Elements, CAS version, *Handbook of Chemistry and Physics,* 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5th ed., John Wiley & Sons, Inc., New York, 2001; Larock, *Comprehensive Organic Transformations*, VCH Publishers, Inc., New York, 1989; and Carruthers, Some *Modern Methods of Organic Synthesis,* 3rd ed., Cambridge University Press, Cambridge, 1987.

"Protecting group" has the meaning conventionally associated with it in organic synthesis, e.g., a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, *Protective Groups in Organic Synthesis*, Fourth Edition, John Wiley & Sons, New York (2006), incorporated herein by reference in its entirety. For example, a hydroxy protected form is where at least one of the hydroxy groups present in a compound is protected with a hydroxy protecting group. Likewise, amines and other reactive groups can similarly be protected.

As used herein and unless otherwise indicated, the term "process(es)" provided herein refers to the methods provided herein which are useful for preparing a compound as described herein or a solid form thereof (e.g., a crystalline form, partially crystalline form, or an amorphous form) provided herein. Modifications to the methods provided herein (e.g., starting materials, reagents, protecting groups, solvents, temperatures, reaction times, purification) are also provided herein. In general, the technical teaching of one embodiment provided herein can be combined with that disclosed in any other embodiments provided herein.

As used herein, and unless otherwise indicated, the term "adding," "reacting," "treating," or the like, used in the context of a process, such as a reaction process or a crystallization process, means contacting one reactant, reagent, solvent, catalyst, reactive group or the like with another reactant, reagent, solvent, catalyst, reactive group, or the like. Reactants, reagents, solvents, catalysts, reactive group, or the like can be added individually, simultaneously, or separately and can be added in any order. Reactants, reagents, solvents, catalysts, reactive group, or the like can each respectively be added in one portion, which may be delivered all at once or over a period of time, or in discrete portions, which also may be delivered all at once or over a period of time. They can be added in the presence or absence of heat and can optionally be added under an inert atmosphere. "Reacting" can refer to in situ formation or intramolecular reaction where the reactive groups are in the same molecule.

As used herein, the term "combining" refers to bringing one or more chemical entities into association with another one or more chemical entities. Combining includes the processes of adding one or more compounds to a solid, liquid, or gaseous mixture of one or more compounds (the same or other chemical entities), or a liquid solution or multiphasic liquid mixture. The act of combining includes the process or processes of one or more compounds reacting (e.g., bond formation or cleavage; salt formation, solvate formation, chelation, or other non-bond altering association) with one or more compounds (the same or other chemical entities). The act of combining can include alteration of one or more compounds, such as by isomerization (e.g., tautomerization, resolution of one isomer from another, or racemization).

As used herein, and unless otherwise indicated, the term "transforming" refers to subjecting the compound at hand to reaction conditions suitable to effect the formation of the desired compound at hand.

As used herein, the term "recovering" includes, but is not limited to, the action of obtaining one or more compounds by collection during and/or after a process step as disclosed herein, and the action of obtaining one or more compounds by separation of one or more compounds from one or more other chemical entities during and/or after a process step as disclosed herein. The term "collection" refers to any action(s) known in the art for this purpose, including, but not limited to, filtration, decanting a mother liquor from a solid to obtain one or more compounds, and evaporation of liquid media in a solution or other mixture to afford a solid, oil, or other residue that includes one or more compounds. The solid can be crystalline, acrystalline, partially crystalline, or amorphous, a powder, granular, of varying particle sizes, of uniform particle size, among other characteristics known in the art. An oil can vary in color and viscosity, and include one or more solid forms as a heterogeneous mixture, among other characteristics known in the art. The term "separation" refers to any action(s) known in the art for this purpose, including, but not limited to, isolating one or more compounds from a solution or mixture using, for example, seeded or seedless crystallization or other precipitation techniques (e.g., adding an anti-solvent to a solution to induce compound precipitation; heating a solution, then cooling to induce compound precipitation; scratching the surface of a solution with an implement to induce compound precipitation), and distillation techniques. Recovering one or more compounds can involve preparation of a salt, solvate, hydrate, chelate or other complexes of the same, then collecting or separating as described above.

As used herein, the term "catalyst precursor" refers to a chemical composition wherein one or more components of an active catalyst (e.g., metal center and supporting ligand) are added to the reaction mixture such that formation of an active catalyst occurs in situ. Those skilled in the art will recognize that even when the metal source and supporting ligand are added to a reaction mixture in the form of a single chemical entity (e.g., $Pd(dppf)Cl_2$), further activation and/or reaction in situ may be required to produce an active catalyst. Notwithstanding, as used herein, the term "catalyst" includes, but is not limited to a chemical composition wherein more than one component of an active catalyst (e.g., metal center and supporting ligand) is added to a reaction mixture in the form of a single chemical entity (e.g., $Pd(dppf)Cl_2$), even if further activation and/or reaction in situ is required to produce an active catalyst.

As used herein, and unless otherwise specified, the terms "solvent," "organic solvent," or "inert solvent," used in the context of a process, such as a reaction process or a crystallization process, each mean a solvent inert under the conditions of the reaction being described. Unless specified to the contrary, for each gram of a limiting reagent, one cc (or mL) of solvent constitutes a volume equivalent (or "vol.").

As used herein, the term "precipitates selectively" refers to a precipitate that forms when a mixture of Compound 1 and Compound 2, such as Compound 19, is reacted with a chiral acid in a solvent to form a pair of diastereomeric salts, wherein the precipitate is enantiomerically enriched in one of Compound 1 or Compound 2, e.g., has an increased % ee relative to the starting mixture. As used herein, the term "selectively soluble" refers to the mother liquor that forms when a mixture of Compound 1 and Compound 2, such as Compound 19, is reacted with a chiral acid to form a pair of diastereomeric salts in a solvent, wherein the mother liquor is enantiomerically enriched in one of Compound 1 or Compound 2, e.g., has an increased % ee relative to the starting mixture.

As used herein, the term "HNSCC" refers to head and neck squamous cell carcinoma (HNSCC). Head and neck squamous cell carcinoma (HNSCC) is the seventh most common invasive carcinoma worldwide, with about 830,000 new diagnoses annually worldwide and 200,000 deaths per year worldwide, and about 54,000 new cases per year in the US. It is also the most common cancer in central Asia. HNSCC has 2 different etiologies and corresponding tumor types. The first subtype is associated with tobacco smoking and alcohol consumption, and unrelated to Human papillomavirus (HPV− or HPV negative). The second subtype is associated with infection with high-risk HPV (HPV+ or HPV positive). The second subtype is largely limited to oropharyngeal cancers. HPV+ tumors are distinct entity with better prognosis and may require differential treatments. Significant proportion of HNSCC, particularly oropharyngeal cancers, are caused by HPV infection. High-risk HPV subtype 16 accounts for 85% of all HPV+tumors in HNSCC. P16 can be used as surrogate marker of HPV infection in HNSCC, particularly in the oropharynx. More accurate HPV testing is available and based on E6/E7 detection (Liang C, et al. Cancer Res. 2012; 72:5004-5013).

The terms "HRAS mutation" or "H-Ras mutation" as used herein refer to an activation mutation in an HRAS gene or H-Ras protein. An H-Ras mutation can refer to either a genetic alteration in the DNA sequence of the HRAS gene that results in oncogenic activation of the corresponding H-Ras protein, or the alteration in the amino acid sequence of an H-Ras protein that results in its oncogenic activation. Thus, the terms "HRAS mutation" or "H-Ras mutation" as used herein do not refer to an alteration in a HRAS gene that does not result in the oncogenic activation of the H-Ras protein, or an alteration of an H-Ras protein sequence that does not lead to its oncogenic activation, although such mutations may also be present in a sample or subject. Accordingly, a sample or a subject that does not have any "H-Ras mutation" as used herein can still have a mutation in the HRAS gene that does not affect the activity of the H-Ras protein or a mutation that impairs the activity of the H-Ras protein, or have a mutation in an H-Ras protein that does not affect its activity or a mutation that impairs its activity. A sample or a subject can have multiple copies of the HRAS gene. A sample or a subject can also have both wild type and mutant H-Ras proteins. As used herein, a sample or a subject having an H-Ras mutation can also have a copy of wild type HRAS gene and/or the wild type H-Ras protein. A sample or a subject that is determined to "have wild type H-Ras," as used herein, refers to the sample or subject that only has the wild type HRAS gene and the wild type H-Ras protein, and no H-Ras mutation. In some embodiments, the mutant HRAS gene encodes a mutant H-Ras protein, wherein the HRAS gene mutation is or comprises a modification in a codon that encodes an amino acid substitution at a specific position selected from a group consisting of G12, G13, Q61, Q22, K117, A146, and any combination thereof, in the corresponding mutant H-Ras protein. In some embodiments, the HRAS gene mutation is a mutation at a codon that encodes an amino acid substitution at a position of G12 in the mutant H-Ras protein. In some embodiments, the HRAS gene mutation is at a codon that encodes a G12R substitution in the mutant H-Ras protein. The HRAS gene mutation can be a mutation at a codon that encodes a G12C, G12D, G12A, G12V, G12S, G12F, G12R, or G12N, substitution in the mutant H-Ras protein. In some embodiments, the HRAS gene mutation is a mutation at a codon that encodes a G12V substitution in the mutant H-Ras protein. In some embodiments, the HRAS gene mutation is a mutation at a codon that encodes an amino acid substitution at a position of G13 in the mutant H-Ras protein. The HRAS gene mutation can be a mutation at a codon that encodes a G13A, G13C, G13V, G13D, G13R, G13S, G13N, or G13V, substitution in the mutant H-Ras protein. In some embodiments, the HRAS gene mutation is a mutation at a codon that encodes a G13C substitution in the mutant H-Ras protein. In some embodiments, the HRAS gene mutation is a mutation at a codon that encodes a G13R substitution in the mutant H-Ras protein. In some embodiments, the HRAS gene mutation is a mutation at a codon that encodes an amino acid substitution at a position of Q61 in the mutant H-Ras protein. The HRAS gene mutation can be a mutation at a codon that encodes a Q61E, Q61K, Q61H, Q61L, Q61P, or Q61R, substitution in the mutant H-Ras protein. In some embodiments, the HRAS gene mutation is a mutation at a codon that encodes a Q61L substitution in the mutant H-Ras protein. In some embodiments, the HRAS gene mutation is a mutation at a codon that encodes a Q61R substitution in the mutant H-Ras protein. In some embodiments, the HRAS gene mutation is a mutation at a codon that encodes an amino acid substitution at a position of Q22 in the mutant H-Ras protein. In some embodiments, the HRAS gene mutation is a mutation at a codon that encodes a Q22K or Q22T substitution in the mutant H-Ras protein. In some embodiments, the HRAS gene mutation is a mutation at a codon that encodes an amino acid substitution at a position of K117 in the mutant H-Ras protein. In some embodiments, the HRAS gene mutation is a mutation at a codon that encodes a K117N or K117L substitution in the mutant H-Ras protein. In some embodiments, the HRAS gene mutation is a mutation at a codon that encodes an amino acid substitution at a position of A146 in the mutant H-Ras protein. The HRAS gene mutation can be a mutation at a codon that encodes an A146V, A146T, or A146P substitution in the mutant H-Ras protein. In some embodiments, the HRAS gene mutation is a mutation at a codon that encodes an A146P substitution in the mutant H-Ras protein. In some embodiments, the mutation can be a mutation at another codon that results in activation of H-Ras protein.

As used herein and unless otherwise indicated, the term "subject" to which administration is contemplated, can be an animal, including, but not limited to, a human (e.g., a male or female of any age group, such as an adult subject or an adolescent subject); primates (e.g., cynomolgus monkeys, rhesus monkeys), and/or other mammals, including commercially relevant mammals such as cattle, pigs, horses, sheep, goats, cats, dogs, rabbits, rodents, and/or birds (e.g., commercially relevant birds such as chickens, ducks, geese, quail, and/or turkeys). In some embodiments, the subject is a mammal. In some embodiments, the subject is a human. In some embodiments, the subject is an adolescent human. In some embodiments, the subject is an adult human. In some embodiments, the subject is a patient, for example, a human patient. In some embodiments, the subject can be a patient, for example, a patient having a cancer dependent on a farnesylated protein.

As used herein, the terms "prevention" and "preventing" are used herein to refer to an approach for obtaining beneficial or desired results including, but not limited, to prophylactic benefit. For prophylactic benefit, the compounds and pharmaceutical compositions disclosed herein can be administered to a patient at risk of developing a particular disease, or to a patient reporting one or more of the physiological symptoms of a disease or disorder, even though a diagnosis of this disease or disorder may not have been made.

A "therapeutic effect," as that term is used herein, encompasses a therapeutic benefit and/or a prophylactic benefit as described herein. A prophylactic effect includes delaying or eliminating the appearance of a disease or disorder, delaying, or eliminating the onset of symptoms of a disease or disorder, slowing, halting, or reversing the progression of a disease or disorder, or any combination thereof.

As used herein, the terms "treat," "treating," "treatment," and "ameliorating" are used interchangeably herein. These terms refer to an approach for obtaining beneficial or desired results including, but not limited to, therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disease or disorder. For example, when used in reference to a patient having cancer dependent on a farnesylated protein, refers to an action that reduces the severity of the cancer, or retards or slows the progression of the cancer, including (a) inhibiting the cancer growth, or arresting development of the cancer, and (b) causing regression of the cancer, or delaying or minimizing one or more symptoms associated with the presence of the cancer.

The disclosure can be understood more fully by reference to the following detailed description and illustrative examples, which are intended to exemplify non-limiting embodiments.

5.1 Compounds

In some embodiments, provided herein, is a Compound 1, which can be named (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile, and which has the structure:

Compound 1

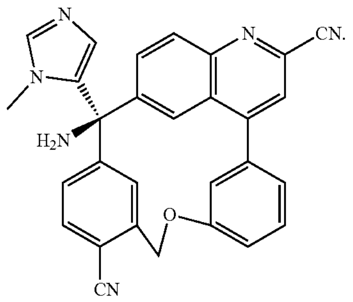

In some embodiments, provided herein, is a Compound 2, which can be named (R)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile, and which has the structure;

Compound 2

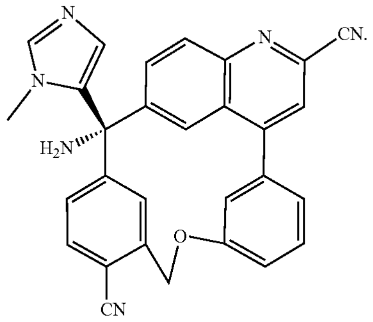

In some embodiments, provided herein, is a Compound 19, which can be named (3-amino-3-(1-methyl-1H-imidazol-5-yl)-6-oxa-2(4,6)-quinolina-1,4(1,3)-dibenzenacyclohexaphane-$2^2$,$4^4$-dicarbonitrile, and which has the structure:

Compound 19

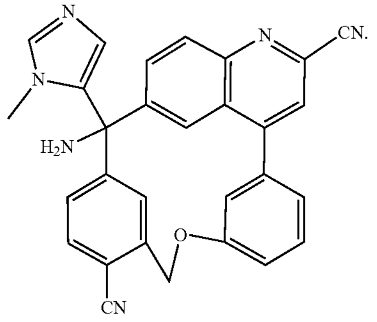

As used herein, Compound 19 depicts a racemic mixture of Compound 1 and Compound 2, but non-equal mixtures of Compound 1 and Compound 2 are also contemplated as described herein.

Compounds useful as described herein include the Compounds 1, 2, and 19, and pharmaceutically acceptable forms thereof, such as Compound 1, and pharmaceutically acceptable forms thereof.

As used herein, compounds disclosed herein include, but are not limited to, free base forms or pharmaceutically acceptable salts thereof, and solvates or hydrates thereof, and isotopologues of such compounds. In some embodiments are contemplated a free base or pharmaceutically acceptable salt of Compound 1, or a hydrate or solvate and/or isotopologue thereof. Throughout the instant application, disclosures involving Compound 1, Compound 2, Compound 19, or any intermediate compounds as disclosed herein in the synthesis of the same, are understood to also include isotopologues as provided herein of said compounds.

A synthesis and certain uses, inhibition activities, and metabolic stabilities, of the Compounds 1, 2, and 19, and pharmaceutically acceptable forms thereof, as provided herein, is described in International Patent Application No. PCT/US2022/80565, the entirety of which is incorporated herein by reference. Improved processes for preparing Compounds 1, 2, and 19, and pharmaceutically acceptable forms thereof, are provided herein. In some embodiments, the compound for use in the methods of treating or the methods of inhibiting provided herein is Compound 1, or a pharmaceutically acceptable form thereof. In some embodiments, the compound for use in the methods of treating or the methods of inhibiting provided herein is a pharmaceutically acceptable salt of Compound 1, or a pharmaceutically acceptable solvate and/or isotopologue thereof. In some embodiments, the compound or solid form for use in the methods of treating or the methods of inhibiting provided herein is a solid form of Compound 1, or a pharmaceutically acceptable form thereof. In some embodiments, the compound for use in the methods of treating or the methods of inhibiting provided herein is a crystalline solid form of Compound 1, or a pharmaceutically acceptable form thereof. Throughout the instant application, disclosures involving the use of the Compound 1, or pharmaceutically acceptable form thereof, such disclosures equally apply to the Compound 2, or pharmaceutically acceptable form thereof, or the Compound 19, or pharmaceutically acceptable form thereof.

In some embodiments, provided herein is a compound that is an intermediate compound as disclosed in the synthesis of Compound 1, or a pharmaceutically acceptable form thereof, as provided herein.

5.2 Solid Forms

Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42). A change in solid form may affect a variety of physical and chemical properties, which may provide benefits or drawbacks in processing, formulation, stability, and bioavailability, among other important pharmaceutical characteristics.

Whether crystalline or amorphous, potential solid forms of a pharmaceutical compound may include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette).

Additional diversity among the potential solid forms of a pharmaceutical compound may arise from the possibility of multiple-component solids. Crystalline solids comprising two or more ionic species are termed salts (see, e.g., *Handbook of Pharmaceutical Salts: Properties, Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (see, e.g., S. R. Byrn et al., *Solid State Chemistry of Drugs*, (1999) SSCI, West Lafayette). Multiple-component crystal forms may potentially be susceptible to polymorphism, wherein a given multiple-component composition may exist in more than one three-dimensional crystalline arrangement. The discovery of solid forms is of great importance in the development of a safe, effective, stable, and marketable pharmaceutical compound.

Notably, it is not possible to predict a priori if crystalline forms of a compound even exist, let alone whether such forms have properties suitable for pharmaceutical development (physical properties, stability, dissolution, purity, etc.) or how to successfully prepare them (see, e.g., Braga and Grepioni, 2005, "Making crystals from crystals: a green route to crystal engineering and polymorphism," *Chem. Commun.:* 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable and marketable pharmaceutical product.

The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, and/or a multiple-component crystal form comprising Compound 1 and a pharmaceutically acceptable excipient.

Solid form and related terms refer to a physical form which is not predominantly in a liquid or a gaseous state. Solid forms may be crystalline or mixtures of crystalline and amorphous forms. A "single-component" solid form comprising a particular compound consists essentially of that compound. A "multiple-component" solid form comprising a particular compound comprises that compound and a significant quantity of one or more additional species, such as ions and/or molecules, for example, solvent molecules, within the solid form. The solid forms provided herein may be crystalline or an intermediate form (e.g., a mixture of crystalline and amorphous forms). The crystal forms described herein, therefore, may have varying degrees of crystallinity or lattice order. The solid forms described herein are not limited to any particular degree of crystallinity or lattice order, and may be 0-100% crystalline. Methods of determining the degree of crystallinity are known to those of ordinary skill in the art, such as those described in Suryanarayanan, R., *X-Ray Powder Diffractometry*, Physical Characterization of Pharmaceutical Solids, H. G. Brittain, Editor, Marcel Dekker, Murray Hill, N.J., 1995, pp. 187-199, which is incorporated herein by reference in its entirety. In some embodiments, the solid forms described herein are about 0, 5, 10, 15, 20, 25, 30, 35, 40, 45, 50, 55, 60, 65, 70, 75, 80, 85, 90, 91, 92, 93, 94, 95, 96, 97, 98, 99, or 100% crystalline.

Solid forms may exhibit distinct physical characterization data that are unique to a particular solid form, such as the crystal forms described herein. These characterization data may be obtained by various techniques known to those skilled in the art, including for example, XRPD, DSC, TGA, and NMR spectroscopy. The data provided by these techniques may be used to identify a particular solid form. One skilled in the art can determine whether a solid form is one of the forms described herein by performing one of these characterization techniques and determining whether the resulting data is "substantially similar" to the reference data provided herein, which is identified as being characteristic of a particular solid form. Characterization data that is "substantially similar" to those of a reference solid form is understood by those skilled in the art to correspond to the same solid form as the reference solid form. In analyzing whether data is "substantially similar," a person of ordinary skill in the art understands that particular characterization data points may vary to a reasonable extent while still describing a given solid form, due to, for example, experimental error and routine sample-to-sample analysis.

In some embodiments, provided herein, are solid forms comprising Compound 1, or a pharmaceutically acceptable salt or solvate thereof:

Compound 1

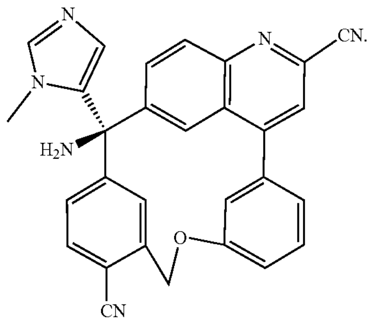

In some embodiments, the solid form comprising Compound 1 or pharmaceutically acceptable salt or solvate thereof can be a crystalline form, a substantially crystalline form, a partially crystalline form, or a mixture of crystalline form(s), or amorphous form(s). In some embodiments, the solid form is crystalline. In some embodiments, the solid form is an amorphous form. In some embodiments, the solid form is exclusive of an amorphous form. In some embodiments, the solid form is a pharmaceutically acceptable salt of the Compound 1, a pharmaceutically acceptable solvate of the Compound 1, or a pharmaceutically acceptable solvate of a pharmaceutically acceptable salt of the Compound 1. In some embodiments, the solid form comprises a free base of the Compound 1. In some embodiments, the solid form is a free base of the Compound 1. In some embodiments, the solid form is a pharmaceutically acceptable salt of the Compound 1. In some embodiments, the solid form is a pharmaceutically acceptable solvate of the Compound 1. In some embodiments, the solid form is a pharmaceutically acceptable solvate of a pharmaceutically acceptable salt of the Compound 1. In some embodiments, the solid form is a non-solvate of the Compound 1 or pharmaceutically acceptable salt thereof. In some embodiments, the solid form is an anhydrate of the Compound 1 or pharmaceutically acceptable salt thereof. In some embodiments, the solid form is a crystalline, free base, hemi-hydrate of the Compound 1. In some embodiments, the solid form is substantially pure. In some embodiments, the solid form is substantially chemically pure. In some embodiments, the solid form is substantially physically pure. In some embodiments, the solid form is substantially enantiomerically pure. In some embodiments, the solid form of Compound 1 or pharmaceutically acceptable salt and or solvate thereof has an enantiomeric purity of at least about 98% (e.g., about 98.5%, about 99%, or about 99.5%).

In some embodiments, the pharmaceutically acceptable solvate of the solid form is selected from the group consisting of: a hydrate, a hemi-hydrate, an iso-butyl acetate solvate, an iso-propyl acetate solvate, a tetrahydrofuran solvate, an acetone solvate, an acetonitrile solvate, or combinations thereof. In some embodiments, the pharmaceutically acceptable solvate of the solid form is a hydrate. In some embodiments, the solid form is a hydrate of the Compound 1 or pharmaceutically acceptable salt thereof. In some embodiments, the Compound 1 or pharmaceutically acceptable salt thereof and the pharmaceutically acceptable solvent in the solid form are present in a molar ratio in the range of 2:1 to 1:2. In some embodiments, the molar ratio of the Compound 1 or pharmaceutically acceptable salt thereof to the solvent in the solid form ranges from about 2:1 to about 1:1. In some embodiments, the molar ratio of the Compound 1 or pharmaceutically acceptable salt thereof to the solvent in the solid form ranges from about 1:1 to about 1:2. In some embodiments, the molar ratio of the Compound 1 or pharmaceutically acceptable salt thereof to the solvent in the solid form is about 1:2 (i.e., bis-solvate). In some embodiments, the molar ratio of the Compound 1 or pharmaceutically acceptable salt thereof to the solvent in the solid form is about 1:1 (i.e., mono-solvate). In some embodiments, the molar ratio of the Compound 1 or pharmaceutically acceptable salt thereof to the solvent in the solid form is about 2:1 (i.e., hemi-solvate). In some embodiments, the solvent is water, and the Compound 1 or pharmaceutically acceptable salt thereof and the water are present in the solid form in a molar ratio of about 2:1 (hemi-hydrate). In some embodiments, the solid form is a hemi-hydrate of the Compound 1 or pharmaceutically acceptable salt thereof.

In some embodiments, the pharmaceutically acceptable salt of the solid form is selected from the group consisting of: a benzoate salt, a besylate salt, a chloride salt, a citrate salt, a fumarate salt, a gentisate salt, a glycolate salt, a 1-hydroxy-2-naphthoate salt, a malate salt, a maleate salt, a mesylate salt, an oxalate salt, a phosphate salt, a tartrate salt, and a tosylate salt. In some embodiments, the pharmaceutically acceptable salt of the solid form is a benzoate salt. In some embodiments, the pharmaceutically acceptable salt of the solid form is a fumarate salt. In some embodiments, the pharmaceutically acceptable salt of the solid form is a 1-hydroxy-2-naphthoate salt. In some embodiments, the Compound 1 or pharmaceutically acceptable solvate thereof and the pharmaceutically acceptable salt (conjugate acid) in the solid form are present in a molar ratio in the range of 2:1 to 1:2. In some embodiments, the molar ratio of the Compound 1 or pharmaceutically acceptable solvate thereof to the conjugate acid in the solid form ranges from about 2:1 to about 1:1. In some embodiments, the molar ratio of the Compound 1 or pharmaceutically acceptable solvate thereof to the conjugate acid in the solid form ranges from about 1:1 to about 1:2. In some embodiments, the molar ratio of the Compound 1 or pharmaceutically acceptable solvate thereof to the conjugate acid in the solid form is about 1:1.

5.2.1 Form 1 of Compound 1

In some embodiments, provided herein is Form 1 of Compound 1. In some embodiments, Form 1 of Compound 1 is a crystalline free base, hemi-hydrate of Compound 1. In some embodiments, Form 1 of Compound 1 is substantially free of amorphous Compound 1. In some embodiments, Form 1 of Compound 1 is substantially free of other crystalline forms (i.e., polymorphs) of Compound 1. In some embodiments, Form 1 of Compound 1 is substantially free of salt forms of Compound 1. In some embodiments, Form 1 of Compound 1 is provided as substantially pure Form 1 of Compound 1.

A representative XRPD pattern of Form 1 of Compound 1 is provided in FIG. 3.

In some embodiments, Form 1 has an enantiomeric purity of about 98%, about 98.5%, about 99%, or about 99.5%, or greater. In some embodiments, Form 1 is crystalline. In some embodiments, Form 1 is substantially crystalline. In some embodiments, Form 1 is about 90%, about 95%, about 96%, about 97%, about 98%, about 98.5%, about 99%, or about 99.5%, crystalline, or greater.

In some embodiments, Form 1 has an X-ray powder diffraction (XRPD) pattern comprising peaks at approximately 9.0, 12.8, 16.6, and 18.4° 2θ. In some embodiments, the XRPD pattern further comprises peaks at approximately 8.6, 12.0, 18.1, and 23.2° 2θ. In some embodiments, the XRPD pattern further comprises peaks at approximately 16.1, 17.1, 24.1, and 25.6° 2θ. In some embodiments, the XRPD pattern comprises peaks at approximately 8.6, 9.0, 12.0, 12.8, 16.1, 16.6, 17.1, 18.1, 18.4, 23.2, 24.1, and 25.6° 2θ.

In some embodiments, provided herein is a solid form comprising a free base, hemi-hydrate of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 8.6, 9.0, 12.0, 12.8, 16.1, 16.6, 17.1, 18.1, 18.4, 23.2, 24.1, and 25.6° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by all of the peaks.

In some embodiments, Form 1 has an XRPD pattern that substantially matches the XRPD pattern presented in FIG. 3.

In some embodiments, Form 1 has approximately unit cell dimensions of: a=15.2 Å, b=7.9 Å, c=20.7 Å, α=90°, β=107.8°, and γ=90°. In some embodiments, Form 1 has a unit cell of a space group of $P2_1$. In some embodiments, Form 1 has a volume of about 2393.3 $Å^3$/cell. In some embodiments, Form 1 has a Z value of 2. In some embodiments, Form 1 has a density of about 1.325 $g/cm^3$.

A representative overlay of thermal gravimetric analysis (TGA) and differential scanning calorimetry (DSC) thermograms for Form 1 of Compound 1 is provided in FIG. 4.

In some embodiments, Form 1 exhibits a thermal (endothermic) event with an onset temperature of about 83° C. and a thermal (endothermic) event with an onset temperature of about 212° C., and/or an endothermic peak at about 137° C. and at about 221° C., as characterized by DSC with a temperature ramp of about 10° C./min. In some embodiments, Form 1 is characterized by a DSC thermogram substantially as shown in the DSC thermogram presented in FIG. 4.

In some embodiments, Form 1 exhibits no weight loss upon heating below about 75° C., as characterized by TGA. In some embodiments, Form 1 exhibits weight loss of about 1.8% upon heating from about 75° C. to about 170° C., as characterized by TGA. In some embodiments, Form 1 is characterized by a TGA thermogram substantially as shown in the TGA thermogram presented in FIG. 4.

In some embodiments, Form 1 has a purity of at least 98%, 98.5%, 99%, or 99.5%.

In some embodiments, Form 1 has a solubility of about 4.69, 5.04, and 3.67 mg/mL in SGF media, at 0.5 h, 2 h, and 24 h, respectively. In some embodiments, Form 1 has a solubility of about 0.29, 0.31, and 0.33 mg/mL in FeSSIF media, at 0.5 h, 2 h, and 24 h, respectively.

In some embodiments, Form 1 is prepared according to the procedures of Example 1.

All of the combinations of the above embodiments are encompassed by this application.

5.2.2 Form 2 of Compound 1

In some embodiments, provided herein is Form 2 of Compound 1. In some embodiments, Form 2 of Compound 1 is a crystalline benzoate salt of Compound 1. In some embodiments, Form 2 has a Compound 1/benzoic acid molar ratio of about 1:1. In some embodiments, Form 2 of Compound 1 is substantially free of amorphous Compound 1. In some embodiments, Form 2 of Compound 1 is substantially free of other crystalline forms (i.e., polymorphs) of Compound 1. In some embodiments, Form 2 of Compound 1 is provided as substantially pure Form 2 of Compound 1.

A representative XRPD pattern of Form 2 of Compound 1 is provided in FIG. 5.

In some embodiments, Form 2 has an enantiomeric purity of about 98%, about 98.5%, about 99%, or about 99.5%, or greater. In some embodiments, Form 2 is crystalline. In some embodiments, Form 2 is substantially crystalline. In some embodiments, Form 2 is partially crystalline. In some embodiments, Form 2 is about 90%, about 95%, about 96%, about 97%, about 98%, about 98.5%, about 99%, or about 99.5%, crystalline, or greater.

In some embodiments, Form 2 has an X-ray powder diffraction (XRPD) pattern comprising peaks at approximately 4.7, 17.0, and 19.4° 2θ. In some embodiments, the XRPD pattern further comprises peaks at approximately 12.7, 16.6, 17.8, 18.9, and 21.4° 2θ. In some embodiments, the XRPD pattern further comprises peaks at approximately 13.5, 13.7, 14.3, 23.0, 23.9, and 24.6° 2θ. In some embodiments, the XRPD pattern comprises peaks at approximately 4.7, 12.7, 13.5, 13.7, 14.3, 16.6, 17.0, 17.8, 18.9, 19.4, 21.4, 23.0, 23.9, and 24.6° 2θ.

In some embodiments, provided herein is a solid form comprising a benzoate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 4.7, 12.7, 13.5, 13.7, 14.3, 16.6, 17.0, 17.8, 18.9, 19.4, 21.4, 23.0, 23.9, and 24.6° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by at least 13 of the peaks. In some embodiments, the solid form is characterized by all of the peaks.

In some embodiments, Form 2 has an XRPD pattern that substantially matches the XRPD pattern presented in FIG. 5.

A representative overlay of thermal gravimetric analysis (TGA) and differential scanning calorimetry (DSC) thermograms for Form 2 of Compound 1 is provided in FIG. 6.

In some embodiments, Form 2 exhibits a thermal (endothermic) event with an onset temperature of about 209° C., and/or an endothermic peak at about 216° C., as characterized by DSC with a temperature ramp of about 10° C./min. In some embodiments, Form 2 is characterized by a DSC thermogram substantially as shown in the DSC thermogram presented in FIG. 6.

In some embodiments, Form 2 exhibits no weight loss upon heating below about 180° C., as characterized by TGA. In some embodiments, Form 2 is characterized by a TGA thermogram substantially as shown in the TGA thermogram presented in FIG. 6.

In some embodiments, Form 2 has (a) a purity of at least 98%, 98.5%, 99%, or 99.5%; (b) a solubility of about 4.17, 4.47, and 4.49 mg/mL in SGF media, at 0.5 h, 2 h, and 24 h, respectively; (c) a solubility of about 0.72, 0.68, and 0.54 mg/mL in FeSSIF media, at 0.5 h, 2 h, and 24 h, respectively; or (d) a combination of any of (a)-(c).

In some embodiments, Form 2 is prepared according to the procedures of Example 2.

All of the combinations of the above embodiments are encompassed by this application.

5.2.3 Form 3 of Compound 1

In some embodiments, provided herein is Form 3 of Compound 1. In some embodiments, Form 3 of Compound 1 is a crystalline besylate salt of Compound 1. In some embodiments, Form 3 has a Compound 1/benzenesulfonic acid molar ratio of about 1:0.9. In some embodiments, Form 3 of Compound 1 is substantially free of amorphous Compound 1. In some embodiments, Form 3 of Compound 1 is substantially free of other crystalline forms (i.e., polymorphs) of Compound 1. In some embodiments, Form 3 of Compound 1 is provided as substantially pure Form 3 of Compound 1.

A representative XRPD pattern of Form 3 of Compound 1 is provided in FIG. 7.

In some embodiments, Form 3 has an enantiomeric purity of about 98%, about 98.5%, about 99%, or about 99.5%, or greater. In some embodiments, Form 3 is crystalline. In some embodiments, Form 3 is substantially crystalline. In some embodiments, Form 3 is moderately crystalline. In some embodiments, Form 3 is partially crystalline. In some embodiments, Form 3 is about 90%, about 95%, about 96%, about 97%, about 98%, about 98.5%, about 99%, or about 99.5%, crystalline, or greater.

In some embodiments, Form 3 has an X-ray powder diffraction (XRPD) pattern comprising peaks at approximately 7.6, 8.9, and 14.3° 2θ. In some embodiments, the XRPD pattern further comprises peaks at approximately 17.9, and 19.7° 2θ. In some embodiments, the XRPD pattern further comprises peaks at approximately 21.0, and 24.8° 2θ. In some embodiments, the XRPD pattern comprises peaks at approximately 7.6, 8.9, 14.3, 17.9, 19.7, 21.0, and 24.8° 2θ.

In some embodiments, provided herein is a solid form comprising a besylate salt of Compound 1, characterized by 1, 2, 3, 4, 5, 6, or all of the XRPD peaks located at approximately the following positions (e.g., degrees 2θ±0.2) when measured using Cu Kα radiation: 7.6, 8.9, 14.3, 17.9, 19.7, 21.0, and 24.8° 2θ. In some embodiments, the solid form is characterized by at least 3 of the peaks. In some embodiments, the solid form is characterized by at least 5 of the peaks. In some embodiments, the solid form is characterized by all of the peaks.

In some embodiments, Form 3 has an XRPD pattern that substantially matches the XRPD pattern presented in FIG. 7.

A representative overlay of thermal gravimetric analysis (TGA) and differential scanning calorimetry (DSC) thermograms for Form 3 of Compound 1 is provided in FIG. 8.

In some embodiments, Form 3 exhibits a thermal (endothermic) event with an onset temperature of about 186° C. and/or an endothermic peak at about 206° C., as characterized by DSC with a temperature ramp of about 10° C./min. In some embodiments, Form 3 is characterized by a DSC thermogram substantially as shown in the DSC thermogram presented in FIG. 8.

In some embodiments, Form 3 exhibits a weight loss of about 5.7% upon heating across the range of about 95 to about 230° C., as characterized by TGA. In some embodiments, Form 3 is characterized by a TGA thermogram substantially as shown in the TGA thermogram presented in FIG. 8.

In some embodiments, Form 3 is prepared according to the procedures of Example 3.

All of the combinations of the above embodiments are encompassed by this application.

5.2.4 Form 4 of Compound 1

In some embodiments, provided herein is Form 4 of Compound 1. In some embodiments, Form 4 of Compound 1 is a crystalline hydrochloride salt of Compound 1. In some embodiments, Form 4 has a Compound 1/hydrochloric acid molar ratio of about 1:1, optionally wherein the solid form is a hydrate. In some embodiments, Form 4 of Compound 1 is substantially free of amorphous Compound 1. In some embodiments, Form 4 of Compound 1 is substantially free of other crystalline forms (i.e., polymorphs) of Compound 1. In some embodiments, Form 4 of Compound 1 is provided as substantially pure Form 4 of Compound 1.

A representative XRPD pattern of Form 4 of Compound 1 is provided in FIG. 9.

In some embodiments, Form 4 has an enantiomeric purity of about 98%, about 98.5%, about 99%, or about 99.5%, or greater. In some embodiments, Form 4 is crystalline. In some embodiments, Form 4 is substantially crystalline. In some embodiments, Form 4 is moderately crystalline. In some embodiments, Form 4 is partially crystalline. In some embodiments, Form 4 is about 90%, about 95%, about 96%, about 97%, about 98%, about 98.5%, about 99%, or about 99.5%, crystalline, or greater.

In some embodiments, Form 4 has an X-ray powder diffraction (XRPD) pattern comprising peaks at approximately 5.3, 16.7, 19.1, and 26.0° 2θ. In some embodiments, the XRPD pattern further comprises peaks at approximately 5.3, 16.7, 19.1, and 26.0° 2θ. In some embodiments, the XRPD pattern further comprises peaks at approximately 5.3, 16.7, 19.1, and 26.0° 2θ. In some embodiments, the XRPD pattern comprises peaks at approximately 5.3, 8.6, 11.2, 12.6, 15.3, 15.9, 16.7, 17.8, 19.1, 24.3, 26.0, and 28.2° 2θ.

In some embodiments, provided herein is a solid form comprising a hydrochloride salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 5.3, 8.6, 11.2, 12.6, 15.3, 15.9, 16.7, 17.8, 19.1, 24.3, 26.0, and 28.2° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by all of the peaks.

In some embodiments, Form 4 has an XRPD pattern that substantially matches the XRPD pattern presented in FIG. 9.

A representative overlay of thermal gravimetric analysis (TGA) and differential scanning calorimetry (DSC) thermograms for Form 4 of Compound 1 is provided in FIG. 10.

In some embodiments, Form 4 exhibits thermal (endothermic) events with onset temperatures of about 28° C., about 98° C., and about 242° C. and/or endothermic peak temperatures at about 64° C. and about 116° C., and at about 258° C. (two overlapping peaks), respectively, as characterized by DSC with a temperature ramp of about 10° C./min. In some embodiments, Form 4 is characterized by a DSC thermogram substantially as shown in the DSC thermogram presented in FIG. 10.

In some embodiments, Form 4 exhibits a weight loss of about 3.2% upon heating from rt to about 90° C. and a weight loss of about 2.7% upon heating from about 90 to 140° C., as characterized by TGA. In some embodiments, Form 4 is characterized by a TGA thermogram substantially as shown in the TGA thermogram presented in FIG. 10.

In some embodiments, Form 4 is prepared according to the procedures of Example 4.

All of the combinations of the above embodiments are encompassed by this application.

5.2.5 Form 5 of Compound 1

In some embodiments, provided herein is Form 5 of Compound 1. In some embodiments, Form 5 of Compound 1 is a crystalline hydrochloride salt of Compound 1. In some embodiments, Form 4 has a Compound 1/hydrochloric acid molar ratio of about 1:1, optionally wherein the solid form is a hydrate. In some embodiments, Form 5 of Compound 1 is substantially free of amorphous Compound 1. In some embodiments, Form 5 of Compound 1 is substantially free of other crystalline forms (i.e., polymorphs) of Compound 1. In some embodiments, Form 5 of Compound 1 is provided as substantially pure Form 5 of Compound 1.

A representative XRPD pattern of Form 5 of Compound 1 is provided in FIG. 11.

In some embodiments, Form 5 has an enantiomeric purity of about 98%, about 98.5%, about 99%, or about 99.5%, or greater. In some embodiments, Form 5 is crystalline. In some embodiments, Form 5 is substantially crystalline. In some embodiments, Form 5 is moderately crystalline. In some embodiments, Form 5 is partially crystalline. In some embodiments, Form 5 is about 90%, about 95%, about 96%, about 97%, about 98%, about 98.5%, about 99%, or about 99.5%, crystalline, or greater.

In some embodiments, Form 5 has an X-ray powder diffraction (XRPD) pattern comprising peaks at approximately 6.3, 8.4, 15.1, and 23.5° 2θ. In some embodiments, the XRPD pattern further comprises peaks at approximately 10.7 and 17.9° 2θ. In some embodiments, the XRPD pattern further comprises peaks at approximately 20.8, and 21.6° 2θ. In some embodiments, the XRPD pattern comprises peaks at approximately 6.3, 8.4, 10.7, 15.1, 17.9, 20.8, 21.6, and 23.5° 2θ.

In some embodiments, provided herein is a solid form comprising a hydrochloride salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 6.3, 8.4, 10.7, 15.1, 17.9, 20.8, 21.6, and 23.5° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by all of the peaks.

In some embodiments, Form 5 has an XRPD pattern that substantially matches the XRPD pattern presented in FIG. 11.

A representative overlay of thermal gravimetric analysis (TGA) and differential scanning calorimetry (DSC) thermograms for Form 5 of Compound 1 is provided in FIG. 12.

In some embodiments, Form 5 exhibits a thermal (endothermic) event with an onset temperature of about 244° C. and/or an endothermic peak temperature at about 247° C., as characterized by DSC with a temperature ramp of about 10° C./min. In some embodiments, Form 5 is characterized by a DSC thermogram substantially as shown in the DSC thermogram presented in FIG. 12.

In some embodiments, Form 5 exhibits a weight loss of about 5.3% prior to about 130° C. and a weight loss of about 12% over the range of about 175 to about 300° C., as characterized by TGA. In some embodiments, Form 5 is characterized by a TGA thermogram substantially as shown in the TGA thermogram presented in FIG. 12.

In some embodiments, Form 5 is prepared according to the procedures of Example 5.

All of the combinations of the above embodiments are encompassed by this application.

5.2.6 Form 6 of Compound 1

In some embodiments, provided herein is Form 6 of Compound 1. In some embodiments, Form 6 of Compound 1 is a crystalline citrate salt of Compound 1. In some embodiments, Form 6 has a Compound 1/citric acid molar ratio of about 1:0.8, optionally wherein the solid form is a solvate. In some embodiments, Form 6 of Compound 1 is substantially free of amorphous Compound 1. In some embodiments, Form 6 of Compound 1 is substantially free of other crystalline forms (i.e., polymorphs) of Compound 1. In some embodiments, Form 6 of Compound 1 is provided as substantially pure Form 6 of Compound 1.

A representative XRPD pattern of Form 6 of Compound 1 is provided in FIG. 13.

In some embodiments, Form 6 has an enantiomeric purity of about 98%, about 98.5%, about 99%, or about 99.5%, or greater. In some embodiments, Form 6 is crystalline. In some embodiments, Form 6 is substantially crystalline. In some embodiments, Form 6 is moderately crystalline. In some embodiments, Form 6 is partially crystalline. In some embodiments, Form 6 is about 90%, about 95%, about 96%, about 97%, about 98%, about 98.5%, about 99%, or about 99.5%, crystalline, or greater.

In some embodiments, Form 6 has an X-ray powder diffraction (XRPD) pattern comprising peaks at approximately 12.0, 16.6, and 18.1° 2θ. In some embodiments, the XRPD pattern further comprises peaks at approximately 12.9, 19.5, and 23.3° 2θ. In some embodiments, the XRPD pattern further comprises peaks at approximately 24.2, 25.6, and 26.1° 2θ. In some embodiments, the XRPD pattern comprises peaks at approximately 12.0, 12.9, 16.6, 18.1, 19.5, 23.3, 24.2, 25.6, and 26.1° 2θ.

In some embodiments, provided herein is a solid form comprising a citrate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 12.0, 12.9, 16.6, 18.1, 19.5, 23.3, 24.2, 25.6, and 26.1° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by all of the peaks.

In some embodiments, Form 6 has an XRPD pattern that substantially matches the XRPD pattern presented in FIG. 13.

A representative overlay of thermal gravimetric analysis (TGA) and differential scanning calorimetry (DSC) thermograms for Form 6 of Compound 1 is provided in FIG. 14.

In some embodiments, Form 6 exhibits exhibits thermal (endothermic) events with onset temperatures of about 92 and 144° C. and/or endothermic peak temperatures at about 102 and 177° C., respectively, as characterized by DSC with a temperature ramp of about 10° C./min. In some embodiments, Form 6 is characterized by a DSC thermogram substantially as shown in the DSC thermogram presented in FIG. 14.

In some embodiments, Form 6 exhibits a weight loss of about 5.1% upon heating from about 26 to about 150° C., as characterized by TGA. In some embodiments, Form 6 is characterized by a TGA thermogram substantially as shown in the TGA thermogram presented in FIG. 14.

In some embodiments, Form 6 is prepared according to the procedures of Example 6.

All of the combinations of the above embodiments are encompassed by this application.

5.2.7 Form 7 of Compound 1

In some embodiments, provided herein is Form 7 of Compound 1. In some embodiments, Form 7 of Compound 1 is a crystalline citrate salt of Compound 1. In some embodiments, Form 7 has a Compound 1/citric acid molar ratio of about 1:1, optionally wherein the solid form is a hydrate. In some embodiments, Form 7 of Compound 1 is substantially free of amorphous Compound 1. In some embodiments, Form 7 of Compound 1 is substantially free of other crystalline forms (i.e., polymorphs) of Compound 1. In some embodiments, Form 7 of Compound 1 is provided as substantially pure Form 7 of Compound 1.

A representative XRPD pattern of Form 7 of Compound 1 is provided in FIG. 15.

In some embodiments, Form 7 has an enantiomeric purity of about 98%, about 98.5%, about 99%, or about 99.5%, or greater. In some embodiments, Form 7 is crystalline. In some embodiments, Form 7 is substantially crystalline. In some embodiments, Form 7 is moderately crystalline. In some embodiments, Form 7 is partially crystalline. In some embodiments, Form 7 is about 90%, about 95%, about 96%, about 97%, about 98%, about 98.5%, about 99%, or about 99.5%, crystalline, or greater.

In some embodiments, Form 7 has an X-ray powder diffraction (XRPD) pattern comprising peaks at approximately 11.0, 15.0, 19.0, 22.1, 27.7, and 29.8° 2θ. In some embodiments, the XRPD pattern further comprises peaks at approximately 22.1, 24.2, 24.6, 25.2, 25.8, and 26.5° 2θ. In some embodiments, the XRPD pattern further comprises peaks at approximately 8.5, 8.8, 12.7, 13.3, 13.8, 16.7, 17.1, 17.5, and 17.9° 2θ. In some embodiments, the XRPD pattern comprises peaks at approximately 8.5, 8.8, 11.0, 12.7, 13.3, 13.8, 15.0, 16.7, 17.1, 17.5, 17.9, 19.0, 21.1, 22.1, 24.2, 24.6, 25.2, 25.8, 26.5, 27.7, and 29.8° 2θ.

In some embodiments, provided herein is a solid form comprising a citrate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 8.5, 8.8, 11.0, 12.7, 13.3, 13.8, 15.0, 16.7, 17.1, 17.5, 17.9, 19.0, 21.1, 22.1, 24.2, 24.6, 25.2, 25.8, 26.5, 27.7, and 29.8° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by at least 13 of the peaks. In some embodiments, the solid form is characterized by all of the peaks.

In some embodiments, Form 7 has an XRPD pattern that substantially matches the XRPD pattern presented in FIG. 15.

A representative overlay of thermal gravimetric analysis (TGA) and differential scanning calorimetry (DSC) thermograms for Form 7 of Compound 1 is provided in FIG. 16.

In some embodiments, Form 7 exhibits thermal (endothermic) events with onset temperatures of about 41, about 135, and about 169° C. and/or endothermic peak temperatures at about 58, about 139, and about 188° C., respectively, as characterized by DSC with a temperature ramp of about 10° C./min. In some embodiments, Form 7 is characterized by a DSC thermogram substantially as shown in the DSC thermogram presented in FIG. 16.

In some embodiments, Form 7 exhibits a weight loss of about 2.8% upon heating from about 25 to about 100° C., as characterized by TGA. In some embodiments, Form 7 is characterized by a TGA thermogram substantially as shown in the TGA thermogram presented in FIG. 16.

In some embodiments, Form 7 is prepared according to the procedures of Example 7.

All of the combinations of the above embodiments are encompassed by this application.

5.2.8 Form 8 of Compound 1

In some embodiments, provided herein is Form 8 of Compound 1. In some embodiments, Form 8 of Compound 1 is a crystalline fumarate salt of Compound 1. In some embodiments, Form 8 has a Compound 1/fumaric acid molar ratio of about 1:1, optionally wherein the solid form is a solvate, optionally wherein the solvate is a hydrate. In some embodiments, Form 8 of Compound 1 is substantially free of amorphous Compound 1. In some embodiments, Form 8 of Compound 1 is substantially free of other crystalline forms (i.e., polymorphs) of Compound 1. In some embodiments, Form 8 of Compound 1 is provided as substantially pure Form 8 of Compound 1.

A representative XRPD pattern of Form 8 of Compound 1 is provided in FIG. 17.

In some embodiments, Form 8 has an enantiomeric purity of about 98%, about 98.5%, about 99%, or about 99.5%, or greater. In some embodiments, Form 8 is crystalline. In some embodiments, Form 8 is substantially crystalline. In some embodiments, Form 8 is about 90%, about 95%, about 96%, about 97%, about 98%, about 98.5%, about 99%, or about 99.5%, crystalline, or greater.

In some embodiments, Form 8 has an X-ray powder diffraction (XRPD) pattern comprising peaks at approximately 8.6, 10.9, 16.7, and 23.3° 2θ. In some embodiments, the XRPD pattern further comprises peaks at approximately 4.9, 11.4, and 17.6° 2θ. In some embodiments, the XRPD pattern further comprises peaks at approximately 12.7, 14.6 and 26.0° 2θ. In some embodiments, the XRPD pattern comprises peaks at approximately 4.9, 8.6, 10.9, 11.4, 12.7, 14.6, 16.7, 17.6, 23.3, and 26.0° 2θ.

In some embodiments, provided herein is a solid form comprising a fumarate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 4.9, 8.6, 10.9, 11.4, 12.7, 14.6, 16.7, 17.6, 23.3, and 26.0° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by all of the peaks.

In some embodiments, Form 8 has an XRPD pattern that substantially matches the XRPD pattern presented in FIG. 17.

A representative overlay of thermal gravimetric analysis (TGA) and differential scanning calorimetry (DSC) thermograms for Form 8 of Compound 1 is provided in FIG. 18.

In some embodiments, Form 8 exhibits a thermal (endothermic) event with an onset temperature of about 28° C., and/or an endothermic peak at about 100° C., and a thermal (endothermic) event with an onset temperature of about 206° C. and/or a peak temperature of about 214° C., as characterized by DSC with a temperature ramp of about 10° C./min. In some embodiments, Form 8 is characterized by a DSC thermogram substantially as shown in the DSC thermogram presented in FIG. 18.

In some embodiments, Form 8 exhibits a weight loss of about 2.0% upon heating from about 24.5° C. to about 150° C., as characterized by TGA. In some embodiments, Form 8 is characterized by a TGA thermogram substantially as shown in the TGA thermogram presented in FIG. 18.

In some embodiments, Form 8 has a purity of at least 98%, 98.5%, 99%, or 99.5%.

In some embodiments, Form 8 has a solubility of about ≥5, ≥5, and ≥5 mg/mL in SGF media, at 0.5 h, 2 h, and 24 h, respectively. In some embodiments, Form 8 has a solubility of a solubility of about 1.27, 1.26, and 1.15 mg/mL in FeSSIF media, at 0.5 h, 2 h, and 24 h, respectively.

In some embodiments, Form 8 is prepared according to the procedures of Example 8.

All of the combinations of the above embodiments are encompassed by this application.

5.2.9 Form 9 of Compound 1

In some embodiments, provided herein is Form 9 of Compound 1. In some embodiments, Form 9 of Compound 1 is a crystalline gentisate salt of Compound 1. In some embodiments, Form 9 has a Compound 1/gentisic acid molar ratio of about 1:1, optionally wherein the solid form is a solvate. In some embodiments, Form 9 of Compound 1 is substantially free of amorphous Compound 1. In some embodiments, Form 9 of Compound 1 is substantially free of other crystalline forms (i.e., polymorphs) of Compound 1. In some embodiments, Form 9 of Compound 1 is provided as substantially pure Form 9 of Compound 1.

A representative XRPD pattern of Form 9 of Compound 1 is provided in FIG. 19.

In some embodiments, Form 9 has an enantiomeric purity of about 98%, about 98.5%, about 99%, or about 99.5%, or greater. In some embodiments, Form 9 is crystalline. In some embodiments, Form 9 is substantially crystalline. In some embodiments, Form 9 is partially crystalline. In some embodiments, Form 9 is about 90%, about 95%, about 96%, about 97%, about 98%, about 98.5%, about 99%, or about 99.5%, crystalline, or greater.

In some embodiments, Form 9 has an X-ray powder diffraction (XRPD) pattern comprising peaks at approximately 8.0, 9.6, 16.5, 17.6, 18.7, and 24.6° 2θ. In some embodiments, the XRPD pattern further comprises peaks at approximately 11.7, 12.2, 19.9, and 26.5° 2θ. In some embodiments, the XRPD pattern further comprises peaks at approximately 13.8, 15.4, 16.1, 20.8, and 21.7° 2θ. In some embodiments, the XRPD pattern comprises peaks at approximately 8.0, 9.6, 11.7, 12.2, 13.8, 15.4, 16.1, 16.5, 17.6, 18.7, 19.9, 20.8, 21.7, 24.6, and 26.5° 2θ.

In some embodiments, provided herein is a solid form comprising a gentisate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 8.0, 9.6, 11.7, 12.2, 13.8, 15.4, 16.1, 16.5, 17.6, 18.7, 19.9, 20.8, 21.7, 24.6, and 26.5° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by at least 13 of the peaks. In some embodiments, the solid form is characterized by all of the peaks.

In some embodiments, Form 9 has an XRPD pattern that substantially matches the XRPD pattern presented in FIG. 19.

A representative overlay of thermal gravimetric analysis (TGA) and differential scanning calorimetry (DSC) thermograms for Form 9 of Compound 1 is provided in FIG. 20.

In some embodiments, Form 9 exhibits thermal (endothermic) events with onset temperatures of about 56 and about 256° C. and/or endothermic peak temperatures at about 81 and about 263° C., respectively, as characterized by DSC with a temperature ramp of about 10° C./min. In some embodiments, Form 9 is characterized by a DSC thermogram substantially as shown in the DSC thermogram presented in FIG. 20.

In some embodiments, Form 9 exhibits a weight loss of about 2.2% upon heating from about 26.5 to about 100° C., as characterized by TGA. In some embodiments, Form 9 is characterized by a TGA thermogram substantially as shown in the TGA thermogram presented in FIG. 20.

In some embodiments, Form 9 is prepared according to the procedures of Example 9.

All of the combinations of the above embodiments are encompassed by this application.

5.2.10 Form 10 of Compound 1

In some embodiments, provided herein is Form 10 of Compound 1. In some embodiments, Form 10 of Compound 1 is a crystalline gentisate salt of Compound 1. In some embodiments, Form 10 has a Compound 1/gentisic acid molar ratio of about 1:1 and wherein the solid form is an anhydrate. In some embodiments, Form 10 of Compound 1 is substantially free of amorphous Compound 1. In some embodiments, Form 10 of Compound 1 is substantially free of other crystalline forms (i.e., polymorphs) of Compound 1. In some embodiments, Form 10 of Compound 1 is provided as substantially pure Form 10 of Compound 1.

A representative XRPD pattern of Form 10 of Compound 1 is provided in FIG. 21.

In some embodiments, Form 10 has an enantiomeric purity of about 98%, about 98.5%, about 99%, or about 99.5%, or greater. In some embodiments, Form 10 is crystalline. In some embodiments, Form 10 is substantially crystalline. In some embodiments, Form 10 is moderately crystalline. In some embodiments, Form 10 is partially crystalline. In some embodiments, Form 10 is about 90%, about 95%, about 96%, about 97%, about 98%, about 98.5%, about 99%, or about 99.5%, crystalline, or greater.

In some embodiments, Form 10 has an X-ray powder diffraction (XRPD) pattern comprising peaks at approximately 4.7, 13.2, and 16.9° 2θ. In some embodiments, the XRPD pattern further comprises peaks at approximately 8.39, 17.5, 18.6, 21.8, and 25.3° 2θ. In some embodiments, the XRPD pattern further comprises peaks at approximately 11.8, 12.6, 19.0, 19.4, and 23.8° 2θ. In some embodiments, the XRPD pattern comprises peaks at approximately 4.7, 8.39, 11.8, 12.6, 13.2, 16.9, 17.5, 18.6, 19.0, 19.4, 21.8, 23.8, and 25.3° 2θ.

In some embodiments, provided herein is a solid form comprising a gentisate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 4.7, 8.39, 11.8, 12.6, 13.2, 16.9, 17.5, 18.6, 19.0, 19.4, 21.8, 23.8, and 25.3° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by all of the peaks.

In some embodiments, Form 10 has an XRPD pattern that substantially matches the XRPD pattern presented in FIG. 21.

A representative overlay of thermal gravimetric analysis (TGA) and differential scanning calorimetry (DSC) thermograms for Form 10 of Compound 1 is provided in FIG. 22.

In some embodiments, Form 10 exhibits a thermal (endothermic) event with an onset temperature of about 240° C. and/or endothermic peak temperature at about 245° C., as characterized by DSC with a temperature ramp of about 10° C./min. In some embodiments, Form 10 is characterized by a DSC thermogram substantially as shown in the DSC thermogram presented in FIG. 22.

In some embodiments, Form 10 exhibits a weight loss of about 0.4% upon heating from about 120 to about 200° C., as characterized by TGA. In some embodiments, Form 10 is characterized by a TGA thermogram substantially as shown in the TGA thermogram presented in FIG. 22.

In some embodiments, Form 10 is prepared according to the procedures of Example 10.

All of the combinations of the above embodiments are encompassed by this application.

5.2.11 Form 11 of Compound 1

In some embodiments, provided herein is Form 11 of Compound 1. In some embodiments, Form 11 of Compound 1 is a crystalline glycolate salt of Compound 1. In some embodiments, Form 11 has a Compound 1/glycolic acid molar ratio of about 1:1, optionally wherein the solid form is a hydrate. In some embodiments, Form 11 of Compound 1 is substantially free of amorphous Compound 1. In some embodiments, Form 11 of Compound 1 is substantially free of other crystalline forms (i.e., polymorphs) of Compound 1. In some embodiments, Form 11 of Compound 1 is provided as substantially pure Form 11 of Compound 1.

A representative XRPD pattern of Form 11 of Compound 1 is provided in FIG. 23.

In some embodiments, Form 11 has an enantiomeric purity of about 98%, about 98.5%, about 99%, or about 99.5%, or greater. In some embodiments, Form 11 is crystalline. In some embodiments, Form 11 is substantially crystalline. In some embodiments, Form 11 is moderately crystalline. In some embodiments, Form 11 is partially crystalline. In some embodiments, Form 11 is about 90%, about 95%, about 96%, about 97%, about 98%, about 98.5%, about 99%, or about 99.5%, crystalline, or greater.

In some embodiments, Form 11 has an X-ray powder diffraction (XRPD) pattern comprising peaks at approximately 7.4, 12.6, 16.7, and 23.8° 2θ. In some embodiments, the XRPD pattern further comprises peaks at approximately 16.2, 23.4, 25.7, and 28.9° 2θ. In some embodiments, the XRPD pattern further comprises peaks at approximately 19.0, 20.3, and 26.1° 2θ. In some embodiments, the XRPD pattern comprises peaks at approximately 7.4, 12.6, 16.2, 16.7, 19.0, 20.3, 23.4, 23.8, 25.7, 26.1, and 28.9° 2θ.

In some embodiments, provided herein is a solid form comprising a glycolate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 7.4, 12.6, 16.2, 16.7, 19.0, 20.3, 23.4, 23.8, 25.7, 26.1, and 28.9° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by all of the peaks.

In some embodiments, Form 11 has an XRPD pattern that substantially matches the XRPD pattern presented in FIG. 23.

A representative overlay of thermal gravimetric analysis (TGA) and differential scanning calorimetry (DSC) thermograms for Form 11 of Compound 1 is provided in FIG. 24.

In some embodiments, Form 11 exhibits thermal (endothermic) events with onset temperatures of about 35, about 116, and about 152° C. and/or endothermic peak temperatures at about 59, about 94, and about 170° C., respectively, as characterized by DSC with a temperature ramp of about 10° C./min. In some embodiments, Form 11 is characterized by a DSC thermogram substantially as shown in the DSC thermogram presented in FIG. 24.

In some embodiments, Form 11 exhibits a weight loss of about 1.7% upon heating from about 27° C. to about 80° C. and a weight loss of about 3.2% upon heating from about 110 to about 200° C., as characterized by TGA. In some embodiments, Form 11 is characterized by a TGA thermogram substantially as shown in the TGA thermogram presented in FIG. 24.

In some embodiments, Form 11 is prepared according to the procedures of Example 11.

All of the combinations of the above embodiments are encompassed by this application.

5.2.12 Form 12 of Compound 1

In some embodiments, provided herein is Form 12 of Compound 1. In some embodiments, Form 12 of Compound 1 is a crystalline 1-hydroxy-2-naphthoate salt of Compound 1. In some embodiments, Form 12 has a Compound 1/1-hydroxy-2-naphthoic acid molar ratio of about 1:1, optionally wherein the solid form is a solvate. In some embodiments, Form 12 of Compound 1 is substantially free of amorphous Compound 1. In some embodiments, Form 12 of Compound 1 is substantially free of other crystalline forms (i.e., polymorphs) of Compound 1. In some embodiments, Form 12 of Compound 1 is provided as substantially pure Form 12 of Compound 1.

A representative XRPD pattern of Form 12 of Compound 1 is provided in FIG. 25.

In some embodiments, Form 12 has an enantiomeric purity of about 98%, about 98.5%, about 99%, or about 99.5%, or greater. In some embodiments, Form 12 is crystalline. In some embodiments, Form 12 is substantially crystalline. In some embodiments, Form 12 is moderately crystalline. In some embodiments, Form 12 is partially crystalline. In some embodiments, Form 12 is about 90%, about 95%, about 96%, about 97%, about 98%, about 98.5%, about 99%, or about 99.5%, crystalline, or greater.

In some embodiments, Form 12 has an X-ray powder diffraction (XRPD) pattern comprising peaks at approximately 6.2, 11.2, 14.4, and 22.3° 2θ. In some embodiments, the XRPD pattern further comprises peaks at approximately 5.1, 14.9, and 18.3° 2θ. In some embodiments, the XRPD pattern further comprises peaks at approximately 5.6 and 25.3° 2θ. In some embodiments, the XRPD pattern comprises peaks at approximately 5.1, 5.6, 6.2, 11.2, 14.4, 14.9, 18.3, 22.3, and 25.3° 2θ.

In some embodiments, provided herein is a solid form comprising a 1-hydroxy-2-naphthoate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 5.1, 5.6, 6.2, 11.2, 14.4, 14.9, 18.3, 22.3, and 25.3° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 8 of the peaks. In some embodiments, the solid form is characterized by all of the peaks.

In some embodiments, Form 12 has an XRPD pattern that substantially matches the XRPD pattern presented in FIG. 25.

A representative overlay of thermal gravimetric analysis (TGA) and differential scanning calorimetry (DSC) thermograms for Form 12 of Compound 1 is provided in FIG. 26.

In some embodiments, Form 12 exhibits thermal (endothermic) events with onset temperatures of about 25 and about 178° C. and/or endothermic peak temperatures at about 32 and about 186° C., respectively, as characterized by DSC with a temperature ramp of about 10° C./min. In some embodiments, Form 12 is characterized by a DSC thermogram substantially as shown in the DSC thermogram presented in FIG. 26.

In some embodiments, Form 12 exhibits a weight loss of about 0.5% upon heating from about 25° C. to about 80° C. and a weight loss of about 7.4% upon heating from about 100 to about 190° C., as characterized by TGA. In some embodiments, Form 12 is characterized by a TGA thermogram substantially as shown in the TGA thermogram presented in FIG. 26.

In some embodiments, Form 12 is prepared according to the procedures of Example 12.

All of the combinations of the above embodiments are encompassed by this application.

5.2.13 Form 13 of Compound 1

In some embodiments, provided herein is Form 13 of Compound 1. In some embodiments, Form 13 of Compound 1 is a crystalline 1-hydroxy-2-naphthoate salt of Compound 1. In some embodiments, Form 13 has a Compound 1/1-hydroxy-2-naphthoic acid molar ratio of about 1:1, wherein the solid form is an anhydrate. In some embodiments, Form 13 of Compound 1 is substantially free of amorphous Compound 1. In some embodiments, Form 13 of Compound 1 is substantially free of other crystalline forms (i.e., polymorphs) of Compound 1. In some embodiments, Form 13 of Compound 1 is provided as substantially pure Form 13 of Compound 1.

A representative XRPD pattern of Form 13 of Compound 1 is provided in FIG. 27.

In some embodiments, Form 13 has an enantiomeric purity of about 98%, about 98.5%, about 99%, or about 99.5%, or greater. In some embodiments, Form 13 is crystalline. In some embodiments, Form 13 is substantially crystalline. In some embodiments, Form 13 is about 90%, about 95%, about 96%, about 97%, about 98%, about 98.5%, about 99%, or about 99.5%, crystalline, or greater.

In some embodiments, Form 13 has an X-ray powder diffraction (XRPD) pattern comprising peaks at approximately 16.6, 18.1, 19.1, and 24.7° 2θ. In some embodiments, the XRPD pattern further comprises peaks at approximately 8.9, 12.5, 14.7, 19.7, 21.6, and 29.7° 2θ. In some embodiments, the XRPD pattern further comprises peaks at approximately 11.8, 12.0, 15.4, 23.3, 25.8, and 27.9° 2θ. In some embodiments, the XRPD pattern comprises peaks at approximately 8.9, 11.8, 12.0, 12.5, 14.7, 15.4, 16.6, 18.1, 19.1, 19.7, 21.6, 23.3, 24.7, 25.8, 27.9, and 29.7° 2θ.

In some embodiments, provided herein is a solid form comprising a 1-hydroxy-2-naphthoate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 8.9, 11.8, 12.0, 12.5, 14.7, 15.4, 16.6, 18.1, 19.1, 19.7, 21.6, 23.3, 24.7, 25.8, 27.9, and 29.7° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by at least 13 of the peaks. In some embodiments, the solid form is characterized by at least 15 of the peaks. In some embodiments, the solid form is characterized by all of the peaks.

In some embodiments, Form 13 has an XRPD pattern that substantially matches the XRPD pattern presented in FIG. 27.

A representative overlay of thermal gravimetric analysis (TGA) and differential scanning calorimetry (DSC) thermograms for Form 13 of Compound 1 is provided in FIG. 28.

In some embodiments, Form 13 exhibits a thermal (endothermic, melting/decomposition) event with an onset temperature of about 187° C., and/or an endothermic peak at about 194° C., as characterized by DSC with a temperature ramp of about 10° C./min. In some embodiments, Form 13 is characterized by a DSC thermogram substantially as shown in the DSC thermogram presented in FIG. 28.

In some embodiments, Form 13 exhibits exhibits no weight loss upon below about 160° C., as characterized by TGA. In some embodiments, Form 13 is characterized by a TGA thermogram substantially as shown in the TGA thermogram presented in FIG. 28.

In some embodiments, Form 13 has a purity of at least 98%, 98.5%, 99%, or 99.5%.

In some embodiments, Form 13 has a solubility of about 3.86, 4.05, and 4.12 in SGF media, at 0.5 h, 2 h, and 24 h, respectively. In some embodiments, Form 13 has a solubility of about 0.74, 0.82, and 0.78 mg/mL in FeSSIF media, at 0.5 h, 2 h, and 24 h, respectively.

In some embodiments, Form 13 is prepared according to the procedures of Example 13.

All of the combinations of the above embodiments are encompassed by this application.

5.2.14 Form 14 of Compound 1

In some embodiments, provided herein is Form 14 of Compound 1. In some embodiments, Form 14 of Compound 1 is a crystalline malate salt of Compound 1. In some embodiments, Form 14 has a Compound 1/malic acid molar ratio of about 1:1, optionally wherein the solid form is a hydrate. In some embodiments, Form 14 of Compound 1 is substantially free of amorphous Compound 1. In some embodiments, Form 14 of Compound 1 is substantially free of other crystalline forms (i.e., polymorphs) of Compound 1. In some embodiments, Form 14 of Compound 1 is provided as substantially pure Form 14 of Compound 1.

A representative XRPD pattern of Form 14 of Compound 1 is provided in FIG. 29.

In some embodiments, Form 14 has an enantiomeric purity of about 98%, about 98.5%, about 99%, or about 99.5%, or greater. In some embodiments, Form 14 is crystalline. In some embodiments, Form 14 is substantially crystalline. In some embodiments, Form 14 is about 90%, about 95%, about 96%, about 97%, about 98%, about 98.5%, about 99%, or about 99.5%, crystalline, or greater.

In some embodiments, Form 14 has an X-ray powder diffraction (XRPD) pattern comprising peaks at approximately 4.7, 16.9, 17.3, 20.8, and 22.7° 2θ. In some embodiments, the XRPD pattern further comprises peaks at approximately 8.3, 12.5, 13.0, 14.5, 16.3, 19.1, 23.5, 24.6, 25.5, and 28.2° 2θ. In some embodiments, the XRPD pattern further comprises peaks at approximately 10.9, 14.1, 18.4, 24.9, 26.1, 26.7, and 27.1° 2θ. In some embodiments, the XRPD pattern comprises peaks at approximately 4.7, 8.3, 10.9, 12.5, 13.0, 14.1, 14.5, 16.3, 16.9, 17.3, 18.4, 19.1, 20.8, 22.7, 23.5, 24.6, 24.9, 25.5, 26.1, 26.7, 27.1, and 28.2° 2θ.

In some embodiments, provided herein is a solid form comprising a malate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 4.7, 8.3, 10.9, 12.5, 13.0, 14.1, 14.5, 16.3, 16.9, 17.3, 18.4, 19.1, 20.8, 22.7, 23.5, 24.6, 24.9, 25.5, 26.1, 26.7, 27.1, and 28.2° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by at least 13 of the peaks. In some embodiments, the solid form is characterized by at least 15 of the peaks. In some embodiments, the solid form is characterized by at least 17 of the peaks. In some embodiments, the solid form is characterized by at least 19 of the peaks. In some embodiments, the solid form is characterized by all of the peaks.

In some embodiments, Form 14 has an XRPD pattern that substantially matches the XRPD pattern presented in FIG. 29.

A representative overlay of thermal gravimetric analysis (TGA) and differential scanning calorimetry (DSC) thermograms for Form 14 of Compound 1 is provided in FIG. 30.

In some embodiments, Form 14 exhibits thermal (endothermic) events with onset temperatures of about 28 and about 178° C. and/or endothermic peak temperatures at about 69 and about 216° C., respectively, as characterized by DSC with a temperature ramp of about 10° C./min. In some embodiments, Form 14 is characterized by a DSC thermogram substantially as shown in the DSC thermogram presented in FIG. 3.

In some embodiments, Form 14 exhibits a weight loss of about 3.6% upon heating from about 30° C. to about 120° C., as characterized by TGA. In some embodiments, Form 14 is characterized by a TGA thermogram substantially as shown in the TGA thermogram presented in FIG. 30.

In some embodiments, Form 14 is prepared according to the procedures of Example 14.

All of the combinations of the above embodiments are encompassed by this application.

5.2.15 Form 15 of Compound 1

In some embodiments, provided herein is Form 15 of Compound 1. In some embodiments, Form 15 of Compound 1 is a crystalline malate salt of Compound 1. In some embodiments, Form 15 has a Compound 1/malic acid molar ratio of about 1:1 and wherein the solid form is a solvate. In some embodiments, Form 15 of Compound 1 is substantially free of amorphous Compound 1. In some embodiments, Form 15 of Compound 1 is substantially free of other crystalline forms (i.e., polymorphs) of Compound 1. In some embodiments, Form 15 of Compound 1 is provided as substantially pure Form 15 of Compound 1.

A representative XRPD pattern of Form 15 of Compound 1 is provided in FIG. 31.

In some embodiments, Form 15 has an enantiomeric purity of about 98%, about 98.5%, about 99%, or about 99.5%, or greater. In some embodiments, Form 15 is crystalline. In some embodiments, Form 15 is substantially crystalline. In some embodiments, Form 15 is moderately crystalline. In some embodiments, Form 15 is about 90%, about 95%, about 96%, about 97%, about 98%, about 98.5%, about 99%, or about 99.5%, crystalline, or greater.

In some embodiments, Form 15 has an X-ray powder diffraction (XRPD) pattern comprising peaks at approximately 11.1, 12.5, 16.6, and 17.8° 2θ. In some embodiments, the XRPD pattern further comprises peaks at approximately 8.39, 22.0, 23.3, and 25.5° 2θ. In some embodiments, the XRPD pattern further comprises peaks at approximately 13.9, 14.7, and 24.1° 2θ. In some embodiments, the XRPD pattern comprises peaks at approximately 8.39, 11.1, 12.5, 13.9, 14.7, 16.6, 17.8, 22.0, 23.3, 24.1, and 25.5° 2θ.

In some embodiments, provided herein is a solid form comprising a malate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 8.39, 11.1, 12.5, 13.9, 14.7, 16.6, 17.8, 22.0, 23.3, 24.1, and 25.5° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by all of the peaks.

In some embodiments, Form 15 has an XRPD pattern that substantially matches the XRPD pattern presented in FIG. 31.

A representative overlay of thermal gravimetric analysis (TGA) and differential scanning calorimetry (DSC) thermograms for Form 15 of Compound 1 is provided in FIG. 32.

In some embodiments, Form 15 exhibits thermal (endothermic) events with onset temperatures of about 127 and about 159° C. and/or endothermic peak temperatures at about 145 and about 182° C., respectively, as characterized by DSC with a temperature ramp of about 10° C./min. In some embodiments, Form 15 is characterized by a DSC thermogram substantially as shown in the DSC thermogram presented in FIG. 32.

In some embodiments, Form 15 exhibits a weight loss of about 3.1% upon heating from about 90° C. to about 160° C., and a weight loss of about 3.6% upon heating from about 160 to about 190° C., as characterized by TGA. In some embodiments, Form 15 is characterized by a TGA thermogram substantially as shown in the TGA thermogram presented in FIG. 32.

In some embodiments, Form 15 is prepared according to the procedures of Example 15.

All of the combinations of the above embodiments are encompassed by this application.

5.2.16 Form 16 of Compound 1

In some embodiments, provided herein is Form 16 of Compound 1. In some embodiments, Form 16 of Compound 1 is a crystalline maleate salt of Compound 1. In some embodiments, Form 16 has a Compound 1/maleic acid molar ratio of about 1:1, optionally wherein the solid form is a hydrate. In some embodiments, Form 16 of Compound 1 is substantially free of amorphous Compound 1. In some embodiments, Form 16 of Compound 1 is substantially free of other crystalline forms (i.e., polymorphs) of Compound 1.

In some embodiments, Form 16 of Compound 1 is provided as substantially pure Form 16 of Compound 1.

A representative XRPD pattern of Form 16 of Compound 1 is provided in FIG. 33.

In some embodiments, Form 16 has an enantiomeric purity of about 98%, about 98.5%, about 99%, or about 99.5%, or greater. In some embodiments, Form 16 is crystalline. In some embodiments, Form 16 is substantially crystalline. In some embodiments, Form 16 is moderately crystalline. In some embodiments, Form 16 is about 90%, about 95%, about 96%, about 97%, about 98%, about 98.5%, about 99%, or about 99.5%, crystalline, or greater.

In some embodiments, Form 16 has an X-ray powder diffraction (XRPD) pattern comprising peaks at approximately 12.2, 12.6, 26.1, and 29.2° 2θ. In some embodiments, the XRPD pattern further comprises peaks at approximately 4.8, 16.7, 24.7, and 25.2° 2θ. In some embodiments, the XRPD pattern further comprises peaks at approximately 14.5, 17.3, and 24.3° 2θ. In some embodiments, the XRPD pattern comprises peaks at approximately 4.8, 12.2, 12.6, 14.5, 16.7, 17.3, 24.3, 24.7, 25.2, 26.1, and 29.2° 2θ.

In some embodiments, provided herein is a solid form comprising a maleate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 4.8, 12.2, 12.6, 14.5, 16.7, 17.3, 24.3, 24.7, 25.2, 26.1, and 29.2° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by all of the peaks.

In some embodiments, Form 16 has an XRPD pattern that substantially matches the XRPD pattern presented in FIG. 33.

A representative overlay of thermal gravimetric analysis (TGA) and differential scanning calorimetry (DSC) thermograms for Form 16 of Compound 1 is provided in FIG. 34.

In some embodiments, Form 16 exhibits thermal (endothermic) events with onset temperatures of about 26 and about 198° C. and/or endothermic peak temperatures at about 53 and about 206° C., respectively, as characterized by DSC with a temperature ramp of about 10° C./min. In some embodiments, Form 16 is characterized by a DSC thermogram substantially as shown in the DSC thermogram presented in FIG. 34.

In some embodiments, Form 16 exhibits a weight loss of about 1.8% upon heating from about 24° C. to about 100° C., as characterized by TGA. In some embodiments, Form 16 is characterized by a TGA thermogram substantially as shown in the TGA thermogram presented in FIG. 34.

In some embodiments, Form 16 is prepared according to the procedures of Example 16.

All of the combinations of the above embodiments are encompassed by this application.

0.2.17 Form 17 of Compound 1

In some embodiments, provided herein is Form 17 of Compound 1. In some embodiments, Form 17 of Compound 1 is a crystalline maleate salt of Compound 1. In some embodiments, Form 17 has a Compound 1/maleic acid molar ratio of about 1:1, optionally wherein the solid form is a hydrate. In some embodiments, Form 17 of Compound 1 is substantially free of amorphous Compound 1. In some embodiments, Form 17 of Compound 1 is substantially free of other crystalline forms (i.e., polymorphs) of Compound 1.

In some embodiments, Form 17 of Compound 1 is provided as substantially pure Form 17 of Compound 1.

A representative XRPD pattern of Form 17 of Compound 1 is provided in FIG. 35.

In some embodiments, Form 17 has an enantiomeric purity of about 98%, about 98.5%, about 99%, or about 99.5%, or greater. In some embodiments, Form 17 is crystalline. In some embodiments, Form 17 is substantially crystalline. In some embodiments, Form 17 is moderately crystalline. In some embodiments, Form 17 is about 90%, about 95%, about 96%, about 97%, about 98%, about 98.5%, about 99%, or about 99.5%, crystalline, or greater.

In some embodiments, Form 17 has an X-ray powder diffraction (XRPD) pattern comprising peaks at approximately 9.5, 15.2, and 18.6° 2θ. In some embodiments, the XRPD pattern further comprises peaks at approximately 4.8, 8.2, 16.6, 17.3, 20.9, 27.0, and 29.1° 2θ. In some embodiments, the XRPD pattern further comprises peaks at approximately 12.8, 14.4, 24.0, 25.2, and 25.7° 2θ. In some embodiments, the XRPD pattern comprises peaks at approximately 4.8, 8.2, 9.5, 12.8, 14.4, 15.2, 16.6, 17.3, 18.6, 20.9, 24.0, 25.2, 25.7, 27.0, and 29.1° 2θ.

In some embodiments, provided herein is a solid form comprising a maleate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 4.8, 8.2, 9.5, 12.8, 14.4, 15.2, 16.6, 17.3, 18.6, 20.9, 24.0, 25.2, 25.7, 27.0, and 29.1° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by at least 13 of the peaks. In some embodiments, the solid form is characterized by all of the peaks.

In some embodiments, Form 17 has an XRPD pattern that substantially matches the XRPD pattern presented in FIG. 35.

A representative overlay of thermal gravimetric analysis (TGA) and differential scanning calorimetry (DSC) thermograms for Form 17 of Compound 1 is provided in FIG. 36.

In some embodiments, Form 17 exhibits thermal (endothermic) events with onset temperatures of about 27 and about 195° C. and/or endothermic peak temperatures at about 60 and about 205° C., respectively, as characterized by DSC with a temperature ramp of about 10° C./min. In some embodiments, Form 17 is characterized by a DSC thermogram substantially as shown in the DSC thermogram presented in FIG. 36.

In some embodiments, Form 17 exhibits a weight loss of about 1.2% upon heating from about 26° C. to about 100° C., as characterized by TGA. In some embodiments, Form 17 is characterized by a TGA thermogram substantially as shown in the TGA thermogram presented in FIG. 36.

In some embodiments, Form 17 is prepared according to the procedures of Example 17.

All of the combinations of the above embodiments are encompassed by this application.

5.2.18 Form 18 of Compound 1

In some embodiments, provided herein is Form 18 of Compound 1. In some embodiments, Form 18 of Compound 1 is a crystalline mesylate salt of Compound 1. In some embodiments, Form 18 has a Compound 1/methanesulfonic acid molar ratio of about 1:0.8, optionally wherein the solid form is a solvate. In some embodiments, Form 18 of Compound 1 is substantially free of amorphous Compound 1. In some embodiments, Form 18 of Compound 1 is substantially free of other crystalline forms (i.e., polymorphs) of Compound 1. In some embodiments, Form 18 of Compound 1 is provided as substantially pure Form 18 of Compound 1.

A representative XRPD pattern of Form 18 of Compound 1 is provided in FIG. 37.

In some embodiments, Form 18 has an enantiomeric purity of about 98%, about 98.5%, about 99%, or about 99.5%, or greater. In some embodiments, Form 18 is crystalline. In some embodiments, Form 18 is substantially crystalline. In some embodiments, Form 18 is moderately crystalline. In some embodiments, Form 18 is partially crystalline. In some embodiments, Form 18 is about 90%, about 95%, about 96%, about 97%, about 98%, about 98.5%, about 99%, or about 99.5%, crystalline, or greater.

In some embodiments, Form 18 has an X-ray powder diffraction (XRPD) pattern comprising peaks at approximately 9.0, 9.2, 18.6, and 19.2° 2θ. In some embodiments, the XRPD pattern further comprises peaks at approximately 17.5, 18.1, and 23.1° 2θ. In some embodiments, the XRPD pattern further comprises peaks at approximately 20.4, 21.0, and 21.2° 2θ. In some embodiments, the XRPD pattern comprises peaks at approximately 9.0, 9.2, 17.5, 18.1, 18.6, 19.2, 20.4, 21.0, 21.2, and 23.1° 2θ.

In some embodiments, provided herein is a solid form comprising a mesylate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 9.0, 9.2, 17.5, 18.1, 18.6, 19.2, 20.4, 21.0, 21.2, and 23.1° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by all of the peaks.

In some embodiments, Form 18 has an XRPD pattern that substantially matches the XRPD pattern presented in FIG. 37.

A representative overlay of thermal gravimetric analysis (TGA) and differential scanning calorimetry (DSC) thermograms for Form 18 of Compound 1 is provided in FIG. 38.

In some embodiments, Form 18 exhibits a thermal (endothermic) event with an onset temperature of about 142° C. and/or an endothermic peak temperature at about 146° C., as characterized by DSC with a temperature ramp of about 10° C./min. In some embodiments, Form 18 is characterized by a DSC thermogram substantially as shown in the DSC thermogram presented in FIG. 38.

In some embodiments, Form 18 exhibits a weight loss of about 5.6% upon heating from about rt to about 145° C. and a weight loss of about 9.5% upon heating from about 145 to about 200° C., as characterized by TGA. In some embodiments, Form 18 is characterized by a TGA thermogram substantially as shown in the TGA thermogram presented in FIG. 38.

In some embodiments, Form 18 is prepared according to the procedures of Example 18.

All of the combinations of the above embodiments are encompassed by this application.

5.2.19 Form 19 of Compound 1

In some embodiments, provided herein is Form 19 of Compound 1. In some embodiments, Form 19 of Compound 1 is a crystalline oxalate salt of Compound 1. In some embodiments, Form 19 has a Compound 1/oxalic acid molar ratio of about 1:1, optionally wherein the solid form is a solvate. In some embodiments, Form 19 of Compound 1 is substantially free of amorphous Compound 1. In some embodiments, Form 19 of Compound 1 is substantially free of other crystalline forms (i.e., polymorphs) of Compound 1. In some embodiments, Form 19 of Compound 1 is provided as substantially pure Form 19 of Compound 1.

A representative XRPD pattern of Form 19 of Compound 1 is provided in FIG. 39.

In some embodiments, Form 19 has an enantiomeric purity of about 98%, about 98.5%, about 99%, or about 99.5%, or greater. In some embodiments, Form 19 is crystalline. In some embodiments, Form 19 is substantially crystalline. In some embodiments, Form 19 is moderately crystalline. In some embodiments, Form 19 is about 90%, about 95%, about 96%, about 97%, about 98%, about 98.5%, about 99%, or about 99.5%, crystalline, or greater.

In some embodiments, Form 19 has an X-ray powder diffraction (XRPD) pattern comprising peaks at approximately 4.7, 13.2, 19.8, and 25.0° 2θ. In some embodiments, the XRPD pattern further comprises peaks at approximately 8.5, 11.4, 14.2, 15.7, and 17.1° 2θ. In some embodiments, the XRPD pattern further comprises peaks at approximately 8.8, 9.7, 20.5, and 25.9° 2θ. In some embodiments, the XRPD pattern comprises peaks at approximately 4.7, 8.5, 8.8, 9.7, 11.4, 13.2, 14.2, 15.7, 17.1, 19.8, 20.5, 25.0, and 25.9° 2θ.

In some embodiments, provided herein is a solid form comprising a oxalate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 4.7, 8.5, 8.8, 9.7, 11.4, 13.2, 14.2, 15.7, 17.1, 19.8, 20.5, 25.0, and 25.9° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by all of the peaks.

In some embodiments, Form 19 has an XRPD pattern that substantially matches the XRPD pattern presented in FIG. 3.

A representative overlay of thermal gravimetric analysis (TGA) and differential scanning calorimetry (DSC) thermograms for Form 19 of Compound 1 is provided in FIG. 40.

In some embodiments, Form 19 exhibits thermal (endothermic) events with onset temperatures of about 92, about 137, and about 194° C. and/or endothermic peak temperatures at about 137, about 190, and about 194° C., respectively, as characterized by DSC with a temperature ramp of about 10° C./min. In some embodiments, Form 19 is characterized by a DSC thermogram substantially as shown in the DSC thermogram presented in FIG. 40.

In some embodiments, Form 19 exhibits a weight loss of about 7.4% upon heating from about 90 to about 190° C. and a weight loss of about 19.0% upon heating from about 190 to about 240° C., as characterized by TGA. In some embodiments, Form 19 is characterized by a TGA thermogram substantially as shown in the TGA thermogram presented in FIG. 40.

In some embodiments, Form 19 is prepared according to the procedures of Example 19.

All of the combinations of the above embodiments are encompassed by this application.

5.2.20 Form 20 of Compound 1

In some embodiments, provided herein is Form 20 of Compound 1. In some embodiments, Form 20 of Compound 1 is a crystalline phosphate salt of Compound 1. In some embodiments, Form 20 is a monophosphate of the Compound 1, optionally wherein the solid form is a hydrate. In some embodiments, Form 20 of Compound 1 is substantially free of amorphous Compound 1. In some embodiments, Form 20 of Compound 1 is substantially free of other crystalline forms (i.e., polymorphs) of Compound 1. In some embodiments, Form 20 of Compound 1 is provided as substantially pure Form 20 of Compound 1.

A representative XRPD pattern of Form 20 of Compound 1 is provided in FIG. 41.

In some embodiments, Form 20 has an enantiomeric purity of about 98%, about 98.5%, about 99%, or about 99.5%, or greater. In some embodiments, Form 20 is crystalline. In some embodiments, Form 20 is substantially crystalline. In some embodiments, Form 20 is moderately crystalline. In some embodiments, Form 20 is about 90%, about 95%, about 96%, about 97%, about 98%, about 98.5%, about 99%, or about 99.5%, crystalline, or greater.

In some embodiments, Form 20 has an X-ray powder diffraction (XRPD) pattern comprising peaks at approximately 9.4, 15.1, 16.6, and 18.2° 2θ. In some embodiments, the XRPD pattern further comprises peaks at approximately 8.5, 10.6, 12.3, 14.1, 17.5, 20.1, 22.5, and 23.6° 2θ. In some embodiments, the XRPD pattern further comprises peaks at approximately 11.1, 12.8, 22.0, 24.4, 25.3, 26.9, and 31.7° 2θ. In some embodiments, the XRPD pattern comprises peaks at approximately 8.5, 9.4, 10.6, 11.1, 12.3, 12.8, 14.1, 15.1, 16.6, 17.5, 18.2, 20.1, 22.0, 22.5, 23.6, 24.4, 25.3, 26.9, and 31.7° 2θ.

In some embodiments, provided herein is a solid form comprising a phosphate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 8.5, 9.4, 10.6, 11.1, 12.3, 12.8, 14.1, 15.1, 16.6, 17.5, 18.2, 20.1, 22.0, 22.5, 23.6, 24.4, 25.3, 26.9, and 31.7° 20. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by at least 13 of the peaks. In some embodiments, the solid form is characterized by at least 15 of the peaks. In some embodiments, the solid form is characterized by at least 17 of the peaks. In some embodiments, the solid form is characterized by all of the peaks.

In some embodiments, Form 20 has an XRPD pattern that substantially matches the XRPD pattern presented in FIG. 41.

A representative overlay of thermal gravimetric analysis (TGA) and differential scanning calorimetry (DSC) thermograms for Form 20 of Compound 1 is provided in FIG. 42.

In some embodiments, Form 20 exhibits a thermal (endothermic) event with onset temperature of about 34° C. and/or an endothermic peak temperature at about 74° C., as characterized by DSC with a temperature ramp of about 10° C./min. In some embodiments, Form 20 is characterized by a DSC thermogram substantially as shown in the DSC thermogram presented in FIG. 42.

In some embodiments, Form 20 exhibits a weight loss of about 4.5% upon heating from about 25 to about 110° C., as characterized by TGA. In some embodiments, Form 20 is characterized by a TGA thermogram substantially as shown in the TGA thermogram presented in FIG. 42.

In some embodiments, Form 20 is prepared according to the procedures of Example 20.

All of the combinations of the above embodiments are encompassed by this application.

5.2.21 Form 21 of Compound 1

In some embodiments, provided herein is Form 21 of Compound 1. In some embodiments, Form 21 of Compound 1 is a crystalline tartrate salt of Compound 1. In some embodiments, Form 21 has a Compound 1/tartaric acid molar ratio about of 1:1, optionally wherein the solid form is a hydrate. In some embodiments, Form 21 of Compound 1 is substantially free of amorphous Compound 1. In some embodiments, Form 21 of Compound 1 is substantially free of other crystalline forms (i.e., polymorphs) of Compound 1. In some embodiments, Form 21 of Compound 1 is provided as substantially pure Form 21 of Compound 1.

A representative XRPD pattern of Form 21 of Compound 1 is provided in FIG. 43.

In some embodiments, Form 21 has an enantiomeric purity of about 98%, about 98.5%, about 99%, or about 99.5%, or greater. In some embodiments, Form 21 is crystalline. In some embodiments, Form 21 is substantially crystalline. In some embodiments, Form 21 is moderately crystalline. In some embodiments, Form 21 is about 90%, about 95%, about 96%, about 97%, about 98%, about 98.5%, about 99%, or about 99.5%, crystalline, or greater.

In some embodiments, Form 21 has an X-ray powder diffraction (XRPD) pattern comprising peaks at approximately 13.2, 16.9, 17.2, 17.7, 18.4, and 25.3° 2θ. In some embodiments, the XRPD pattern further comprises peaks at approximately 8.3, 12.3, 20.9, and 24.0° 2θ. In some embodiments, the XRPD pattern further comprises peaks at approximately 14.5, 19.9, and 22.4° 2θ. In some embodiments, the XRPD pattern comprises peaks at approximately 8.3, 12.3, 13.2, 14.5, 16.9, 17.2, 17.7, 18.4, 19.9, 20.9, 22.4, 24.0, and 25.3° 2θ.

In some embodiments, provided herein is a solid form comprising a tartrate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 8.3, 12.3, 13.2, 14.5, 16.9, 17.2, 17.7, 18.4, 19.9, 20.9, 22.4, 24.0, and 25.3° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by all of the peaks.

In some embodiments, Form 21 has an XRPD pattern that substantially matches the XRPD pattern presented in FIG. 43.

A representative overlay of thermal gravimetric analysis (TGA) and differential scanning calorimetry (DSC) thermograms for Form 21 of Compound 1 is provided in FIG. 44.

In some embodiments, Form 21 exhibits thermal (endothermic) events with onset temperatures of about 29 and about 201° C. and/or endothermic peak temperatures at about 70 and about 204° C., as characterized by DSC with a temperature ramp of about 10° C./min. In some embodiments, Form 21 is characterized by a DSC thermogram substantially as shown in the DSC thermogram presented in FIG. 44.

In some embodiments, Form 21 exhibits a weight loss of about 6.8% upon heating from about 30 to about 140° C., as characterized by TGA. In some embodiments, Form 21 is characterized by a TGA thermogram substantially as shown in the TGA thermogram presented in FIG. 44.

In some embodiments, Form 21 is prepared according to the procedures of Example 21.

All of the combinations of the above embodiments are encompassed by this application.

5.2.22 Form 22 of Compound 1

In some embodiments, provided herein is Form 22 of Compound 1. In some embodiments, Form 22 of Compound 1 is a crystalline tartrate salt of Compound 1. In some embodiments, Form 22 has a Compound 1/tartaric acid molar ratio about of 1:1 and, optionally wherein the solid form is a solvate. In some embodiments, Form 22 of Compound 1 is substantially free of amorphous Compound 1. In some embodiments, Form 22 of Compound 1 is substantially free of other crystalline forms (i.e., polymorphs) of Compound 1. In some embodiments, Form 22 of Compound 1 is provided as substantially pure Form 22 of Compound 1.

A representative XRPD pattern of Form 22 of Compound 1 is provided in FIG. 45.

In some embodiments, Form 22 has an enantiomeric purity of about 98%, about 98.5%, about 99%, or about 99.5%, or greater. In some embodiments, Form 22 is crystalline. In some embodiments, Form 22 is substantially crystalline. In some embodiments, Form 22 is moderately crystalline. In some embodiments, Form 22 is about 90%, about 95%, about 96%, about 97%, about 98%, about 98.5%, about 99%, or about 99.5%, crystalline, or greater.

In some embodiments, Form 22 has an X-ray powder diffraction (XRPD) pattern comprising peaks at approximately 10.6, 11.2, 16.6, 17.6, 18.1, and 22.5° 2θ. In some embodiments, the XRPD pattern further comprises peaks at approximately 8.5, 14.6, 22.0, 25.2, 25.6, and 29.9° 2θ. In some embodiments, the XRPD pattern further comprises peaks at approximately 12.3, 14.2, 23.7, 23.9, and 27.4° 2θ. In some embodiments, the XRPD pattern comprises peaks at approximately 8.5, 10.6, 11.2, 12.3, 14.2, 14.6, 16.6, 17.6, 18.1, 22.0, 22.5, 23.7, 23.9, 25.2, 25.6, 27.4, and 29.9° 2θ.

In some embodiments, provided herein is a solid form comprising a tartrate salt of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 8.5, 10.6, 11.2, 12.3, 14.2, 14.6, 16.6, 17.6, 18.1, 22.0, 22.5, 23.7, 23.9, 25.2, 25.6, 27.4, and 29.9° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by at least 13 of the peaks. In some embodiments, the solid form is characterized by at least 15 of the peaks. In some embodiments, the solid form is characterized by all of the peaks.

In some embodiments, Form 22 has an XRPD pattern that substantially matches the XRPD pattern presented in FIG. 45.

A representative overlay of thermal gravimetric analysis (TGA) and differential scanning calorimetry (DSC) thermograms for Form 22 of Compound 1 is provided in FIG. 46.

In some embodiments, Form 22 exhibits thermal (endothermic) events with onset temperatures of about 27, about 106, and about 209° C. and/or endothermic peak temperatures at about 51, about 141, and about 222° C., as characterized by DSC with a temperature ramp of about 10° C./min. In some embodiments, Form 22 is characterized by a DSC thermogram substantially as shown in the DSC thermogram presented in FIG. 46.

In some embodiments, Form 22 exhibits a weight loss of about 2.8% upon heating from about 80 to about 170° C., as characterized by TGA. In some embodiments, Form 22 is characterized by a TGA thermogram substantially as shown in the TGA thermogram presented in FIG. 46.

In some embodiments, Form 22 is prepared according to the procedures of Example 22.

All of the combinations of the above embodiments are encompassed by this application.

5.2.23 Form 23 of Compound 1

In some embodiments, provided herein is Form 23 of Compound 1. In some embodiments, Form 23 of Compound 1 is a crystalline tosylate salt of Compound 1. In some embodiments, Form 23 has a Compound 1/p-toluenesulfonic acid molar ratio of about 1:0.8, optionally wherein the solid form is a solvate. In some embodiments, Form 23 of Compound 1 is substantially free of amorphous Compound 1. In some embodiments, Form 23 of Compound 1 is substantially free of other crystalline forms (i.e., polymorphs) of Compound 1. In some embodiments, Form 23 of Compound 1 is provided as substantially pure Form 23 of Compound 1.

A representative XRPD pattern of Form 23 of Compound 1 is provided in FIG. 47.

In some embodiments, Form 23 has an enantiomeric purity of about 98%, about 98.5%, about 99%, or about 99.5%, or greater. In some embodiments, Form 23 is crystalline. In some embodiments, Form 23 is substantially crystalline. In some embodiments, Form 23 is moderately crystalline. In some embodiments, Form 23 is partially crystalline. In some embodiments, Form 23 is about 90%, about 95%, about 96%, about 97%, about 98%, about 98.5%, about 99%, or about 99.5%, crystalline, or greater.

In some embodiments, Form 23 has an X-ray powder diffraction (XRPD) pattern comprising peaks at approximately 8.5, 14.6, 18.1, and 21.7° 2θ. In some embodiments, the XRPD pattern further comprises peaks at approximately 6.8, 17.7, and 23.8° 2θ. In some embodiments, the XRPD pattern further comprises peaks at approximately 18.8 and 22.9° 2θ. In some embodiments, the XRPD pattern comprises peaks at approximately 6.8, 8.5, 14.6, 17.7, 18.1, 18.8, 21.7, 22.9, and 23.8° 2θ.

In some embodiments, provided herein is a solid form comprising a tosylate salt of Compound 1, characterized by 1, 2, 3, 4, 5, 6, 7, 8, or all of the XRPD peaks located at approximately the following positions (e.g., degrees 2θ±0.2) when measured using Cu Kα radiation: 6.8, 8.5, 14.6, 17.7, 18.1, 18.8, 21.7, 22.9, and 23.8° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 8 of the peaks. In some embodiments, the solid form is characterized by all of the peaks.

In some embodiments, Form 23 has an XRPD pattern that substantially matches the XRPD pattern presented in FIG. 47.

A representative overlay of thermal gravimetric analysis (TGA) and differential scanning calorimetry (DSC) thermograms for Form 23 of Compound 1 is provided in FIG. 48.

In some embodiments, Form 23 exhibits thermal (endothermic) events with onset temperatures of about 83 and about 186° C. and/or endothermic peak temperatures at about 120 and about 202° C., respectively, as characterized by DSC with a temperature ramp of about 10° C./min. In some embodiments, Form 23 is characterized by a DSC thermogram substantially as shown in the DSC thermogram presented in FIG. 48.

In some embodiments, Form 23 exhibits a weight loss of about 1.8% upon heating from about rt to about 100° C. and a weight loss of about 5.6% upon heating from about 100 to about 180° C., as characterized by TGA. In some embodiments, Form 23 is characterized by a TGA thermogram substantially as shown in the TGA thermogram presented in FIG. 48.

In some embodiments, Form 23 is prepared according to the procedures of Example 23.

All of the combinations of the above embodiments are encompassed by this application.

5.2.24 Form 24 of Compound 1

In some embodiments, provided herein is Form 24 of Compound 1. In some embodiments, Form 24 of Compound 1 is a crystalline anhydrate of Compound 1. In some embodiments, Form 24 of Compound 1 is substantially free of amorphous Compound 1. In some embodiments, Form 24 of Compound 1 is substantially free of other crystalline forms (i.e., polymorphs) of Compound 1. In some embodiments, Form 24 of Compound 1 is substantially free of salt forms of Compound 1. In some embodiments, Form 24 of Compound 1 is provided as substantially pure Form 24 of Compound 1.

A representative XRPD pattern of Form 24 of Compound 1 is provided in FIG. 49.

In some embodiments, Form 24 has an enantiomeric purity of about 98%, about 98.5%, about 99%, or about 99.5%, or greater. In some embodiments, Form 24 is crystalline. In some embodiments, Form 24 is substantially crystalline. In some embodiments, Form 24 is about 90%, about 95%, about 96%, about 97%, about 98%, about 98.5%, about 99%, or about 99.5%, crystalline, or greater.

In some embodiments, Form 24 has an X-ray powder diffraction (XRPD) pattern comprising peaks at approximately 9.5, 11.8, 14.6, and 20.9° 2θ. In some embodiments, the XRPD pattern further comprises peaks at approximately 14.8, 16.4, 22.3, and 23.8° 2θ. In some embodiments, the XRPD pattern further comprises peaks at approximately 16.6, 17.1, 24.2, and 25.1° 2θ. In some embodiments, the XRPD pattern comprises peaks at approximately 9.5, 11.8, 14.6, 14.8, 16.4, 16.6, 17.1, 20.9, 22.3, 23.8, 24.2, and 25.1° 2θ.

In some embodiments, provided herein is a solid form comprising a anhydrate of Compound 1, characterized by 1, 2, 3, 4, 5, 6, 7, 8, 9, 10, or all of the XRPD peaks located at approximately the following positions (e.g., degrees 2θ±0.2) when measured using Cu Kα radiation: 9.5, 11.8, 14.6, 14.8, 16.4, 16.6, 17.1, 20.9, 22.3, 23.8, 24.2, and 25.1° 2θ. In some embodiments, the solid form is characterized by at least 3 of the peaks. In some embodiments, the solid form is characterized by at least 5 of the peaks. In some embodiments, the solid form is characterized by at least 7 of the peaks. In some embodiments, the solid form is characterized by at least 9 of the peaks. In some embodiments, the solid form is characterized by at least 11 of the peaks. In some embodiments, the solid form is characterized by all of the peaks.

In some embodiments, Form 24 has an XRPD pattern that substantially matches the XRPD pattern presented in FIG. 49.

A representative overlay of thermal gravimetric analysis (TGA) and differential scanning calorimetry (DSC) thermograms for Form 24 of Compound 1 is provided in FIG. 50.

In some embodiments, Form 24 exhibits a thermal (endothermic) event with an onset temperature of about 240° C. and/or an endothermic peak at about 246° C., as characterized by DSC with a temperature ramp of about 10° C./min. In some embodiments, Form 24 is characterized by a DSC thermogram substantially as shown in the DSC thermogram presented in FIG. 50.

In some embodiments, Form 24 exhibits no weight loss upon heating up to about 200° C., as characterized by TGA. In some embodiments, Form 24 is characterized by a TGA thermogram substantially as shown in the TGA thermogram presented in FIG. 50.

In some embodiments, Form 24 is prepared according to the procedures of Example 14.

All of the combinations of the above embodiments are encompassed by this application.

5.3 Pharmaceutically Acceptable Salts of Compound 1

In some embodiments, provided herein, is a pharmaceutically acceptable salt of Compound 1:

Compound 1

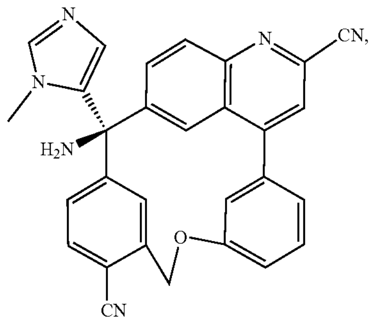

or an isotopologue thereof, or a pharmaceutically acceptable solvate of the pharmaceutically acceptable salt. In some embodiments, the pharmaceutically acceptable salt is a benzoate salt, a besylate salt, a chloride salt, a citrate salt, a fumarate salt, a gentisate salt, a glutarate salt, a glycolate salt, a hippurate salt, a 1-hydroxy-2-naphthoate salt, a malate salt, a maleate salt, a mesylate salt, an oxalate salt, a phosphate salt, a sulfate salt, a tartrate salt, or a tosylate salt. In some embodiments, the pharmaceutically acceptable salt of Compound 1, or pharmaceutically acceptable solvate thereof, is substantially pure. In some embodiments, the pharmaceutically acceptable salt of Compound 1, or pharmaceutically acceptable solvate thereof, is substantially chemically pure. In some embodiments, the pharmaceutically acceptable salt of Compound 1, or pharmaceutically acceptable solvate thereof, is substantially physically pure. In some embodiments, the pharmaceutically acceptable salt of Compound 1, or pharmaceutically acceptable solvate thereof, is substantially enantiomerically pure. In some embodiments, the pharmaceutically acceptable salt of Compound 1, or pharmaceutically acceptable solvate thereof, has an enantiomeric purity of at least about 98% (e.g., about 98.5%, about 99%, or about 99.5%). In some embodiments, the pharmaceutically acceptable salt of Compound 1, or pharmaceutically acceptable solvate thereof, has a Compound 1/conjugate acid molar ratio in the range of about 2:1 to about 1:2. In some embodiments, the pharmaceutically acceptable salt of Compound 1, or pharmaceutically acceptable solvate thereof, has a Compound 1/conjugate acid molar ratio in the range of about 2:1 to about 1:1. In some embodiments, the pharmaceutically acceptable salt of Compound 1, or pharmaceutically acceptable solvate thereof, has a Compound 1/conjugate acid molar ratio in the range of about 1:1 to about 1:2. In some embodiments, the pharmaceutically acceptable salt of Compound 1, or pharmaceutically acceptable solvate thereof, has a Compound 1/conjugate acid molar ratio is about 1:1. In some embodiments, the pharmaceutically acceptable salt of Compound 1 is a non-solvate of the pharmaceutically acceptable salt of the Compound 1. In some embodiments, the pharmaceutically acceptable salt of Compound 1 is an anhydrate of the pharmaceutically acceptable salt of the Compound 1. In some embodiments, the pharmaceutically acceptable salt of Compound 1 is a pharmaceutically acceptable solvate of the pharmaceutically acceptable salt of the Compound 1. In some embodiments, the pharmaceutically acceptable salt of Compound 1 is a pharmaceutically acceptable solvate of the pharmaceutically acceptable salt of the Compound 1, wherein the pharmaceutically acceptable solvate is a hydrate, a hemi-hydrate, an iso-butyl acetate, an iso-propyl acetate, a tetrahydrofuran solvate, an acetone solvate, an acetonitrile solvate, or combinations thereof. In some embodiments, the pharmaceutically acceptable solvate is a hydrate. In some embodiments, the pharmaceutically acceptable solvate of the pharmaceutically acceptable salt of the Compound 1 has a Compound 1/solvent molar ratio in the range of about 2:1 to about 1:2. In some embodiments, the pharmaceutically acceptable solvate of the pharmaceutically acceptable salt of the Compound 1 has a Compound 1/solvent molar ratio in the range of about 2:1 to about 1:1. In some embodiments, the pharmaceutically acceptable solvate of the pharmaceutically acceptable salt of the Compound 1 has a Compound 1/solvent molar ratio in the range of about 1:1 to about 1:2. In some embodiments, the pharmaceutically acceptable solvate of the pharmaceutically acceptable salt of the Compound 1 has a Compound 1/solvent molar ratio that is about 1:1.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile benzoate salt, or a pharmaceutically acceptable solvate thereof. In some embodiments, the benzoate salt of Compound 1 has a Compound 1/benzoic acid molar ratio in the range of about 2:1 to about 1:2, such as about 2:1 to about 1:1, or about 1:1 to about 1:2. In some embodiments, the benzoate salt of Compound 1 has a Compound 1/benzoic acid molar ratio of about 1:1.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile besylate salt, or a pharmaceutically acceptable solvate thereof.

In some embodiments, the pharmaceutically acceptable salt of the Compound 1 is (S)-3-dicarbonitrile chloride salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile citrate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile fumarate salt, or a pharmaceutically acceptable solvate thereof. In some embodiments, the fumarate salt of Compound 1 has a Compound 1/fumaric acid molar ratio in the range of about 2:1 to about 1:2, such as about 2:1 to about 1:1, or about 1:1 to about 1:2. In some embodiments, the fumarate salt of Compound 1 has a Compound 1/fumaric acid molar ratio of about 1:1.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile gentisate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile glutarate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile glycolate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile hippurate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile 1-hydroxy-2-naphthoate salt, or a pharmaceutically acceptable solvate thereof.

In some embodiments, the 1-hydroxy-2-naphthoate salt of Compound 1 has a Compound 1/1-hydroxy-2-naphthoic acid molar ratio in the range of about 2:1 to about 1:2, such as about 2:1 to about 1:1, or about 1:1 to about 1:2. In some embodiments, the 1-hydroxy-2-naphthoate salt of Compound 1 has a Compound 1/1-hydroxy-2-naphthoic acid molar ratio of about 1:1.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile malate salt, or a pharmaceutically acceptable solvate thereof.

In some embodiments, the pharmaceutically acceptable salt of the Compound 1 is (S)-3-dicarbonitrile maleate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile mesylate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile oxalate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile phosphate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile sulfate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile tartrate salt, or a pharmaceutically acceptable solvate thereof.

In some embodiments, the pharmaceutically acceptable salt of the Compound 1 is (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile tosylate salt, or a pharmaceutically acceptable solvate thereof.

5.4 Pharmaceutical Compositions and Methods of Preparing

In some embodiments, provided herein, is a pharmaceutical composition comprising i) a solid form comprising Compound 1, or a pharmaceutically acceptable salt and/or solvate thereof:

Compound 1

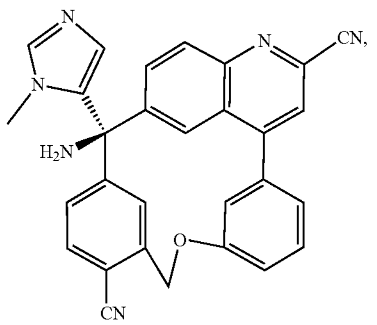

in an amount from about 0.1 mg to about 200 mg, and, ii) one or more pharmaceutically acceptable excipients. In some embodiments, the solid form contained in the pharmaceutical composition is crystalline. In some embodiments, the amount of Compound 1 contained in the pharmaceutical composition is about 0.2 mg free base equivalent. In some embodiments, the amount of Compound 1 contained in the pharmaceutical composition is about 1.0 mg free base equivalent. In some embodiments, the amount of Compound 1 contained in the pharmaceutical composition is about 10 mg free base equivalent. In some embodiments, the amount of Compound 1 contained in the pharmaceutical composition is about 50 mg free base equivalent. In some embodiments, the pharmaceutical composition comprises a solid form of Compound 1, as disclosed herein. In some embodiments, the pharmaceutical composition comprises any one of Forms 1-24 of Compound 1, as disclosed herein. In some embodiments, the pharmaceutical composition comprises a solid form of a crystalline, free base, hemi-hydrate of the Compound 1, as disclosed herein. In some embodiments, the pharmaceutical composition comprises Form 1 of Compound 1, as disclosed herein. In some embodiments, the pharmaceutical composition is formulated as an immediate release oral dosage form. In some embodiments, the pharmaceutical composition is a tablet. In some embodiments, the tablet is a coated tablet. In some embodiments, the tablet coating is a spray dry film coating. In some embodiments, the tablet coating comprises a polymer, a plasticizer, and a pigment. In some embodiments, the tablet coating comprises polyvinyl alcohol, titanium dioxide, polyethylene glycol, and talc. In some embodiments, the one or more pharmaceutically acceptable excipients comprises a filler, a glidant, a disintegrant, a lubricant, or a binder, or combinations thereof.

In some embodiments, the pharmaceutical composition comprises a filler. In some embodiments, the filler is present in an amount of from about 40 to about 95% w/w (or weight %; referring to weight of particular ingredient per total weight of composition; typically, for a tablet composition, relative to the uncoated core tablet weight). In some embodiments, the filler is silicified microcrystalline cellulose, microcrystalline cellulose, D-mannitol, or a combination thereof. In some embodiments, the filler is silicified microcrystalline cellulose.

In some embodiments, the pharmaceutical composition comprises a glidant. In some embodiments, the amount of glidant is colloidal silicon dioxide. In some embodiments, the colloidal silicon dioxide is present in an amount of about 0.5 to about 5% w/w, or about 0.5, about 1.0, or about 1.5% w/w, or about 1.0% w/w.

In some embodiments, the pharmaceutical composition comprises a disintegrant. In some embodiments, the disintegrant is croscarmellose sodium. In some embodiments, the disintegrant is present in an amount of from about 1 to about 6% w/w, or about 2.0, about 2.5, about 3.0, about 3.5, or about 4.0% w/w, or about 3.0% w/w. In some embodiments, the pharmaceutical composition comprises a lubricant.

In some embodiments, the lubricant is magnesium stearate. In some embodiments, the lubricant is present in an amount of from about 0.5 to about 2.5% w/w, or about 0.5, about 1.0, about 1.5, or about 2.0% w/w, or about 1.0% w/w, or about 1.5% w/w.

In some embodiments, the pharmaceutical composition comprises a binder. In some embodiments, the binder is povidone. In some embodiments, the binder is present in an amount of about 3 to about 10% w/w and about 3 to about 15 mg.

In some embodiments, provided herein is a pharmaceutical composition wherein (a) the solid form is present in an amount of from about 0.1 mg to about 25 mg free base equivalent, and the silicified microcrystalline cellulose is present in an amount from about 70 to about 97% w/w, or (b) the solid form is present in an amount of from about 25 mg to about 200 mg free base equivalent, and the silicified microcrystalline cellulose is present in an amount from about 40 to about 70% w/w. In some embodiments, the solid form is present in an amount of about 0.2 mg free base equivalent, and the silicified microcrystalline cellulose is present in an amount of about 75 to about 95% w/w and about 73 to about 75.4 mg. In some embodiments, the solid form is present in an amount of about 1.0 mg free base equivalent, and the silicified microcrystalline cellulose is present in an amount of about 75 to about 95% w/w and (a) about 80 to about 380 mg, or (b) about 80 to about 90 mg, or (c) about 370 to about 378 mg. In some embodiments, the solid form is present in an amount of about 10 mg free base equivalent, and the silicified microcrystalline cellulose is present in an amount of about 75 to about 95% w/w and about 75 to about 85 mg. In some embodiments, the solid form is present in an amount of about 50 mg free base equivalent, and the silicified microcrystalline cellulose is present in an amount of about 40 to about 50% w/w and about 40 to about 50 mg or the silicified microcrystalline cellulose is present in about 60 to about 70% w/w and about 60 to about 70 mg.

In some embodiments, the pharmaceutical composition comprises: (a) a core tablet comprising about 0.21 mg Compound 1 (Form 1), about 75.4 mg silicified microcrystalline cellulose, about 0.8 mg colloidal silicon dioxide, about 2.4 mg croscarmellose sodium, and about 1.2 mg magnesium stearate; and (b) a tablet coating. In some embodiments, this pharmaceutical composition is a 0.2 mg Compound 1 (free base equivalent) strength composition.

In some embodiments, the pharmaceutical composition comprises: (a) a core tablet comprising about 1.03 mg Compound 1 (Form 1), about 377 mg silicified microcrystalline cellulose, about 4.0 mg colloidal silicon dioxide, about 12.0 mg croscarmellose sodium, and about 6.0 mg magnesium stearate; and (b) a tablet coating. In some embodiments, this pharmaceutical composition is a 1 mg Compound 1 (free base equivalent) strength composition.

In some embodiments, the pharmaceutical composition comprises: (a) a core tablet comprising about 10.3 mg Compound 1 (Form 1), about 84.2 mg silicified microcrystalline cellulose, about 1.0 mg colloidal silicon dioxide, about 3.0 mg croscarmellose sodium, and about 1.5 mg magnesium stearate; and (b) a tablet coating. In some embodiments, this pharmaceutical composition is a 10 mg Compound 1 (free base equivalent) strength composition.

In some embodiments, the pharmaceutical composition comprises: (a) a core tablet comprising about 51.5 mg Compound 1 (Form 1), about 43.0 mg silicified microcrystalline cellulose, about 1.0 mg colloidal silicon dioxide, about 3.0 mg croscarmellose sodium, and about 1.5 mg magnesium stearate; and (b) a tablet coating. In some embodiments, the core tablet comprises: (a) an intragranular portion comprising 51.5 mg Compound 1 (Form 1), about 43.0 mg silicified microcrystalline cellulose, about 1.0 mg colloidal silicon dioxide, about 2.0 mg croscarmellose sodium, and about 1.0 mg magnesium stearate; and (b) an extragranular portion comprising about 1.0 mg croscarmellose sodium and about 0.5 mg magnesium stearate. In some embodiments, these pharmaceutical compositions are 50 mg Compound 1 (free base equivalent) strength compositions.

In some embodiments, the pharmaceutical composition comprises: (a) a core tablet comprising about 51.4 mg Compound 1 (Form 1), about 43.1 mg silicified microcrystalline cellulose, about 1.0 mg colloidal silicon dioxide, about 3.0 mg croscarmellose sodium, and about 1.5 mg magnesium stearate; and (b) a tablet coating. In some embodiments, the core tablet comprises: (a) an intragranular portion comprising 51.4 mg Compound 1 (Form 1), about 43.1 mg silicified microcrystalline cellulose, about 1.0 mg colloidal silicon dioxide, about 2.0 mg croscarmellose sodium, and about 1.0 mg magnesium stearate; and (b) an extragranular portion comprising about 1.0 mg croscarmellose sodium and about 0.5 mg magnesium stearate. In some embodiments, these pharmaceutical compositions are 50 mg Compound 1 (free base equivalent) strength compositions.

In some embodiments, the pharmaceutical composition comprises: (a) a core tablet comprising about 1.0 mg Compound 1 (Form 1), about 5.0 mg povidone, about 89 mg silicified microcrystalline cellulose, about 1.0 mg colloidal silicon dioxide, about 3.0 mg croscarmellose sodium, and about 1.0 mg magnesium stearate; and (b) a tablet coating.

In some embodiments, this pharmaceutical composition is a 1 mg Compound 1 (free base equivalent) strength composition.

In some embodiments, the pharmaceutical composition comprises: (a) a core tablet comprising about 10 mg Compound 1 (Form 1), about 5.0 mg povidone, about 80 mg silicified microcrystalline cellulose, about 1.0 mg colloidal silicon dioxide, about 3.0 mg croscarmellose sodium, and about 1.0 mg magnesium stearate; and (b) a tablet coating. In some embodiments, this composition is a 10 mg Compound 1 (free base equivalent) strength composition.

In some embodiments, the pharmaceutical composition comprises: (a) a core tablet comprising about 52 mg Compound 1 (Form 1), about 10.0 mg povidone, about 128 mg silicified microcrystalline cellulose, about 2.0 mg colloidal silicon dioxide, about 6.0 mg croscarmellose sodium, and about 2.0 mg magnesium stearate; and (b) a tablet coating. In some embodiments, the pharmaceutical composition comprises: (a) a core tablet comprising about 51.5 mg Compound 1 (Form 1), about 10.0 mg povidone, about 128.5 mg silicified microcrystalline cellulose, about 2.0 mg colloidal silicon dioxide, about 6.0 mg croscarmellose sodium, and about 2.0 mg magnesium stearate; and (b) a tablet coating. In some embodiments, the core tablet comprises: (a) an intragranular portion comprising the Compound 1 (Form 1), the silicified microcrystalline cellulose, the colloidal silicon dioxide, the croscarmellose sodium, and povidone; and (b) an extragranular portion comprising the magnesium stearate. In some embodiments, this composition is a 50 mg Compound 1 (free base equivalent) strength composition.

In some embodiments, provided herein, is a method of preparing a pharmaceutical composition, as disclosed herein, the method comprising: i) optionally, de-lumping the solid form of the Compound 1, or pharmaceutically acceptable salt and/or solvate thereof; ii) mixing the solid form of the Compound 1, or pharmaceutically acceptable salt and/or solvate thereof, with a disintegrant, a glidant, and a first portion of a filler to form a first blend; iii) de-lumping the first blend to form a de-lumped first blend; iv) de-lumping a second portion of the filler; v) blending the de-lumped first blend and the de-Jumped second portion of the filler to form a second blend; vi) blending the second blend with a lubricant to form a lubricated blend; and vii) compressing the lubricated blend, optionally with a rotary press, into a tablet. In some embodiments, the method comprises de-lumping the solid form of the Compound 1, or pharmaceutically acceptable salt and/or solvate thereof. In some embodiments, the method further comprises viii) coating the compressed tablet. In some embodiments, the coating is a spray dry film coating. In some embodiments, the method further comprises ix) packaging the film coated tablets into a container. In some embodiments, the amount of the solid form of the Compound 1, or pharmaceutically acceptable salt and/or solvate thereof, present in the pharmaceutical composition is about 0.2 mg, about 1 mg, or about 10 mg free base equivalent.

In some embodiments, provided herein, is a method of preparing a pharmaceutical composition, as disclosed herein, the method comprising: i) optionally, de-lumping the solid form of the Compound 1, or pharmaceutically acceptable salt and/or solvate thereof; ii) mixing the solid form of the Compound 1, or pharmaceutically acceptable salt and/or solvate thereof, with a filler, a glidant, and a first portion of a disintegrant to form a first blend; iii) de-lumping and then blending the first blend to form a second blend; iv) blending the second blend with a first portion of a lubricant to form a lubricated intragranular blend; v) forming granules from the intragranular blend, for example, with a roller compactor and screen; vi) blending the granules with a second portion of the disintegrant and a second portion of the lubricant to form a lubricated final blend; and vii) compressing the lubricated final blend, optionally with a rotary press, into a tablet. In some embodiments, the method comprises de-lumping the solid form of the Compound 1, or pharmaceutically acceptable salt and/or solvate thereof. In some embodiments, the method further comprises viii) coating the compressed tablet. In some embodiments, the coating is a spray dry film coating. In some embodiments, the method further comprises ix) packaging the film coated tablets into a container. In some embodiments, the amount of the solid form of the Compound 1, or pharmaceutically acceptable salt and/or solvate thereof, present in the film coated tablet is 50 mg free base equivalent.

In some embodiments, provided herein, is a method of preparing a pharmaceutical composition, as disclosed herein, the method comprising: i) optionally, de-lumping the solid form of the Compound 1, or pharmaceutically acceptable salt and/or solvate thereof; ii) granulating the solid form of the Compound 1, or pharmaceutically acceptable salt and/or solvate thereof, a filler, a glidant, and a disintegrant with a binder and water to form wet granules; iii) drying the wet granules to form dry granules; iv) blending the granules with a lubricant to form a lubricated final blend; and v) compressing the lubricated final blend, optionally with a rotary press, into a tablet. In some embodiments, the method comprises de-lumping the solid form of the Compound 1, or pharmaceutically acceptable salt and/or solvate thereof. In some embodiments, the method further comprises vii) coating the compressed tablet. In some embodiments, the coating is a spray dry film coating. In some embodiments, the method further comprises viii) packaging the film coated tablets into a container. In some embodiments, the amount of the solid form of the Compound 1, or pharmaceutically acceptable salt and/or solvate thereof, present in the film coated tablet is 1 mg, 10 mg, or 50 mg free base equivalent. In some embodiments, the dry granules are milled prior to blending with the lubricant to form the lubricated final blend. In some embodiments, the granules are milled using a screen of about 0.5 mm to about 2 mm mesh, or about 1 mm mesh. In some embodiments, the wet granules are milled prior to drying using, for example, a 3/8 inch screen.

5.5 Synthesis

In some embodiments, provided herein, is a process for preparing Compound 1:

Compound 1

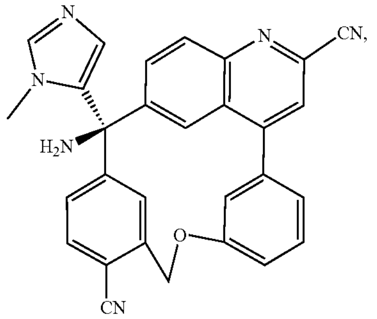

or a pharmaceutically acceptable form thereof, comprising one or more of the following steps as shown in Schemes A-F:

Scheme A.
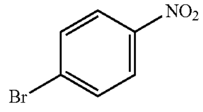
A
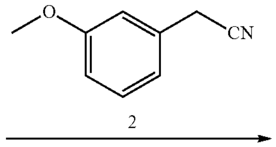
2
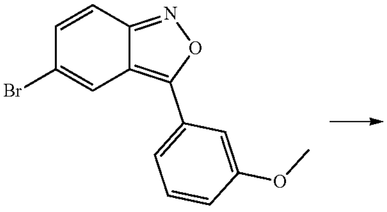
3
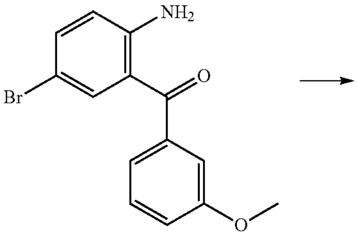
4
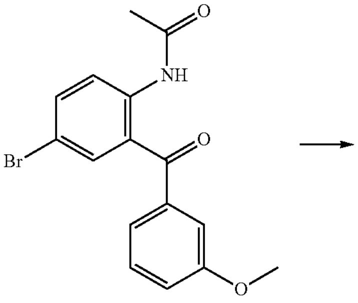
5
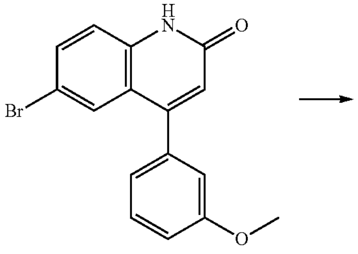
6
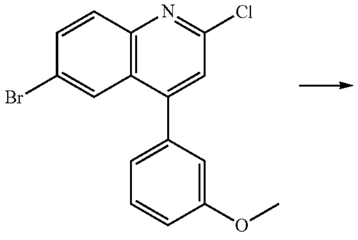
7
-continued
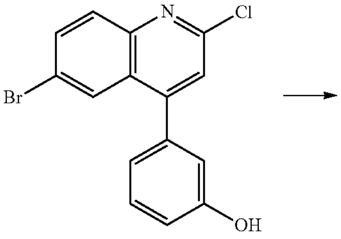
8
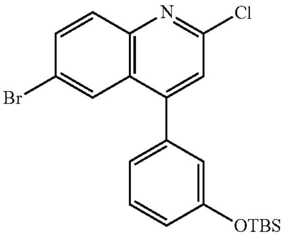
9
Scheme B.
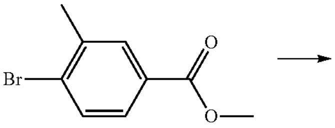
20
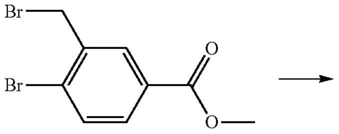
21
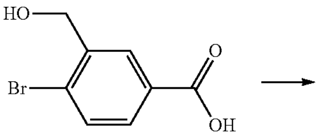
22
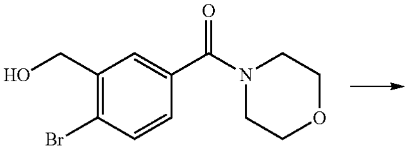
23
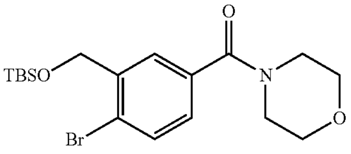
11

Scheme C.
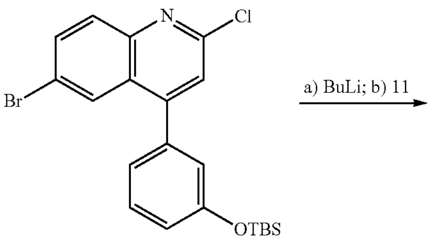
9
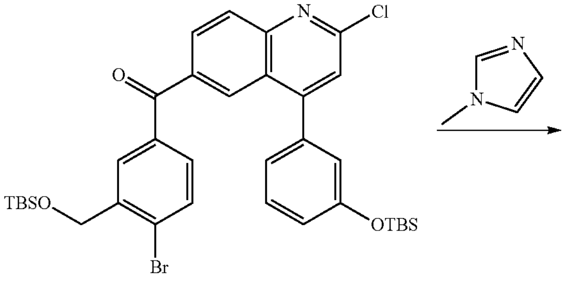
12
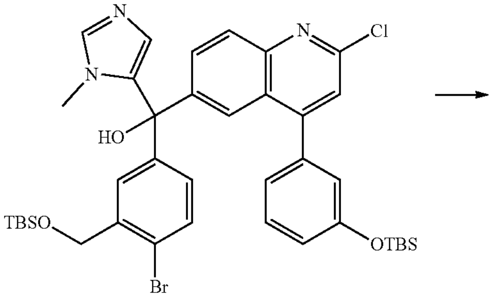
13
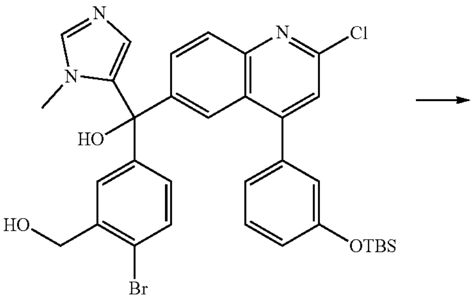
14
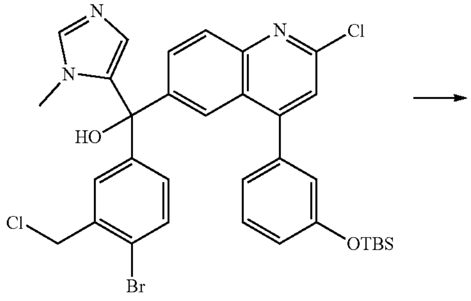
15
-continued
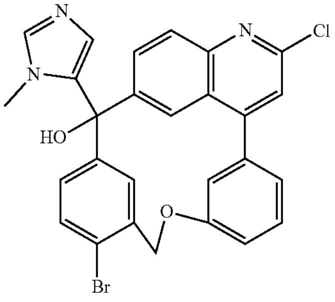
16
Scheme D.
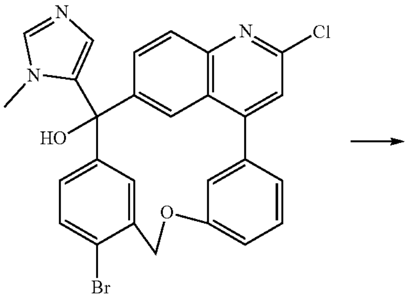
16
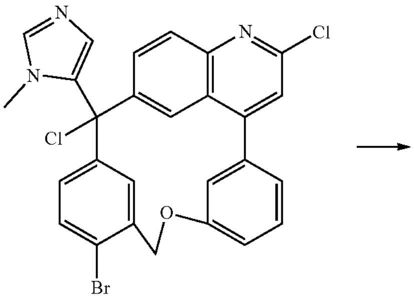
17A
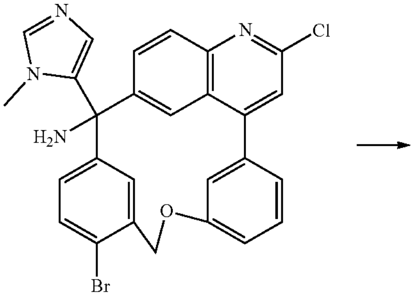
18A -continued

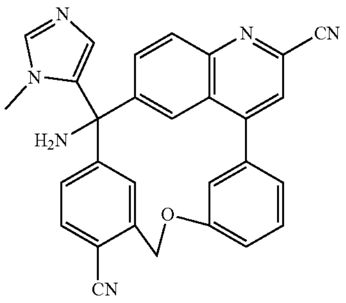

19

Scheme E.

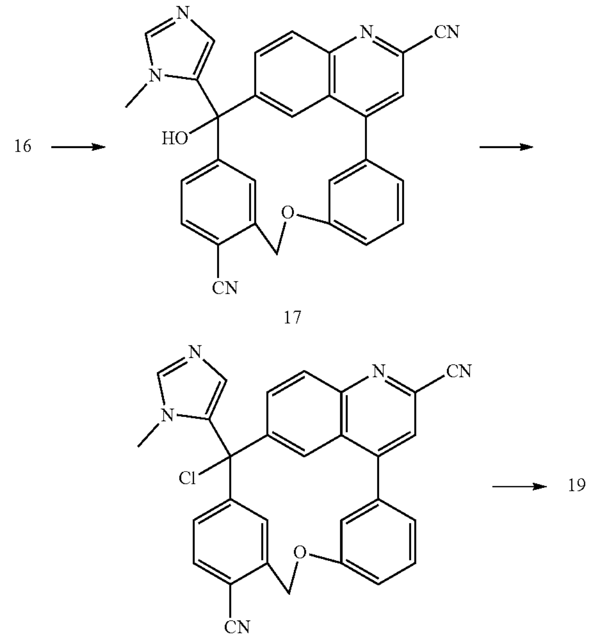

Scheme F.

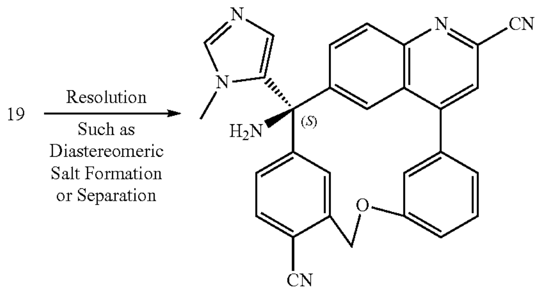

1

In some embodiments, provided herein is a process for preparing Compound 1, or a pharmaceutically acceptable form thereof, comprising:

(a) reacting racemic Compound 19:

Compound 19

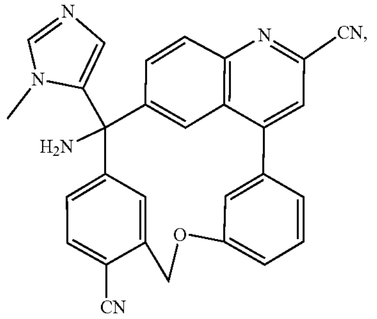

with a chiral acid in a solvent to form a diastereomeric salt of Compound 1 and a diastereomeric salt of Compound 2:

Compound 2

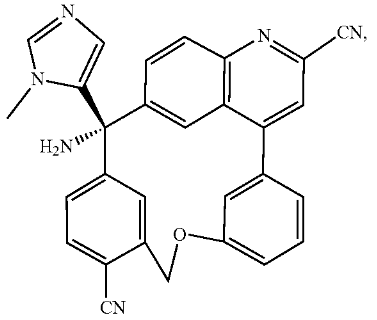

wherein one of the two diastereomeric salts precipitates selectively from the solvent and the other of the two diastereomeric salts is selectively soluble in the solvent;

(b) separating the precipitate from the solvent;

(c) reacting the diastereomeric salt of Compound 1 with a base to provide Compound 1, and (d) optionally, recrystallizing Compound 1, optionally from ACN/water in a ratio of about 2:1 to about 1:5, optionally about 1:1 to about 1:3.

In some embodiments, the chiral acid is (R)-chlocyphos, (S)-chlocyphos, (+)-tartaric acid, (−)-tartaric acid, (+)-camphorsulfonic acid, (−)-camphorsulfonic acid, L-(−)-di-p-anisoyltartaric acid, D-(+)-di-p-anisoyltartaric acid, L-(−)-di-toluoyltartaric acid, D-(+)-di-toluoyltartaric acid, (R)-BINAP phosphate, (S)-BINAP phosphate, di-benzoyl-l-tartaric acid, or di-benzoyl-D-tartaric acid. In some embodiments, the chiral acid is dibenzoyl-D-tartaric acid or dibenzoyl-L-tartaric acid, and the solvent is acetone or DCM. In some embodiments, the chiral acid is (R)-BINAP phosphate or (S)-BINAP phosphate, and the solvent is dioxane, acetone, ACN, IPAc, MEK, THF, 2-MeTHE, dioxolane, or glyme, for example, in some embodiments, the solvent is THF or dioxolane. In some embodiments, the chiral acid is dibenzoyl-D-tartaric acid, and the diastereomeric salt of Compound 1 is the diastereomeric salt that is selectively soluble in the solvent. In some embodiments, the chiral acid is dibenzoyl-L-tartaric acid, and the diastereomeric salt of Compound 1 is the diastereomeric salt that precipitates selectively from the solvent. In some embodiments, the base is $Na_2CO_3$, $K_2CO_3$, NaOH, or KOH, or wherein the base is $Na_2CO_3$. In some embodiments, the solvent is DCM.

In some embodiments, the method disclosed herein comprises reacting Compound 18:

Compound 18

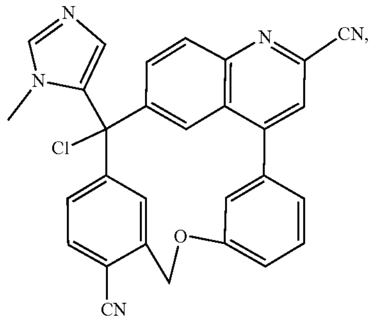

with an ammonia equivalent to form Compound 19. In some embodiments, the ammonia equivalent is $NH_3$, optionally in an amount of about 15 to about 50 equivalents, or about 40 to 50 equivalents. In some embodiments, the reacting of the Compound 18 is performed in a polar solvent. In some embodiments, the polar solvent is selected from IPA, EtOH, MeOH, 1,4-dioxane, DMI, and mixtures thereof. In some embodiments, the polar solvent is MeOH. In some embodiments, the reacting of the Compound 18 is performed at a temperature from about 0 to about 40° C.

In some embodiments, the method disclosed herein comprises chlorinating Compound 17:

Compound 17

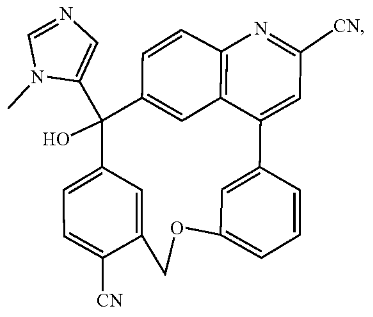

with a chlorinating agent to form Compound 18. In some embodiments, the chlorinating agent is thionyl chloride, $POCl_3$, $PCl_3$, or oxalyl chloride. In some embodiments, the chlorinating agent is thionyl chloride. In some embodiments, the chlorinating agent is used in an amount of about 2 to about 3.5 equivalents. In some embodiments, the chlorinating of the Compound 17 is performed in a polar, aprotic solvent. In some embodiments, the polar, aprotic solvent is DMI. In some embodiments, the chlorinating of the Compound 17 is performed at a temperature of about 10 to about 60° C.

In some embodiments, the method disclosed herein comprises reacting Compound 16:

Compound 16

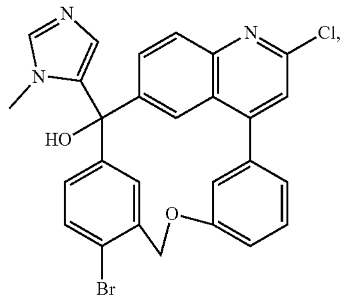

with a cyanide equivalent and a palladium catalyst, optionally in the presence of zine source and/or a phosphine ligand, to provide Compound 17. In some embodiments, the cyanide source is $Cu(CN)_2$ or $Zn(CN)_2$. In some embodiments, the cyanide source is $Zn(CN)_2$. In some embodiments, the cyanide source is used in an amount of about 1 to about 1.7 equivalents. In some embodiments, the palladium catalyst is $[PdCl(allyl)]_2$, $Pd_2(dba)_3$, $Pd(OAc)_2$, $Pd(PPh_3)_4$, $Pd(dppf)_2Cl_2$, $PdCl_2$, or a combination thereof, or is $Pd_2(dba)$; and $Pd(OAc)_2$. In some embodiments, the phosphine ligand is $PPh_3$, R-BINAP, or dppf, or is dppf. In some embodiments, the phosphine ligand is present in an amount of about 0.02 to about 0.15 equivalents. In some embodiments, the zinc source is zinc metal. In some embodiments, the reacting of the Compound 16 is performed at a temperature of from about 60 to about 110° C., or from about 90 to about 110° C. In some embodiments, the reacting of the Compound 16 is performed in a polar solvent. In some embodiments, the polar solvent is DMA or DMF.

In some embodiments, provided herein, is a process for preparing Compound 1:

Compound 1

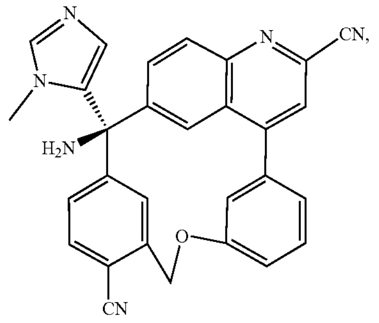

or a pharmaceutically acceptable form thereof, comprising reacting Compound 18A:

Compound 19

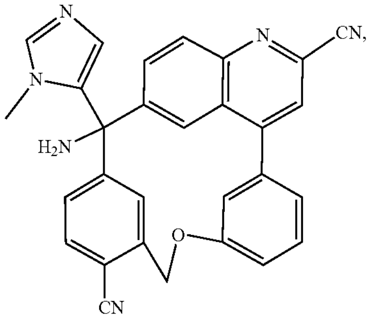

with a cyanide equivalent and a palladium catalyst, optionally in the presence of zinc source and/or a phosphine ligand, to provide Compound 19:

Compound 19

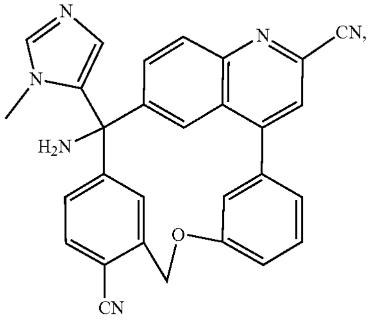

and purifying racemic Compound 19 by chiral separation to provide Compound 1. In some embodiments, the cyanide source is $Cu(CN)_2$ or $Zn(CN)_2$. In some embodiments, the cyanide source is $Zn(CN)_2$. In some embodiments, the cyanide source used in an amount of about 1 to about 1.7 equivalents. In some embodiments, the palladium catalyst is $[PdCl(allyl)]_2$, $Pd_2(dba)_3$, $Pd(OAc)_2$, $Pd(PPh_3)_4$, $Pd(dppf)_2Cl_2$, $PdCl_2$, or a combination thereof, or is $Pd_2(dba)_3$ and $Pd(OAc)_2$. In some embodiments, the phosphine ligand is $PPh_3$, R-BINAP, or dppf. In some embodiments, the phosphine ligand is dppf. In some embodiments, the phosphine ligand is present in an amount of about 0.02 to about 0.15 equivalents. In some embodiments, the zinc source is zinc metal. In some embodiments, the reacting of the Compound 18A is performed at a temperature of from about 60 to about 110° C., or from about 90 to about 110° C. In some embodiments, the reacting of the Compound 18A is performed in a polar solvent. In some embodiments, the polar solvent is DMA or DMF.

In some embodiments, the method disclosed herein comprises reacting Compound 17A:

Compound 16

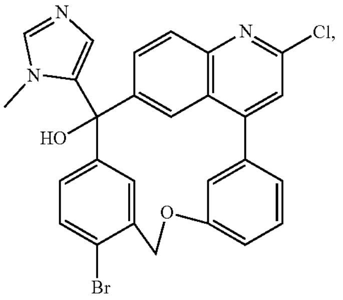

with an ammonia equivalent to form Compound 18A. In some embodiments, the ammonia equivalent is $NH_3$. In some embodiments, the ammonia equivalent is used in an amount of about 15 to about 50 equivalents, or about 17 to 21 equivalents. In some embodiments, the reacting of the Compound 17A is performed in a polar solvent. In some embodiments, the polar solvent is selected from IPA, EtOH, MeOH, 1,4-dioxane, DMI, and mixtures thereof. In some embodiments, the polar solvent is IPA. In some embodiments, the reacting of the Compound 17A is performed at a temperature from about 0 to about 40° C.

In some embodiments, the method disclosed herein comprises chlorinating Compound 16:

Compound 16

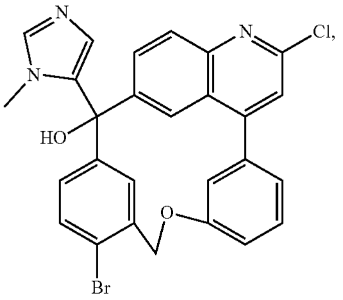

with a chlorinating agent to form Compound 17A. In some embodiments, the chlorinating agent is thionyl chloride, POCH, PCI, or oxalyl chloride. In some embodiments, the chlorinating agent is thionyl chloride. In some embodiments, the chlorinating agent is used in an amount of about 2 to about 3.5 equivalents. In some embodiments, the chlorinating of the Compound 16 is performed in a polar, aprotic solvent. In some embodiments, the polar, aprotic solvent is DMI. In some embodiments, the chlorinating of the Compound 16 is performed at a temperature of about 10 to about 60° C.

In some embodiments, the method disclosed herein comprises cyclizing Compound 15X:

Compound 15X

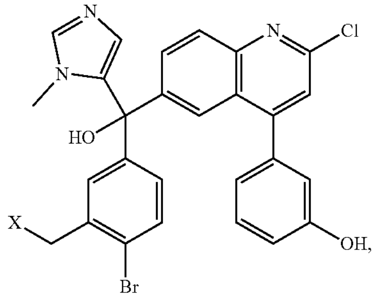

or a salt thereof, wherein X is a leaving group selected from —Cl, —Br, —I, -OTs, or -OMs, optionally wherein X is —Cl (Compound 15), in the presence of a base to form Compound 16. In some embodiments, the base is $Cs_2CO_3$, $K_2CO_3$, or $Li_2CO_3$. In some embodiments, the base is $Cs_2CO_3$. In some embodiments, the base is $KH_2PO_4$. In some embodiments, X is —OH, and the reaction is performed under Mitsunobu conditions. In some embodiments, Compound 15X is used in free base form, and the base is present in an amount of about 1.5 to 4 equivalents. In some embodiments, Compound 15X is used in salt form, and the base is present in an amount of about 4 to 12 equivalents. In some embodiments, the reacting of the Compound 15X is done in a polar, aprotic solvent. In some embodiments, the polar, aprotic solvent is DME, DMF, MTBE, DMAc, or diglyme, or a mixture thereof, for example, the polar, aprotic solvent is DMF or DMAc. In some embodiments, the reacting of the Compound 15X is performed at a temperature of about 40 to about 80° C.

In some embodiments, the method disclosed herein comprises reacting Compound 14:

Compound 14

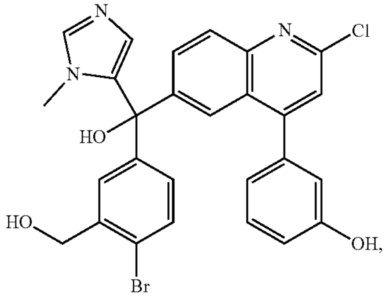

or a salt thereof, with a hydroxyl activating agent to form Compound 15X or a salt thereof. In some embodiments, the hydroxyl activating agent is thionyl chloride, POCH, PCB, or oxalyl chloride (X is —Cl), NaBr or LiBr (X is —Br), TsCl (X is -OTs), or MsCl (X is -OMs). In some embodiments, the hydroxyl activating agent is thionyl chloride and X is —Cl. In some embodiments, the hydroxyl activating agent is used in an amount of about 2 to about 4 equivalents, or about 3 equivalents. In some embodiments, the reacting of the Compound 14 is done in a polar, aprotic solvent, for example, selected from THE, 2-MeTHF, DMF, or DMA. In some embodiments, the reacting of the Compound 14 is performed at a temperature of about 10 to about 60° C.

In some embodiments, the process comprises reacting Compound 14 or a salt thereof under Mitsunobu conditions to form Compound 16. In some embodiments, the Mitsunobu conditions comprise a dialkyl azodicarboxylate and a trialkyl- or triarylphosphine, for example, the dialkyl azodicarboxylate is DEAD or DIAD, and the trialkyl- or triarylphosphine is triphenylphosphine.

In some embodiments, the method disclosed herein comprises deprotecting Compound 13PG:

Compound 13PG

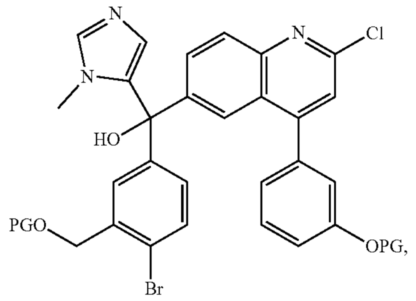

wherein each PG is independently a hydroxyl protecting group, under suitable deprotecting conditions to form Compound 14 or a salt thereof. In some embodiments, both PG groups are silyl protecting groups, such as tert-butyldimethylsilyl, tri-isopropylsilyl, triethylsilyl, or tert-butyldiphenylsilyl. In some embodiments, both PG groups are tri-isopropylsilyl or tert-butyldimethylsilyl (Compound 13). In some embodiments, the deprotecting conditions comprise TBAF, MSA, $MSA/H_2O$, or $HCl/H_2O$, optionally in a polar solvent. In some embodiments, the solvent is THE, ACN, EtOAc, acetone, toluene, or a mixture thereof. In some embodiments, the deprotecting conditions comprise 3 N HCl in THF or THE/toluene (optionally about 4:1 to about 1:4 THF/toluene, or about 2:1 to about 3:1 THF/toluene). In some embodiments, the deprotecting of the Compound 13PG is performed at a temperature of about 0 to about 40° C.

In some embodiments, the method disclosed herein comprises coupling Compound 12PG:

Compound 12PG

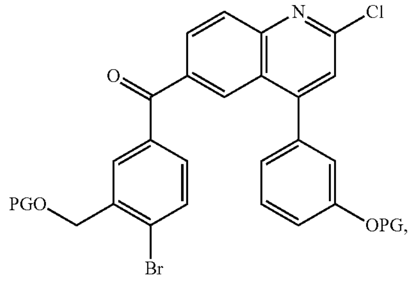

wherein each PG is independently a hydroxyl protecting group. In some embodiments, both PG groups are silyl protecting groups, such as tert-butyldimethylsilyl, tri-isopropylsilyl, triethylsilyl, or tert-butyldiphenylsilyl. In some embodiments, both PG groups are tri-isopropylsilyl or tert-butyldimethylsilyl (Compound 12), and wherein 1-methylimidazole is used to form Compound 13PG, In some embodiments, the coupling of the Compound 12PG is performed at a temperature of about −50 to about-90° C. In some embodiments, the reacting comprises metalating 1-methylimidazole at the 5-position to form a reactive species, and mixing the reactive species with Compound 12PG, optionally wherein the reactive species is (1-methyl-2-(protecting group)-1H-imidazol-5-yl)lithium, optionally wherein the 1-methyl-2-(protecting group)-1H-imidazol-5-yl)lithium is (1-methyl-2-(triethylsilyl)-1H-imidazol-5-yl) lithium. In some embodiments, the metalating comprises reacting 1-methyl-imidazole with (i) BuLi, (ii) TESCl, and (iii) BuLi, to form the (1-methyl-2-(triethylsilyl)-1H-imidazol-5-yl)lithium. In some embodiments, the metalating and coupling are performed at temperatures of about −30 to about −90° C.

In some embodiments, the method disclosed herein comprises condensing Compound 11PG:

with Compound 9PG:

Compound 11PG

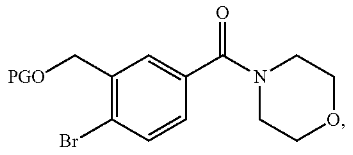

Compound 9PG

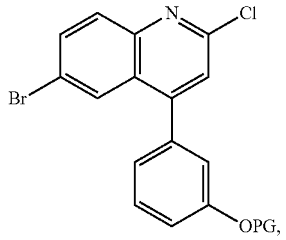

wherein each PG is independently a hydroxyl protecting group, optionally wherein the PG groups in Compound 9PG and Compound 11PG are both silyl protecting groups, such as tert-butyldimethylsilyl, tri-isopropylsilyl, triethylsilyl, or tert-butyldiphenylsilyl, optionally wherein both PG groups are tri-isopropylsilyl or tert-butyldimethylsilyl (Compound 9 and Compound 11), to form Compound 12PG. In some embodiments, the method comprises reacting Compound 9PG with a metalating agent, such as BuLi or isopropylMgCl/LiCl, to form a reactive species. In some embodiments, the metalating agent is used in an amount of from about 1 to about 1.3 equivalents, optionally in a polar, aprotic solvent. In some embodiments, the polar, aprotic solvent is THF. In some embodiments, the method further comprises mixing the reactive species with Compound 11PG. In some embodiments, the reacting of the Compound 9PG and the mixing with Compound 11PG are performed at a temperature from about −60 to about −85° C.

In some embodiments, the method disclosed herein comprises reacting Compound 8:

Compound 8

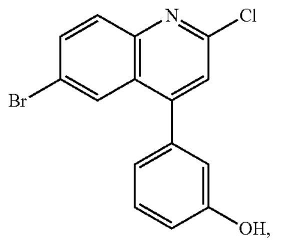

with a hydroxyl protecting group reagent to form Compound 9PG. In some embodiments, the PG is a silyl protecting group. In some embodiments, the hydroxyl protecting group reagent is a silyl chloride reagent. In some embodiments, the PG is tert-butyldimethylsilyl and the hydroxyl protecting group reagent is TBSCl. In some embodiments, wherein the reacting of the Compound 8 is performed in the presence of a base, optionally wherein the base is imidazole, TEA, TEA/DMAP, DIPEA, or pyridine, optionally in a polar, aprotic solvent. In some embodiments, the polar, aprotic solvent is DCM or THF.

In some embodiments, the method disclosed herein comprises reacting Compound 7:

Compound 7

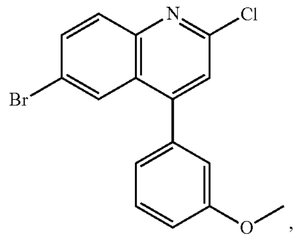

with a demethylating agent to form Compound 8. In some embodiments, the demethylating agent is $BCl_3$ or $BBr_3$. In some embodiments, the demethylating agent is used in an amount of about 1.5 to 2.5 equivalents, optionally in the presence of a phase transfer agent. In some embodiments, the phase transfer agent is a tetraalkylammonium salt, such as tetrabutylammonium iodide, optionally in a polar, aprotic solvent. In some embodiments, the polar, aprotic solvent is THF. In some embodiments, the reacting of the Compound 7 is performed at a temperature of about 0 to about 40° C.

In some embodiments, the method disclosed herein comprises reacting Compound 6:

Compound 6

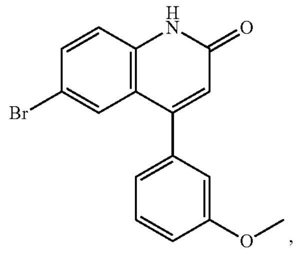

with a dehydrating reagent to form Compound 7. In some embodiments, the dehydrating reagent is $POCl_3$, oxalyl chloride, thionyl chloride, $PCl_3$, or $PCl_5$, for example, the dehydrating reagent is $POCl_3$. In some embodiments, the dehydrating reagent is used in an amount of about 2 to about 6 equivalents, optionally in a polar, aprotic solvent. In some embodiments, the polar, aprotic solvent is ACN, THE, 2-MeTHF, toluene, or DCM. In some embodiments, the reacting of the Compound 6 is performed at a temperature of about 40 to about 85° C.

In some embodiments, the method disclosed herein comprises reacting Compound 5:

Compound 5

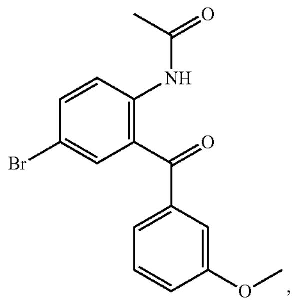, with (i) a base and (ii) an acid to form Compound 6. In some embodiments, the base is potassium tert-butoxide or sodium tert-butoxide. In some embodiments, the base is used in an amount of about 1.5 to about 3 equivalents. In some embodiments, the acid is HCl or $H_2SO_4$. In some embodiments, the acid is used in a stoichiometric or catalytic amount. In some embodiments, the reacting of the Compound 5 is done in a polar solvent. In some embodiments, the polar solvent is THF or toluene. In some embodiments, step (i) is performed at a temperature from about 10 to about 40° C. In some embodiments, step (ii) is performed at a temperature from about 10 to about 75° C.

In some embodiments, the method disclosed herein comprises acetylating Compound 4:

Compound 4

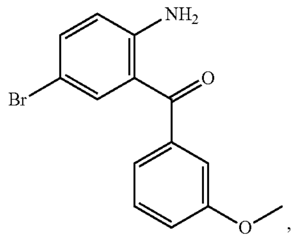, in the presence of an acetylating agent to form Compound 5. In some embodiments, the acetylating agent is (a) $Ac_2O$ or (b) AcCl and a base. In some embodiments, the base is TEA or DIPEA. In some embodiments, where (a) or (b) is performed in a polar solvent such as DCM or toluene, optionally at a temperature of about 15 to about 110° C., or (c) AcCl in water and an organic solvent such as $Et_2O$ or DCM. In some embodiments, the reaction work-up may comprise adding water, separating the layers, washing the organic phase with aq. $NaHCO_3$ and aq. NaCl. The resulting organic solution, e.g., toluene solution, may be used directly in the next step.

In some embodiments, the method disclosed herein comprises treating Compound 3:

Compound 3

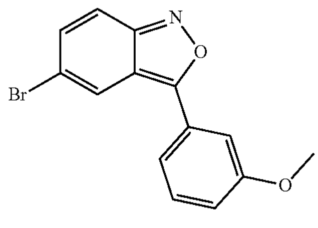, with a reducing agent to form Compound 4. In some embodiments, the reducing agent is $TiCl_3$ and a proton source. In some embodiments, the proton source is water. In some embodiments, the TiCl3 is used in an amount of about 1.5 to about 3 equivalents, optionally in a polar, aprotic solvent. In some embodiments, the polar, aprotic solvent is THF. In some embodiments, the reducing agent is $H_2$ and a hydrogenation catalyst. In some embodiments, the hydrogenation catalyst is Pd/C or Pt/C.

In some embodiments, the method disclosed herein comprises reacting 1-bromo-4-nitrobenzene with 2-(3-methoxyphenyl)acetonitrile in the presence of a base to form Compound 3. In some embodiments, the base is NaOH, KOH, or an alkoxide base. In some embodiments, the alkoxide base is sodium methoxide, sodium ethoxide, or potassium tert-butoxide, optionally in an amount of about 2 to about 10 equivalents, optionally in a polar solvent. In some embodiments, the polar solvent is MeOH, EtOH, MeOH/DCM, or EtOH/DCM, optionally at a temperature of about 0 to about 60° C. In some embodiments, the work-up may comprise washing with aq. $Na_2S_2O_3$, optionally preceded by quenching by the addition of aq. NaOCl. In some embodiments, the crude material may be purified by diluting with MeOH, stirring at a temperature of about 30 to about 60° C., then concentrating to about 4.5-5.5 V, cooling, and filtering the resulting solid.

In some embodiments, the method disclosed herein comprises reacting Compound 23:

Compound 23

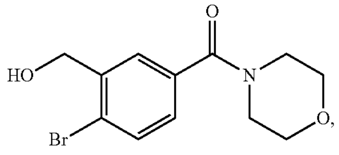

with a hydroxyl protecting group reagent to form Compound 11PG. In some embodiments, the PG is a silyl protecting group and the hydroxyl protecting group reagent is a silyl chloride reagent. In some embodiments, the PG is tert-butyldimethylsilyl and the hydroxyl protecting group reagent is TBSCl in the presence of a base. In some embodiments, the base is imidazole, TEA, TEA/DMAP, DIPEA, or pyridine, optionally in a polar, aprotic solvent. In some embodiments, the polar, aprotic solvent is DCM or THF.

In some embodiments, the method disclosed herein comprises reacting Compound 22:

Compound 22

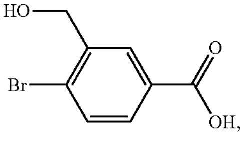

with morpholine under amide coupling conditions to form Compound 23. In some embodiments, the amide coupling conditions comprise a carbodiimide and a base. In some embodiments, the carbodiimide is EDC, EDCI, or DCC. In some embodiments, the base is TEA, DIPEA, or TEA/DMAP. In some embodiments, the amide coupling conditions comprise BOP, PyBOP, HOAt, HOBt, or $T_3P$.

In some embodiments, the method disclosed herein comprises converting Compound 21:

Compound 21

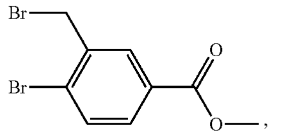

to Compound 22 by treating Compound 21 with a base and water. In some embodiments, the base is $Na_2CO_3$, $K_2CO_3$, NaOH, or KOH, optionally in a polar, protic solvent. In some embodiments, the polar, protic solvent is water, MeOH, EtOH, IPA, or a mixture thereof. In some embodiments, the polar, protic solvent is EtOH/water. In some embodiments, the treating of Compound 21 is performed at a temperature of about 50 to about 110° C. In some embodiments, Compound 21 is in a mixture with methyl 4-bromo-3-(dibromomethyl)benzoate, and the converting further comprises mixing the product of the treating step with a reducing agent. In some embodiments, the reducing agent is $NaBH_4$, $NaCNBH_3$, or $BH_3$·DMS.

In some embodiments, the method disclosed herein comprises reacting Compound 20:

Compound 20

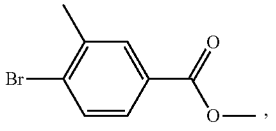

with a brominating agent and a radical initiator to form Compound 21. In some embodiments, the brominating agent is NBS, Br2, $NaBrO_3$/HBr, or 1,3-dibromo-5,5-dimethylhydantoin, and the radical initiator is light, heat, or AIBN. In some embodiments, the brominating agent is NBS and the radical initiator is light. In some embodiments, the reacting of the Compound 20 is performed in a continuous flow reactor with a photolysis flow cell with a wavelength in the range of about 300 to about 500 nm. In some embodiments, the reacting of the Compound 20 produces a mixture of Compound 21 and methyl 4-bromo-3-(dibromomethyl)benzoate.

In some embodiments, provided herein, is a process for preparing Compound 9 comprising reacting Compound 7:

Compound 7

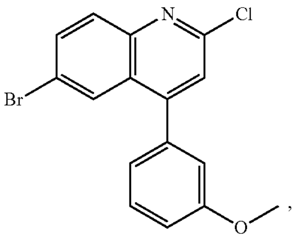

with a demethylating agent to form Compound 8:

Compound 8

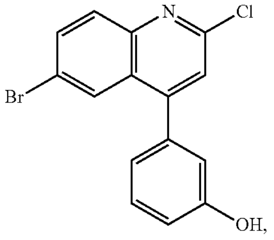

and reacting Compound 8 with TBSCl and a base to form Compound 9. In some embodiments, the demethylating agent is $BCl_3$ or $BBr_3$, optionally in an amount of about 1.5 to 2.5 equivalents, optionally in the presence of a phase transfer agent. In some embodiments, the phase transfer agent is a tetraalkylammonium salt, such as tetrabutylammonium iodide, optionally in a polar, aprotic solvent. In some embodiments, the polar, aprotic solvent is THF. In some embodiments, the reacting of the Compound 7 is performed at a temperature of about 0 to about 40° C. In some embodiments, the base is imidazole, TEA, TEA/DMAP, DIPEA, or pyridine. In some embodiments, the reacting is in a polar, aprotic solvent. In some embodiments, the polar, aprotic solvent is DCM or THF.

In some embodiments, the method disclosed herein comprises reacting Compound 6:

Compound 6

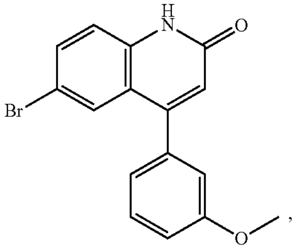

with a dehydrating reagent to form Compound 7. In some embodiments, the dehydrating reagent is $POCl_3$, oxalyl chloride, thionyl chloride, PCI, or PCL. In some embodiments, the dehydrating reagent is $POCl_3$. In some embodiments, the dehydrating reagent is used in an amount of about 2 to about 6 equivalents, optionally in a polar, aprotic solvent. In some embodiments, the polar, aprotic solvent is ACN, THF, 2-MeTHE, toluene, or DCM. In some embodiments, the reacting of the Compound 6 is performed at a temperature of about 40 to about 85° C.

In some embodiments, provided herein, is a process for preparing Compound 11:

Compound 11

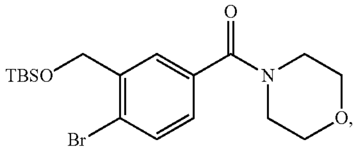

comprising reacting Compound 23:

Compound 23

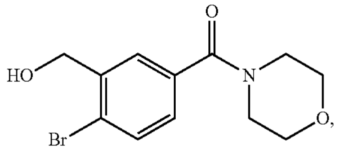

with TBSCl in the presence of a base to form Compound 11. In some embodiments, the base is imidazole, TEA, TEA/DMAP, DIPEA, or pyridine. In some embodiments, the reacting of the Compound 11 is performed in a polar, aprotic solvent. In some embodiments, the polar, aprotic solvent is DCM or THF.

In some embodiments, provided herein, is a process for preparing Compound 19:

Compound 19

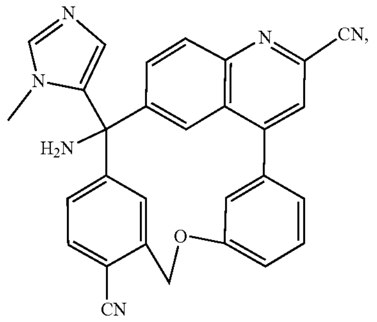

comprising chlorinating Compound 17:

Compound 17

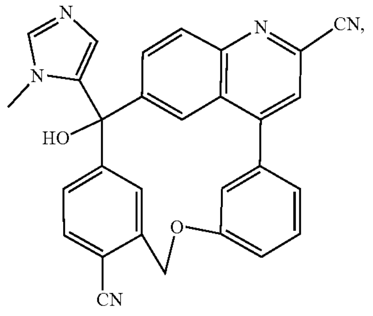

with a chlorinating agent to form Compound 18:

Compound 18

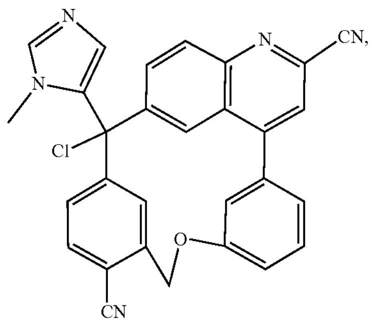

and reacting Compound 18 with an ammonia equivalent to form Compound 19. In some embodiments, the chlorinating agent is thionyl chloride, POCH, PC, or oxalyl chloride. In some embodiments, the chlorinating agent is thionyl chloride. In some embodiments, the chlorinating agent is used in an amount of about 2 to about 3.5 equivalents. In some embodiments, the chlorinating is performed in a polar, aprotic solvent. In some embodiments, the polar, aprotic solvent is DMI. In some embodiments, the chlorinating of the Compound 17 is performed at a temperature of about 10 to about 60° C.

In some embodiments, the ammonia equivalent is $NH_3$. In some embodiments, the ammonia equivalent is used in an amount of about 15 to about 50 equivalents, or about 40 to 50 equivalents. In some embodiments, the reacting of the Compound 18 is performed in a polar solvent, wherein the polar solvent is optionally selected from IPA, EtOH, MeOH, 1,4-dioxane, DMI, and mixtures thereof. In some embodiments, the polar solvent is MeOH. In some embodiments, the reacting of the Compound 18 is performed at a temperature from about 0 to about 40° C.

In some embodiments, provided herein, is a process for preparing Compound 14:

Compound 14

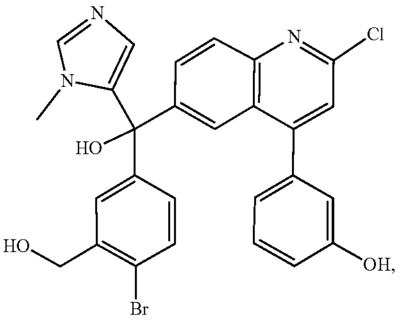

comprising deprotecting Compound 13:

Compound 13

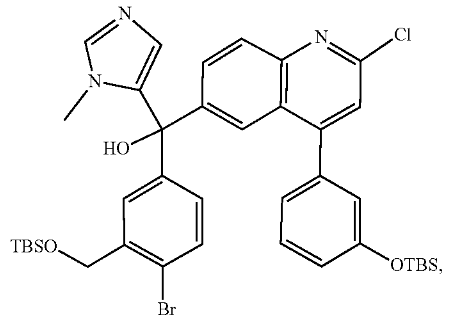

under deprotecting conditions to form Compound 14. In some embodiments, the deprotecting conditions comprise TBAF, MSA, MSA/$H_2O$, or HCl/$H_2O$, optionally in a polar solvent. In some embodiments, the solvent is THE, ACN, EtOAc, acetone, toluene, or a mixture thereof. In some embodiments, the deprotecting conditions comprise 3 N HCl in THF or THF/toluene (optionally about 4:1 to about 1:4 THF/toluene, or about 2:1 to about 3:1 THF/toluene). In some embodiments, the deprotecting of the Compound 14 at a temperature of about 0 to about 40° C.

In some embodiments, provided herein, is a process for preparing Compound 12:

Compound 12

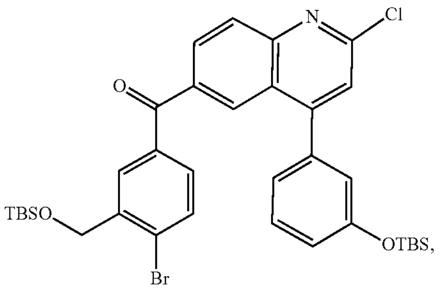

comprising condensing Compound 11:

Compound 11

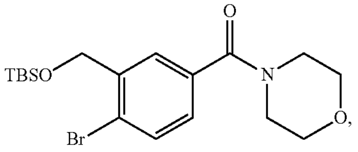

with Compound 9:

Compound 9

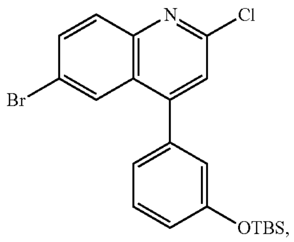

to form Compound 12. In some embodiments, the process comprises reacting Compound 9 with a metalating agent, such as BuLi or isopropylMgCl/LiCl, to form a reactive species. In some embodiments, the metalating agent is used in an amount of from about 1 to about 1.3 equivalents, optionally in a polar, aprotic solvent. In some embodiments, the polar, aprotic solvent is THF. In some embodiments, mixing the reactive species with Compound 11, optionally wherein the reacting of the Compound 9 and the mixing of the reactive species with Compound 11 are performed at a temperature from about −60 to about −85° C.

In some embodiments, provided herein, is a process for preparing Compound 13, comprising coupling Compound 12 with 1-methylimidazole to form Compound 13. In some embodiments, the process comprises comprising metalating 1-methylimidazole at the 5-position to form a reactive species, and mixing the reactive species with Compound 12. In some embodiments, the reactive species is (1-methyl-2-(protecting group)-1H-imidazol-5-yl)lithium, optionally wherein the 1-methyl-2-(protecting group)-1H-imidazol-5-yl)lithium is (1-methyl-2-(triethylsilyl)-1H-imidazol-5-yl)lithium. In some embodiments, the metalating comprises reacting 1-methyl-imidazole with (i) BuLi, (ii) TESCl, and (iii) BuLi, to form the (1-methyl-2-(triethylsilyl)-1H-imidazol-5-yl)lithium. In some embodiments, the metalating is performed at a temperature of about −30 to about −90° C. In some embodiments, the coupling is performed at a temperature of about −30 to about −90° C.

In some embodiments, where one or more steps of the processes disclosed herein employ a transition metal catalyst, the process may comprise reducing the amount of transition metal materials, such as palladium-based materials or zinc-based materials, from a reaction product or a subsequent reaction product. In some embodiments, the reducing is performed on Compound 1 or an intermediate in the synthetic process, so that Compound 1 meets transition metal or palladium specification guidelines ("Guideline on the Specification Limits for Residues of Metal Catalysts" European Medicines Agency *Preauthorisation Evaluation of Medicines for Human Use*, London, January 2007, Doc. Ref. CPMP/SWP/QWP/4446/00 corr). In some embodiments, the process comprises reducing the amount of palladium and/or zinc in Compound 1 or an intermediate. In some embodiments, reducing the amount of palladium and/or zinc mixed with a reaction product such as Compound 1 comprises treating the reaction product/transition metal mixture with an adsorbing agent, and extracting agent, or a crystallizing agent, or a combination thereof. In some embodiments, reducing the amount of palladium comprises treating the reaction product with an extracting agent and then treating the resulting material with an adsorbing agent. In some embodiments, the reaction product may be treated once, more than once, or twice with an adsorbing agent.

Examples of adsorbing agents include, but are not limited to, trithiocyanuric acid (trimercaptotriazine; TMT), a TMT derivative (such as solid TMT, polystyrene-bound TMT, silica gel-bound TMT, SiliaMetS® DMT, mercapto-porous polystyrene-bound TMT, or TMT-3Na), derivatized silica gel (such as silica gel-linker-thiol, silica gel-$(CH_2)_3$—SH, silica gel-$(CH_2)_3$—S—$(CH_2)_2$—SH, or such as silica gel-linker-amine, such as silica gel-$(CH_2)_3$—$NH_2$, or silica gel-$(CH_2)_3$—[NH—$(CH_2)_2]_{1-2}$—$NH_2$, or silica gel-$(CH_2)_3$—NHC(S)$NHCH_3$, such as SiliaMetS® metal scavengers), polystyrene-bound ethylenediamine, derivatized polyolefin fibers (e.g., grafted with acrylic acid, vinyl pyridine, styrene sulfonic acid, styryl thiol, styryl diphenylphosphine, mercaptoethylacrylate, or acrylate alpha-hydroxyl thiol, such as Smopex® metal scavengers), activated charcoal (such as DARCO® KB-G and DARCO® KB-WJ), or glass bead sponges. Examples of crystallizing agents include, but are not limited to, N-acetylcysteine, thiourea, 2-methyl-thiourea, thioglycerol, a hemi-maleate salt, or $Bu_3P$. Examples of extracting agents include, but are not limited to, N-acetylcysteine, L-cysteine, and $Bu_3P$ in lactic acid. See, e.g., Garrett et al., *Adv. Synth. Catal.* 2004, 346, 889-900.

Examples of additional adsorbing agents suitable for zine removal include zine chelators such as EDTA and EDTA derivatives, for example tetrasodium EDTA, and SiliaMetS® metal scavengers such as SiliaMetS DEAM, SiliaMetS diamine, SiliaMetS DOTA, SiliaMetS Imidazole, and SiliaMetS Triamine.

In some embodiments, Compound 1 is treated with a mixture of tetrasodium EDTA and TMT-3Na in water at a temperature of about 20 to about 40° C., then optionally purified by column chromatography.

In some embodiments, after the reducing, the amount of palladium and/or in the reaction product is about 100 ppm or less, or about 10 ppm, or is undetectable. In some embodiments, the presence and/or amount of residual heavy metal (e.g., palladium or zine) impurities is determined using methods known in the art. In some embodiments, the presence and/or amount of residual heavy metal (e.g., palladium or zinc) impurities is determined using inductively coupled plasma mass spectrometry (ICP-MS). In some embodiments, the presence and/or amount of residual heavy metal (e.g., palladium) impurities is determined using techniques described in U.S. Pharmacopeia General Chapter <232> Elemental Impurities—Limits.

In some embodiments, provided herein, is a compound selected from:

(12)

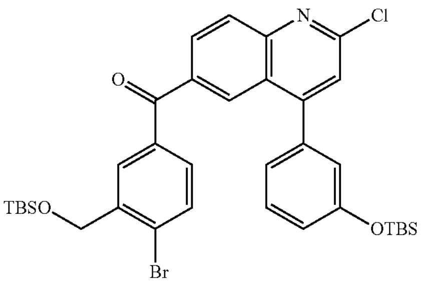

(13)

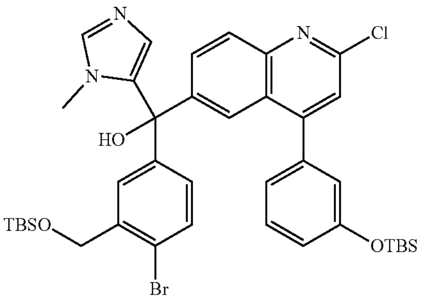

(7)

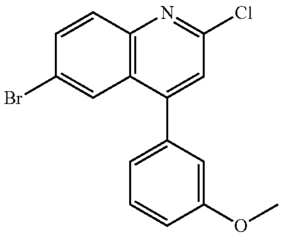

, (11)

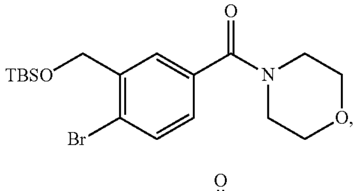

, (23)

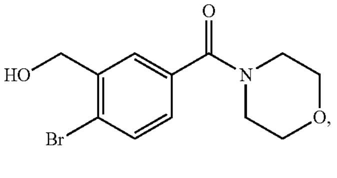

, and salts thereof.

In some embodiments, provided herein, is a compound selected from: (R)-chlocyphos, (S)-chlocyphos, (+)-tartaric acid, (−)-tartaric acid, (+)-camphorsulfonic acid, (−)-camphorsulfonic acid, L-(−)-di-p-anisoyltartaric acid, D-(+)-di-p-anisoyltartaric acid, L-(−)-di-toluoyltartaric acid, D-(+)-di-toluoyltartaric acid, (R)-BINAP phosphate, (S)-BINAP phosphate, di-benzoyl-l-tartaric acid, or di-benzoyl-D-tartaric acid salt of Compound 1 or Compound 2. In some embodiments, the salt is the di-benzoyl-l-tartaric acid or di-benzoyl-D-tartaric acid salt of Compound 1 or Compound 2. In some embodiments, the salt is Compound 1 L-DBTA salt.

5.6 Uses and Methods 5.6.1 Therapeutic Uses and Methods

RAS isoforms associate with the inner surface of the plasma membrane to transduce extracellular signals. To become active, RAS undergoes several post-translational modifications. Among the first steps in becoming activated is the farnesylation of the cysteine in the CAAX box at the C-terminal end (where C represents cysteine, A represents an aliphatic amino acid, and X represents any amino acid). Rowinsky, E. K., et al., J. Clin. Oncol. 1999, 17, 3631-3652. The enzyme farnesyltransferase (FTase) recognizes the CAAX motif and transfers a 15-carbon farnesyl isoprenoid from farnesyl diphosphate to the cysteine residue. The AAX amino acids subsequently are cleaved by Ras-converting enzyme I, and the farnesylated cysteine is carboxymethylated by isoprenylcysteine carboxyl methyltransferase. Prior, I. A., et al., J. Cell Sci. 2001, 114, 1603-1608. Further palmitoylation (KRAS4A, NRAS, and HRAS or the presence of a polybasic domain (KRAS4B) leads to anchoring of the protein in the plasma membrane. Hancock, J. F., et al., Cell 1990, 63, 133-139. The observations suggest prenylation is required for the function of all RAS isoforms, including their mutated forms. However, some farnesylated proteins—including KRAS and NRAS—can be rescued from membrane displacement in the presence of a farnesyltransferase inhibitor (FTI) by an alternative prenylation by the enzyme geranylgeranyltransferase (GGTase). Zhang, F. L., et al., J. Biol. Chem. 1997, 272, 10232-10239; Whyte, D. B., et al., J. Biol. Chem. 1997, 272, 14459-14464. Conversely, the third family member, HRAS, is not a GGTase substrate, and thus its membrane localization and cellular function are diminished by an FTI. Whyte, D. B., et al. Accordingly, the use of FTIs to target enriched patient populations of tumors, for example tumors dependent on farnesylated proteins, such as HRAS, for example tumors harboring HRAS mutations, should provide clinical benefit.

One particular FTI that is in clinical development is tipifarnib. The efficacy of tipifarnib was examined in a series of cell- and patient-derived xenograft models of head and neck squamous cell carcinoma (HNSCC). Gilardi, M., et al., Mol. Cancer Ther. 2020, 19, 1784-1796. Genomic analyses have revealed that HRAS mutations occur in 6% of HNSCC at initial diagnosis (Hoadley, K. A., et al., Cell 2018, 173, 291-304) and in 15% of patients during acquisition of resistance to cetuximab (Braig, F., et al., Oncotarget 2016, 7, 42988-42995), and HRAS mutations have been demonstrated to correlate with reduced response of HNSCC patients to cetuximab treatment. “Rampias, T., et al., Clin. Cancer Res. 2014, 20, 2933-2946.

HRAS is also recurrently mutated in other cancer types, including urothelial cell carcinoma and salivary gland tumors, and 24% of HRAS mutant metastatic urothelial carcinoma patients treated with tipifarnib experienced an objective response. In addition, of 13 pts with recurrent/metastatic salivary gland tumors (SGT) treated with tipifarnib, one experienced an objective response and an additional seven patients had stable disease as best response. Ho, A. L., et al., J. Clin. Oncol. 2020, 38, 6504. Other tumor types exhibiting recurrent HRAS driver mutations include lung squamous cell carcinoma, thyroid cancer, pheochromocytoma and paraganglioma. Hoadley, K. A., et al.

In some embodiments, a pharmaceutically acceptable salt of Compound 1, or a pharmaceutically acceptable solvate thereof, or a solid form comprising Compound 1, or a pharmaceutically acceptable salt thereof, or a pharmaceutically acceptable solvate thereof, is a farnesyltransferase inhibitor. In some embodiments, the pharmaceutically acceptable salt of Compound 1, or pharmaceutically acceptable solvate thereof, or the solid form comprising Compound 1, or pharmaceutically acceptable salt thereof, or a pharmaceutically acceptable solvate thereof, is a selective farnesyltransferase inhibitor, relative to inhibition of geranylgeranyl transferase type-1, such as geranylgeranyl transferase type-1. In some embodiments, provided herein is a method of inhibiting a farnesyltransferase, comprising contacting the farnesyltransferase with an effective amount of the pharmaceutically acceptable salt of Compound 1, or pharmaceutically acceptable solvate thereof, or the solid form comprising Compound 1, or pharmaceutically acceptable salt thereof, or a pharmaceutically acceptable solvate thereof. In some embodiments, the method of inhibiting a farnesyltransferase comprises contacting the farnesyltransferase with an effective amount of a pharmaceutical composition, as disclosed herein, comprising a pharmaceutically acceptable salt of Compound 1, or a pharmaceutically acceptable solvate thereof, or a solid form comprising Compound 1, or a pharmaceutically acceptable salt thereof, or a pharmaceutically acceptable solvate thereof, and a pharmaceutically acceptable excipient. In some embodiments, the contacting of the farnesyltransferase takes place in a cell. In some embodiments, the farnesyltransferase is present in a cell. In some embodiments, the cell is in a subject. In some embodiments, the cell is a mammalian cell. In some embodiments, the cell a human cell. In some embodiments, the subject suffers from a cancer dependent on a farnesylated protein. In some embodiments, the subject is a human.

In some embodiments, the method inhibits farnesylation of H-Ras protein. In some embodiments, the H-Ras protein has a mutation. In some embodiments, the H Ras protein mutation is or comprises a modification in a codon that encodes an amino acid substitution at a specific position selected from G12, G13, Q61, Q22, K117, A146, and any combination thereof, in the corresponding mutant H-Ras protein. In some embodiments, the inhibiting of the farnesylation of the H-Ras protein, such as an H-Ras protein having a mutation, takes place in a cell. In some embodiments, the cell is in a subject. In some embodiments, the cell is a mammalian cell. In some embodiments, the cell a human cell. In some embodiments, the inhibition of the farnesyltransferase present in the cell takes place in a subject suffering from cancer dependent on a farnesylated protein. In some embodiments, the cancer dependent on a farnesylated protein is a solid tumor. In some embodiments, the cancer dependent on a farnesylated protein is a cancer dependent on one or more farnesylated proteins. In some embodiments, the cancer dependent on a farnesylated protein is dependent on the farnesylated protein(s) for the progression and/or survival of said cancer. In some embodiments, the cancer dependent on a farnesylated protein is a cancer dependent on farnesylated H-Ras protein. In some embodiments, the cancer dependent on a farnesylated protein has an H-Ras protein mutation. In some embodiments, the H Ras protein mutation is or comprises a modification in a codon that encodes an amino acid substitution at a specific position selected from G12, G13, Q61, Q22, K117, A146, and any combination thereof, in the corresponding mutant H-Ras protein. In some embodiments, the cancer dependent on a farnesylated protein is head and neck cancer. In some embodiments, the head and neck cancer is head and neck squamous cell carcinoma (HNSCC). In some embodiments, the head and neck cancer, for example, HNSCC, is dependent on one or more farnesylated proteins, such as dependent on a farnesylated H-Ras protein. In some embodiments, the head and neck cancer, for example, HNSCC, has an H-Ras protein mutation. In some embodiments, the cancer dependent on a farnesylated protein is carcinoma, melanoma, sarcoma, or chronic granulomatous disease. For example, in some embodiments, the cancer dependent on a farnesylated protein is thyroid cancer, head and neck cancers, urothelial cancers, salivary cancers, cancers of the upper digestive tract, bladder cancer, breast cancer, ovarian cancer, brain cancer, gastric cancer, prostate cancer, lung cancer, colon cancer, skin cancer, liver cancer, or pancreatic cancer. In some embodiments, the cancer is squamous cell carcinoma (SCC). For example, in some embodiments, the SCC is head and neck SCC (HNSCC), lung SCC (LSCC), thyroid SCC (TSCC), esophagus SCC (ESCC), bladder SCC (BSCC) or urothelial carcinoma (UC). In some embodiments, the SCC is HNSCC. In some embodiments, the SCC is human papillomavirus (HPV)-negative SCC. In some embodiments, the HNSCC is HPV-negative HNSCC. For example, in some embodiments, the HNSCC is HNSCC of the trachea, HNSCC of the maxilla, HNSCC of the oral cavity. In some embodiments, the SCC, for example, HNSCC, lung SCC, thyroid SCC, esophagus SCC, bladder SCC or urothelial carcinoma, is dependent on one or more farnesylated proteins, such as dependent on a farnesylated H-Ras protein. In some embodiments, the HNSCC is dependent on one or more farnesylated proteins, such as dependent on a farnesylated H-Ras protein. In some embodiments, the SCC, for example, HNSCC, lung SCC, thyroid SCC, esophagus SCC, bladder SCC or urothelial carcinoma, has an H-Ras protein mutation. In some embodiments, the HNSCC has an H-Ras protein mutation. In some embodiments, the subject is a human.

In some embodiments, provided herein is a method of treating cancer dependent on a farnesylated protein in a subject, comprising administering a therapeutically effective amount of a pharmaceutically acceptable salt of Compound 1, or a pharmaceutically acceptable solvate thereof, or a solid form comprising Compound 1, or a pharmaceutically acceptable salt thereof, or a pharmaceutically acceptable solvate thereof, to the subject having cancer dependent on a farnesylated protein. In some embodiments, the method of treating cancer dependent on a farnesylated protein in a subject comprises administering a therapeutically effective amount of a pharmaceutical composition, as disclosed herein, containing a pharmaceutically acceptable salt of Compound 1, or a pharmaceutically acceptable solvate thereof, or a solid form comprising Compound 1, or a pharmaceutically acceptable salt thereof, or a pharmaceutically acceptable solvate thereof, and a pharmaceutically acceptable excipient, to the subject having cancer dependent on a farnesylated protein. In some embodiments, the cancer dependent on a farnesylated protein is a solid tumor. In some embodiments, the cancer dependent on a farnesylated protein is a cancer dependent on one or more farnesylated proteins. In some embodiments, the cancer dependent on a farnesylated protein is dependent on the farnesylated protein(s) for the progression and/or survival of said cancer. In some embodiments, the cancer dependent on a farnesylated protein is a cancer dependent on farnesylated H-Ras protein. In some embodiments, the cancer dependent on a farnesylated protein has an H-Ras protein mutation. In some embodiments, the H Ras protein mutation is or comprises a modification in a codon that encodes an amino acid substitution at a specific position selected from G12, G13, Q61, Q22, K117, A146, and any combination thereof, in the corresponding mutant H-Ras protein. In some embodiments, the cancer dependent on a farnesylated protein is head and neck cancer. In some embodiments, wherein the head and neck cancer is head and neck squamous cell carcinoma (HNSCC). In some embodiments, the head and neck cancer, for example, HNSCC, is dependent on one or more farnesylated proteins, such as dependent on a farnesylated H-Ras protein. In some embodiments, the head and neck cancer, for example, HNSCC, has an H-Ras protein mutation. In some embodiments, the cancer dependent on a farnesylated protein is carcinoma, melanoma, sarcoma, or chronic granulomatous disease. For example, in some embodiments, the cancer dependent on a farnesylated protein is thyroid cancer, head and neck cancers, urothelial cancers, salivary cancers, cancers of the upper digestive tract, bladder cancer, breast cancer, ovarian cancer, brain cancer, gastric cancer, prostate cancer, lung cancer, colon cancer, skin cancer, liver cancer, or pancreatic cancer. In some embodiments, the cancer dependent on a farnesylated protein is Squamous Cell Carcinoma (SCC). For example, in some embodiments, the SCC is head and neck SCC (HNSCC), lung SCC (LSCC), thyroid SCC (TSCC), esophagus SCC (ESCC), bladder SCC (BSCC) or urothelial carcinoma (UC). In some embodiments, the SCC is HNSCC. In some embodiments, the SCC is human papillomavirus (HPV)-negative SCC. In some embodiments, the HNSCC is HPV-negative HNSCC. For example, in some embodiments, the HNSCC is HNSCC of the trachea, HNSCC of the maxilla, HNSCC of the oral cavity. In some embodiments, the SCC, for example, HNSCC, lung SCC, thyroid SCC, esophagus SCC, bladder SCC or urothelial carcinoma, is dependent on one or more farnesylated proteins, such as dependent on a farnesylated H-Ras protein. In some embodiments, the HNSCC is dependent on one or more farnesylated proteins, such as dependent on a farnesylated H-Ras protein. In some embodiments, the SCC, for example, HNSCC, lung SCC, thyroid SCC, esophagus SCC, bladder SCC or urothelial carcinoma, has an H-Ras protein mutation. In some embodiments, the HNSCC has an H-Ras protein mutation. In some embodiments, the subject is a human.

In some embodiments, the method of treating cancer dependent on a farnesylated protein, as disclosed herein, the presence or absence of the H-Ras mutation has been determined prior to the treating. In some embodiments, determining the presence or absence of the H-Ras mutation comprises analyzing nucleic acids obtained from a sample from the subject. In some embodiments, said sample is a tissue biopsy. In some embodiments, said sample is a tumor biopsy. In some embodiments, the H-Ras mutation is determined by sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay. In some embodiments, the H-Ras mutation is determined by PCR. In some embodiments, the H-Ras mutation is determined by sequencing.

In some embodiments, the pharmaceutically acceptable salt of Compound 1, or pharmaceutically acceptable solvate thereof, or the solid form comprising Compound 1, or pharmaceutically acceptable salt or solvate thereof, as disclosed herein, is metabolically stable, for example, metabolically stable to liver metabolism in a subject, such as metabolically stable to liver metabolism in a human.

5.6.2 Doses and Regimens

A compound described herein can be delivered in the form of a pharmaceutical composition which comprises a therapeutically effective amount of a pharmaceutically acceptable salt of Compound 1, or a pharmaceutically acceptable solvate thereof, or a solid form comprising Compound 1, or a pharmaceutically acceptable salt thereof, or a pharmaceutically acceptable solvate thereof, and a pharmaceutically acceptable excipient. In some embodiments, the therapeutically effective amount in the pharmaceutical composition is determined based on the free base equivalent amount of the pharmaceutically acceptable salt of Compound 1, or pharmaceutically acceptable solvate thereof, or the solid form comprising Compound 1, or pharmaceutically acceptable salt thereof, or a pharmaceutically acceptable solvate thereof. The pharmaceutical compositions disclosed herein are intended to be administered by a suitable route, including but not limited to orally, parenterally, rectally, topically and locally. In some embodiments, a selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A suitable daily dose of a compound described herein administered to a subject will be that amount of the compound which, in some embodiments, can be the lowest dose effective to produce a therapeutic effect. Such an effective dose will generally depend upon the factors described herein. In some embodiments, a therapeutically effective amount of the pharmaceutically acceptable salt of Compound 1, or pharmaceutically acceptable solvate thereof, or the solid form comprising Compound 1, or pharmaceutically acceptable salt thereof, or a pharmaceutically acceptable solvate thereof, as the active ingredient, is in an amount of from about 0.01 up to about 500 mg/kg daily, either as a single dose or subdivided into more than one dose, or more particularly in an amount of from about 0.01 to about 400 mg/kg daily, such as in an amount of from about 0.01 to about 300 mg/kg daily, about 0.01 to about 200 mg/kg daily, about 0.01 to 100 mg/kg daily, about 0.01 to about 50 mg/kg daily, about 0.01 to about 25 mg/kg daily, or about 0.01 to about 10 mg/kg daily, such as in an amount of about 0.01 mg/kg daily, about 0.025 mg/kg daily, about 0.05 mg/kg daily, about 0.075 mg/kg daily, about 0.1 mg/kg daily, about 0.25 mg/kg daily, about 0.5 mg/kg daily, about 0.75 mg/kg daily, about 1 mg/kg daily, about 2.5 mg/kg daily, about 5 mg/kg daily, about 7.5 mg/kg daily, about 10 mg/kg daily, about 15 mg/kg daily, about 20 mg/kg daily, about 25 mg/kg daily, about 50 mg/kg daily, about 75 mg/kg daily, about 100 mg/kg daily, about 100 mg/kg daily, about 200 mg/kg daily, about 300 mg/kg daily, about 400 mg/kg daily, or about 500 mg/kg daily. For example, in some embodiments, the dosage or therapeutically effective amount of the pharmaceutically acceptable salt of Compound 1, or pharmaceutically acceptable solvate thereof, or the solid form comprising Compound 1, or pharmaceutically acceptable salt thereof, or a pharmaceutically acceptable solvate thereof, as disclosed herein, is in an amount of from about 0.01 to about 25 mg/kg daily, about 0.01 to about 20 mg/kg daily, about 0.01 to about 15 mg/kg daily, about 0.01 to about 10 mg/kg daily, about 0.01 to about 7.5 mg/kg daily, about 0.01 to about 5 mg/kg daily, or about 0.01 to about 2.5 mg/kg daily, such as in an amount of about 0.01 mg/kg daily, about 0.025 mg/kg daily, about 0.05 mg/kg daily, about 0.075 mg/kg daily, about 0.1 mg/kg daily, about 0.25 mg/kg daily, about 0.5 mg/kg daily, about 0.75 mg/kg daily, about 1 mg/kg daily, about 2.5 mg/kg daily, about 5 mg/kg daily, about 7.5 mg/kg daily, about 10 mg/kg daily, about 15 mg/kg daily, about 20 mg/kg daily. In some embodiments, the therapeutically effective amount of the pharmaceutically acceptable salt of Compound 1, or pharmaceutically acceptable solvate thereof, or the solid form comprising Compound 1, or pharmaceutically acceptable salt thereof, or a pharmaceutically acceptable solvate thereof, is contained in a pharmaceutical composition as described herein. Actual dosage levels of the active ingredients in the pharmaceutical compositions described herein can be varied so as to obtain an amount of the active ingredient which is effective to achieve the desired therapeutic response for a particular subject, such as a human patient, composition, and mode of administration, without being toxic to the subject. In some instances, dosage levels below the lower limit of the aforesaid range can be more than adequate, while in other cases still larger doses can be employed without causing any harmful side effect, e.g., by dividing such larger doses into several small doses for administration throughout the day. Dosages may reflect the amount of compound, or the amount of compound in a particular pharmaceutical form, or the free base form equivalent of the particular pharmaceutical form.

In some embodiments, the treatment with a pharmaceutically acceptable salt of Compound 1, or a pharmaceutically acceptable solvate thereof, or a solid form comprising Compound 1, or a pharmaceutically acceptable salt thereof, or a pharmaceutically acceptable solvate thereof, is administered in combination with radiotherapy, or radiation therapy.

It is understood that subheadings throughout this document do not limit the subject matter discussed to only those sections, but apply, and are contemplated to apply, to each embodiment disclosed in the instant application.

The disclosed compounds herein, including exemplified compounds and intermediate compounds, were named using ChemDraw® version 18.1.4.4 or later.

6. EXAMPLES

| Abbreviations: | |
|---|---|
| ACN: Acetonitrile | MTBE: tert-Butyl methyl ether |
| CPME: Cyclopentyl methyl ether | NaOMe: Sodium methoxide |
| DCM: Dichloromethane | NBS: N-Bromosuccinimide |
| DEA: Diethylamine | n-BuLi: n-Butyllithium |
| DMA: Dimethylacetamide | Pd(Ph3)4: Tetrakis(triphenylphosphine)palladium(0) |
| DMAc: Dimethylacetamide | Pd2(dba)3: Tris(dibenzylideneacetone)dipalladium(0) |
| DMF: Dimethylformamide | PPh3: Triphenylphosphine |
| DMI: 1,3-Dimethyl-2-imidazolidinone | SFC: Supercritical fluid chromatography |
| DMSO: Dimethyl sulfoxide | T3P: Propanephosphonic acid anhydride |
| DPPF: 1,1'-Bis(diphenylphosphino)ferrocene | TBAF: Tetra-n-butylammonium fluoride |
| Et3SiCl: Chlorotriethylsilane | t BuOK: Potassium tert-butoxide |
| EtOAc: Ethyl acetate | TEA: Triethylamine |
| EtOH: Ethanol | TFA: Trifluoroacetic acid |
| IPA: Isopropanol | THF: Tetrahydrofuran |
| IPAc: Isopropyl acetate | TBSCl: Tri(n-butyl)silyl chloride |
| 2-MeTHF: 2-Methyl-Tetrahydrofuran | TIPSCl: Triisopropylsilyl chloride |
| MEK: Butanone | TMEDA: Tetramethylethylenediamine |
| MeOH: Methanol | |

Analytical Methods

XRPD: XRPD diffractograms were collected with an X-ray diffractometer (Instrument: PANalytical, Empyrean; Radiation, Cu Kα (λ=1.5418 Å); Detector, PIXcel$^{1D}$; Scan angle, 3-40° (2θ); Scan step, 0.013° (2θ); Tube voltage/current, 45 kV/40 mA; Divergence slit, ⅛°; Rotation, On; Sample holder, Zero-background sample pan). The sample was prepared on a zero-background silicon wafer by gently pressing onto the flat surface.

PLM: Light microscopy analysis was performed using an ECLIPSE LV100POL microscope (Nikon, Japan). Each sample was placed on a glass slide with a drop of immersion oil and covered with a glass slip. The sample was observed using a 4-20× objective with polarized light.

DSC: DSC analysis was performed with a TA instrument (Discovery DSC 250). About 1-3 mg of sample was placed into an aluminum pan with a pin hole and heated from 25 to 300° C. at a heating rate of 10° C./min under $N_2$ purge gas at a flow rate of 50 mL/min.

TGA: TGA analysis was performed with a TA instrument (Discovery TGA 55). About 1-5 mg of sample was loaded onto a pre-tared aluminum pan and heated from rt to 300° C. at a heating rate of 10° C./min under $N_2$ purge gas at flow rates of 40 mL/min (balance chamber) and 60 mL/min (sample chamber).

HPLC: unless otherwise indicated, HPLC analysis for all polymorph, salt, and solubility in media experiments, was conducted on an Agilent 1260 series instrument, with a Waters XBridge Shield RP18 4.6*150 mm, 3.5 μm column, column temperature 40° C., mobile phase A: 0.1% $H_3PO_4$ in water; B: MeOH:ACN 3:7 v/v, with a flow rate of 1.5 mL/min, an injection volume of 5 μL, a DAD detector at a 210 nm wavelength, and a gradient of 12 min, 100% A, 3 min 50% A, 2.1 min 5% A, 5 min 100% A.

HPLC: unless otherwise indicated, HPLC analysis for all chiral salt screen experiments was conducted on an Agilent 1290 series HPLC instrument, with Waters XBridge BEH C18 XP (2.1×50 mm, 2.5 μm) column, with a flow rate of 0.6 mL/min, a DAD detector, at 215 nm and 252 nm wavelengths, Mobile phase A: 10 mM $NH_4OAc$ (water/MeOH/ACN 900/60/40); Mobile phase B: 10 mM $NH_4OAc$ (water/MeOH/ACN 100/540/360), with a gradient of 1.5 min 80% A, 1.5 min 0% A.

UPC: Unless otherwise indicated, UPC analysis was conducted on a Waters Acquity UPC$^2$ system with UV detector and QDA detector, using a Daicel Chiralpak ID-3

(3.0×150 mm, 3 μm) column, mobile phase A: 65% $CO_2$, mobile phase B: 35% MeOH+0.2% $NH_4OH$ (25%, aq.), isocratic pump program, run time of 10 min, a flow rate of 1.2 mL/min, UV detection at 250 nm, and a column temperature of 40° C.

The following Examples are presented by way of illustration, not limitation. Unless stated otherwise, the Compound 1 starting material used in the preparation of Forms 1-24, as detailed in Examples 1-24, was Compound 1 (amorphous, free base), prepared according to Example 52.

EXAMPLE 1: Preparation of Compound 1, Free Base, Hemi-Hydrate (Form 1)

Method A: Compound 1, free base (20 mg), was characterized as amorphous by polarized light microscopy and by XRPD (FIG. 1).

The material was diluted with (a) acetone/$H_2O$ (1/9 v/v), (b) ACN/$H_2O$ (1/9 v/v), or THF/$H_2O$ (1/9 v/v) (0.5 mL). The resulting mixtures were stirred at 50° C. for 4 d (acetone/$H_2O$) or 11 d (ACN/$H_2O$ or THF/$H_2O$). The resulting solids were collected by filtration and analyzed as Compound 1, free base, hemi-hydrate (Form 1) by XRPD analysis.

Method B: Amorphous Compound 1, free base (250 mg), was mixed with 3 mL of acetone/$H_2O$ (1/9, v/v) at 50° C. for 17 h. The resulting suspension was stirred at rt for 1 h and then filtered. The solid was collected and vacuum-dried at 40° C. for 4 h. Compound 1, free base, hemi-hydrate, was obtained in 91% yield and 99.61% purity (HPLC) with 0.4% residual acetone ($^1$H NMR, Bruker, 400 MHz, DMSO-d6).

Method C: To a solution of Compound 1, free base, in ACN (3 V) at 45±5° C. was added purified water (3 V) over 1 h, followed by seed crystals of Compound 1, free base, hemi-hydrate (Form 1). The resulting mixture was stirred for 0.5 h at 45±5° C. and then treated with purified water (6 V) over 2 h. The resulting mixture was stirred for 2 h at 45±5° C., then cooled to 25±5° C. and stirred for 7 h. The resulting solid was collected by filtration, washed with purified water, and oven-dried at 60° C. under vacuum for 8 d to obtain Compound 1, free base, hemi-hydrate (Form 1). HPLC: 98.8% Compound 1, 0.4% Compound 2.

Method D: Single Crystal Analysis of Compound 1, Free Base, Hemi-Hydrate (Form 1). A crystal structure of Form 1 was collected and solved. Crystalline Compound 1, free base, hemi-hydrate, was dissolved in ACN/$H_2O$ (0.3 mL) at 50.0 mg/mL at 60° C. The solution was filtered at rt and the filtrate was covered with pin-hole film and held at rt for 20 h to allow evaporative crystallization. The resulting plate crystals with agglomerates were collected and analyzed by single crystal X-ray diffraction (180 K, Rigaku XtaLAB Synergy-DW diffractometer, with Cu Kα radiation (λ=1.54184 Å). All non-hydrogen atoms could be located directly from the difference Fourier maps. Framework hydrogen atoms were placed geometrically and constrained using the riding model to the parent atoms. Final structure refinement was done using the SHELXL program by minimizing the sum of squared deviations of $F^2$ using a full-matrix technique. The single crystal structure of Form 1 is monoclinic in $P2_1$ space group with formula of $2(C_{29}H_{20}N_6O)\cdot H_2O$, a hemi-hydrate. As shown in FIG. 2, analysis confirmed two Compound 1 molecules and one water molecule in each asymmetric unit, the unit cell contains two asymmetric units, and the "S" absolute configuration for the chiral carbon. A summary of structural data for Compound 1 (Form 1) is provided in Table 1,

TABLE 1

Summary of structural data for Compound 1, free base, hemi-hydrate (Form 1)

| | |
|---|---|
| Empirical formula | $C_{58}H_{42}N_{12}O_3$ |
| Formula weight | 955.03 |
| Temperature/K | 293(2) |
| Crystal system | monoclinic |
| Space group | $P2_1$ |
| a/Å | 15.2657(2) |
| b/Å | 7.93780(10) |
| c/Å | 20.7456(3) |
| α/° | 90 |
| β/° | 107.8170(10) |
| γ/° | 90 |
| Volume/Å$^3$ | 2393.30(6) |
| Z | 2 |
| $\rho_{calc}$/g/cm$^3$ | 1.325 |
| μ/mm$^{-1}$ | 0.688 |
| F(000) | 996.0 |
| Crystal size/mm$^3$ | 0.35 × 0.23 × 0.02 |
| Radiation | Cu Kα (λ = 1.54184 Å) |
| 2Θ range for data collection/° | 4.474 to 153.708 |
| Index ranges | −19 ≤ h ≤ 19, −9 ≤ k ≤ 10, −26 ≤ l ≤ 26 |
| Reflections collected | 72611 |
| Independent reflections | 9940 [$R_{int}$ = 0.0362, $R_{sigma}$ = 0.0191] |
| Data/restraints/parameters | 9940/10/678 |
| Goodness-of-fit on $F^2$ | 1.071 |
| Final R indexes [I >= 2σ (I)] | $R_1$ = 0.0324, $wR_2$ = 0.0968 |
| Final R indexes [all data] | $R_1$ = 0.0364, $wR_2$ = 0.0991 |
| Largest diff. peak/hole /e Å$^{-3}$ | 0.14/−0.12 |
| Flack parameter | 0.07(7) |

$^1$H NMR (300 MHz, DMSO-$d_6$) δ 8.43 (s, 1H), 8.26 (s, 1H), 8.16 (s, 1H), 7.74 (d, J=87.4 Hz, 3H), 7.48-7.19 (m, 3H), 7.12-7.03 (m, 1H), 5.50 (d, J=12.8 Hz, 2H), 3.60 (s, 2H).

Analytical data for material obtained from Method B are provided (XRPD, FIG. 3); DSC/TGA (FIG. 4). Methods A, C, and D produced material with consistent analytical data.

DSC: The product exhibited a thermal (endothermic) event with an onset temperature of about 83° C. and an endothermic peak at about 138° C., and a thermal (endothermic, melting) event with an onset temperature of about 212° C. and an endothermic peak at about 221° C. TGA: The product exhibited no weight loss upon heating below about 75° C. and a weight loss of about 1.8% upon heating from about 75° C. to about 170° C.

EXAMPLE 2: Preparation of Compound 1, Benzoate Salt (Form 2)

Method A: Amorphous Compound 1, free base (30 mg), was mixed with 0.5 mL (a) IPA, (b) acetone, (c) IPAc, or (d) ACN/water (19/1) at rt, and treated with benzoic acid (1.1 equiv.), and the resulting mixtures were stirred at rt for 16 h. For (b), 1 mL n-heptane was added, and the mixture was stirred for another 24 h at 50° C. In each case, the resulting solids were collected by filtration and dried under vacuum at 40° C. for 4 h, to provide Compound 1, benzoate salt (Form 2). Analytical data is provided (XRPD, FIG. 5; DSC/TGA, FIG. 6). $^1$H NMR for (a) (Bruker, 400 MHz, DMSO-d6) showed 0.2 wt % residual IPA.

Method B: Amorphous Compound 1, free base (350 mg), and benzoic acid (86.6 mg, 1 equiv.) were added to 3.5 mL of acetone at rt. The resulting mixture was stirred for 5 min at rt, then seeded with 4 wt % of Compound 1, benzoate salt (Form 2), and stirred for 4 h. The resulting suspension was treated with n-heptane (7 mL) and stirred for 20 h. The resulting solid was collected by filtration and dried under vacuum at 40° C. for 4 h to provide Compound 1, benzoate salt (Form 2). Characterization data were obtained as follows. Analytical data for material obtained from Method B were comparable to Method A material. $^1$H NMR (Bruker, 400 MHz, DMSO-d6) showed 0.5 wt % residual acetone.

$^1$H NMR (400 MHZ, DMSO-$d_6$) δ 8.44 (s, 1H), 8.25 (d, J=8.9 Hz, 1H), 8.16 (s, 1H), 8.05-7.79 (m, 3H), 7.69-7.54 (m, 2H), 7.54-7.35 (m, 3H), 7.30-7.00 (m, 3H), 6.31 (s, 1H), 5.49 (d, J=12.7 Hz, 2H), 3.59 (s, 3H).

DSC: The product exhibited a thermal (endothermic, melting/decomposition) event with an onset temperature of about 209° C. and a peak temperature of about 216° C. TGA: The product exhibited no weight loss upon heating below about 180° C. Based on these data, Compound 1, benzoate salt (Form 2) was identified as an anhydrate.

EXAMPLE 3: Preparation of Compound 1, Besylate (Benzenesulfonic Acid) Salt (Form 3)

Amorphous Compound 1, free base (30 mg), and benzenesulfonic acid (1.0 equiv.) were mixed with IPAc (0.5 mL) at rt and stirred for 4 d. The mixture was concentrated, treated with acetone (0.2 mL), and stirred at rt for 4 d, then treated with n-heptane (1 mL). The resulting solid was collected and dried to obtain Compound 1, besylate salt (Form 3). Analytical data are provided (XRPD, FIG. 7; DSC/TGA, FIG. 8).

$^1$H NMR (400 MHZ, DMSO-$d_6$) δ 8.95 (s, 1H), 8.52-8.14 (m, 3H), 7.98 (s, 2H), 7.66-7.53 (m, 2H), 7.46 (t, J=7.9 Hz, 1H), 7.41-7.21 (m, 4H), 7.11 (dd, J=8.2, 2.4 Hz, 1H), 6.89 (s, 1H), 5.86-5.22 (m, 2H), 3.43 (s, 3H), 1.24 (s, 2H), 1.17 (d, J=6.2 Hz, 1H).

DSC: The product exhibited multiple thermal events, including a thermal (endothermic) event with an onset temperature of about 186° C. and a peak temperature of about 206° C. TGA: The product exhibited 5.7% of weight loss upon heating across the range of about 95 to about 230° C. These data, along with $^1$H NMR data (Bruker, 400 MHz, DMSO-d6), identified material with a molar ratio of 1:0.9 of Compound 1 to acid, and residual IPAc (3%), n-heptane (1.3%), and acetone (0.2%), indicating a solvate form.

EXAMPLE 4: Preparation of Compound 1, Chloride Salt (Form 4)

Amorphous Compound 1, free base form (30 mg), was mixed with IPA (0.5 mL), treated with HCl solution (1 M, prepared by diluting conc. HCl in IPA), and stirred at rt for 4 d. The resulting solid was isolated by centrifugation and vacuum-dried at 40° C. for 4 h to provide Compound 1, chloride salt (Form 4). Analytical data are provided (XRPD, FIG. 9; DSC/TGA, FIG. 10). Purity, 98.9% (HPLC). $^1$H NMR (Bruker, 400 MHz, DMSO-d6) identified 0.3% residual IPA.

$^1$H-NMR (400 MHZ, DMSO-$d_6$) δ 8.73 (s, 1H), 8.31 (d, J=8.8 Hz, 2H), 8.21 (s, 1H), 7.97 (s, 2H), 7.46 (t, J=7.9 Hz, 1H), 7.41-7.16 (m, 2H), 7.10 (dd, J=8.2, 2.4 Hz, 1H), 6.79 (s, 1H), 5.52 (d, J=10.5 Hz, 2H), 4.14-3.54 (m, 3H).

DSC: Four endothermic peaks were observed with onset temperatures of about 28° C., 98° C., and 242° C., respectively, and peak temperatures at about 64° C. and 116° C. (loss of water and residual solvent), and at about 258° C. (two overlapping peaks; melting, decomposition), respectively. TGA: The product exhibited two stages of weight loss, 3.2% prior to 90° C. and 2.7% over the range of 90 to 140° C. These data indicated Form 4 as a hydrate.

EXAMPLE 5: Preparation of Compound 1, Chloride Salt (Form 5)

Form 5 was prepared using the procedure described for Example 4, substituting ACN for IPA. Analytical data are provided (XRPD, FIG. 11; DSC/TGA, FIG. 12). Purity, 98.9% (HPLC).

$^1$H NMR (400 MHZ, DMSO-$d_6$) δ 8.95 (s, 1H), 8.51-8.15 (m, 3H), 7.99 (s, 2H), 7.46 (t, J=7.9 Hz, 1H), 7.26 (d, J=7.5 Hz, 2H), 7.11 (dd, J=8.1, 2.4 Hz, 1H), 6.88 (s, 1H), 5.52 (d, J=11.2 Hz, 2H), 3.77 (dt, J=12.2, 6.2 Hz, 3H).

DSC: The product exhibited multiple thermal events, including a thermal (endothermic) event with an onset temperature of about 244° C. and a peak temperature of about 247° C., and indicated loss of water and residual solvents. TGA: The product exhibited 5.3% of weight loss prior to 130° C. (loss of water and residual solvents) and about 12% of weight loss over the range of about 175 to about 300° C. $^1$H NMR indicated trace levels of remaining ACN (0.3%).

EXAMPLE 6: Preparation of Compound 1, Citrate Salt (Form 6)

Amorphous Compound 1, free base (30 mg), was mixed with IPAc (0.5 mL) at rt and treated with citric acid (1.1 equiv.). After 19 h, the resulting solid was isolated by filtration and dried under vacuum at 40° C. for 4 h. Analytical data are provided (XRPD, FIG. 13; DSC/TGA, FIG. 14).

$^1$H NMR (400 MHZ, DMSO-$d_6$) δ 8.43 (s, 1H), 8.25 (d, J=8.9 Hz, 1H), 8.16 (s, 1H), 7.81 (d, J=71.5 Hz, 3H), 7.43 (t, J=7.9 Hz, 2H), 7.23 (d, J=7.5 Hz, 2H), 7.08 (dd, J=8.3, 2.4 Hz, 1H), 6.36 (s, 1H), 5.49 (d, J=12.2 Hz, 2H), 3.60 (s, 3H), 2.78-2.57 (m, 3H), 1.96 (s, 1H), 1.17 (d, J=6.3 Hz, 2H).

DSC: The product exhibited multiple endothermic peaks, including peaks with onset temperatures of about 92 and 144° C. and peak temperatures of about 102 and 177° C., respectively. TGA: The product exhibited about 5.1% of weight loss over the range of about 26 to about 150° C. Based on these data, along with $^1$H NMR results (Bruker, 400 MHz, DMSO-d6), Compound 1, citrate salt (Form 6) was identified an IPAc solvate. with a molar ratio of base to acid of 1:0.8

EXAMPLE 7: Preparation of Compound 1, Citrate Salt (Form 7)

The product was prepared as described in Example 6, using ACN/$H_2O$ (19/1) in place of IPAc. Analytical data are provided (XRPD, FIG. 15; DSC/TGA, FIG. 16).

$^1$H NMR (400 MHZ, DMSO-d6) δ 8.42 (s, 1H), 8.25 (d, J=8.9 Hz, 1H), 8.16 (s, 1H), 7.81 (d, J=62.1 Hz, 3H), 7.43 (t, J=7.9 Hz, 2H), 7.23 (d. J=7.5 Hz, 2H), 7.11-7.01 (m, 1H), 6.35 (s, 1H), 5.49 (d, J=12.6 Hz, 2H), 3.61 (s, 3H), 2.74 (d, J=15.4 Hz, 2H), 2.64 (d, J=15.4 Hz, 2H).

DSC: The product exhibited four endothermic peaks, including peaks with onset temperatures of about 41, about 135, and about 169° C., and peak temperatures of about 58, about 139, and about 188° C., respectively. TGA: The product exhibited about 2.8% of weight loss over the range of 25 to about 100° C. $^1$H NMR (Bruker, 400 MHz, DMSO-d6) indicated about 0.2% residual ACN. These data indicated Form 7 to be a hydrate.

EXAMPLE 8: Preparation of Compound 1, Fumarate Salt (Form 8)

Method A: Amorphous Compound 1, free base (30 mg), was mixed with acetone (0.5 mL), treated with fumaric acid (1.1 equiv.), and stirred at rt for 19 h. The resulting mixture was treated with n-heptane (1 mL) and stirred at 50° C. for 20 h. The resulting solid was isolated by filtration and dried under vacuum at 40° C. for 4 h.

Method B: Amorphous Compound 1, free base (30 mg), was mixed with ACN/water (19/1, 0.5 mL), treated with 1.1 equiv. fumaric acid (1.1 equiv.), and stirred at rt for 2 h. ACN/water (19/1, 0.3 mL) was added and the mixture was stirred for another 17 h. The resulting solid was isolated by filtration and dried under vacuum at 40° C. for 4 h. Analytical data are provided (XRPD, FIG. 17; DSC/TGA, FIG. 18). $^1$H NMR (Bruker, 400 MHz, DMSO-d6) indicated 0.2% residual ACN.

Method C: Amorphous Compound 1, free base (350 mg) and fumaric acid (90 mg, 1.1 equiv.) were mixed in acetone (3.5 mL) and the mixture was stirred for 30 min at rt. The resulting solution was added dropwise to a dispersion of Compound 1, fumarate salt (Form 8) seeds in n-heptane. After stirring for 24 h at rt, the resulting solid was isolated by filtration and dried under vacuum at 40° C. for 5 h. To remove residual acetone, the solid was ground by mortar and pestle and dried further under vacuum at 90° C. for 3 h.

Material obtained from Methods A and C showed comparable results to data provided for Method B material.

$^1$H NMR (400 MHZ, DMSO-d$_6$) δ 8.44 (s, 1H), 8.25 (d, J=8.9 Hz, 1H), 8.16 (s, 1H), 8.01-7.52 (m, 3H), 7.43 (t, J=7.9 Hz, 2H), 7.22 (d, J=7.5 Hz, 1H), 7.08 (dd, J=8.3, 2.4 Hz, 1H), 6.62 (s, 2H), 6.32 (s, 1H), 5.49 (d, J=13.2 Hz, 2H), 3.59 (s, 4H).

DSC: The product exhibited a thermal (endothermic, dehydration) event with an onset temperature of about 28° C. and a peak temperature of about 100° C., and a thermal (endothermic, melting/decomposition) event with an onset temperature of about 206° C. and a peak temperature of about 214° C. TGA: The product exhibited a weight loss of about 2.0% upon heating from about 24.5° C. to about 150.0° C.

EXAMPLE 9: Preparation of Compound 1, Gentisate Salt (Form 9)

The product was prepared as described in Example 6, using gentisic acid and IPA or IPAc as the solvent. Analytical data are provided (XRPD, FIG. 19; DSC/TGA, FIG. 20).

$^1$H NMR (400 MHZ, DMSO-d$_6$) δ 9.03 (s, 1H), 8.42 (s, 1H), 8.25 (d, J=8.9 Hz, 1H), 8.16 (s, 1H), 7.82 (d, J=53.1 Hz, 3H), 7.43 (t, J=7.9 Hz, 2H), 7.29-7.00 (m, 4H), 6.91 (dd, J=8.8, 3.1 Hz, 1H), 6.74 (d, J=8.8 Hz, 1H), 6.37 (s, 1H), 5.50 (d, J=12.6 Hz, 2H), 1.17 (d, J=6.2 Hz, 1H).

DSC: The product exhibited two endothermic peaks (desolvation, IPAc; melting/decomposition) with onset temperatures of about 56 and about 256° C. and peak temperatures of about 81 and about 263° C., respectively. TGA: The product exhibited a 2.2% weight loss over the range of about 26.5 to about 100° C. $^1$H NMR (Bruker, 400 MHz, DMSO-d6) indicated residual IPAc (about 1.9%), collectively indicated a solvate form.

EXAMPLE 10: Preparation of Compound 1, Gentisate Salt (Form 10)

The product was prepared as described in Example 6, using gentisic acid and acetone or ACN/$H_2O$ (19/1) as the solvent. Data is provided below from the ACN/$H_2O$ experiment. Analytical data are provided (XRPD, FIG. 21; DSC/TGA, FIG. 22). $^1$H NMR (Bruker, 400 MHz, DMSO-d6) indicated residual IPAc (0.4%).

$^1$H NMR (400 MHZ, DMSO-d6) δ 9.04 (s, 1H), 8.42 (s, 1H), 8.25 (d, J=8.9 Hz, 1H), 8.16 (s, 1H), 7.82 (d. J=54.8 Hz, 3H), 7.43 (t, J=7.9 Hz, 2H), 7.28-6.96 (m, 4H), 6.91 (dd, J=8.8, 3.1 Hz, 1H), 6.74 (d, J=8.9 Hz, 1H), 6.37 (s, 1H), 5.49 (d, J=12.6 Hz, 2H).

DSC (FIG. 22): The product exhibited one endothermic peak (melting/decomposition) with an onset temperature of about 240° C. and a peak temperature of about 245° C. TGA (FIG. 22): The product exhibited a weight loss of about 0.4% upon heating over the range of about 120 to 200° C. The form was indicated as an anhydrate.

EXAMPLE 11: Preparation of Compound 1, Glycolate Salt (Form 11)

Method A: The product was prepared as described in Example 6, using glycolic acid and IPAc as the solvent. Analytical data are provided (XRPD, FIG. 23; DSC/TGA, FIG. 24). $^1$H NMR (Bruker, 400 MHz, DMSO-d6) indicated residual IPAc (0.4%).

Method B: Amorphous Compound 1, free base (30 mg) and glycolic acid (1.1 equiv.) were mixed in acetone (0.5 mL) and stirred at rt for 16 h. The solution was treated with n-heptane (1 mL) and stirred for 2 d at 50° C. The resulting solid was isolated by filtration and dried under vacuum at 40° C. for 4 h. Data was comparable to that obtained from the product of Method A.

$^1$H NMR (400 MHZ, DMSO-d$_6$) δ 8.44 (s, 1H), 8.24 (d, J=8.9 Hz, 1H), 8.16 (s, 1H), 7.90 (s, 1H), 7.58 (s, 1H), 7.48-7.17 (m, 3H), 7.08 (dd, J=8.2, 2.4 Hz, 1H), 6.32 (s, 1H), 5.49 (d, J=13.5 Hz, 2H), 3.91 (s, 2H), 3.59 (s, 2H).

DSC: The product exhibited multiple endothermic events, including peaks with onset temperatures at about 35, about 116, and about 152° C., and peak temperatures at about 59, about 94, and about 170° C., respectively. TGA: The product exhibited a weight loss of about 1.7% upon heating from 27° C. to about 80° C. and a weight loss of about 3.2% upon heating from about 110 to about 200° C. The data indicated the form may be a hydrate.

EXAMPLE 12: Preparation of Compound 1, 1-Hydroxy-2-Naphthoate Salt (Form 12)

The product was prepared as described in Example 6, using 1-hydroxy-2-naphthoic acid and IPAc. Analytical data are provided (XRPD, FIG. 25; DSC/TGA, FIG. 26).

$^1$H NMR (400 MHz, DMSO-d$_6$) δ 8.42 (s, 1H), 8.26 (dd, J=8.7, 1.4 Hz, 2H), 8.17 (s, 1H), 7.85 (d, J=8.1 Hz, 3H), 7.74 (d, J=8.7 Hz, 1H), 7.66-7.58 (m, 1H), 7.52 (ddd, J=8.2, 6.9, 1.3 Hz, 1H), 7.44 (t, J=7.9 Hz, 1H), 7.26 (dd, J=19.8, 8.1 Hz, 3H), 7.09 (dd, J=8.2, 1.9 Hz, 1H), 6.47 (s, 1H), 5.52 (s, 2H), 4.86 (hept, J=6.3 Hz, 1H), 1.96 (s, 1H), 1.17 (d, J=6.3 Hz, 2H).

DSC: The product exhibited multiple endothermic events, including peaks with onset temperatures of about 25 and about 178° C., and peak temperatures of about 32 and about 186° C., respectively. TGA: The product exhibited 0.5% of weight loss upon heating from 25 to about 80° C. and 7.4% of weight loss upon heating from about 100 to about 190° C. $^1$H NMR (Bruker, 400 MHz, DMSO-d6) indicated the presence of residual IPAc (about 5.1%).

EXAMPLE 13: Preparation of Compound 1, 1-Hydroxy-2-Naphthoate Salt (Form 13)

Method A: The product was obtained as described in Example 9, using ACN/water (19/1) as the solvent. XRPD analytical data are provided (FIG. 27).

Method B: Amorphous Compound 1, free base (300 mg), and 1-hydroxy-2-naphthoic acid (1.1 equiv.) were added to ACN/$H_2O$ (19/1, 5 mL) and the resulting mixture was stirred for 5 min. The solution was treated with Compound 1, 1-hydroxy-2-naphthoic acid salt (Form 13) seeds and the mixture was stirred at rt for 16 h. The resulting thick suspension was diluted with ACN/$H_2O$ (19/1, 2.5 mL) and stirred for 2 h. The solid was collected by filtration and dried under vacuum at 40° C. for 4 h. DSC/TGA data are provided (FIG. 28). Materials obtained from Methods A and B had comparable analytical data.

$^1H$ NMR (400 MHz, DMSO-$d_6$) δ 8.42 (s, 1H), 8.26 (d, J=9.0 Hz, 2H), 8.17 (s, 1H), 8.08-7.82 (m, 3H), 7.74 (d, J=8.7 Hz, 1H), 7.62 (ddd, J=8.2, 6.8, 1.4 Hz, 1H), 7.53 (ddd, J=8.2, 6.9, 1.3 Hz, 1H), 7.44 (t, J=7.9 Hz, 1H), 7.26 (dd, J=20.2, 8.1 Hz, 3H), 7.09 (dd, J=8.2, 2.4 Hz, 1H), 6.48 (s, 1H), 5.52 (s, 2H).

DSC: The product exhibited a thermal (endothermic, melting/decomposition) event with an onset temperature of about 187° C. and a peak temperature of about 194° C. TGA: The product exhibited no weight loss upon heating below about 160° C.

EXAMPLE 14: Preparation of Compound 1, Malate Salt (Form 14)

Amorphous Compound 1, free base (30 mg), and malic acid (1.1 equiv.) were mixed in ACN/$H_2O$ (0.5 mL) and stirred at rt for 2 h. The mixture was treated with ACN/$H_2O$ (19/1, 0.3 mL), and was stirred for 17 h at rt. The resulting solid was isolated by filtration and dried under vacuum at 40° C. for 4 h. Analytical data are provided (XRPD, FIG. 29; DSC/TGA, FIG. 30).

$^1H$ NMR (400 MHz, DMSO-$d_6$) δ 8.44 (s, 1H), 8.25 (d, J=8.9 Hz, 1H), 8.16 (s, 1H), 7.77 (d, J=100.4 Hz, 3H), 7.43 (t, J=7.9 Hz, 2H), 7.23 (d, J=7.6 Hz, 2H), 7.08 (dd, J=8.3, 2.4 Hz, 1H), 6.33 (s, 1H), 5.49 (d, J=12.7 Hz, 2H), 4.24 (dd, J=7.6, 5.1 Hz, 1H), 3.59 (s, 3H), 2.61 (dd, J=15.6, 5.1 Hz, 1H), 2.43 (dd, J=15.7, 7.6 Hz, 1H).

DSC: The product exhibited multiple thermal events, including peaks with onset temperatures of about 28 and about 178° C., and peak temperatures of about 69 and about 216° C., respectively. TGA: The product exhibited a weight loss of about 3.6% weight loss upon heating from about 30 to about 120° C. The data indicated the form is a hydrate.

EXAMPLE 15; Preparation of Compound 1, Malate Salt (Form 15)

Amorphous Compound 1, free base (30 mg), and malic acid (1.1 equiv.) were mixed in acetone (0.5 mL) and stirred for 19 h at rt. The mixture was treated with n-heptane (1 mL) and stirred for 2 d at 50° C. The resulting solid was isolated by filtration and dried under vacuum at 40° C. for 4 h. Analytical data are provided (XRPD (FIG. 31; DSC/TGA, FIG. 32). $^1H$ NMR (Bruker, 400 MHZ, DMSO-d6) indicated residual acetone (6.0%) and n-heptane (3.7%).

$^1H$ NMR (400 MHz, DMSO-$d_6$) δ 8.43 (s, 1H), 8.24 (d, J=8.9 Hz, 1H), 8.15 (s, 1H), 7.77 (d, J=94.0 Hz, 3H), 7.41 (q, J=19.6, 13.7 Hz, 2H), 7.29-7.00 (m, 3H), 6.32 (s, 1H), 5.49 (d, J=11.5 Hz, 2H), 4.24 (dd, J=7.6, 5.1 Hz, 1H), 3.60 (s, 2H), 2.61 (dd, J=15.7, 5.1 Hz, 1H), 2.43 (dd, J=15.7, 7.6 Hz, 1H), 2.09 (s, 2H), 1.33-1.17 (m, 1H), 0.90-0.81 (m, 1H).

DSC: The product exhibited multiple thermal events, including peaks with onset temperatures of about 127 and about 159° C., and peak temperatures of about 145 and about 182° C. TGA: The product exhibited a weight loss of about 3.1% upon heating from about 90 to about 160° C. and a weight loss of about 3.6% upon heating from about 160 to about 190° C. The data indicated the form is a solvate.

EXAMPLE 16: Preparation of Compound 1, Maleate Salt (Form 16)

A mixture of amorphous Compound 1, free base (30 mg), and maleic acid (1.1 equiv.) in IPA (0.5 mL) was stirred at rt for 2 h, then treated with IPA (0.3 mL) and stirred an additional 14 h. The resulting solid was isolated by filtration and dried under vacuum at 40° C. for 4 h. Analytical data are provided (XRPD, FIG. 33; DSC/TGA, FIG. 34).

$^1H$ NMR (400 MHZ, DMSO-$d_6$) δ 8.44 (d, J=47.0 Hz, 2H), 8.30 (d, J=8.8 Hz, 1H), 8.20 (s, 1H), 7.95 (s, 2H), 7.45 (t, J=7.9 Hz, 1H), 7.25 (d, J=7.5 Hz, 2H), 7.10 (dd, J=8.3, 2.4 Hz, 1H), 6.70 (s, 1H), 6.10 (d, J=1.8 Hz, 2H), 5.74-5.36 (m, 2H), 3.72 (s, 4H).

DSC: The product exhibited 2-3 endothermic peaks at onset temperatures of about 26° C. and about 198° C. and peak temperatures of about 53° C. and about 206° C. TGA: The product exhibited weight loss of about 1.8% upon heating from 24 to about 100° C. (loss of water), indicating the material was a hydrate.

EXAMPLE 17: Preparation of Compound 1, Maleate Salt (Form 17)

The product was obtained as described in Example 6, using maleic acid and ACN/$H_2O$ (19/1). Analytical data are provided (XRPD, FIG. 35; DSC/TGA, FIG. 36).

$^1H$ NMR (400 MHz, DMSO-$d_6$) δ 8.59-8.26 (m, 2H), 8.20 (s, 1H), 7.95 (s, 2H), 7.53-7.18 (m, 3H), 7.10 (dd, J=8.4, 2.4 Hz, 1H), 6.69 (s, 1H), 6.11 (s, 2H), 5.52 (d, J=9.9 Hz, 2H), 3.72 (s, 3H).

DSC: The product exhibited multiple endothermic events, including peaks with onset temperatures of about 27 and about 195° C., and peak temperatures of about 60 and about 205° C., respectively. TGA: The product exhibited weight loss of about 1.2% upon heating from about 26 to about 100° C., indicating the material was a hydrate.

EXAMPLE 18: Preparation of Compound 1, Mesylate Salt (Form 18)

Methanesulfonic acid (1.0 equiv.) was dissolved in IPAc (0.5 mL) and amorphous Compound 1, free base (30 mg), was added. The resulting mixture was stirred at rt for 4 d. The resulting solid was collected by centrifugation and vacuum-dried at 40° C. for 4 h. Analytical data are provided (XRPD, FIG. 37; DSC/TGA, FIG. 38). Purity (99.2%, HPLC).

$^1H$ NMR (400 MHZ, DMSO-$d_6$) δ 8.89 (s, 1H), 8.32 (d. J=8.6 Hz, 2H), 8.22 (s, 1H), 8.07-7.73 (m, 2H), 7.46 (t, J=7.9 Hz, 1H), 7.40-7.19 (m, 2H), 7.14-7.06 (m, 1H), 6.86 (s, 1H), 5.54 (d, J=11.4 Hz, 2H), 4.86 (hept, J=6.3 Hz, 1H), 3.36 (s, 3H), 2.29 (s, 2H), 1.96 (s, 2H), 1.17 (d, J=6.3 Hz, 5H).

DSC: The product exhibited an endothermic peak with an onset temperature of about 142° C. and a peak temperature of about 146° C. (desolvation). TGA: The product exhibited a weight loss of about 5.6% upon heating from rt to about 145° C. and a weight loss of about 9.5% upon heating from about 145 to about 200° C. $^1H$ NMR (Bruker, 400 MHz, DMSO-d6) indicated a molar ratio of 1:0.8 (free base: acid) and residual IPAc (12%). The data indicated the form was an IPAc solvate.

EXAMPLE 19: Preparation of Compound 1, Oxalate Salt (Form 19)

ACN (0.25 mL) was added to a mixture of amorphous Compound 1, free base (30 mg), and oxalic acid (1.0 equiv.) and the resulting mixture was stirred at rt for 4 d. The resulting solid was collected by centrifugation and dried under vacuum at 40° C. for 4 h. Analytical data are provided (XRPD, FIG. 39; DSC/TGA, FIG. 40). Purity, 99.1% (HPLC).

$^1$H NMR (400 MHz, DMSO-$d_6$) δ 8.64-7.59 (m, 5H), 7.53-6.94 (m, 4H), 6.54 (s, 1H), 5.52 (s, 2H), 2.08 (s, 2H).

DSC: The product exhibited endothermic peaks at onset temperatures of about 92° C. (peak temperature of about 137° C.) (solvent loss), about 187° C. (peak temperature of about 190° C.) (melting), and about 194° C. (peak temperature of about 202° C.) (decomposition). TGA: The product exhibited a weight loss of about 7.4% upon heating from about 90 to about 190° C. (solvent loss) and a weight loss of 19.0% upon heating from about 190 to about 240° C. (decomposition). These data and $^1$H NMR (Bruker, 400 MHz, DMSO-d6) (6.4% residual ACN) indicated the form was an ACN solvate.

EXAMPLE 20: Preparation of Compound 1, Phosphate Salt (Form 20)

Amorphous Compound 1, free base (30 mg), was dissolved in ACN/$H_2O$ (19/1, 0.5 mL) and treated with $H_3PO_4$ (1-1.1 equiv.; 85% molarity in water). The resulting mixture was stirred for 19 h at rt. The resulting solid was collected by filtration and dried under vacuum at 40° C. for 4 h. Analytical data are provided (XRPD, FIG. 41; DSC/TGA, FIG. 42). $^1$H NMR (Bruker, 400 MHz, DMSO-d6) indicated 0.1% residual ACN.

$^1$H NMR (400 MHZ, DMSO-d6) δ 8.44 (s, 1H), 8.25 (d, J=8.9 Hz, 1H), 8.16 (s, 1H), 7.78 (d, J=92.7 Hz, 3H), 7.43 (t, J=7.9 Hz, 2H), 7.23 (d. J=7.5 Hz, 2H), 7.08 (dd, J=8.1, 2.4 Hz, 1H), 6.34 (s, 2H), 5.49 (d, J=12.7 Hz, 5H).

DSC: The product exhibited 2-3 endothermic peaks, including an endothermic peak with an onset temperature of about 34° C. and a peak temperature of about 74° C. TGA: The product exhibited a weight loss of about 4.5% upon heating from 25 to about 110° C. The data indicated the form may be a hydrate. Analysis by ion chromatography confirmed the form as a mono-phosphate.

EXAMPLE 21: Preparation of Compound 1, Tartrate Salt (Form 21)

Amorphous Compound 1, free base (30 mg), was mixed with ACN/$H_2O$ (19/1, 0.5 mL) at rt and treated with tartaric acid (1.1 equiv.). After stirring for 2 h, ACN/$H_2O$ (19/1, 0.3 mL) was added and the mixture was stirred another 17 h. The resulting solid was isolated by filtration and dried under vacuum at 40° C. for 4 h. Analytical data are provided (XRPD, FIG. 43; DSC/TGA, FIG. 44). $^1$H NMR (Bruker, 400 MHz, DMSO-d6) indicated about 0.8% residual ACN.

$^1$H NMR (400 MHZ, DMSO-d6) δ 8.44 (s, 1H), 8.25 (d, J=8.9 Hz, 1H), 8.16 (s, 1H), 8.04-7.54 (m, 3H), 7.43 (t, J=7.9 Hz, 2H), 7.23 (d, J=7.5 Hz, 2H), 7.08 (dd, J=8.4, 2.4 Hz, 1H), 6.33 (s, 1H), 5.49 (d, J=12.7 Hz, 2H), 4.29 (s, 2H).

DSC: The product exhibited multiple endothermic peaks including two with onset temperatures of about 29 and about 201° C., and peak temperatures of about 70 and about 204° C. TGA: The product exhibited a weight loss of about 6.8% upon heating from about 30 to about 140° C. The data indicated the form as a hydrate.

EXAMPLE 22: Preparation of Compound 1, Tartrate Salt (Form 22)

The product was prepared as described in Example 6, using tartaric acid and acetone. Analytical data are provided (XRPD, FIG. 45; DSC/TGA, FIG. 46).

$^1$H NMR (400 MHZ, DMSO-d6) δ 8.44 (s, 1H), 8.25 (d, J=8.9 Hz, 1H), 8.16 (s, 1H), 8.06-7.53 (m, 3H), 7.43 (t, J=7.9 Hz, 2H), 7.23 (d, J=7.5 Hz, 2H), 7.12-7.00 (m, 1H), 6.33 (s, 2H), 5.49 (d, J=12.7 Hz, 2H), 4.29 (s, 2H), 2.09 (s, 2H).

DSC: The product exhibited multiple endothermic peaks including peaks with the following temperatures (onset/peak): about 27° C./about 51° C., about 106° C./about 141° C., and about 209° C./about 222° C. TGA: The product exhibited a weight loss of about 2.8% upon heating from about 80 to about 170° C. $^1$H NMR (Bruker, 400 MHz, DMSO-d6) indicated 5.1 wt % of residual acetone. The data indicated the form as an acetone solvate.

EXAMPLE 23: Preparation of Compound 1, Tosylate Salt (Form 23)

IPAc (0.5 mL) was added to a mixture of amorphous Compound 1, free base (30 mg), and p-toluenesulfonic acid (1.0 equiv.) with stirring, and the resulting mixture was stirred at rt for 4 d. The resulting solid was collected by centrifugation and vacuum-dried at 40° C. for 4 h. $^1$H NMR (Bruker, 400 MHz, DMSO-d6) indicated 10.7% residual IPAc (molar ratio of base to acid of 1:0.8). Analytical data are provided (XRPD, FIG. 47; DSC/TGA, FIG. 48). Purity, 99.1% (HPLC).

1H-NMR (400 MHZ, DMSO-$d_6$) δ 8.89 (s, 1H), 8.32 (d, J=8.6 Hz, 2H), 8.22 (s, 1H), 7.99 (s, 2H), 7.55-7.16 (m, 3H), 7.10 (dd, J=8.3, 1.7 Hz, 1H), 6.86 (s, 1H), 5.54 (d, J=11.4 Hz, 2H), 4.86 (hept, J=6.3 Hz, 1H), 3.35 (s, 3H), 2.29 (s, 2H), 1.96 (s, 2H), 1.24 (s, 1H), 1.17 (d, J=6.3 Hz, 4H).

DSC: The product exhibited an endothermic peak with an onset temperature of about 83° C. and a peak temperature of about 120° C. (loss of solvent and water) and an endothermic peak with an onset temperature of about 186° C. and a peak temperature of about 202° C. (melting), TGA: The product exhibited a weight loss of about 1.8% upon heating from rt to about 100° C. and a weight loss of about 5.6% upon heating from about 100 to about 180° C. (loss of water and solvent). The data indicate the form to be an IPAc solvate.

EXAMPLE 24; Preparation of Compound 1, Free Base, Anhydrate (Form 24)

Amorphous Compound 1, free base (20 mg), was dissolved in Solvent (1 mL) at 70° C., and treated with Anti-Solvent (2 mL) and the resulting mixture was stirred for at least 1 d and up to 4 d. The resulting solid was collected and dried to provide Compound 1, free base, anhydrate (Form 24). Solvent/Anti-Solvent pairs included: EtOH/MTBE, EtOAc/n-heptane, and anisole/MTBE. Analytical data are provided (XRPD, FIG. 49; DSC/TGA, FIG. 50). $^1$H NMR analysis (Bruker, 400 MHz, DMSO-d6) on material obtained from the EtOAc/n-heptane solvent pair showed the presence of 0.2% residual EtOAc.

$^1$H-NMR (400 MHZ, DMSO-$d_6$) δ 8.45 (s, 1H), 8.25 (d, J=9.0 Hz, 1H), 8.16 (s, 1H), 7.74 (d, J=135.7 Hz, 3H), 7.43

(t, J=7.9 Hz, 2H), 7.22 (d, J=7.6 Hz, 2H), 7.12-7.03 (m, 1H), 6.44 (d, J=92.5 Hz, 1H), 5.51 (s, 2H), 3.58 (s, 3H), 3.28 (s, 2H).

DSC: The product exhibited an endothermic peak with an onset temperature of about 240° C. and a peak temperature of about 246° C. (melting). TGA: The product exhibited no weight loss upon heating below about 200° C. The data indicate the form to be an anhydrate.

EXAMPLE 25: Solubility Testing of Solid Forms in SGF and FeSSIF Media

About 15 mg of test material was weighed into a sample vial and then 3.0 mL of water, simulated gastric fluid (SGF), fasted state simulated intestinali fluid (FaSSIF), or fed state simulated intestinal fluid (FeSSIF) media was added. The resulting suspensions were shaken at 37° C. for up to 24 hours. At 0.5, 2, and 24 hours, suspensions were filtered, and test material concentrations in the filtrates were analyzed by HPLC. Residual solids were collected for analysis. Solubilities for tested compounds are shown in Table 2.

TABLE 2

Solubilities of Solid Forms

| Sample | Media | pH of media | Solubility (mg/mL) 0.5 h | 2 h | 24 h |
|---|---|---|---|---|---|
| Benzoate (Form 2) | Water | 5.7 | 0.093 | 0.094 | 0.067 |
| | SGF | 1.2 | 4.17 | 4.47 | 4.49 |
| | FeSSIF | 5.0 | 0.72 | 0.68 | 0.54 |
| | FaSSIF | 6.5 | 0.074 | 0.077 | 0.095 |
| 1-Hydroxy-2-naphthoate (Form 13) | Water | 5.7 | 0.014 | 0.020 | 0.013 |
| | SGF | 1.2 | 3.86 | 4.05 | 4.12 |
| | FeSSIF | 5.0 | 0.74 | 0.82 | 0.78 |
| | FaSSIF | 6.5 | 0.097 | 0.086 | 0.13 |
| Fumarate (Form 8) | Water | 5.8 | 0.38 | 0.43 | 0.34 |
| | SGF | 1.2 | ~5 | ~5 | ~5 |
| | FeSSIF | 5.0 | 1.27 | 1.26 | 1.15 |
| | FaSSIF | 6.5 | 0.13 | 0.16 | 0.45 |
| Free base (Form 1) | Water | 6.0 | <LOD | <LOD | <LOD |
| | SGF | 1.2 | 4.69 | 5.04 | 3.67 |
| | FeSSIF | 5.0 | 0.29 | 0.31 | 0.33 |
| | FaSSIF | 6.5 | 0.0046 | 0.0066 | 0.011 |
| Amorphous free base | Water | 6.0 | 0.001 | 0.002 | 0.0009 |
| | SGF | 1.2 | ~5 | ~5 | ~5 |
| | FeSSIF | 5.0 | 1.24 | 1.22 | 1.29 |
| | FaSSIF | 6.5 | 0.087 | 0.085 | 0.09 |

Formulation Examples

In the formulation examples that follow, where the form of Compound 1 is not specified, the mg/tablet amounts for Compound 1 are based on the free base form of Compound 1 (free base equivalent amount). Where another form of Compound 1 is used, such as a solvate, for example a hydrate, salt, or combination thereof, the mg/tablet of Compound 1 material is increased as needed to achieve the free base equivalent strength listed, e.g., by accounting for purity of Compound 1, and solvent (solvate and/or residual solvent) or conjugate acid in the Compound 1 material. The amount of silicified microcrystalline cellulose is reduced mg for mg so that the total mass of Compound 1 plus silicified microcrystalline cellulose in the tablet matches the totals listed in Tables 3 and 5 below.

EXAMPLE 26: Tablet Formulation 1

Tablet compositions comprising Compound 1 (as free base, non-solvate) may include the ingredients and dosage strengths shown in Table 3.

TABLE 3

Tablet Formulation 1 Components

| Component | 0.2 mg Strength % w/w | mg/tablet | 1 mg Strength % w/w | mg/tablet | 10 mg Strength % w/w | mg/tablet | 50 mg Strength % w/w | mg/tablet |
|---|---|---|---|---|---|---|---|---|
| Compound 1 | 0.25 | 0.2 | 0.25 | 1.0 | 10.00 | 10.0 | 50.00 | 50.0 |
| Silicified microcrystalline cellulose (ProSolv ® SMCC HD90, NF; filler) | 94.25 | 75.4 | 94.25 | 377.0 | 84.50 | 84.5 | 44.50 | 44.5 |
| Colloidal silicon dioxide (Cabosil M-5P; glidant) | 1.00 | 0.8 | 1.00 | 4.0 | 1.00 | 1.0 | 1.00 | 1.0 |
| Croscarmellose sodium (Ac-Di-Sol ® SD-711; disintegrant) | 3.00 | 2.4 | 3.00 | 12.0 | 3.00 | 3.0 | 3.00 | 3.0 |
| Magnesium stearate (Hyqual ® NF-GenAR ®; lubricant) | 1.50 | 1.2 | 1.50 | 6.0 | 1.50 | 1.5 | 1.50 | 1.5 |
| Core Tablet Total | 100.0 | 80.0 | 100.0 | 400.0 | 100.0 | 100.0 | 100.0 | 100.0 |
| Core Tablet | 96.62 | 80.0 | 96.62 | 400.0 | 96.62 | 100.0 | 96.62 | 100.0 |
| Opadry II white [a] | 3.38 | 2.8 | 3.38 | 14.0 | 3.38 | 3.5 | 3.38 | 3.5 |
| Coated Tablet Total | 100.0 | 82.8 | 100.0 | 414.0 | 100.0 | 103.5 | 100.0 | 103.5 |

[a] comprised of polyvinyl alcohol, titanium dioxide, polyethylene glycol, and talc.

For Compound 1 (Form 1), a free base hemi-hydrate, an API correction factor of 0.9716 is used to maintain the target Compound 1 tablet strength, yielding the proportions shown in Table 4 (mg or % w/w free base equivalent/0.9716=mg or % w/w for Compound 1 (Form 1)). The API correction factor for the particular lot of Compound 1 evaluated in the instant example was determined as follows: API correction factor=(purity of API)*(1−water content−residual solvent−ROI)=(0.994)*(1−0.022−0.000073−0.0005)=0.9716. For the 50 mg strength batch, API with an API correction factor of 0.9724 was used (in which case, the amount of Compound 1 (Form 1) material was 51.4 mg or 51.4% w/w, and the amount of silicified microcrystalline cellulose was 43.1 mg or 43.1% w/w). The correction factor can range from about 0.96 to 0.99, or from about 0.97 to 0.98, or can be about 0.9716, about 0.9717, or about 0.9724.

TABLE 4

Tablet Formulation 1 Components-Compound 1 (Form 1)

| | 0.2 mg Strength | | 1 mg Strength | | 10 mg Strength | | 50 mg Strength | |
|---|---|---|---|---|---|---|---|---|
| Component | % w/w | mg/tablet | % w/w | mg/tablet | % w/w | mg/tablet | % w/w | mg/tablet |
| Compound 1 (Form 1) | 0.26 | 0.21 | 0.26 | 1.03 | 10.29 | 10.29 | 51.46 | 51.46 |
| Silicified microcrystalline cellulose (ProSoly ® SMCC HD90, NF; filler) | 94.24 | 75.39 | 94.24 | 376.97 | 84.21 | 84.21 | 43.04 | 43.04 |
| Colloidal silicon dioxide (Cabosil M-5P; glidant) | 1.00 | 0.8 | 1.00 | 4.0 | 1,00 | 1.0 | 1.00 | 1.0 |
| Croscarmellose sodium (Ac-Di-Sol ® SD-711; disintegrant) | 3.00 | 2.4 | 3.00 | 12.0 | 3.00 | 3.0 | 3.00 | 3.0 |
| Magnesium stearate (Hyqual ® NF-GenAR ®; lubricant) | 1.50 | 1.2 | 1.50 | 6.0 | 1.50 | 1.5 | 1.50 | 1.5 |
| Core Tablet Total | 100.0 | 80.0 | 100.0 | 400.0 | 100.0 | 100.0 | 100.0 | 100.0 |
| Core Tablet | 96.62 | 80.0 | 96.62 | 400.0 | 96.62 | 100.0 | 96.62 | 100.0 |
| Opadry II white [a] | 3.38 | 2.8 | 3.38 | 14.0 | 3.38 | 3.5 | 3.38 | 3.5 |
| Coated Tablet Total | 100.0 | 82.8 | 100,0 | 414.0 | 100.0 | 103.5 | 100.0 | 103.5 |

[a] comprised of polyvinyl alcohol, titanium dioxide, polyethylene glycol, and talc.

Tablet Preparation:

Compound 1, free base, hemi-hydrate (Form 1) is comprised of fine, irregular-shaped crystals with agglomerates, and has low bulk density (about 0.2 g/mL) and poor flowability (Carr Index of 31), Use of silicified microcrystalline cellulose showed improved uniformity of the blend. Use of a glidant, disintegrant, and lubricant allowed for acceptable tableting and disintegration characteristics.

For the 0.2 mg, 1 mg, and 10 mg strength tablets, Compound 1 may be de-lumped by sieving through a 150 μm hand screen as needed. Compound 1 was blended with colloidal silicon dioxide, croscarmellose sodium, and about half of the silicified microcrystalline cellulose in a suitably sized blender (e.g., V-blender) to obtain a first blend. The first blend and the remaining silicified microcrystalline cellulose were sieved through a screen manually or mechanically using a suitable screen (e.g., 300 μm hand screen or 813 μm Comil (milling) screen) and blended in a suitably sized blender to obtain a second blend. Magnesium stearate was de-lumped by sieving through a 500 μm screen, and was blended with the second blend to produce a lubricated blend. The lubricated blend was compressed into tablets of predetermined weights using a rotary tablet press to produce uncoated tablets. The uncoated tablets were coated in a perforated pan coater using an aqueous suspension of Opadry II (about 15% w/w) to yield the final cosmetically coated tablets.

For 50 mg strength tablets, Compound 1 may be de-lumped by sieving through a 150 μm hand screen as needed. Compound 1 was blended with silicified microcrystalline cellulose, colloidal silicon dioxide, and about two-thirds of the croscarmellose sodium in a blender (e.g., V-blender) to obtain a first blend. The first blend was passed through a 1143 μm Comil screen to form a de-lumped first blend, which was blended in a blender to form a second blend. Approximately two-thirds of the magnesium stearate was de-lumped by passing through a 500 μm screen and then blended with the second blend to yield a lubricated intragranular blend. Ribbons of the intragranular blend were formed using a roller compactor and then passed through a 1.0 mm screen to yield granules. The remaining magnesium stearate was de-lumped by passing through a 500 μm screen. The remaining croscarmellose sodium and de-lumped magnesium stearate were blended with the granules to provide a lubricated final blend. The final blend was compressed into tablets of predetermined tablet weights using a rotary tablet press to provide uncoated tablets. The uncoated tablets were coated in a perforated pan coater using Opadry II dispersed in water (about 15% w/w) to yield the final coated tablets. The dry granulation by roller compaction process was used for the 50 mg tablets to increase flowability and compactability at the higher drug loading level.

Exemplary processes for preparing tablets having strengths of 0.2 mg, 1 mg, 10 mg, and 50 mg of Compound 1, or a pharmaceutically acceptable salt and/or solvate thereof (free base equivalent amount) is illustrated in FIG. 51.

Stability Testing:

A four-week excipient compatibility study at 40° C./75% relative humidity and 60° C. accelerated stress conditions showed no incompatibility of Compound 1 with Tablet Formulation 1 excipients.

Dissolution Testing:

Dissolution testing of the 0.2 mg and 50 mg tablets (tablets were tested in 900 mL of aqueous solution at pH 4.5, sodium acetate with 0.5% sodium lauryl sulfate, mixed with a paddle at 75 rpm) showed rapid dissolution suitable for an immediate release product.

EXAMPLE 27; Tablet Formulation 2

Tablet compositions comprising Compound 1 (as free base, non-solvate) may include the ingredients and dosage strengths shown in Table 5. Exemplary tablet compositions for Compound 1 (Form 1), assuming an API correction factor of 0.9716 for the 1 mg and 10 mg strengths, and 0.965 for the 50 mg strength, are shown in Table 6. API correction factors of about 0.96 to 0.99, or about 0.97 to 0.98, may be used as appropriate. A wet-granulation approach may be used to further improve granule characteristics for downstream processing.

TABLE 5

Tablet Formulation 2 Components

| Component | 1 mg Strength | | 10 mg Strength | | 50 mg Strength | |
|---|---|---|---|---|---|---|
| | % w/w | mg/tablet | % w/w | mg/tablet | % w/w | mg/tablet |
| Compound 1 | 1.0 | 1.0 | 10.00 | 10.0 | 25.0 | 50.0 |
| Povidone (binder) | 5.0 | 5.0 | 5.0 | 5.0 | 5.0 | 10.0 |
| Silicified microcrystalline cellulose (filler) | 89.0 | 89.0 | 80.0 | 80.0 | 65.0 | 130.0 |
| Colloidal silicon dioxide (glidant) | 1.0 | 1.0 | 1.0 | 1.0 | 1.0 | 2.0 |
| Croscarmellose sodium (disintegrant) | 3.0 | 3.0 | 3.0 | 3.0 | 3.0 | 6.0 |
| Magnesium stearate (lubricant) | 1.0 | 1.0 | 1.0 | 1.0 | 1.0 | 2.0 |
| Core Tablet Total | 100.0 | 100.0 | 100.0 | 100.0 | 100.0 | 200.0 |
| Core Tablet | 96.62 | 100.0 | 96.62 | 100.0 | 96.62 | 200.0 |
| Opadry II white | 3.38 | 3.5 | 3.38 | 3.5 | 3.38 | 7.0 |
| Coated Tablet Total | 100.0 | 103.5 | 100.0 | 103.5 | 100.0 | 207.0 |

TABLE 6

Tablet Formulation 2 Components-Compound 1 (Form 1)

| Component | 1 mg Strength | | 10 mg Strength | | 50 mg Strength | |
|---|---|---|---|---|---|---|
| | % w/w | mg/tablet | % w/w | mg/tablet | % w/w | mg/tablet |
| Compound 1 (Form 1) | 1.03 | 1.03 | 10.29 | 10.29 | 25.91 | 51.8 |
| Povidone (binder) | 5.0 | 5.0 | 5.0 | 5.0 | 5.0 | 10.0 |
| Silicified microcrystalline cellulose (filler) | 88.97 | 88.97 | 79.71 | 79.71 | 64.09 | 128.2 |
| Colloidal silicon dioxide (glidant) | 1.0 | 1.0 | 1.0 | 1.0 | 1,0 | 2.0 |
| Croscarmellose sodium (disintegrant) | 3.0 | 3.0 | 3.0 | 3.0 | 3.0 | 6.0 |
| Magnesium stearate (lubricant) | 1.0 | 1.0 | 1.0 | 1.0 | 1.0 | 2.0 |
| Core Tablet Total | 100.0 | 100,0 | 100.0 | 100.0 | 100.0 | 200.0 |
| Core Tablet | 96.62 | 100.0 | 96.62 | 100.0 | 96.62 | 200.0 |
| Opadry II white | 3.38 | 3.5 | 3.38 | 3.5 | 3.38 | 7.0 |
| Coated Tablet Total | 100.0 | 103.5 | 100.0 | 103.5 | 100.0 | 207.0 |

Tablet Preparation: Compound 1, silicified microcrystalline cellulose, colloidal silicon dioxide, and croscarmellose sodium are transferred into a suitable-sized high shear granulator bowl and granulated using povidone dissolved in water (about 15% w/w). Additional water may be used to achieve desired granule properties along with wet-massing. The wet granules are passed through a screen (e.g., 3/8 in.) and dried in a dryer until the water is sufficiently removed to form dry granules. The dry granules are passed through a screen (e.g., 1 mm, or in the range of about 0.5 to 2 mm) and then mixed with magnesium stearate (de-lumped by passing through a 500 μm screen) in a blender to form the lubricated final blend. The final blend is compressed into tablets with predetermined weights on a rotary tablet press and cosmetically coated in a perforated pan coater using Opadry II dispersed in water (about 15% w/w) to yield the final coated tablets.

In some aspects, tablets may be prepared from a blend of ingredients by direct compression. In some aspects, tablets may be prepared by preparing a dry granulated blend of ingredients followed by direct compression. In some aspects, at drug loading levels of ≥ about 20%, or ≥ about 25%, direct compression of the ingredient blend leads to elevated ejection pressures during tooling, causing damage to tablets upon ejections across a range of compression pressures, and which was not alleviated by adjusting tooling parameters such as increasing the die perimeter. In some cases, addition of a lubricant or increasing the lubricant level to ≥ about 1.5% w/w or ≥ about 1.75% w/w, wherein the lubricant may be magnesium stearate, reduced the ejection pressure. In some aspects, use of wet granulation produced tablets with significantly lower ejection pressure and thus, ejection force (e.g., 162-188 N vs. 244 N), than for dry granulation, while maintaining suitable tablet thickness, compressibility, and elastic recovery.

EXAMPLE 28: Tablet Formulation 3

Additional tablet formulations are prepared with components as shown in Table 7.

TABLE 7

| Tablet Formulation 3 Components | | | | |
|---|---|---|---|---|
| | 0.5 mg Strength | | 50 mg Strength | |
| Component | % w/w | mg/blend | % w/w | mg/blend |
| Compound 1 | 0.50 | 0.50 | 50.00 | 50.0 |
| Microcrystalline cellulose (Avicel PH 102; filler) | 47.25 | 47.25 | 22.50 | 22.5 |
| D-Mannitol (Pearlitol 100 SD; filler) | 47.25 | 47.25 | 22.50 | 22.5 |
| Colloidal silicon dioxide (Cabosil M-5P; glidant) | 1.00 | 1.0 | 1.00 | 1.0 |
| Croscarmellose sodium (Ac-Di-Sol; disintegrant) | 3.00 | 3.0 | 3.00 | 3.0 |
| Magnesium stearate (lubricant) | 1.00 | 1.0 | 1.00 | 1.0 |
| Core Tablet Total | 100.0 | 100.0 | 100.0 | 100.0 |
| Core Tablet | 95.0 | 95.0 | 95.0 | 95.0 |
| Opadry II | 5.0 | 5.0 | 5.0 | 5.0 |
| Coated Tablet Total | 100.0 | 100.0 | 100.0 | 100.0 |

Compound 1, microcrystalline cellulose, D-mannitol, croscarmellose sodium, and magnesium stearate were blended using standard methods. Results from stability testing from exposure of blended samples to high temperature and/or humidity for four weeks are provided in Table 8.

TABLE 8

| | % Purity | |
|---|---|---|
| Sample | 40° C./75% relative humidity | 60° C. |
| Compound 1 (control) | 99.35 | 99.35 |
| 0.5 mg formulation | 99.48 | 95.95 |
| 50 mg formulation | 99.28 | 99.36 |

Blends described may be compressed into tablets and coated with film coating using methods analogous to those described herein.

Synthesis Examples

In the synthesis examples that follow, it is understood that reference to a compound as disclosed herein having one or more stereocenters without designating the specific chirality (e.g., R- or S-enantiomer) will be understood to refer to the compound as racemic mixture (or a mixture of diastereomers), while inclusion of R- or S-designations will be understood to refer to an enantiomer (or a diastereomer) form of the compound, such as an enantiomerically (or diastereomerically) enriched form of the compound, or an enantiomeric excess of the specified enantiomer form of the compound, in accordance with discussion above regarding enantiomeric enriched and enantiomeric excess. Notation of a compound with an R- or S-designation is understood to include an enantiomerically enriched or an enantiomeric excess of the specified enantiomer of the compound, and not limited to only 100% of the single specified enantiomer of the compound. For example, reference to Compound 19 will be understood to refer to the compound prepared in Example 47 and in its racemic form: (rac)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile. Similarly, reference to Compound 1 will be understood to refer to the compound prepared in Example 48 and in its single stereoisomer(S) form: (S)-3-amino-3-(1-methyl-1H-imidazol-5-yl)-6-oxa-2(4,6)-quinolina-1,4(1,3)-dibenzenacyclohexaphane-$2^2$,$4^4$-dicarbonitrile.

EXAMPLE 29: Synthesis of 5-bromo-3-(3-methoxyphenyl)benzo[c]isoxazole (3)

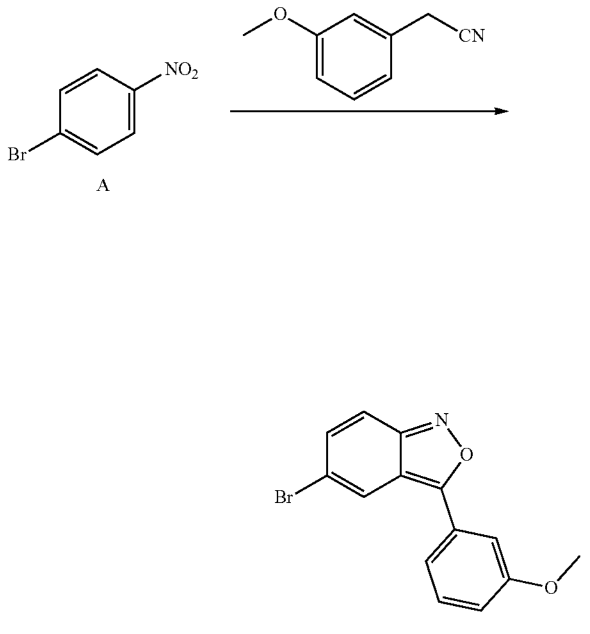

A

3

To a mixture of NaOH (5 equiv.) in MeOH (4 V) at about 10° C. was added 1-bromo-4-nitrobenzene (A) (1.0 equiv.) and 2-(3-methoxyphenyl)acetonitrile (1.8 equiv.) and the resulting mixture was stirred at rt for 16 h. The mixture was diluted with MeOH (4 V) and the resulting solid was collected by filtration. The collected solid was dissolved in DCM (20 V), washed with aq. $Na_2S_2O_3$(10 V×2) and satd. aq. NaCl, and concentrated to obtain Compound 3(83% yield). $^1H$ NMR (400 MHZ, $CDCl_3$) δ=8.01 (s, 1H), 7.64-7.43 (m, 4H), 7.36 (dd, J=1.6, 9.6 Hz, 1H), 7.10-7.03 (m, 1H), 3.91 (s, 3H).

EXAMPLE 30: Synthesis of (2-amino-5-bromophenyl)(3-methoxyphenyl) methanone (4)

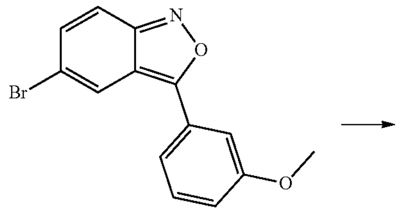

3

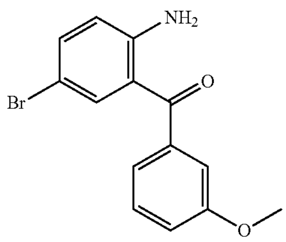

4

A solution of Compound 3(1.0 equiv.) in THF (5 V) at 10° C. was treated with $TiCl_3$ (20% in HCl; 2.5 equiv.) and the resulting solution was stirred at rt for 16 h. The mixture was diluted with water (5 V) and toluene (10 V). The aqueous phase was separated and re-extracted with toluene (10 V). The combined organic phases were washed with 10% aq. NaCl and concentrated to about 6 V to provide a toluene solution of Compound 4, which was used without purification. $^1H$ NMR (400 MHZ, DMSO-$d_6$) δ=7.48-7.38 (m, 2H), 7.33-7.28 (m, 1H), 7.21-7.14 (m, 1H), 7.11-7.05 (m, 2H), 6.85 (dd, J=9.2, 1.2 Hz, 1H), 3.80 (s, 3H). MS ESI calcd. for $C_{14}H_{13}NO_2Br$ $[M+H]^+$ 306.0, found 305.9.

EXAMPLE 31: Synthesis of N-(4-bromo-2-(3-methoxybenzoyl)phenyl)acetamide (5)

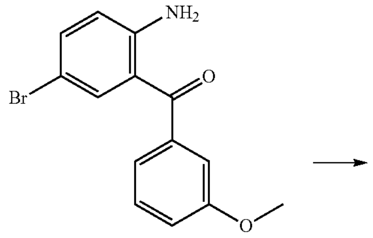

4

-continued

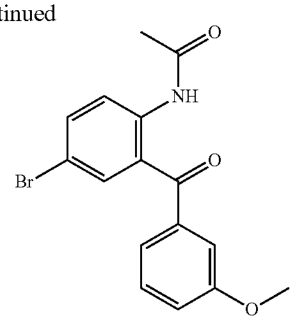

5

A solution of Compound 4(1.0 equiv.) in toluene (6 V) was treated with $Ac_2O$ (1.5 equiv.), and the resulting mixture was stirred at rt for 16 h. The mixture was diluted with heptane (8 V), concentrated to about 3 V, and stirred at rt for 1 h. The resulting solid was collected by filtration and dried in a vacuum oven to provide Compound 5(90% yield over two steps). MS: m/z calcd for $C_{16}H_{15}BrNO_3$ $[M+H]^+$ 350.0, found 349.9.

EXAMPLE 32: Synthesis of 6-bromo-4-(3-methoxyphenyl) quinolin-2(1H)-one (6)

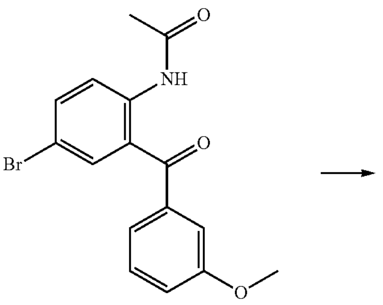

5

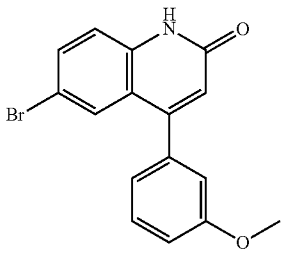

6

A solution of Compound 5(1.0 equiv.) in toluene (10 V) at about 30° C. was treated with potassium tert-butoxide (1.8 M in THF; 2.0 equiv.), and the resulting mixture was stirred at about 30° C. for 16 h. The mixture was cooled to about 20° C. and was treated with HCl (2 M; 5 V). The resulting mixture was stirred for 1 h. The resulting solid was collected by centrifugation (2×), diluted with methanol (10 V), heated to about 50° C., and stirred for 6 h. The reaction mixture was cooled to about 20° C. The resulting solid was collected by centrifugation (2×). The filter cakes were combined and dried in a vacuum oven at about 50° C. for 12 h to provide Compound 6(94% yield; 100% purity by HPLC). 1H NMR (400 MHz, $CF_3COOD$) δ 7.98 (d, J=1.9 Hz, 1H), 7.84 (dd, J=8.8, 2.0 Hz, 1H), 7.60 (d, J=8.9 Hz, 1H), 7.43 (t, J=8.0 Hz, 1H), 7.13 (d, J=6.8 Hz, 2H), 7.03 (d, J=9.0 Hz, 2H), 3.87 (s, 3H); LCMS m/z: [M+H]+ calcd for $C_{16}H_{12}BrNO_2$, 330.01; found, 330.2.

EXAMPLE 33: Synthesis of 6-bromo-2-chloro-4-(3-methoxyphenyl)quinoline (7)

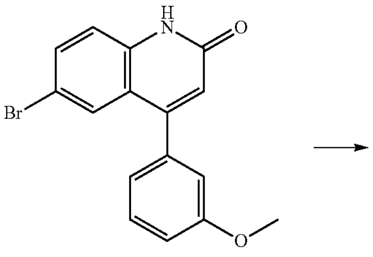

6

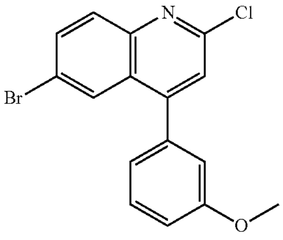

7

A solution of Compound 6(1.0 equiv.) in ACN (10 V) was heated to 50° C. and treated with $POCl_3$(2.0 equiv.), and the resulting mixture was heated to 65° C. over 1.5 h and stirred for 5 h. The mixture was cooled to about 25° C. and then was added to an excess of 20% aq. $KH_2PO_4$ and the resulting mixture was stirred for 1 h. The mixture was diluted with toluene (9 V) and stirred for 1 h. The aqueous phase was separated and the organic phase was washed with 10% aq. NaCl (10 V) and concentrated to 8 to 11 V to obtain Compound 7(96% yield, 99.7% purity by HPLC). $^1$H NMR (400 MHZ, $CDCl_3$) δ 8.03 (d, J=2.3 Hz, 1H), 7.96 (d, J=8.9 Hz, 1H), 7.81 (dd, J=9.0, 2.2 Hz, 1H), 7.47 (dd, J=8.4, 7.5 Hz, 1H), 7.37 (s, 1H), 7.06 (dddd, J=14.3, 7.5, 2.1, 1.0 Hz, 2H), 6.98 (dd, J=2.6, 1.6 Hz, 1H), 3.88 (s, 3H); LCMS m/z: [M+H]+ calcd for $C_{16}H_{11}BrClNO$, 347.97; found, 348.0.

EXAMPLE 34: Synthesis of 3-(6-bromo-2-chloroquinolin-4-yl)phenol (8)

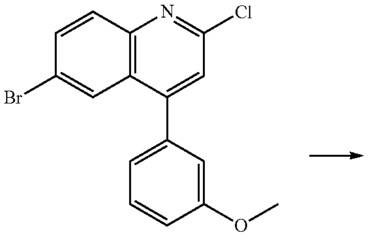

7

-continued

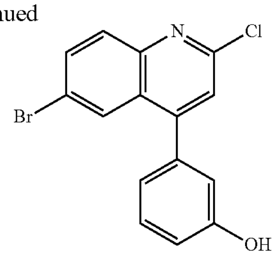

8

A solution of Compound 6(1.0 equiv.) in toluene (obtained as in Example 5) at about 20° C. was treated with $Bu_4NI$ (1.1 equiv.) and then slowly with $BCl_3$ (2.0 equiv.), maintaining the temperature from about 10 to about 35° C., and the resulting mixture was stirred for 2 h. The mixture was diluted with THF (5 V), stirred for 30 min, diluted with water (10 V), and stirred for 30 min. The aqueous phase was removed and the organic phase was washed with 10% aq. $NaHCO_3$ and 10% aq. NaCl, and concentrated to 3 to 5 V. The resulting mixture was diluted with ACN (10 V) and concentrated to 3 to 5 V (2×), then cooled to 0° C. and stirred for 2 h. The resulting solid was collected by centrifugation and dried in a vacuum oven at 50° C. for 12 h to provide Compound 8(85% yield, 98% purity). $^1$H NMR (300 MHZ, DMSO-$d_6$) δ 9.85 (s, 1H), 7.98 (d, J=7.4 Hz, 3H), 7.57 (s, 1H), 7.41 (t, J=7.8 Hz, 1H), 7.01-6.95 (m, 2H), 6.93 (t, J=1.9 Hz, 1H); LCMS m/z: [M+H]+ calcd for $C_{15}H_9BrClNO$, 333.96; found, 334.0.

EXAMPLE 35: Synthesis of 6-bromo-4-(3-((tert-butyldimethylsilyl)oxy)phenyl)-2-chloroquinoline (9)

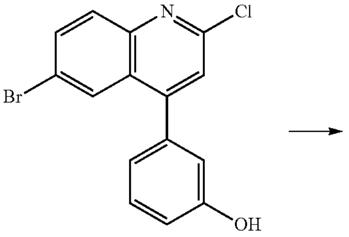

8

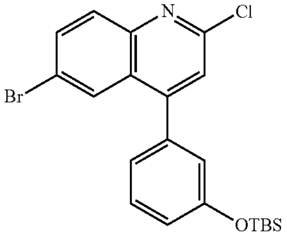

9

A mixture of Compound 8(1.0 equiv.), DMAP (0.1 equiv.), $Et_3N$ (2.0 equiv.), and TBSCl (1.5 equiv.). in DCM (0.5 V) was stirred at rt for 4 h. The reaction mixture was washed with water and 10% aq. NaCl, concentrated to 3 to 5 V, diluted with MeOH, concentrated to 3 to 5 V, cooled to rt, and stirred for 2 h. The resulting solid was collected by centrifugation and dried in a vacuum over at 50° C. for 17 h to obtain Compound 9(94% yield, 99.5% purity). $^1$H NMR (400 MHZ, $CDCl_3$) δ 8.04 (d, J=2.2 Hz, 1H), 7.95 (d, J=9.0 Hz, 1H), 7.81 (dd, J=8.9, 2.2 Hz, 1H), 7.44-7.34 (m, 2H), 7.03 (dddd, J=15.6, 8.2, 2.1, 1.0 Hz, 2H), 6.94-6.92 (m, 1H), 1.01 (s, 9H), 0.26 (s, 6H); LCMS m/z: [M+H]+ calcd for $C_{21}H_{23}BrClNOSi$, 448.04; found, 448.2.

EXAMPLE 36: Synthesis of methyl 4-bromo-3-(bromomethyl)benzoate (21)

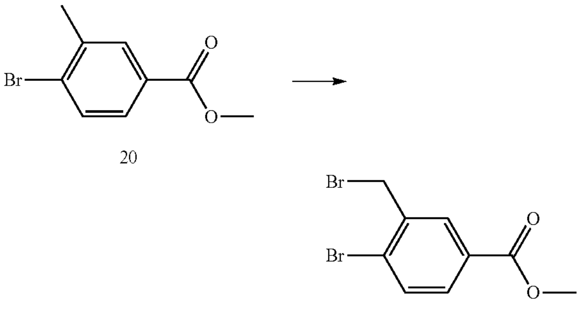

20

21

A solution of methyl 4-bromo-3-methylbenzoate (1.0 equiv.) in ACN (15 V) was treated with NBS (1.35 equiv.) and the mixture was exposed to light in a continuous flow reactor with a photolysis flow cell (wavelength, 450 nm and optionally 365 nm). The reaction mixture was concentrated to about 5 to 7 V, treated with water at rt, and stirred for 4 h. The resulting solid was collected by centrifugation, washing with water, and dried in a vacuum oven at 50° C. for 12 h to provide Compound 21 in 94% yield as a 75:25 mixture of Compound 21 and methyl 4-bromo-3-(dibromomethyl) benzoate. Compound 21: $^1$H NMR (400 MHZ, DMSO-$d_6$) δ 8.21 (d, J=2.0 Hz, 1H), 7.86-7.78 (m, 2H), 4.83 (s, 2H), 3.87 (s, 3H). Methyl 4-bromo-3-(dibromomethyl)benzoate: $^1$H NMR (400 MHz, DMSO-$d_6$) δ 8.48 (d, J=1.8 Hz, 1H), 7.89-7.80 (m, 2H), 7.41 (s, 1H), 3.90 (s, 3H).

EXAMPLE 37: Synthesis of 4-bromo-3-(hydroxymethyl)benzoic acid (22)

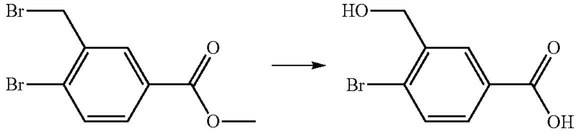

21 22

The mixture of Compound 21 and methyl 4-bromo-3-(dibromomethyl)benzoate (1.0 equiv.) from Example 8 was diluted with $H_2O$ (6.5 V) and ethanol (1.5 V) and treated with $Na_2CO_3$(4.0 equiv.). The resulting mixture was stirred at reflux for 16 h. The resulting mixture (a mixture of Compound 22 and 4-bromo-3-formylbenzoic acid) was cooled to about 30° C. and treated with $NaBH_4$(0.3 equiv.). The resulting mixture was stirred at about 50° C. and stirred for 2 h. The mixture was cooled to rt, diluted with THF/EtOAc (1:1, 5 V), and pH adjusted to 2-3 with 6 N HCl. The aqueous phase was separated and extracted with THE/EtOAc (1:1, 5 V). The combined organic phases were washed with 10% aq. NaCl, and concentrated to about 4 to 6 V, and solvent-swapped with THF (2×, 10 V) and concentrated to about 4 to 6 V. The mixture was diluted with heptane (15 V) and stirred at rt for 1 h. The resulting solid was collected by centrifugation and dried in a vacuum oven at about 50 C for 12 h to provide Compound 22 (87% % yield, 97% purity). $^1$H NMR (400 MHZ, DMSO-$d_6$) δ 13.13 (s, 1H), 8.11 (d, J=2.0 Hz, 1H), 7.76-7.68 (m, 2H), 5.61 (t, J=5.6 Hz, 1H), 4.54 (d, J=4.6 Hz, 2H); LCMS m/z: $[M-H]^-$ calcd for $C_8H_7BrO_3$, 229.0; found, 229.0.

EXAMPLE 38: Synthesis of (4-bromo-3-(hydroxymethyl)phenyl)(morpholino)methanone (23)

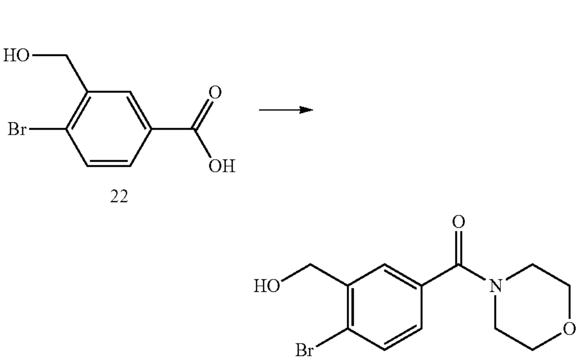

22

23

A mixture of Compound 22 (1.0 equiv.), morpholine (1.5 equiv.), DMAP (0.1 equiv.), and triethylamine (2.0 equiv.) in DCM (10 V) was treated with EDCI (1.6 equiv.), and the resulting mixture was stirred at about 30° C. for 14 h. The mixture was diluted with DCM (3 V) and the aqueous phase was separated. The organic phase was washed with 5% aq. $NaHCO_3$ and 10% aq. NaCl, and concentrated to about 4 to 6 V. The resulting mixture was treated with heptane (15 V) and stirred for 2 h. The resulting solid was collected by centrifugation, washing with heptane, and dried in a vacuum oven at 50° C. for 12 h to provide Compound 23 (85% yield, 98.8% purity). $^1$H NMR (400 MHz, DMSO-$d_6$) δ 7.64 (d, J=8.1 Hz, 1H), 7.55-7.51 (m, 1H), 7.24 (dd, J=8.1, 2.2 Hz, 1H), 5.55 (t, J=5.7 Hz, 1H), 4.53 (d, J=5.6 Hz, 2H), 3.61 (s, 6H); LCMS m/z: [M+H]+ calcd for $C_{12}H_{14}BrNO_3$, 300.0; found, 300.0.

EXAMPLE 39: Synthesis of (4-bromo-3-(((tert-butyldimethylsilyl)oxy)methyl)phenyl)(morpholino) methanone (11)

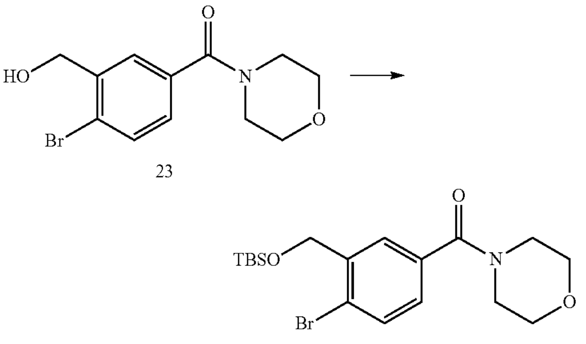

23

11

A mixture of Compound 23, TBSCl (1.3 equiv.), triethylamine (2.0 equiv.), and DMAP (0.1 equiv.) in DCM (10 V) was stirred at rt for 4 h. The reaction mixture was washed with water (6 V) and the aqueous phase was extracted with DCM (3 V). The combined organic phases were washed with 10% aq. NaCl, concentrated to about 7 to 9 V, solvent-swapped with MeOH (2×, 8 V), and concentrated to about 7 to 9 V. The resulting solution was added dropwise to water (8 V) at 3° C. and the resulting mixture was stirred for 2 h. The resulting solid was collected by centrifugation, washing with MeOH/$H_2O$ (0.50 V) and dried at about 30° C. for 12 h to provide Compound 11 (94% yield, 97% purity). $^1H$ NMR (300 MHz, $CDCl_3$) δ 7.61-7.53 (m, 2H), 7.20 (dd, J=8.1, 2.2 Hz, 1H), 4.74 (s, 2H), 3.70 (s, 8H), 0.97 (s, 9H), 0.15 (s, 6H); LCMS m/z: [M+H]+ calcd for $C_{18}H_{28}BrNO_3Si$, 414.10; found, 414.1.sal EXAMPLE 40: Synthesis of (4-bromo-3-(((tert-butyldimethylsilyl)oxy)methyl)phenyl)(4-(3-((tert-butyldimethylsilyl)oxy)phenyl)-2-chloroquinolin-6-yl)methanone (12)

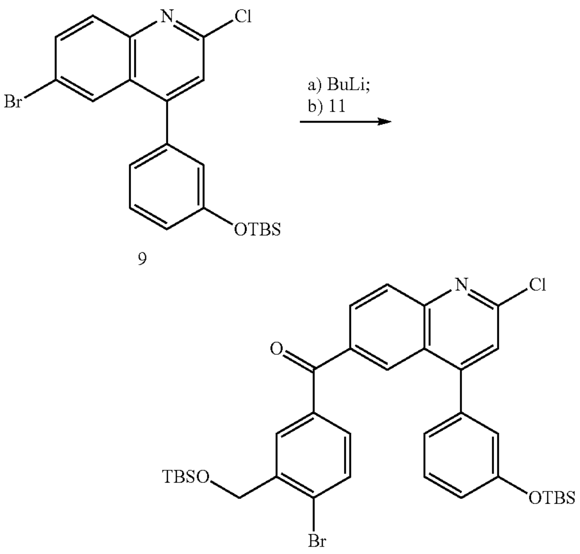

9

12

A solution of Compound 9(1.0 equiv.) in THF (5 V) was cooled to −80° C. was treated with BuLi (2.5 M in hexanes; 1.1 equiv.) and the resulting mixture was stirred at −80° C. for 2 h. To this mixture at −80° C. was added dropwise a pre-cooled solution of Compound 11 (1.05 equiv.) in THF (3 V) and the resulting mixture was stirred at −80° C. for 2 h. The mixture was treated with a solution of glacial acetic acid (2 equiv.) in THF (1 V) and the resulting mixture was stirred at −80° C. for 30 min. The mixture was warmed to rt and the resulting solid was filtered, rinsing with THE. The filtrate was washed with water. The aqueous phase was separated and extracted with MTBE, washed with 10% aq. NaCl, vacuum distilled to about 5 to 8 V, solvent-switched to MeOH, and crystallized by heating to about 50° C., cooling slowly over 3 h to 0° C., and stirring for 2 h (2×). The resulting solid was collected by centrifugation, washing with MeOH, and dried in a vacuum oven at 50° C. for about 12 h to provide Compound 12 (69% yield, 99% purity). $^1H$ NMR (400 MHZ, $CDCl_3$) δ 8.36 (d, J=1.8 Hz, 1H), 8.18 (d, J=8.7 Hz, 1H), 8.10 (dd, J=8.7, 1.9 Hz, 1H), 7.99~7.95 (m, 1H), 7.64~7.55 (m, 2H), 7.43 (s, 1H), 7.36 (t, J=7.8 Hz, 1H), 7.08 (d, J=7.5 Hz, 1H), 6.99~6.91 (m, 2H), 4.74 (s, 2H), 1.90 (s, 1H), 1.27 (s, 1H), 0.98 (s, 9H), 0.82 (s, 9H), 0.19 (s, 6H), 0.07 (s, 6H); LCMS m/z: [M+H]+ calcd for $C_{35}H_{43}BrClNO_3Si_2$, 696.17; found, 696.2.

EXAMPLE 41: Synthesis of (4-bromo-3-(((tert-butyldimethylsilyl)oxy)methyl)phenyl)(4-(3-((tert-butyldimethylsilyl)oxy)phenyl)-2-chloroquinolin-6-yl)(1-methyl-1H-imidazol-5-yl) methanol (13)

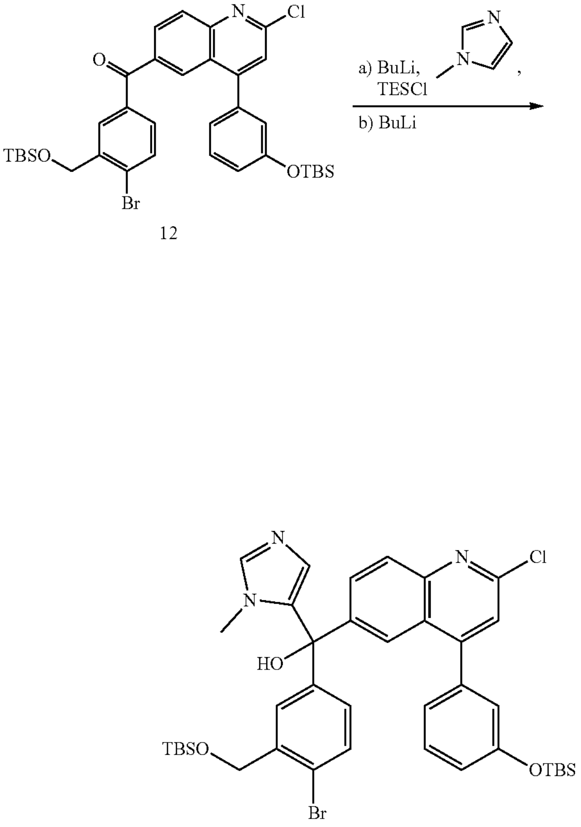

12

13

A solution of 1-methylimidazole (1.6 equiv.) in THF (8 V) at −75° C. was treated with n-BuLi (2.5 M in hexanes; 1.7 equiv.) and the mixture was stirred for 1 h and then treated with TESCl (1.75 equiv). The resulting mixture was stirred for another 1 h at −75° C., then was treated with n-BuLi (2.5 M in hexanes; 1.2 equiv.), and stirred for 1.5 h. The mixture was cooled to about −85° C., treated with a solution of Compound 12 (1.0 equiv.) in toluene (2 V) dropwise, and the resulting mixture was stirred at −85° C. for 30 min. The mixture was warmed to about −30° C. and stirred for 30 min, then quenched at −30° C. with 10% aq. $NH_4Cl$, warmed to rt, and diluted with water. The aqueous phase was separated and extracted with MTBE. The combined organic phases were washed with 5% (w/w) aq. citric acid (2×) and with 10% aq. NaCl to provide a solution of Compound 13 (84% yield, 78% purity), which was used without further purification.

EXAMPLE 42: 3-(6-((4-bromo-3-(hydroxymethyl)phenyl)(hydroxy)(1-methyl-1H-imidazol-5-yl)methyl)-2-chloroquinolin-4-yl)phenol (14)

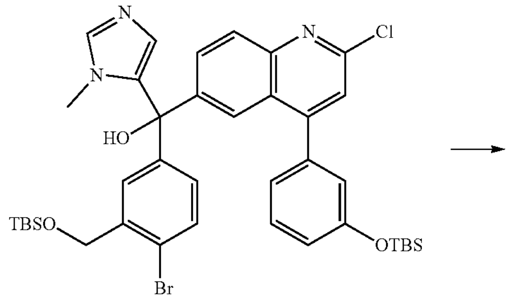

13

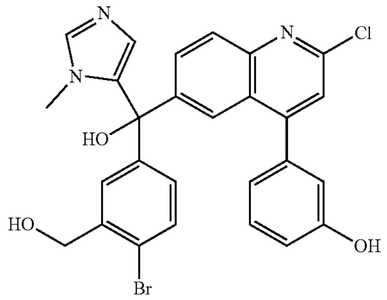

14

The solution of Compound 13 (1.0 equiv.) from Example 13 was solvent-switched to THE (10 V) at 5° C. was treated with 3 N HCl (1.5 equiv.) and the resulting mixture was stirred at 10° C. for 24 h. The pH of the mixture was adjusted to 7-9 with 10% aq. NaOH at 0-5° C. The resulting mixture was extracted with 2-MeTHF (5 V). The organic layer was concentrated and solvent-switched to EtOAc (3 V) and the mixture was stirred for 21 h. The resulting solid was collected by centrifugation, mixed with THE (8 V) and water (0.4 V), and concentrated. The residue was mixed with EtOAc (6 V) and stirred for 21 h. The resulting solid was collected by centrifugation, rinsing with 2:1 EtOAc/THF, and dried at 30° C. for 12 h to provide Compound 14 (85% yield). $^1$H NMR (400 MHZ, DMSO-$d_6$) δ 7.99 (d, J=8.8 Hz, 1H), 7.82 (d. J=2.1 Hz, 1H), 7.74 (dd, J=8.8, 2.1 Hz, 1H), 7.64 (d, J=1.1 Hz, 1H), 7.53~7.46 (m, 3H), 7.29 (t, J=7.8 Hz, 1H), 7.04~6.97 (m, 2H), 6.91 (ddd, J=8.2, 2.4, 1.0 Hz, 1H), 6.87~ 6.79 (m, 2H), 6.07 (d, J=1.1 Hz, 1H), 4.45 (d, J=2.0 Hz, 2H), 3.33 (s, 5H); LCMS m/z: [M+H]+ calcd for $C_{27}H_{22}BrClN_3O_3$, 552; found, 552.

EXAMPLE 43: Synthesis of 3-(6-((4-bromo-3-(chloromethyl)phenyl)(hydroxy)(1-methyl-1H-imidazol-5-yl)methyl)-2-chloroquinolin-4-yl)phenol hydrochloride salt (15)

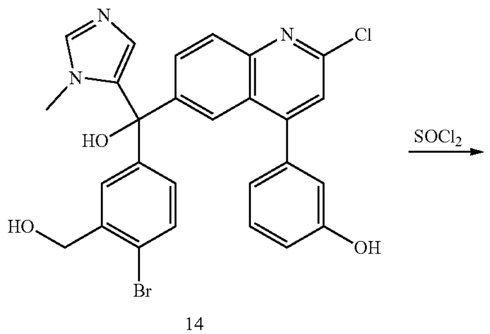

14

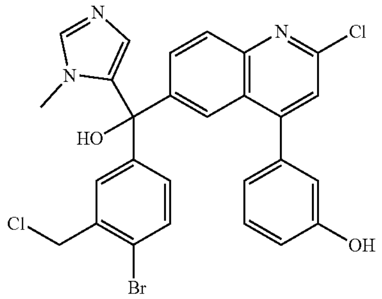

15

A solution of Compound 14 (1.0 equiv.) in 2-MeTHF (20 V) at rt was treated with $SOCl_2$(3.0 equiv.) and the resulting mixture was stirred at 50° C. for 1 h. The reaction mixture was cooled to rt and treated with heptane (20 V). The resulting mixture was stirred for 2 h. The resulting solid was collected by centrifugation, washing with heptane, and slurried with heptane/2-MeTHF (10 V/1 V) for 2 h. The resulting solid was collected by centrifugation and dried at 30° C. for 12 h to provide Compound 15, which was used directly in the next step (90% purity by HPLC). $^1$H NMR (300 MHz, DMSO-$d_6$) δ 14.71 (s, 1H), 9.92 (s, 1H), 9.24 (d, J=1.5 Hz, 1H), 8.11~8.01 (m, 1H), 7.86~7.76 (m, 2H), 7.75~7.62 (m, 2H), 7.62~7.52 (m, 2H), 7.30 (td, J=7.5, 1.7 Hz, 1H), 7.19 (dd, J=8.4, 2.4 Hz, 1H), 6.99~6.89 (m, 3H), 6.83 (dt, J=7.6, 1.3 Hz, 1H), 4.79 (d, J=1.6 Hz, 2H), 3.56 (s, 3H); LCMS m/z: [M+H−HCl]+ calcd for $C_{27}H_{21}BrCl_2N_3O_2$, 570; found, 570.

EXAMPLE 44: Synthesis of $4^4$-bromo-$2^2$-chloro-3-(1-methyl-1H-imidazol-5-yl)-6-oxa-2(4,6)-quinolina-1,4(1,3)-dibenzenacyclohexaphan-3-ol (16)

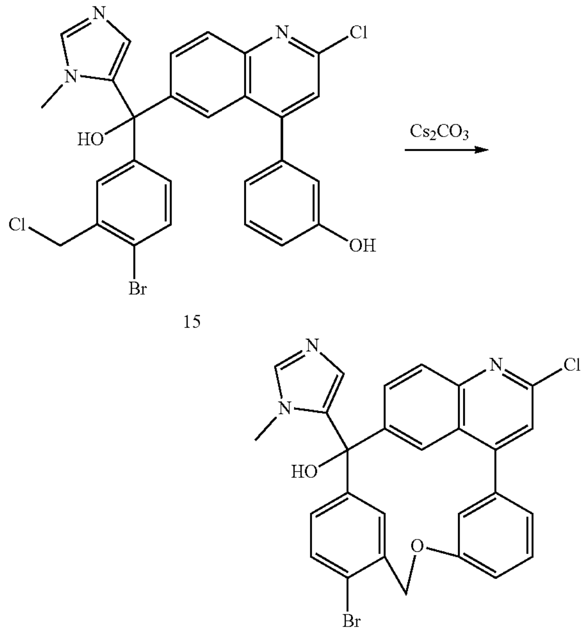

15

16

A solution of Compound 15 (1.0 equiv.) in DMAc (15 V) at 70° C. was added to a mixture of $Cs_2CO_3$(3.0 equiv.) in DMAc (5 V) and the resulting mixture was stirred at 70° C. for 2 h. The mixture was cooled to rt, mixed with water (30 V), and stirred for 6 h. The resulting solid was collected by centrifugation, washing with water, and dried at 50° C. for 12 h. The product could be purified further by iterative slurrying with 2-MeTHF/THF (1:1, 5 V) at 70° C. and DMI/ACN (1:2, 10.5 V). Compound 16 was obtained (60% yield for two steps). $^1$H NMR (400 MHZ, DMSO-d6) δ 8.22 (d, J=8.9 Hz, 1H), 8.10 (d, J=8.8 Hz, 1H), 7.66 (d, J=25.2 Hz, 4H), 7.39 (t, J=7.9 Hz, 1H), 7.19 (d, J=7.5 Hz, 1H), 7.13~6.92 (m, 2H), 6.19 (s, 1H), 5.45 (d, J=10.3 Hz, 2H), 3.58 (s, 3H); LCMS m/z: [M+H]+calcd for $C_{27}H_{20}BrClN_3O_2$, 534; found, 534.

EXAMPLE 45: Synthesis of $4^4$-bromo-$2^2$,3-dichloro-3-(1-methyl-1H-imidazol-5-yl)-6-oxa-2(4,6)-quinolina-1,4(1,3)-dibenzenacyclohexaphane (17A)

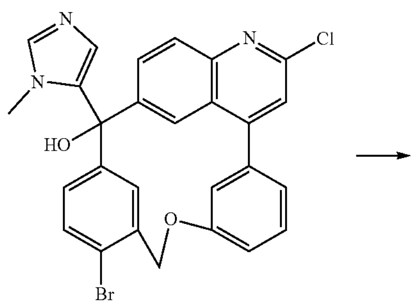

16

-continued

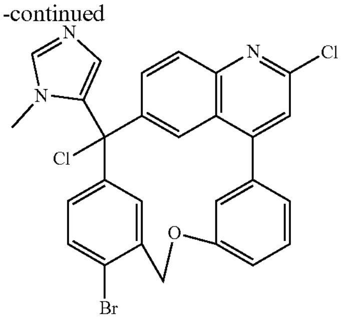

17A

A solution of Compound 16 (1.0 equiv.) in DMI (10 V) was treated with $SOCl_2$ (3.3 equiv.) and stirred at 40° C. for 8 h. The resulting mixture was used directly in the next step.

EXAMPLE 46: Synthesis of $4^4$-bromo-$2^2$-chloro-3-(1-methyl-1H-imidazol-5-yl)-6-oxa-2(4,6)-quinolina-1,4(1,3)-dibenzenacyclohexaphan-3-amine (18A)

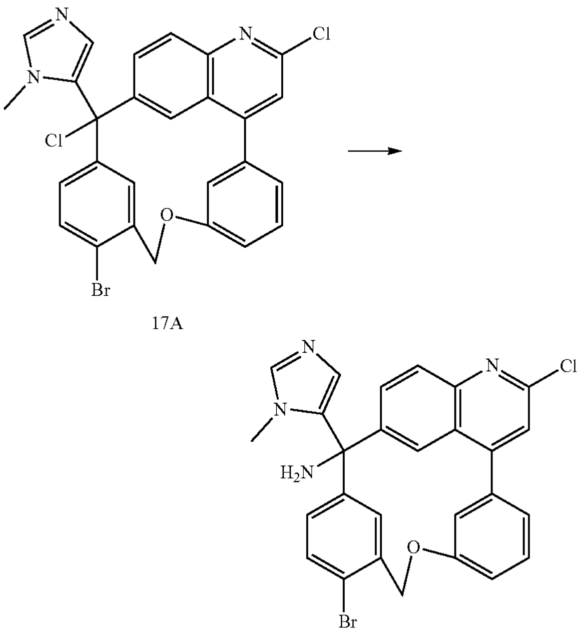

17A

18A

The solution of Compound 17A in DMI from Example 17 at rt added to $NH_3$ (2 M in IPA; 20 equiv.) and stirred at rt for 16 h. The reaction mixture was concentrated under reduced pressure to about 13 to 15 V, treated with water (50 V) over 4 h, and stirred for 16 h. Water (30 V) was added and the resulting solid was collected by centrifugation. Additional purification steps may include dissolving the collected solid in dilute aq. HCl, agitating with DCM, adjusting the pH of the aqueous phase with 10% aq. $Na_2CO_3$ to 8-9 at about 5 C, separating the organic phase, washing the organic phase with water, switching the organic phase to 2-MeTHE, stirring for 2 h at 40° C. and then 16 h at 25° C., and collecting the resulting solid by centrifugation, then optionally slurrying in DMI/2-MeTHF, performing silica gel chromatography, and recrystallization from DCM/heptane. The collected solid was dried in a vacuum oven at 50° C. for 24 h to give Compound 18A (34% yield for two steps). $^1$H NMR (400 MHZ, DMSO-$d_6$) δ 8.19 (d, J=8.9 Hz, 1H), 7.00 (d, J=8.8 Hz, 1H), 7.80 (s, 1H), 7.58 (s, 1H), 7.55~7.48 (m, 2H), 7.34 (t, J=7.9 Hz, 1H), 7.30 (s, 1H), 7.25 (s, 1H), 7.14 (dd, J=7.6, 1.3 Hz, 1H), 7.02 (ddd, J=8.3, 2.6, 1.0 Hz, 2H), 6.39 (s, 1H), 5.46~5.34 (m, 2H), 3.76 (dtd, J=35.9, 7.6, 6.0 Hz, 1H), 3.53 (td, J=8.0, 6.4 Hz, 1H), 3.12 (d, J=1.6 Hz, 3H), 2.99 (s, 2H), 1.98~1.69 (m, 2H), 1.29 (ddt, J=11.7, 8.8, 7.4 Hz, 1H), 1.09 (d, J=6.0 Hz, 2H); LCMS m/z: [M+H]+ calcd for $C_{27}H_{21}BrClN_4O$, 532.85; found, 532.85.

EXAMPLE 47: Synthesis of 3-amino-3-(1-methyl-1H-imidazol-5-yl)-6-oxa-2(4,6)-quinolina-1,4(1,3)-dibenzenacyclohexaphane-2$^2$,4$^4$-dicarbonitrile (19)

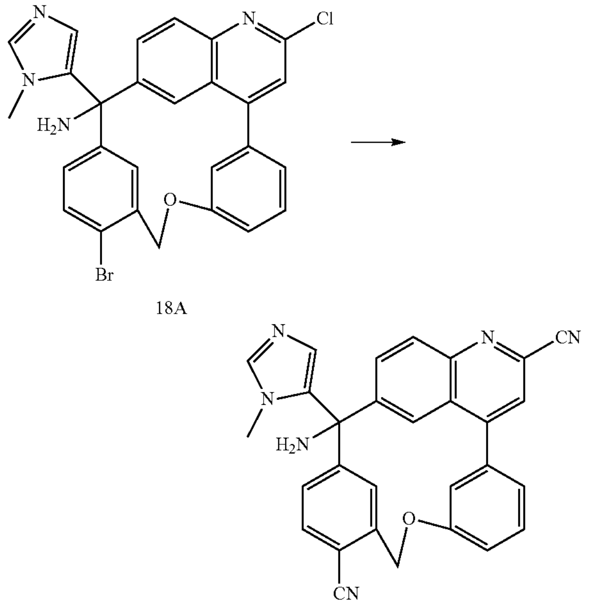

18A

19

A reaction vessel containing a mixture of dppf (0.08 equiv.), $Pd_2(dba)_3$ (0.013 equiv.), and $Pd(OAc)_2$(0.04 equiv.) in DMA (5.75 V) at 25° C. was de-gassed and back-filled with $N_2$ (6×), then stirred at 25° C. for 1.5 h. Compound 18A (1.0 equiv.), $Zn(CN)_2$(1.5 equiv.), Zn (0.05 equiv.), and 0.25 V DMA were added. The resulting mixture was heated to 100° C. and stirred for 8 h, then cooled to 25° C. and filtered, washing with DMA (1 V). To the filtrate at 0° C. was added a pre-mixed solution of tetrasodium EDTA (2.5 equiv.) and trithiocyanuric acid trisodium salt (TMT-3Na; 0.18 equiv.) in water (12 V). The resulting mixture was warmed to 25° C. and stirred for 5 h. The resulting solid was collected by filtration, washing with water, and dried at 45° C. under vacuum for 19 h, then purified by column chromatography (4% MeOH/DCM), and crystallized from ACN. The resulting solid was collected by filtration, washing with ACN, and dried under vacuum at 45° C. for 13 h to give Compound 19 (72% yield). $^1$H NMR (400 MHz, DMSO-$d_6$) δ 8.38~8.36 (d, J=8.4 Hz, 1H), 8.23~8.05 (d, J=9.2 Hz, 1H), 8.08 (s, 1H), 7.94 (s, 1H), 7.87-7.82 (m, 1H), 7.56 (s, 1H), 7.42~7.40 (m, 1H), 7.25 (s, 1H), 7.21~7.20 (m, 1H) 7.12 (s, 1H), 7.09~7.07 (t, J=2.4 Hz, 1H), 6.40 (s, 1H), 5.58~5.47 (m, 2H), 3.17 (s, 2H), 3.14 (s, 3H); LCMS m/z: [M+H]+ calcd for $C_{29}H_{20}N_6O$, 469.17; found, 469.10.

EXAMPLE 48: Synthesis of (S)-3-amino-3-(1-methyl-1H-imidazol-5-yl)-6-oxa-2(4,6)-quinolina-1,4(1,3)-dibenzenacyclohexaphane-2$^2$,4$^4$-dicarbonitrile (1)

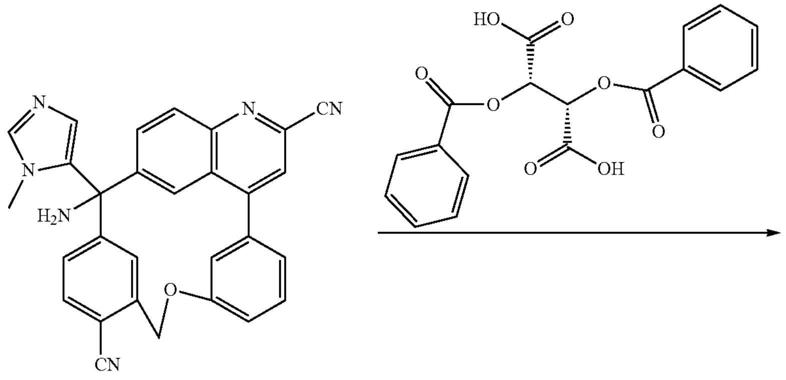

19

-continued

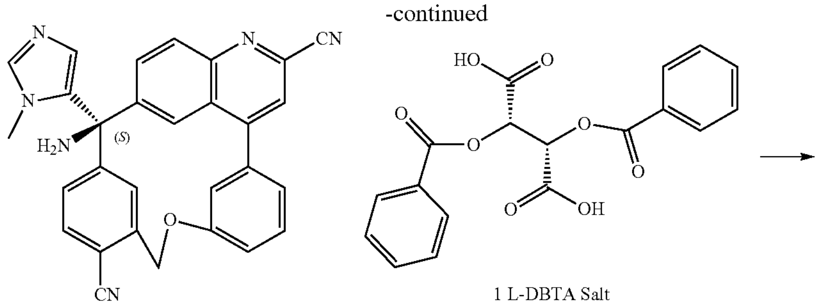

1

1 L-DBTA Salt

To a solution of Compound 19 (1.0 equiv.) in DCM (95 V) was added a solution of dibenzoyl-L-tartaric acid (L-DBTA; 1.2 equiv.) in DCM (20 V) and the resulting mixture was stirred at 25° C. for 12 h. The resulting solid was filtered, washing with DCM (10 V). This procedure was repeated on a second batch of Compound 19. The combined solids (Compound 1 L-DBTA salt) were diluted with DCM (5 V) and washed with a solution of $Na_2CO_3$(1.4 equiv.) in water (20 V). The layers were separated and the aqueous layer was extracted with DCM. The combined organic phases were washed with water, then solvent-switched to ACN, and filtered. The filtrate was treated with 3-mercaptopropyl ethyl sulfide silica at 25° C. and filtered. The filtrate was concentrated to about 3 V, heated to about 45° C., and treated with water (3 V). Seed crystals of Compound 1 (Form 1) were added (1.5% wt) and the mixture was stirred for 30 min, diluted with water (6 V), filtered, and stirred for 2 h, then cooled to 25° C. and stirred for 7 h. The resulting solid was collected by filtration, washing with water, and dried at 60° C. under vacuum for 12 days to provide Compound 1 (16% yield, 98.8% purity with 0.4% (R) enantiomer by ultraperfomance chromatography (UPC)). XRPD analysis was consistent with Compound 1 (Form 1).

EXAMPLE 49: Chiral Resolution Salt Screen with Chiral Acids

Experiment 1. A solution of racemate Compound 19 in acetone was prepared and distributed into 40 1 mL tubes (15 μmol Compound 19 in each). A solution of each test resolving agent (1 equiv. unless 0.5 equiv. indicated below) was added to each tube. The mixtures were concentrated at 45° C. overnight. For each resolving agent, a volume of 0.5 mL of test solvent ($H_2O$, EtOH, IPA, ACN, dioxane, EtOAc, IPAc, MEK, CPME, anisole, toluene, or heptane) was added. The mixtures were heated to 70° C. for 15 to 45 min in an ultrasonic heating bath then cooled to rt. The resulting solids and mother liquors were tested for change in ee of the solids and of the mother liquors. The following resolving agents were tested: dibenzoyl-L-tartaric acid hydrate, (R)-phencyphos hydrate, (R)-chlocyphos, (−)-tartaric acid, (+)-camphor sulfonic acid, D-camphoric acid, L-malic acid, (S)-mandelic acid, L-(−)-di-p-anisoyltartaric acid, L-(−)-di-p-toluoyltartaric acid, (R)-anisyphos, (R)-BINAP phosphate, (R)-(−)-2-chloromandelic acid, N-acetyl-L-phenylalanine, N-acetyl-L-leucine, L-lactic acid, (S)-naproxen, D-(+)-3-phenyllactic acid, N-acetyl-L-proline, L-α-hydroxyisovaleric acid, dibenzoyl-L-tartaric acid hydrate (0.5 eq), (−)-tartaric acid (0.5 eq), L-(−)-di-p-anisoyltartaric acid (0.5 eq), L-(−)-di-p-toluoyltartaric acid (0.5 eq), (R)-methoxy (trifluoromethyl)phenylacetic acid, (R)-phenylsuccinic acid, N-carbobenzyloxy-L-tryptophan, N-carbobenzyloxy-L-valine, Boc-D-phenylalanine, carbobenzyloxy-L-proline, Boc-D-homophenylalanine, (S)-'O-acetyl mandelic acid, D-pyroglutamic acid, N-Boc alanine, (R)-4-methyl-mandelic acid, N-acetyl methionine, abietic acid, (+)-dehydroabietic acid, (R)-(−)-2-phenylpropionic acid, and (R)-α-methoxy-phenyl acetic acid). The resulting solid and mother liquor for each sample were tested by HPLC for change in ee relative to the racemic Compound 19. For the majority of the tests, no significant change in ee was observed for the solid or the mother liquor. Tests that provided a change of at least 10% in one or both ee aspects by UPC relative to the racemic starting material are shown in Table 9. The remaining tests did not provide a change of at least 10% in ee.

TABLE 9

| Resolving agent | Solvent | ee solid | ee mother liquor |
|---|---|---|---|
| (R)-Chlocyphos | EtOH | −2% | +13% |
| | IPAc | −1% | +26% |
| | H2O | +14% | −1% |
| (−)-Tartaric acid | IPAc | −1% | +10% |
| (+)-Camphorsulfonic acid | IPAc | −1% | +16% |
| L-(−)-Di-p-anisoyltartaric acid | EtOH | −3% | +25% |
| L-(−)-Di-toluoyltartaric acid | EtOH | −7% | +61% |
| (R)-BINAP phosphate | Dioxane | +3% | −20% |

Experiment 2. Compound 19 (300 mg, 1 equiv.) was added to a solution of a resolving agent (L-(−)-di-toluoyl tartaric acid, (−)-tartaric acid, L-(−)-di-p-anisoyltartaric acid, or di-benzoyl-L-tartaric acid; 3.15 equiv.) in a solvent (9 V) and the mixture was allowed to stir at rt overnight. The resulting solid was collected and recrystallized twice from acetone. Results for resolving agents that increased ee by at least 10% are shown in Table 10. Experiments using (−)-tartaric acid (acetone, EtOH, IPA, or ACN) or L-(−)-di-p-anisoyltartaric acid (acetone, EtOH, ACN, or MEK) did not produce significant change to ee solid.

TABLE 10

| Resolving Agent (acetone) | After 1st Crystallization ee solid | After 1st Crystallization ee mother liquor | After 2nd Crystallization ee solid | After 2nd Crystallization ee mother liquor | Recovery |
|---|---|---|---|---|---|
| L-(−)-Di-toluoyl tartaric acid | −90.0% | +48.3% | −94.7% | −31.2% | 25.5% |
| Di-benzoyl-L-tartaric acid | −64.4% | +20.4% | 90.0% | 43.0% | 5.0% |

Experiment 3. Compound 19 was dissolved in DMSO with heating and test resolving agent (1 equiv.) was added. The mixture was stirred until all solids dissolved. Water was added and the resulting precipitate was collected by filtration, washed with water, and dried. The salt was dissolved in test solvent (10 V) with heating and the mixture was stirred at rt overnight. Any resulting solid was collected and the solid and mother liquor were analyzed by HPLC for % change in ee. Test resolving agents were (R)-chlocyphos, (+)-camphor sulfonic acid, and (R)-BINAP phosphate, and test solvents were acetone, ACN, EtOH, IPA, dioxolane, MEK, CPME, anisole, toluene, heptanes, water, acetone, IPAc, THF, 2-MeTHF, dioxolane, glyme, and EtOAc. The resulting solid and mother liquor for each sample were tested by UPC for change in ee relative to the racemic Compound 19. For the majority of the tests, no significant change in ee was observed for the solid or the mother liquor. Tests that provided a change of at least 10% in one or both ee aspects relative to the racemic starting material are shown in Table 11. The remaining tests did not provide a change of at least 10% in ee.

TABLE 11

| Resolving agent | Solvent | ee solid | ee ML |
|---|---|---|---|
| (R)-Chlocyphos | Acetone | −11.3% | +39.2% |
| | ACN | −10.7% | +41.7% |
| (R)-BINAP phosphate | Acetone | +48.7% | −34.3% |
| | ACN | +38.4% | −27.3% |
| | IPAc | −3.6% | +14.1 |
| | MEK | +55.9% | −31.0% |
| | THF | +47.0% | −36.0% |
| | 2-MeTHF | +60.7% | −50.5% |
| | Dioxolane | +45.0% | |
| | Glyme | +44.5% | −47.0% |

Successive crystallizations of the recovered solid increased the ee.

Experiment 4. Compound 19 (1 equiv.) and (R)-BINAP phosphate (1 equiv.) were combined with heating in acetone, MEK, dioxolane, THF, glyme, or MeOH, then heated at reflux for 3 h, and stirred at rt overnight. The solid was filtered, washed with solvent, and dried. The solid and mother liquor were tested by HPLC for change in ee relative to racemic Compound 19. Tests that provided a change of at least 10% in one or both ee aspects relative to the racemic starting material are shown in Table 12. The remaining tests did not provide a change of at least 10% in ee.

TABLE 12

| Solvent | ee solid | ee mother liquir |
|---|---|---|
| Acetone | −72.6% | −0.9% |
| MEK | −59.2% | +0.9% |
| Dioxolane | +43.2% | −53.9% |
| THF | +48.7% | −69.7% |
| Glyme (dimethoxyethane) | +28.7% | −73.9% |

Crystallization of the THF and dioxolane products improved the ee, as shown in Table 13.

TABLE 13

| Solvent | 1st crystallization ee solid | 1st crystallization ee ML | 2nd crystallization ee solid | 2nd crystallization ee ML |
|---|---|---|---|---|
| THF | +24.0% | −61.9% | +60.4% | −44.2% |
| Dioxolane | +62.4% | −48.6% | +92.9% | −16.3% |

Repeating the experiment with 10 V dioxolane provided an initial solid with +60.5% ee (mother liquor with −15.98% ee). The solid was dissolved in 10 V dioxolane, heated at reflux for 3 h, and stirred at rt overnight. The collected solid had +97.0% ee and a purity of 99.7% by HPLC.

EXAMPLE 50: Synthesis of 3-hydroxy-3-(1-methyl-1H-imidazol-5-yl)-6-oxa-2(4,6)-quinolina-1,4(1,3)-dibenzenacyclohexaphane-$2^2$,$4^4$-dicarbonitrile (17)

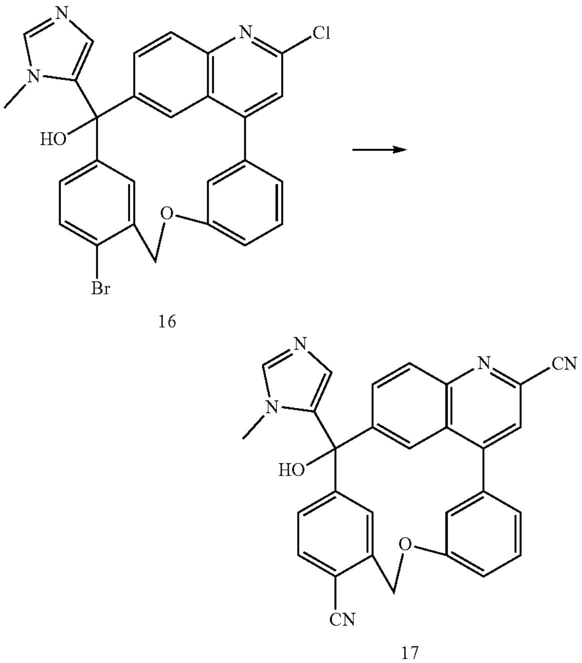

16

17

Compound 16 was converted to Compound 17 using methods analogous to those described in Example 19. After 2 h at 100° C., the reaction mixture was cooled to rt, and the resulting solid was collected by filtration, washing with DMA, and was mixed with water (20 V). The resulting solid was filtered, washing with water, and was dried at 50° C. for 12 h, then was dissolved in THE, treated with HCl (12 M, 1 equiv.), and concentrated. The crude material was dissolved in ACN (10 V), concentrated to about 5 V, diluted with ACN (5 V), heated at 50° C. for 1 h, then cooled to rt, and stirred for 3 h. The resulting solid was collected by filtration, washing with ACN, then dissolved in 2-MeTHF (10 V), and adjusted to pH 7-8 with sat. aq. $NaHCO_3$. The layers were separated and the aqueous phase was extracted with 2-MeTHF (10 V). The combined organic layers were washed with sat. aq. NaCl, and concentrated to obtain Compound 21 (78% yield). $^1H$ NMR (400 MHZ, DMSO-$d_6$) δ=8.36-8.22 (m, 2H), 8.10 (s, 1H), 7.88-7.79 (m, 2H), 7.60 (s, 1H), 7.51-7.40 (m, 2H), 7.27-7.21 (m, 2H), 7.16 (s, 1H), 7.14-7.09 (m, 1H), 7.01 (s, 1H), 6.32 (s, 1H), 5.59-5.49 (m, 2H), 3.54 (s, 3H). MS ESI calcd. for $C_{29}H_{20}N_5O_2$ $[M+H]^+$ 470.2, found 470.1.

EXAMPLE 51: Synthesis of 3-chloro-3-(1-methyl-1H-imidazol-5-yl)-6-oxa-2(4,6)-quinolina-1,4(1,3)-dibenzenacyclohexaphane-$2^2$,$4^4$-dicarbonitrile (18)

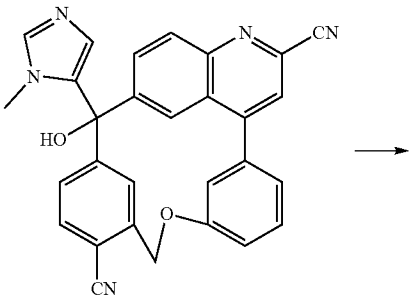

17

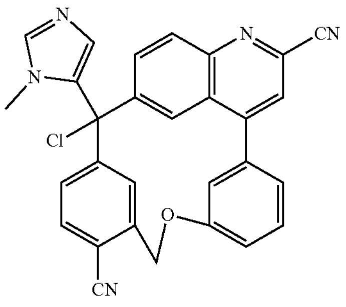

18

A solution of Compound 17 (1.0 equiv.) in DMI (5 V) at 0° C. was treated with $SOCl_2$ (2.8 equiv.) and the resulting mixture was stirred at 40° C. for 2 h. The mixture was used in the next step without work-up or purification.

EXAMPLE 52: Synthesis of 3-amino-3-(1-methyl-1H-imidazol-5-yl)-6-oxa-2(4,6)-quinolina-1,4(1,3)-dibenzenacyclohexaphane-$2^2$,$4^4$-dicarbonitrile (19) and Compound 1

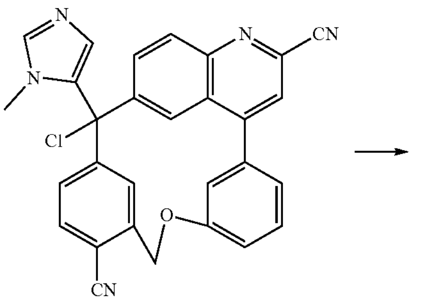

18

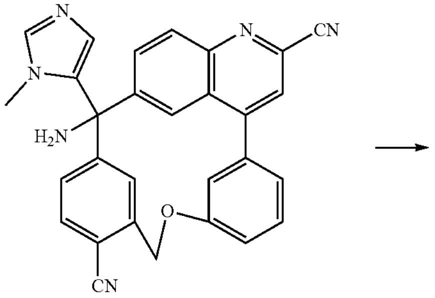

1

19

The mixture of Compound 18 from Example 23 was added to a $NH_3$ (7 M in MeOH; 45 equiv.) at −40° C. and the resulting mixture was stirred at 0° C. for 2 h. The mixture was diluted with water (20 V) at 0° C. and extracted with EtOAc (2×). The combined organic layers were washed with water and extracted with 0.5 N HCl (2×). The combined aqueous phases were adjusted to pH~11 with sat. aq. $Na_2CO_3$ and extracted with EtOAc (2×). The combined organic layers were washed with sat. aq. NaCl and concentrated. The crude product was mixed with IPA (2 V) and stirred for 2 h at rt. The resulting solid was collected by filtration and dried at 50° C. to provide racemic Compound 19 (67% yield over two steps). Compound 19 was resolved by SFC chiral chromatography to get Compound 1 (amorphous, free base). SFC conditions: Column, CHIRALPAK IF (7×25 cm, 10 μm); flow rate, 200 m L/min; mobile phase A, DCM (2 mM $NH_3$ in MeOH); mobile phase B, THF; gradient, 25% B; detector UV 200 nm; column temperature 35° C. The $^1H$ NMR (400 MHz, DMSO-$d_6$) matched that of compound(S)-058, as prepared in Example 58, which is described in International Patent Application No. PCT/US2022/80565.

6.1 INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference in its entirety. Such citations or identifications of any publication, patent, or patent application in this application is not to be construed as an admission that it is prior art to the present application. In case of conflict, the present application, including any definitions herein, will control.

What is claimed is:

1. A solid form comprising Compound 1, or a pharmaceutically acceptable salt and/or a pharmaceutically acceptable solvate thereof:

Compound 1

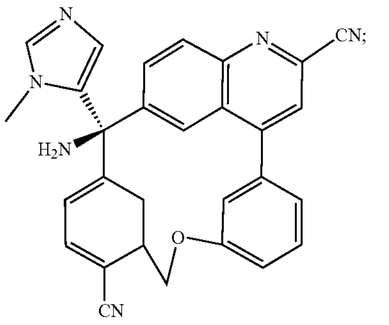

wherein the solid form is crystalline.

2. The solid form of claim 1, wherein the solid form comprises a free base of the Compound 1 or the pharmaceutically acceptable solvate thereof.

3. The solid form of claim 1, wherein the solid form is a non-solvate of the Compound 1 or the pharmaceutically acceptable salt thereof.

4. The solid form of claim 1, wherein the solid form is the pharmaceutically acceptable solvate of the Compound 1 or the pharmaceutically acceptable salt thereof, comprising (i) the Compound 1 or the pharmaceutically acceptable salt thereof, and (ii) a pharmaceutically acceptable solvent.

5. The solid form of claim 4, wherein the pharmaceutically acceptable solvate is selected from the group consisting of: a hydrate, an iso-butyl acetate solvate, an iso-propyl acetate solvate, a tetrahydrofuran solvate, an acetone solvate, and an acetonitrile solvate, and combinations thereof.

6. The solid form of claim 5, wherein the pharmaceutically acceptable solvate comprises (i) the Compound 1 or the pharmaceutically acceptable salt thereof, and (ii) the pharmaceutically acceptable solvent, in a molar ratio in the range of about 2:1 to about 1:2.

7. The solid form of claim 6, wherein the pharmaceutically acceptable solvate is a hydrate.

8. The solid form of claim 7, wherein the hydrate comprises (i) the Compound 1 or the pharmaceutically acceptable salt thereof, and (ii) water, in a molar ratio in the range of about 2:1 to about 1:2.

9. The solid form of claim 1, wherein the solid form is a crystalline, free base, hemi-hydrate of the Compound 1.

10. The solid form of claim 9, wherein the solid form is Compound 1 (Form 1).

11. The solid form of claim 9, which is characterized by an X-ray power diffraction (XRPD) pattern, when measured using Cu Kα radiation, comprising peaks at approximately 9.0, 12.8, 16.6, and 18.4° 2θ.

12. The solid form of claim 1, wherein the solid form comprises the pharmaceutically acceptable salt of the Compound 1 or the pharmaceutically acceptable solvate thereof.

13. The solid form of claim 12, wherein the pharmaceutically acceptable salt is a benzoate salt, a besylate salt, a chloride salt, a citrate salt, a fumarate salt, a gentisate salt, a glycolate salt, a 1-hydroxy-2-naphthoate salt, a malate salt, a maleate salt, a mesylate salt, an oxalate salt, a phosphate salt, a tartrate salt, or a tosylate salt.

14. The solid form of claim 1, wherein the solid form is a free base of the Compound 1 or the pharmaceutically acceptable solvate thereof.

15. The solid form of claim 11, wherein the XRPD pattern comprises a peak selected from the group consisting of approximately 8.6, 12.0, 18.1, and 23.2° 2θ.

16. The solid form of claim 15, wherein the XRPD pattern comprises a peak selected from the group consisting of approximately 16.1, 17.1, 24.1, and 25.6° 2θ.

17. The solid form of claim 9, which is characterized by having approximately unit cell dimensions of a=15.2Å, b=7.9 Å, c=20.7 Å, α=90°, ß=107.8°, and γ=90°, and a unit cell of a space group of $P2_1$.

18. The solid form of claim 9, which exhibits a thermal (endothermic) event with an onset temperature of about 83° C. and a thermal (endothermic, melting) event with an onset temperature of about 212° C., and/or an endothermic peak at about 137° C. and at about 221° C., as characterized by differential scanning calorimetry (DSC) with a temperature ramp of about 10° C./min.

19. The solid form of claim 9, which exhibits no weight loss upon heating below about 75° C. and a weight loss of about 1.8% upon heating from about 75° C. to about 170° C., as characterized by thermal gravimetric analysis (TGA).

20. The solid form of claim 9, wherein the solid form has a purity of at least 98%, 98.5%, 99%, or 99.5%.

21. The solid form of claim 9, wherein the solid form has:

(a) a solubility of about 4.69, 5.04, and 3.67 mg/mL in simulated gastric fluid (SGF) media, at 0.5 h, 2 h, and 24 h, respectively; or (b) a solubility of about 0.29, 0.31, and 0.33 mg/mL in fed state simulated intestinal fluid (FeSSIF) media, at 0.5 h, 2 h, and 24 h, respectively;

or a combination thereof.

22. The solid form of claim 1, wherein the solid form comprises a non-solvate of the Compound 1 or the pharmaceutically acceptable salt thereof.

23. The solid form of claim 1, wherein the solid form comprises the pharmaceutically acceptable solvate of the Compound 1 or the pharmaceutically acceptable salt thereof.

24. The solid form of claim 1, wherein the solid form is the pharmaceutically acceptable salt of the Compound 1 or the pharmaceutically acceptable solvate thereof.

25. A solid form comprising a pharmaceutically acceptable solvate of Compound 1, or a pharmaceutically acceptable salt thereof:

Compound 1

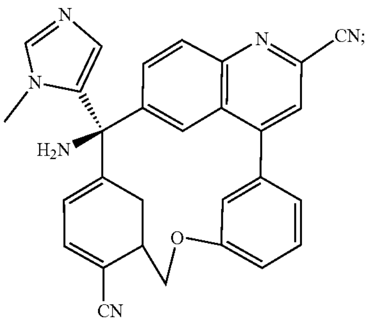

wherein:

i) the pharmaceutically acceptable solvate is selected from the group consisting of: a hydrate, an iso-butyl acetate solvate, an iso-propyl acetate solvate, a tetrahydrofuran solvate, an acetone solvate, and an acetonitrile solvate, and combinations thereof; and ii) the pharmaceutically acceptable solvate comprises (a) the Compound 1 or the pharmaceutically acceptable salt thereof, and (b) a pharmaceutically acceptable solvent, solvent are present in a molar ratio in the range of about 2:1 to about 1:2.

26. The solid form of claim 25, wherein the pharmaceutically acceptable solvate is a hydrate.

27. The solid form of claim 26, wherein the hydrate comprises (i) the Compound 1 or the pharmaceutically acceptable salt thereof, and (ii) water in a molar ratio of about 2:1 (hemi-hydrate).

28. The solid form of claim 25, wherein the pharmaceutically acceptable salt is a benzoate salt, a besylate salt, a chloride salt, a citrate salt, a fumarate salt, a gentisate salt, a glycolate salt, a 1-hydroxy-2-naphthoate salt, a malate salt, a maleate salt, a mesylate salt, an oxalate salt, a phosphate salt, a tartrate salt, or a tosylate salt.

* * * * *